(12) United States Patent
Kamiie et al.

(10) Patent No.: US 7,901,942 B2
(45) Date of Patent: Mar. 8, 2011

(54) METHOD OF QUANTIFYING MEMBRANE PROTEIN BY MASS SPECTROMETRY USING PEPTIDE SELECTION CRITERIA

(75) Inventors: Junichi Kamiie, Sendai (JP); Sumio Otsuki, Sendai (JP); Tetsuya Terasaki, Sendai (JP)

(73) Assignee: Tohoku University, Sendai (JP)

( * ) Notice: Subject to any disclaimer, the term of this patent is extended or adjusted under 35 U.S.C. 154(b) by 143 days.

(21) Appl. No.: 12/093,133

(22) PCT Filed: Oct. 27, 2006

(86) PCT No.: PCT/JP2006/321577
§ 371 (c)(1),
(2), (4) Date: Jun. 27, 2008

(87) PCT Pub. No.: WO2007/055116
PCT Pub. Date: May 18, 2007

(65) Prior Publication Data
US 2010/0029005 A1    Feb. 4, 2010

(30) Foreign Application Priority Data

Nov. 8, 2005  (JP) ................................ 2005-324159

(51) Int. Cl.
*G01N 33/00* (2006.01)
(52) U.S. Cl. .......................................... 436/86; 435/23
(58) Field of Classification Search .................... 436/86; 435/23
See application file for complete search history.

(56) References Cited

FOREIGN PATENT DOCUMENTS

| EP | 1 533 316 A1 | 5/2005 |
|---|---|---|
| JP | 2002-515820 A | 5/2002 |
| JP | 2002-524755 A | 8/2002 |
| JP | 2004-28993 A | 3/2003 |
| JP | 2004-77276 A | 3/2004 |
| JP | 2004-157124 A | 6/2004 |
| JP | 2004-533610 A | 11/2004 |
| JP | 2005-185281 A | 7/2005 |
| WO | WO 97/04297 | 2/1997 |
| WO | WO 00/15321 | 3/2000 |
| WO | WO 02/090929 A2 | 11/2002 |
| WO | WO 03/046148 | 6/2003 |
| WO | WO 2004/002996 | 1/2004 |

OTHER PUBLICATIONS

International Search Report from corresponding PCT Application No. PCT/JP2006/321577 (WO07/055116) and English Translation dated Jan. 23, 2007, 4 pages.

(Continued)

*Primary Examiner* — Yelena G Gakh
*Assistant Examiner* — Michelle M Adams
(74) *Attorney, Agent, or Firm* — Cadwalader, Wickersham & Taft LLP

(57) ABSTRACT

A method is provided for quantifying a plasma membrane protein present by using a stable-isotope labeled peptide as a probe by mass spectrometry in a simple, quick and accurate manner. A plasma membrane protein is fragmented to prepare an oligopeptide fragment, identified by LC/MS/MS. A subject peptide for quantification is selected if the peptide is obtained by fragmenting with a protease, the peptide is specific to a target molecule, and if the peptide has a high total score value based on selective criteria for hydrophobic amino acids content, sequence conditions, number of amino acid residues, specific amino acid sequence conditions, etc. According to these criteria, a subject peptide fragment that can be ionized by ESI method is selected. By using the subject peptide for and a stable-isotope labeled peptide, the plasma membrane protein is quantified accurately by mass spectrometry.

13 Claims, 7 Drawing Sheets
(3 of 7 Drawing Sheet(s) Filed in Color)

OTHER PUBLICATIONS

Barnidge, David R. et al., "Absolute Quantification of the G Protein-Coupled Receptor Rhodopsin by LC/MS/MS Using Proteolysis Product Peptides and Synthetic Peptide Standards," Analytical Chemistry, vol. 75, No. 3, Feb. 1, 2003, pp. 445-451, American Chemical Society.

Romijn, Edwin P., et al., "Recent Liquid Chromatographic- (tandem) Mass Spectrometric Applications in Proteomics," Journal of Chromatography, vol. 1000, No. 1/2, Jun. 6, 2003, pp. 589-608, Elsevier Science B.V.

JP International Preliminary Examination Report (IPER) from corresponding PCT Application No. PCT/JP2006/321577 (WO07/055116), dated Nov. 16, 2007, and English Translation, undated, 9 pages.

JP Written Opinion from corresponding PCT Application No. PCT/JP2006/321577 (WO07/055116), dated Jan. 23, 2007, 4 pages.

Supplementary European Search Report from corresponding European Application No. 06822538.2 dated Mar. 23, 2009, 2 pages.

Kamiie, Junichi et al., "Quantitative Atlas of Membrane Transporter Proteins: Development and Application of a Highly Sensitive Simultaneous LC/MS/MS Method Combined with Novel In-Silico Peptide Selection Criteria," Pharmaceutical Research, vol. 25, No. 6, Jan. 25, 2008, pp. 1469-1483, Springer Netherlands.

Anderson, et al., "Developing Peptide MRM-based Assays for Cardiovascular Biomarker Proteins in Plasma Using a Hybrid Triple Quadrupole Linear Ion Trap Mass Spectrometer," Plasma Proteome Institute, ASMS San Antonio Jun. 9, 2005, pp. 1-14.

Allikmets, et al., "Characterization of the Human ABC Superfamily: Isolation and Mapping of 21 New Genes Using the Expressed Sequence Tags Database," Human Molecular Genetics, 1996, vol. 5, No. 10, pp. 1649-1655.

Doyle, et al., "A Multidrug Resistance Transporter From Human MCF-7 Breast Cancer Cells," Proc. Natl. Acad. Sci. USA, vol. 95, Medical Sciences, Dec. 1998, pp. 15665-15670.

Maliepaard, et al., "Circumvention of Breast Cancer Resistance Protein (BCRP)- Mediated Resistance to Camptothecins in Vitro Using Non-Substrate Drugs or the BCRP Inhibitor GF120918," Clinical Cancer Research, vol. 7, 935-941, Apr. 2001, pp. 935-941.

Kioka, et al., "P-Glycoprotein Gene (MDR1) cDNA from Human Adrenal: Normal P-Glycoprotein Carries Gly[185] with an Altered Pattern of Multidrug Resistance," BioChemical and BioPhysical Research Communications, vol. 162, No. 1, 1989, Jul. 14, 1989, pp. 224-231.

Gros, et al., "Isolation and Expression of a Complementary DNA that Confers Multidrug Resistance," Nature, vol. 323, Oct. 23, 1986, pp. 728-731.

Ponticelli, et al., "Meiotic Recombination-Deficient Mutants of Schizosaccharomyces Pombe," Genetics Society of America 123: 45-54, Sep. 1989, pp. 45-54.

Dean, et al., "Evolution of ATP-Binding Cassette Transporter Genes," Current Opinion in Genetics & Development 1995, 5: 779-785.

Kuhn, et al., "Quantification of C-reactive Protein in the Serum of Patients with Rheumatoid Arthritis Using Multiple Reaction Monitoring Mass Spectrometry and 13C-labeled Peptide Standards," Proteomics 2004, 4, 1175-1186.

Supplementary European Search Report from corresponding European Application No. 06822538.2 dated Mar. 23, 2009, including written opinion, 9 pages.

Kawakami, H. et al. "Simultaneous Absolute Quantification of 11 Cytochrome P450 Isoforms in Liver Microsomes by Liquid Chromatography Tandem Mass Spectrometry with In Silico Target Peptide Selection," J. Pharmaceutical Sci., 1-12, epub ahead of print Jun. 16, 2010 (PMID: 20564338); published online in Wiley InterScience (www.interscience.wiley.com). DOI 10.1002/jps.22255.

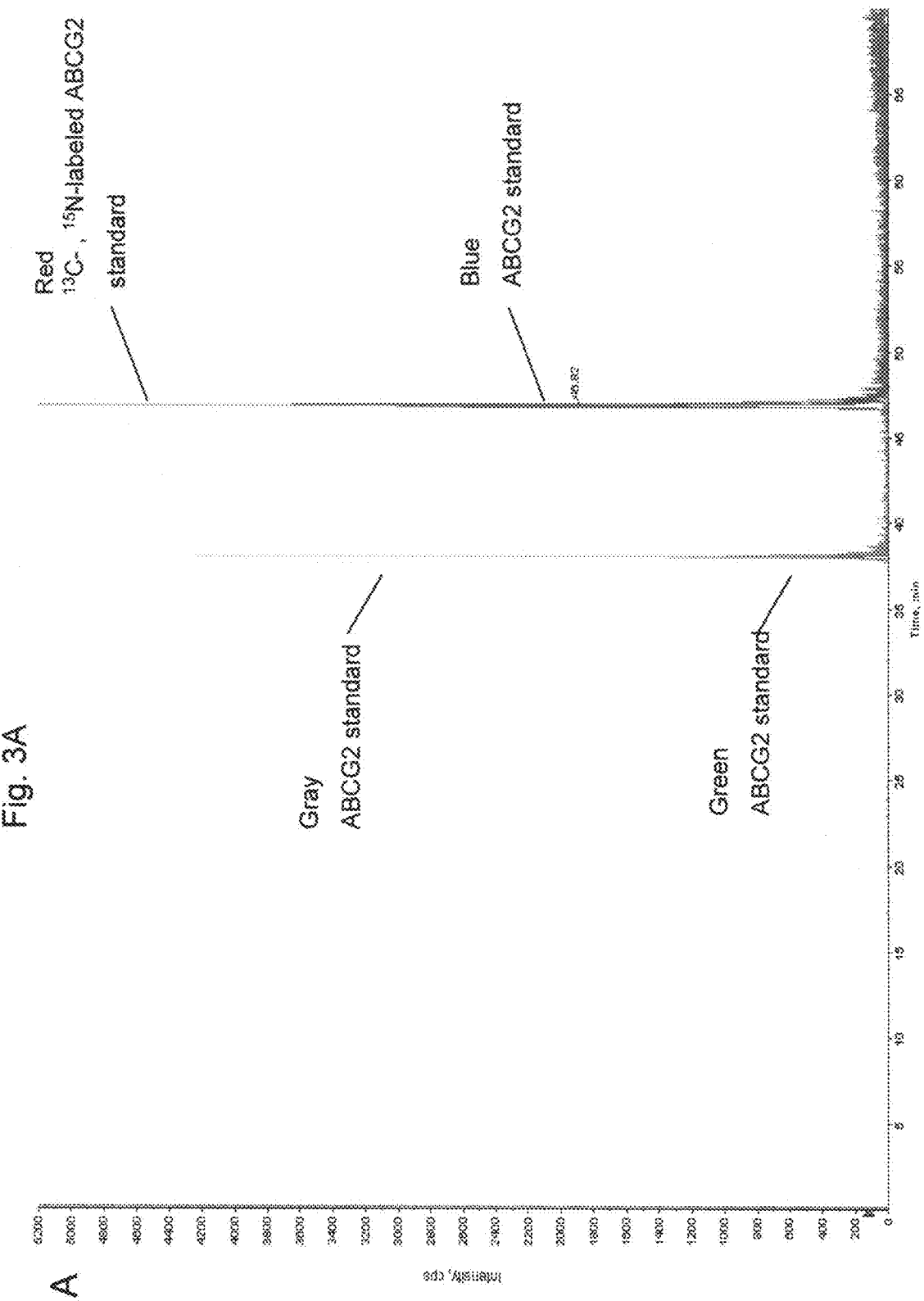

SEQUENCE LISTING

```
<160> NUMBER OF SEQ ID NOS: 1420

<210> SEQ ID NO 1
<211> LENGTH: 10
<212> TYPE: PRT
<213> ORGANISM: Artificial Sequence
<220> FEATURE:
<223> OTHER INFORMATION: Fragment of ATP binding cassette, sub-family
      member G2

<400> SEQUENCE: 1

Glu Asn Leu Gln Phe Ser Ala Ala Leu Arg
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Fragment of ATP binding cassette, sub-family
      member G2

<400> SEQUENCE: 2

Leu Ala Glu Ile Tyr Val Asn Ser Ser Phe Tyr Lys
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Fragment of ATP binding cassette, sub-family
      member G2

<400> SEQUENCE: 3

Leu Phe Asp Ser Leu Thr Leu Leu Ala Ser Gly Arg
1               5                   10
```

```
<210> SEQ ID NO 4
<211> LENGTH: 10
<212> TYPE: PRT
<213> ORGANISM: Artificial Sequence
<220> FEATURE:
<223> OTHER INFORMATION: Fragment of ATP binding cassette, sub-family
      member G2

<400> SEQUENCE: 4

Ser Ser Leu Leu Asp Val Leu Ala Ala Arg
1               5                   10

<210> SEQ ID NO 5
<211> LENGTH: 9
<212> TYPE: PRT
<213> ORGANISM: Artificial Sequence
<220> FEATURE:
<223> OTHER INFORMATION: Fragment of ATP binding cassette, sub-family
      member G2

<400> SEQUENCE: 5

Val Ile Gln Glu Leu Gly Leu Asp Lys
1               5

<210> SEQ ID NO 6
<211> LENGTH: 14
<212> TYPE: PRT
<213> ORGANISM: Artificial Sequence
<220> FEATURE:
<223> OTHER INFORMATION: Fragment of P-glycoprotein

<400> SEQUENCE: 6

Ser Glu Ile Asp Ala Leu Glu Met Ser Ser Asn Asp Ser Arg
1               5                   10

<210> SEQ ID NO 7
<211> LENGTH: 14
<212> TYPE: PRT
<213> ORGANISM: Artificial Sequence
<220> FEATURE:
<223> OTHER INFORMATION: Fragment of P-glycoprotein

<400> SEQUENCE: 7

Glu Ala Leu Asp Glu Ser Ile Pro Pro Val Ser Phe Trp Arg
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Fragment of P-glycoprotein

<400> SEQUENCE: 8

Ile Ala Thr Glu Ala Ile Glu Asn Phe Arg
1               5                   10

<210> SEQ ID NO 9
<211> LENGTH: 16
<212> TYPE: PRT
<213> ORGANISM: Artificial Sequence
<220> FEATURE:
<223> OTHER INFORMATION: Fragment of P-glycoprotein

<400> SEQUENCE: 9

Asn Ala Asp Val Ile Ala Gly Phe Asp Asp Gly Val Ile Val Glu Lys
1               5                   10                  15
```

```
<210> SEQ ID NO 10
<211> LENGTH: 17
<212> TYPE: PRT
<213> ORGANISM: Artificial Sequence
<220> FEATURE:
<223> OTHER INFORMATION: Fragment of P-glycoprotein

<400> SEQUENCE: 10

Leu Tyr Asp Pro Thr Glu Gly Met Val Ser Val Asp Gly Gln Asp Ile
1               5                   10                  15

Arg

<210> SEQ ID NO 11
<211> LENGTH: 25
<212> TYPE: PRT
<213> ORGANISM: Artificial Sequence
<220> FEATURE:
<223> OTHER INFORMATION: Fragment of P-glycoprotein

<400> SEQUENCE: 11

Ile Leu Leu Leu Asp Glu Ala Thr Ser Ala Leu Asp Thr Glu Ser Glu
1               5                   10                  15

Ala Val Val Gln Val Ala Leu Asp Lys
            20                  25

<210> SEQ ID NO 12
<211> LENGTH: 10
<212> TYPE: PRT
<213> ORGANISM: Artificial Sequence
<220> FEATURE:
<223> OTHER INFORMATION: Fragment of P-glycoprotein

<400> SEQUENCE: 12

Thr Val Val Ser Leu Thr Gln Glu Gln Lys
1               5                   10

<210> SEQ ID NO 13
<211> LENGTH: 9
<212> TYPE: PRT
<213> ORGANISM: Artificial Sequence
<220> FEATURE:
<223> OTHER INFORMATION: Fragment of P-glycoprotein

<400> SEQUENCE: 13

Ser Thr Val Val Gln Leu Leu Glu Arg
1               5

<210> SEQ ID NO 14
<211> LENGTH: 10
<212> TYPE: PRT
<213> ORGANISM: Artificial Sequence
<220> FEATURE:
<223> OTHER INFORMATION: Fragment of P-glycoprotein

<400> SEQUENCE: 14

Glu Asn Val Thr Met Asp Glu Ile Glu Lys
1               5                   10

<210> SEQ ID NO 15
<211> LENGTH: 9
<212> TYPE: PRT
<213> ORGANISM: Artificial Sequence
<220> FEATURE:
<223> OTHER INFORMATION: Fragment of P-glycoprotein

<400> SEQUENCE: 15
```

```
Asn Thr Thr Gly Ala Leu Thr Thr Arg
1               5

<210> SEQ ID NO 16
<211> LENGTH: 8
<212> TYPE: PRT
<213> ORGANISM: Artificial Sequence
<220> FEATURE:
<223> OTHER INFORMATION: Fragment of P-glycoprotein

<400> SEQUENCE: 16

Val Val Gln Glu Ala Leu Asp Lys
1               5

<210> SEQ ID NO 17
<211> LENGTH: 8
<212> TYPE: PRT
<213> ORGANISM: Artificial Sequence
<220> FEATURE:
<223> OTHER INFORMATION: Fragment of P-glycoprotein

<400> SEQUENCE: 17

Phe Tyr Asp Pro Leu Ala Gly Lys
1               5

<210> SEQ ID NO 18
<211> LENGTH: 9
<212> TYPE: PRT
<213> ORGANISM: Artificial Sequence
<220> FEATURE:
<223> OTHER INFORMATION: Fragment of P-glycoprotein

<400> SEQUENCE: 18

Ser Thr Thr Val Gln Leu Met Gln Arg
1               5

<210> SEQ ID NO 19
<211> LENGTH: 14
<212> TYPE: PRT
<213> ORGANISM: Artificial Sequence
<220> FEATURE:
<223> OTHER INFORMATION: Fragment of ATP-binding cassette, sub-family
      C member4

<400> SEQUENCE: 19

Ser Gln His Leu Gly Glu Glu Leu Gln Gly Phe Trp Asp Lys
1               5                   10

<210> SEQ ID NO 20
<211> LENGTH: 17
<212> TYPE: PRT
<213> ORGANISM: Artificial Sequence
<220> FEATURE:
<223> OTHER INFORMATION: Fragment of ATP-binding cassette, sub-family
      C member4

<400> SEQUENCE: 20

Met Asp Thr Glu Leu Ala Glu Ser Gly Ser Asn Phe Ser Val Gly Gln
1               5                   10                  15

Arg

<210> SEQ ID NO 21
<211> LENGTH: 21
<212> TYPE: PRT
<213> ORGANISM: Artificial Sequence
<220> FEATURE:
<223> OTHER INFORMATION: Fragment of ATP-binding cassette, sub-family
```

C member4

<400> SEQUENCE: 21

Asp Gly Ala Leu Glu Ser Gln Asp Thr Glu Asn Val Pro Val Thr Leu
1               5                   10                  15

Ser Glu Glu Asn Arg
            20

<210> SEQ ID NO 22
<211> LENGTH: 13
<212> TYPE: PRT
<213> ORGANISM: Artificial Sequence
<220> FEATURE:
<223> OTHER INFORMATION: Fragment of ATP-binding cassette, sub-family
      C member4

<400> SEQUENCE: 22

Ile Thr Ile Leu Val Thr His Gln Leu Gln Tyr Leu Lys
1               5                   10

<210> SEQ ID NO 23
<211> LENGTH: 16
<212> TYPE: PRT
<213> ORGANISM: Artificial Sequence
<220> FEATURE:
<223> OTHER INFORMATION: Fragment of ATP-binding cassette, sub-family
      C member4

<400> SEQUENCE: 23

Ile Ala Tyr Val Ser Gln Gln Pro Trp Val Phe Ser Gly Thr Leu Arg
1               5                   10                  15

<210> SEQ ID NO 24
<211> LENGTH: 13
<212> TYPE: PRT
<213> ORGANISM: Artificial Sequence
<220> FEATURE:
<223> OTHER INFORMATION: Fragment of ATP-binding cassette, sub-family
      C member4

<400> SEQUENCE: 24

Ile Gln Thr Phe Leu Leu Leu Asp Glu Ile Ser Gln Arg
1               5                   10

<210> SEQ ID NO 25
<211> LENGTH: 16
<212> TYPE: PRT
<213> ORGANISM: Artificial Sequence
<220> FEATURE:
<223> OTHER INFORMATION: Fragment of ATP-binding cassette, sub-family
      C member4

<400> SEQUENCE: 25

Asp Leu Gln Leu Leu Glu Asp Gly Asp Leu Thr Val Ile Gly Asp Arg
1               5                   10                  15

<210> SEQ ID NO 26
<211> LENGTH: 13
<212> TYPE: PRT
<213> ORGANISM: Artificial Sequence
<220> FEATURE:
<223> OTHER INFORMATION: Fragment of ATP-binding cassette, sub-family
      C member4

<400> SEQUENCE: 26

Met Val His Val Gln Asp Phe Thr Ala Phe Trp Asp Lys
1               5                   10

```
<210> SEQ ID NO 27
<211> LENGTH: 11
<212> TYPE: PRT
<213> ORGANISM: Artificial Sequence
<220> FEATURE:
<223> OTHER INFORMATION: Fragment of ATP-binding cassette, sub-family
      C member4

<400> SEQUENCE: 27

Val Phe Phe Trp Trp Leu Asn Pro Leu Phe Lys
1               5                   10

<210> SEQ ID NO 28
<211> LENGTH: 17
<212> TYPE: PRT
<213> ORGANISM: Artificial Sequence
<220> FEATURE:
<223> OTHER INFORMATION: Fragment of ATP-binding cassette, sub-family
      C member4

<400> SEQUENCE: 28

Asp Asn Glu Glu Ser Glu Gln Pro Pro Val Pro Gly Thr Pro Thr Leu
1               5                   10                  15

Arg

<210> SEQ ID NO 29
<211> LENGTH: 8
<212> TYPE: PRT
<213> ORGANISM: Artificial Sequence
<220> FEATURE:
<223> OTHER INFORMATION: Fragment of ATP-binding cassette, sub-family
      C member4

<400> SEQUENCE: 29

Ala Pro Val Leu Phe Phe Asp Arg
1               5

<210> SEQ ID NO 30
<211> LENGTH: 9
<212> TYPE: PRT
<213> ORGANISM: Artificial Sequence
<220> FEATURE:
<223> OTHER INFORMATION: Fragment of ATP-binding cassette, sub-family
      C member4

<400> SEQUENCE: 30

Val Ala Met Glx His Met Ile Tyr Arg
1               5

<210> SEQ ID NO 31
<211> LENGTH: 23
<212> TYPE: PRT
<213> ORGANISM: Artificial Sequence
<220> FEATURE:
<223> OTHER INFORMATION: Fragment of ATP-binding cassette, sub-family
      C member4

<400> SEQUENCE: 31

Ser Ser Leu Leu Ser Ala Val Leu Gly Glu Leu Ala Pro Ser His Gly
1               5                   10                  15

Leu Val Ser Val His Gly Arg
            20

<210> SEQ ID NO 32
<211> LENGTH: 18
<212> TYPE: PRT
<213> ORGANISM: Artificial Sequence
```

```
<220> FEATURE:
<223> OTHER INFORMATION: Fragment of ATP-binding cassette, sub-family
      C member4

<400> SEQUENCE: 32

Thr Phe Ser Glu Ser Ser Val Trp Ser Gln Gln Ser Ser Arg Pro Ser
1               5                   10                  15

Leu Lys

<210> SEQ ID NO 33
<211> LENGTH: 9
<212> TYPE: PRT
<213> ORGANISM: Artificial Sequence
<220> FEATURE:
<223> OTHER INFORMATION: Fragment of ATP-binding cassette, sub-family
      C member4

<400> SEQUENCE: 33

Val Ser Glu Ala Ile Val Ser Ile Arg
1               5

<210> SEQ ID NO 34
<211> LENGTH: 10
<212> TYPE: PRT
<213> ORGANISM: Artificial Sequence
<220> FEATURE:
<223> OTHER INFORMATION: Fragment of ATP-binding cassette, sub-family
      C member4

<400> SEQUENCE: 34

Ser Gly Ile Asp Phe Gly Ser Leu Leu Lys
1               5                   10

<210> SEQ ID NO 35
<211> LENGTH: 16
<212> TYPE: PRT
<213> ORGANISM: Artificial Sequence
<220> FEATURE:
<223> OTHER INFORMATION: Fragment of ATP-binding cassette, sub-family
      C member4

<400> SEQUENCE: 35

Asp Leu Gln Leu Leu Glu Asp Gly Asp Leu Thr Val Ile Gly Asp Arg
1               5                   10                  15

<210> SEQ ID NO 36
<211> LENGTH: 16
<212> TYPE: PRT
<213> ORGANISM: Artificial Sequence
<220> FEATURE:
<223> OTHER INFORMATION: Fragment of ATP-binding cassette, sub-family
      C member4

<400> SEQUENCE: 36

Met Ser Ile Ile Pro Gln Glu Pro Val Leu Phe Thr Gly Thr Met Arg
1               5                   10                  15

<210> SEQ ID NO 37
<211> LENGTH: 7
<212> TYPE: PRT
<213> ORGANISM: Artificial Sequence
<220> FEATURE:
<223> OTHER INFORMATION: ABCA1

<400> SEQUENCE: 37

Ala Asp Val Ile Leu His Lys
1               5
```

```
<210> SEQ ID NO 38
<211> LENGTH: 6
<212> TYPE: PRT
<213> ORGANISM: Artificial Sequence
<220> FEATURE:
<223> OTHER INFORMATION: ABCA1

<400> SEQUENCE: 38

Leu Ala Ala Ala Glu Arg
1               5

<210> SEQ ID NO 39
<211> LENGTH: 11
<212> TYPE: PRT
<213> ORGANISM: Artificial Sequence
<220> FEATURE:
<223> OTHER INFORMATION: ABCA1

<400> SEQUENCE: 39

Ser Leu Asn Trp Tyr Glu Asp Asn Asn Tyr Lys
1               5                   10

<210> SEQ ID NO 40
<211> LENGTH: 11
<212> TYPE: PRT
<213> ORGANISM: Artificial Sequence
<220> FEATURE:
<223> OTHER INFORMATION: ABCA1

<400> SEQUENCE: 40

Ile Leu Tyr Thr Pro Asp Thr Pro Ala Thr Arg
1               5                   10

<210> SEQ ID NO 41
<211> LENGTH: 9
<212> TYPE: PRT
<213> ORGANISM: Artificial Sequence
<220> FEATURE:
<223> OTHER INFORMATION: ABCA1

<400> SEQUENCE: 41

Asp Gly Tyr Trp Asp Pro Gly Pro Arg
1               5

<210> SEQ ID NO 42
<211> LENGTH: 11
<212> TYPE: PRT
<213> ORGANISM: Artificial Sequence
<220> FEATURE:
<223> OTHER INFORMATION: ABCA1

<400> SEQUENCE: 42

Ser Tyr Trp Phe Gly Glu Glu Ser Asp Glu Lys
1               5                   10

<210> SEQ ID NO 43
<211> LENGTH: 10
<212> TYPE: PRT
<213> ORGANISM: Artificial Sequence
<220> FEATURE:
<223> OTHER INFORMATION: ABCA1

<400> SEQUENCE: 43

Leu Gly Val Ser Ile Gln Asn Leu Val Lys
1               5                   10

<210> SEQ ID NO 44
```

```
<211> LENGTH: 8
<212> TYPE: PRT
<213> ORGANISM: Artificial Sequence
<220> FEATURE:
<223> OTHER INFORMATION: ABCA1

<400> SEQUENCE: 44

Ile Ala Ile Ile Ser His Gly Lys
1               5

<210> SEQ ID NO 45
<211> LENGTH: 14
<212> TYPE: PRT
<213> ORGANISM: Artificial Sequence
<220> FEATURE:
<223> OTHER INFORMATION: ABCA1

<400> SEQUENCE: 45

Glu Gly Ala Phe Val Glu Leu Phe His Glu Ile Asp Asp Arg
1               5                   10

<210> SEQ ID NO 46
<211> LENGTH: 6
<212> TYPE: PRT
<213> ORGANISM: Artificial Sequence
<220> FEATURE:
<223> OTHER INFORMATION: ABCA1

<400> SEQUENCE: 46

Asp Ser Ser Ala Asp Arg
1               5

<210> SEQ ID NO 47
<211> LENGTH: 7
<212> TYPE: PRT
<213> ORGANISM: Artificial Sequence
<220> FEATURE:
<223> OTHER INFORMATION: ABCA1

<400> SEQUENCE: 47

Phe Leu Asn Ser Leu Gly Arg
1               5

<210> SEQ ID NO 48
<211> LENGTH: 12
<212> TYPE: PRT
<213> ORGANISM: Artificial Sequence
<220> FEATURE:
<223> OTHER INFORMATION: ABCA1

<400> SEQUENCE: 48

Phe Val Ser Pro Leu Ser Trp Asp Leu Val Gly Arg
1               5                   10

<210> SEQ ID NO 49
<211> LENGTH: 14
<212> TYPE: PRT
<213> ORGANISM: Artificial Sequence
<220> FEATURE:
<223> OTHER INFORMATION: ABCA1

<400> SEQUENCE: 49

Ile Leu Asp Gly Gly Gly Gln Asn Asp Ile Leu Glu Ile Lys
1               5                   10

<210> SEQ ID NO 50
<211> LENGTH: 7
<212> TYPE: PRT
```

-continued

```
<213> ORGANISM: Artificial Sequence
<220> FEATURE:
<223> OTHER INFORMATION: ABCA1

<400> SEQUENCE: 50

Gly Asp Ala Phe Leu Asn Lys
1               5

<210> SEQ ID NO 51
<211> LENGTH: 10
<212> TYPE: PRT
<213> ORGANISM: Artificial Sequence
<220> FEATURE:
<223> OTHER INFORMATION: ABCA1

<400> SEQUENCE: 51

Glu His Val Glu Phe Phe Ala Leu Leu Arg
1               5                   10

<210> SEQ ID NO 52
<211> LENGTH: 10
<212> TYPE: PRT
<213> ORGANISM: Artificial Sequence
<220> FEATURE:
<223> OTHER INFORMATION: ABCA1

<400> SEQUENCE: 52

Phe Gly Asp Gly Tyr Thr Ile Val Val Arg
1               5                   10

<210> SEQ ID NO 53
<211> LENGTH: 9
<212> TYPE: PRT
<213> ORGANISM: Artificial Sequence
<220> FEATURE:
<223> OTHER INFORMATION: ABCA1

<400> SEQUENCE: 53

Asp Gln Ser Asp Asp Asp His Leu Lys
1               5

<210> SEQ ID NO 54
<211> LENGTH: 13
<212> TYPE: PRT
<213> ORGANISM: Artificial Sequence
<220> FEATURE:
<223> OTHER INFORMATION: ABCA2

<400> SEQUENCE: 54

Ser Thr Val Ser Ser Phe Ser Leu Asp Ser Val Ala Arg
1               5                   10

<210> SEQ ID NO 55
<211> LENGTH: 7
<212> TYPE: PRT
<213> ORGANISM: Artificial Sequence
<220> FEATURE:
<223> OTHER INFORMATION: ABCA2

<400> SEQUENCE: 55

Asn Pro Gln Glu Leu Trp Arg
1               5

<210> SEQ ID NO 56
<211> LENGTH: 8
<212> TYPE: PRT
<213> ORGANISM: Artificial Sequence
<220> FEATURE:
```

<223> OTHER INFORMATION: ABCA2

<400> SEQUENCE: 56

Leu Gly Gly Asn Pro Leu Phe Arg
1               5

<210> SEQ ID NO 57
<211> LENGTH: 9
<212> TYPE: PRT
<213> ORGANISM: Artificial Sequence
<220> FEATURE:
<223> OTHER INFORMATION: ABCA2

<400> SEQUENCE: 57

Ile Leu Thr Val Pro Glu Ser Gln Lys
1               5

<210> SEQ ID NO 58
<211> LENGTH: 7
<212> TYPE: PRT
<213> ORGANISM: Artificial Sequence
<220> FEATURE:
<223> OTHER INFORMATION: ABCA2

<400> SEQUENCE: 58

Gly Ala Leu Gln Gly Tyr Arg
1               5

<210> SEQ ID NO 59
<211> LENGTH: 7
<212> TYPE: PRT
<213> ORGANISM: Artificial Sequence
<220> FEATURE:
<223> OTHER INFORMATION: ABCA2

<400> SEQUENCE: 59

Asn Gln Leu Asp Val Ala Lys
1               5

<210> SEQ ID NO 60
<211> LENGTH: 12
<212> TYPE: PRT
<213> ORGANISM: Artificial Sequence
<220> FEATURE:
<223> OTHER INFORMATION: ABCA2

<400> SEQUENCE: 60

Ile Leu Tyr Ala Pro Ala Gly Ser Glu Val Asp Arg
1               5                   10

<210> SEQ ID NO 61
<211> LENGTH: 7
<212> TYPE: PRT
<213> ORGANISM: Artificial Sequence
<220> FEATURE:
<223> OTHER INFORMATION: ABCA2

<400> SEQUENCE: 61

Ser Phe Leu Glu Gln Gly Arg
1               5

<210> SEQ ID NO 62
<211> LENGTH: 6
<212> TYPE: PRT
<213> ORGANISM: Artificial Sequence
<220> FEATURE:
<223> OTHER INFORMATION: ABCA2

```
<400> SEQUENCE: 62

Leu Gln Gln His Leu Arg
1               5

<210> SEQ ID NO 63
<211> LENGTH: 10
<212> TYPE: PRT
<213> ORGANISM: Artificial Sequence
<220> FEATURE:
<223> OTHER INFORMATION: ABCA2

<400> SEQUENCE: 63

Trp Leu Gln Gln Tyr Val Ala Glu Leu Arg
1               5                   10

<210> SEQ ID NO 64
<211> LENGTH: 7
<212> TYPE: PRT
<213> ORGANISM: Artificial Sequence
<220> FEATURE:
<223> OTHER INFORMATION: ABCA2

<400> SEQUENCE: 64

Val Ser Val Asp Ile Phe Lys
1               5

<210> SEQ ID NO 65
<211> LENGTH: 8
<212> TYPE: PRT
<213> ORGANISM: Artificial Sequence
<220> FEATURE:
<223> OTHER INFORMATION: ABCA2

<400> SEQUENCE: 65

Ser Tyr Trp Leu Gly Ser Gly Arg
1               5

<210> SEQ ID NO 66
<211> LENGTH: 12
<212> TYPE: PRT
<213> ORGANISM: Artificial Sequence
<220> FEATURE:
<223> OTHER INFORMATION: ABCA2

<400> SEQUENCE: 66

Thr Glu Ala Trp Glu Trp Ser Trp Pro Trp Ala Arg
1               5                   10

<210> SEQ ID NO 67
<211> LENGTH: 12
<212> TYPE: PRT
<213> ORGANISM: Artificial Sequence
<220> FEATURE:
<223> OTHER INFORMATION: ABCA2

<400> SEQUENCE: 67

Leu Thr Val Glu Glu His Leu Trp Phe Tyr Ser Arg
1               5                   10

<210> SEQ ID NO 68
<211> LENGTH: 7
<212> TYPE: PRT
<213> ORGANISM: Artificial Sequence
<220> FEATURE:
<223> OTHER INFORMATION: ABCA2

<400> SEQUENCE: 68
```

```
Leu Phe Gln His Leu Glu Arg
1               5

<210> SEQ ID NO 69
<211> LENGTH: 11
<212> TYPE: PRT
<213> ORGANISM: Artificial Sequence
<220> FEATURE:
<223> OTHER INFORMATION: ABCA2

<400> SEQUENCE: 69

Tyr Gly Ala Ile Thr Phe Gly Asn Val Leu Lys
1               5                   10

<210> SEQ ID NO 70
<211> LENGTH: 9
<212> TYPE: PRT
<213> ORGANISM: Artificial Sequence
<220> FEATURE:
<223> OTHER INFORMATION: ABCA2

<400> SEQUENCE: 70

Ser Ile Pro Ala Ser Phe Gly Thr Arg
1               5

<210> SEQ ID NO 71
<211> LENGTH: 7
<212> TYPE: PRT
<213> ORGANISM: Artificial Sequence
<220> FEATURE:
<223> OTHER INFORMATION: ABCA2

<400> SEQUENCE: 71

Val Val Asn Ser Tyr Leu Lys
1               5

<210> SEQ ID NO 72
<211> LENGTH: 8
<212> TYPE: PRT
<213> ORGANISM: Artificial Sequence
<220> FEATURE:
<223> OTHER INFORMATION: ABCA2

<400> SEQUENCE: 72

Glu His Leu Gln Leu Tyr Thr Arg
1               5

<210> SEQ ID NO 73
<211> LENGTH: 6
<212> TYPE: PRT
<213> ORGANISM: Artificial Sequence
<220> FEATURE:
<223> OTHER INFORMATION: ABCA2

<400> SEQUENCE: 73

Val Gln Tyr Gln Leu Lys
1               5

<210> SEQ ID NO 74
<211> LENGTH: 12
<212> TYPE: PRT
<213> ORGANISM: Artificial Sequence
<220> FEATURE:
<223> OTHER INFORMATION: ABCA2

<400> SEQUENCE: 74

Ser Glu His Ile Ser Leu Ala Gln Val Phe Ser Lys
1               5                   10
```

<210> SEQ ID NO 75
<211> LENGTH: 7
<212> TYPE: PRT
<213> ORGANISM: Artificial Sequence
<220> FEATURE:
<223> OTHER INFORMATION: ABCA2

<400> SEQUENCE: 75

Ser Ala Pro Thr Glu Leu Arg
1               5

<210> SEQ ID NO 76
<211> LENGTH: 8
<212> TYPE: PRT
<213> ORGANISM: Artificial Sequence
<220> FEATURE:
<223> OTHER INFORMATION: ABCA3

<400> SEQUENCE: 76

Gln Leu Ala Leu Leu Leu Trp Lys
1               5

<210> SEQ ID NO 77
<211> LENGTH: 6
<212> TYPE: PRT
<213> ORGANISM: Artificial Sequence
<220> FEATURE:
<223> OTHER INFORMATION: ABCA3

<400> SEQUENCE: 77

Gly Phe Pro Ser Glu Lys
1               5

<210> SEQ ID NO 78
<211> LENGTH: 7
<212> TYPE: PRT
<213> ORGANISM: Artificial Sequence
<220> FEATURE:
<223> OTHER INFORMATION: ABCA3

<400> SEQUENCE: 78

Asp Phe Glu Asp Tyr Ile Arg
1               5

<210> SEQ ID NO 79
<211> LENGTH: 8
<212> TYPE: PRT
<213> ORGANISM: Artificial Sequence
<220> FEATURE:
<223> OTHER INFORMATION: ABCA3

<400> SEQUENCE: 79

Glu Pro Leu Pro Leu Ala Val Lys
1               5

<210> SEQ ID NO 80
<211> LENGTH: 12
<212> TYPE: PRT
<213> ORGANISM: Artificial Sequence
<220> FEATURE:
<223> OTHER INFORMATION: ABCA3

<400> SEQUENCE: 80

Glu Gly Phe Leu Ala Val Gln His Ala Val Asp Arg
1               5                   10

```
<210> SEQ ID NO 81
<211> LENGTH: 8
<212> TYPE: PRT
<213> ORGANISM: Artificial Sequence
<220> FEATURE:
<223> OTHER INFORMATION: ABCA3

<400> SEQUENCE: 81

Leu Thr Leu Gly Glu Tyr Gly Arg
1               5

<210> SEQ ID NO 82
<211> LENGTH: 11
<212> TYPE: PRT
<213> ORGANISM: Artificial Sequence
<220> FEATURE:
<223> OTHER INFORMATION: ABCA3

<400> SEQUENCE: 82

Asp Ala Leu Gln Ala Glu Gly Gln Glu Pro Arg
1               5                   10

<210> SEQ ID NO 83
<211> LENGTH: 13
<212> TYPE: PRT
<213> ORGANISM: Artificial Sequence
<220> FEATURE:
<223> OTHER INFORMATION: ABCA3

<400> SEQUENCE: 83

Glu Val Leu Gly Asp Leu Glu Glu Phe Leu Ile Phe Arg
1               5                   10

<210> SEQ ID NO 84
<211> LENGTH: 11
<212> TYPE: PRT
<213> ORGANISM: Artificial Sequence
<220> FEATURE:
<223> OTHER INFORMATION: ABCA3

<400> SEQUENCE: 84

Ala Ser Val Glu Gly Gly Gly Phe Asn Glu Arg
1               5                   10

<210> SEQ ID NO 85
<211> LENGTH: 7
<212> TYPE: PRT
<213> ORGANISM: Artificial Sequence
<220> FEATURE:
<223> OTHER INFORMATION: ABCA3

<400> SEQUENCE: 85

Ser Ala Leu Gln Ala Ala Lys
1               5

<210> SEQ ID NO 86
<211> LENGTH: 6
<212> TYPE: PRT
<213> ORGANISM: Artificial Sequence
<220> FEATURE:
<223> OTHER INFORMATION: ABCA3

<400> SEQUENCE: 86

Leu Glu Glu Leu Ser Lys
1               5

<210> SEQ ID NO 87
<211> LENGTH: 8
```

```
<212> TYPE: PRT
<213> ORGANISM: Artificial Sequence
<220> FEATURE:
<223> OTHER INFORMATION: ABCA3

<400> SEQUENCE: 87

Val Pro Leu Leu Ala Val Asp Arg
1               5

<210> SEQ ID NO 88
<211> LENGTH: 10
<212> TYPE: PRT
<213> ORGANISM: Artificial Sequence
<220> FEATURE:
<223> OTHER INFORMATION: ABCA3

<400> SEQUENCE: 88

Gly Leu Leu Leu Glu Pro His Ala Asn Lys
1               5                   10

<210> SEQ ID NO 89
<211> LENGTH: 8
<212> TYPE: PRT
<213> ORGANISM: Artificial Sequence
<220> FEATURE:
<223> OTHER INFORMATION: ABCA3

<400> SEQUENCE: 89

Phe Gly Ser Gly Tyr Ser Leu Arg
1               5

<210> SEQ ID NO 90
<211> LENGTH: 14
<212> TYPE: PRT
<213> ORGANISM: Artificial Sequence
<220> FEATURE:
<223> OTHER INFORMATION: ABCA3

<400> SEQUENCE: 90

Val Gln Ser Glu Gly Gln Gln Glu Ala Leu Glu Glu Phe Lys
1               5                   10

<210> SEQ ID NO 91
<211> LENGTH: 6
<212> TYPE: PRT
<213> ORGANISM: Artificial Sequence
<220> FEATURE:
<223> OTHER INFORMATION: ABCA3

<400> SEQUENCE: 91

Asp Leu Ser Trp Ala Lys
1               5

<210> SEQ ID NO 92
<211> LENGTH: 7
<212> TYPE: PRT
<213> ORGANISM: Artificial Sequence
<220> FEATURE:
<223> OTHER INFORMATION: ABCA3

<400> SEQUENCE: 92

Val Phe Gly Ile Leu Glu Lys
1               5

<210> SEQ ID NO 93
<211> LENGTH: 11
<212> TYPE: PRT
<213> ORGANISM: Artificial Sequence
```

<220> FEATURE:
<223> OTHER INFORMATION: ABCA4

<400> SEQUENCE: 93

Asp Glu Glu Thr Leu Thr Leu Phe Leu Ile Lys
1               5                   10

<210> SEQ ID NO 94
<211> LENGTH: 9
<212> TYPE: PRT
<213> ORGANISM: Artificial Sequence
<220> FEATURE:
<223> OTHER INFORMATION: ABCA4

<400> SEQUENCE: 94

Val Leu Pro Thr Leu Leu Asp Ser Arg
1               5

<210> SEQ ID NO 95
<211> LENGTH: 7
<212> TYPE: PRT
<213> ORGANISM: Artificial Sequence
<220> FEATURE:
<223> OTHER INFORMATION: ABCA4

<400> SEQUENCE: 95

Ser Gln Gly Ile Asn Leu Arg
1               5

<210> SEQ ID NO 96
<211> LENGTH: 9
<212> TYPE: PRT
<213> ORGANISM: Artificial Sequence
<220> FEATURE:
<223> OTHER INFORMATION: ABCA4

<400> SEQUENCE: 96

Asp Thr Leu Gly Asn Pro Thr Val Lys
1               5

<210> SEQ ID NO 97
<211> LENGTH: 6
<212> TYPE: PRT
<213> ORGANISM: Artificial Sequence
<220> FEATURE:
<223> OTHER INFORMATION: ABCA4

<400> SEQUENCE: 97

Ser Ile Val Leu Glu Lys
1               5

<210> SEQ ID NO 98
<211> LENGTH: 10
<212> TYPE: PRT
<213> ORGANISM: Artificial Sequence
<220> FEATURE:
<223> OTHER INFORMATION: ABCA4

<400> SEQUENCE: 98

Asp Ile Glu Thr Ser Leu Asp Ala Val Arg
1               5                   10

<210> SEQ ID NO 99
<211> LENGTH: 8
<212> TYPE: PRT
<213> ORGANISM: Artificial Sequence
<220> FEATURE:
<223> OTHER INFORMATION: ABCA4

```
<400> SEQUENCE: 99

Ile Ala Ile Ile Ala Gln Gly Arg
1               5

<210> SEQ ID NO 100
<211> LENGTH: 7
<212> TYPE: PRT
<213> ORGANISM: Artificial Sequence
<220> FEATURE:
<223> OTHER INFORMATION: ABCA4

<400> SEQUENCE: 100

Ala Tyr Ala Ser Leu Phe Arg
1               5

<210> SEQ ID NO 101
<211> LENGTH: 7
<212> TYPE: PRT
<213> ORGANISM: Artificial Sequence
<220> FEATURE:
<223> OTHER INFORMATION: ABCA4

<400> SEQUENCE: 101

Phe Trp Val Asn Glu Gln Arg
1               5

<210> SEQ ID NO 102
<211> LENGTH: 7
<212> TYPE: PRT
<213> ORGANISM: Artificial Sequence
<220> FEATURE:
<223> OTHER INFORMATION: ABCA4

<400> SEQUENCE: 102

Glu Ile Pro Asp Phe Leu Lys
1               5

<210> SEQ ID NO 103
<211> LENGTH: 9
<212> TYPE: PRT
<213> ORGANISM: Artificial Sequence
<220> FEATURE:
<223> OTHER INFORMATION: ABCA4

<400> SEQUENCE: 103

His Leu Glu Thr Glu Asp Asn Ile Lys
1               5

<210> SEQ ID NO 104
<211> LENGTH: 6
<212> TYPE: PRT
<213> ORGANISM: Artificial Sequence
<220> FEATURE:
<223> OTHER INFORMATION: ABCA4

<400> SEQUENCE: 104

Val Trp Phe Asn Asn Lys
1               5

<210> SEQ ID NO 105
<211> LENGTH: 6
<212> TYPE: PRT
<213> ORGANISM: Artificial Sequence
<220> FEATURE:
<223> OTHER INFORMATION: ABCA4

<400> SEQUENCE: 105
```

Ala Ala Gly Ala Ser Arg
1               5

<210> SEQ ID NO 106
<211> LENGTH: 7
<212> TYPE: PRT
<213> ORGANISM: Artificial Sequence
<220> FEATURE:
<223> OTHER INFORMATION: ABCA5

<400> SEQUENCE: 106

Thr Asn Val Ser Leu Trp Lys
1               5

<210> SEQ ID NO 107
<211> LENGTH: 6
<212> TYPE: PRT
<213> ORGANISM: Artificial Sequence
<220> FEATURE:
<223> OTHER INFORMATION: ABCA5

<400> SEQUENCE: 107

Glu Leu Glu Ser Thr Lys
1               5

<210> SEQ ID NO 108
<211> LENGTH: 13
<212> TYPE: PRT
<213> ORGANISM: Artificial Sequence
<220> FEATURE:
<223> OTHER INFORMATION: ABCA5

<400> SEQUENCE: 108

Gly Ile Pro Ala Asn Asn Ile Ile Gln Glu Val Gln Lys
1               5                   10

<210> SEQ ID NO 109
<211> LENGTH: 8
<212> TYPE: PRT
<213> ORGANISM: Artificial Sequence
<220> FEATURE:
<223> OTHER INFORMATION: ABCA5

<400> SEQUENCE: 109

His Ile Val Trp Asn Leu Leu Lys
1               5

<210> SEQ ID NO 110
<211> LENGTH: 7
<212> TYPE: PRT
<213> ORGANISM: Artificial Sequence
<220> FEATURE:
<223> OTHER INFORMATION: ABCA5

<400> SEQUENCE: 110

Asn Ala Val Val Pro Ile Lys
1               5

<210> SEQ ID NO 111
<211> LENGTH: 8
<212> TYPE: PRT
<213> ORGANISM: Artificial Sequence
<220> FEATURE:
<223> OTHER INFORMATION: ABCA5

<400> SEQUENCE: 111

Ile Thr His Ala Leu Asp Leu Lys

<210> SEQ ID NO 112
<211> LENGTH: 7
<212> TYPE: PRT
<213> ORGANISM: Artificial Sequence
<220> FEATURE:
<223> OTHER INFORMATION: ABCA5

<400> SEQUENCE: 112

Gly Tyr Phe Leu Glu Ile Lys
1               5

<210> SEQ ID NO 113
<211> LENGTH: 10
<212> TYPE: PRT
<213> ORGANISM: Artificial Sequence
<220> FEATURE:
<223> OTHER INFORMATION: ABCA5

<400> SEQUENCE: 113

Asp Trp Ile Glu Asn Leu Glu Val Asp Arg
1               5                   10

<210> SEQ ID NO 114
<211> LENGTH: 11
<212> TYPE: PRT
<213> ORGANISM: Artificial Sequence
<220> FEATURE:
<223> OTHER INFORMATION: ABCA5

<400> SEQUENCE: 114

Glu Ile Gln Tyr Ile Phe Pro Asn Ala Ser Arg
1               5                   10

<210> SEQ ID NO 115
<211> LENGTH: 11
<212> TYPE: PRT
<213> ORGANISM: Artificial Sequence
<220> FEATURE:
<223> OTHER INFORMATION: ABCA5

<400> SEQUENCE: 115

Gln Glu Ser Phe Ser Ser Ile Leu Ala Tyr Lys
1               5                   10

<210> SEQ ID NO 116
<211> LENGTH: 8
<212> TYPE: PRT
<213> ORGANISM: Artificial Sequence
<220> FEATURE:
<223> OTHER INFORMATION: ABCA6

<400> SEQUENCE: 116

Thr Ala Leu Ala Pro Leu Leu Lys
1               5

<210> SEQ ID NO 117
<211> LENGTH: 10
<212> TYPE: PRT
<213> ORGANISM: Artificial Sequence
<220> FEATURE:
<223> OTHER INFORMATION: ABCA6

<400> SEQUENCE: 117

Gly Thr Ser Val Ile Gly Ala Pro Asn Lys
1               5                   10

<210> SEQ ID NO 118
<211> LENGTH: 7
<212> TYPE: PRT
<213> ORGANISM: Artificial Sequence
<220> FEATURE:
<223> OTHER INFORMATION: ABCA6

<400> SEQUENCE: 118

Thr Leu Pro Phe Ile Thr Lys
1               5

<210> SEQ ID NO 119
<211> LENGTH: 8
<212> TYPE: PRT
<213> ORGANISM: Artificial Sequence
<220> FEATURE:
<223> OTHER INFORMATION: ABCA6

<400> SEQUENCE: 119

Glu Asn Leu Ser Leu Phe Ala Lys
1               5

<210> SEQ ID NO 120
<211> LENGTH: 8
<212> TYPE: PRT
<213> ORGANISM: Artificial Sequence
<220> FEATURE:
<223> OTHER INFORMATION: ABCA6

<400> SEQUENCE: 120

Asp Gln Val Trp Ser Leu Leu Arg
1               5

<210> SEQ ID NO 121
<211> LENGTH: 9
<212> TYPE: PRT
<213> ORGANISM: Artificial Sequence
<220> FEATURE:
<223> OTHER INFORMATION: ABCA6

<400> SEQUENCE: 121

Leu Val Tyr Thr Leu Pro Leu Glu Arg
1               5

<210> SEQ ID NO 122
<211> LENGTH: 13
<212> TYPE: PRT
<213> ORGANISM: Artificial Sequence
<220> FEATURE:
<223> OTHER INFORMATION: ABCA6

<400> SEQUENCE: 122

Thr Asn Thr Phe Pro Asp Leu Phe Ser Asp Leu Asp Lys
1               5                   10

<210> SEQ ID NO 123
<211> LENGTH: 14
<212> TYPE: PRT
<213> ORGANISM: Artificial Sequence
<220> FEATURE:
<223> OTHER INFORMATION: ABCA6

<400> SEQUENCE: 123

His Gln Asn Ile Leu Leu Glu Val Asp Asp Phe Glu Asn Arg
1               5                   10

<210> SEQ ID NO 124

```
<211> LENGTH: 6
<212> TYPE: PRT
<213> ORGANISM: Artificial Sequence
<220> FEATURE:
<223> OTHER INFORMATION: ABCA6

<400> SEQUENCE: 124

Thr Phe Leu Glu Val Arg
1               5

<210> SEQ ID NO 125
<211> LENGTH: 6
<212> TYPE: PRT
<213> ORGANISM: Artificial Sequence
<220> FEATURE:
<223> OTHER INFORMATION: ABCA6

<400> SEQUENCE: 125

Leu Val Ser Ala Phe Lys
1               5

<210> SEQ ID NO 126
<211> LENGTH: 11
<212> TYPE: PRT
<213> ORGANISM: Artificial Sequence
<220> FEATURE:
<223> OTHER INFORMATION: ABCA6

<400> SEQUENCE: 126

Leu His Glu Gln Leu Asn Val Pro Val Gln Lys
1               5                   10

<210> SEQ ID NO 127
<211> LENGTH: 7
<212> TYPE: PRT
<213> ORGANISM: Artificial Sequence
<220> FEATURE:
<223> OTHER INFORMATION: ABCA6

<400> SEQUENCE: 127

Asp Tyr Ile Leu Glu Leu Lys
1               5

<210> SEQ ID NO 128
<211> LENGTH: 14
<212> TYPE: PRT
<213> ORGANISM: Artificial Sequence
<220> FEATURE:
<223> OTHER INFORMATION: ABCA6

<400> SEQUENCE: 128

Glu Thr Ser Gln Val Thr Leu Val His Thr Glu Ile Leu Lys
1               5                   10

<210> SEQ ID NO 129
<211> LENGTH: 10
<212> TYPE: PRT
<213> ORGANISM: Artificial Sequence
<220> FEATURE:
<223> OTHER INFORMATION: ABCA6

<400> SEQUENCE: 129

Leu Phe Pro Gln Ala Ala Gly Gln Glu Arg
1               5                   10

<210> SEQ ID NO 130
<211> LENGTH: 8
<212> TYPE: PRT
```

```
<213> ORGANISM: Artificial Sequence
<220> FEATURE:
<223> OTHER INFORMATION: ABCA6

<400> SEQUENCE: 130

Tyr Ser Ser Leu Leu Thr Tyr Lys
1               5

<210> SEQ ID NO 131
<211> LENGTH: 15
<212> TYPE: PRT
<213> ORGANISM: Artificial Sequence
<220> FEATURE:
<223> OTHER INFORMATION: ABCA6

<400> SEQUENCE: 131

Leu Pro Val Ala Asp Val Tyr Pro Leu Ser Gln Thr Phe His Lys
1               5                   10                  15

<210> SEQ ID NO 132
<211> LENGTH: 7
<212> TYPE: PRT
<213> ORGANISM: Artificial Sequence
<220> FEATURE:
<223> OTHER INFORMATION: ABCA6

<400> SEQUENCE: 132

Val Phe Leu Glu Leu Ser Lys
1               5

<210> SEQ ID NO 133
<211> LENGTH: 8
<212> TYPE: PRT
<213> ORGANISM: Artificial Sequence
<220> FEATURE:
<223> OTHER INFORMATION: ABCA6

<400> SEQUENCE: 133

Leu Leu Pro His Ser Asp Glu Pro
1               5

<210> SEQ ID NO 134
<211> LENGTH: 7
<212> TYPE: PRT
<213> ORGANISM: Artificial Sequence
<220> FEATURE:
<223> OTHER INFORMATION: ABCA7

<400> SEQUENCE: 134

Gln Phe Gln Ser Pro Leu Arg
1               5

<210> SEQ ID NO 135
<211> LENGTH: 7
<212> TYPE: PRT
<213> ORGANISM: Artificial Sequence
<220> FEATURE:
<223> OTHER INFORMATION: ABCA8

<400> SEQUENCE: 135

Leu Phe Pro Gln Ala Ala Arg
1               5

<210> SEQ ID NO 136
<211> LENGTH: 7
<212> TYPE: PRT
<213> ORGANISM: Artificial Sequence
<220> FEATURE:
```

<223> OTHER INFORMATION: ABCA9

<400> SEQUENCE: 136

Gln His Ile Ser Asp Ala Lys
1               5

<210> SEQ ID NO 137
<211> LENGTH: 12
<212> TYPE: PRT
<213> ORGANISM: Artificial Sequence
<220> FEATURE:
<223> OTHER INFORMATION: ABCA10

<400> SEQUENCE: 137

Asp Gly His Gly Asp Ser Pro Leu Phe Phe Leu Lys
1               5                   10

<210> SEQ ID NO 138
<211> LENGTH: 10
<212> TYPE: PRT
<213> ORGANISM: Artificial Sequence
<220> FEATURE:
<223> OTHER INFORMATION: ABCA12

<400> SEQUENCE: 138

Leu Leu Ala Ile Pro Ile Pro Asp Asn Arg
1               5                   10

<210> SEQ ID NO 139
<211> LENGTH: 12
<212> TYPE: PRT
<213> ORGANISM: Artificial Sequence
<220> FEATURE:
<223> OTHER INFORMATION: ABCA13

<400> SEQUENCE: 139

Phe His Pro Gln Asn Leu Pro Ala Asp Gly Phe Lys
1               5                   10

<210> SEQ ID NO 140
<211> LENGTH: 14
<212> TYPE: PRT
<213> ORGANISM: Artificial Sequence
<220> FEATURE:
<223> OTHER INFORMATION: ABCB1

<400> SEQUENCE: 140

Glu Ala Leu Asp Glu Ser Ile Pro Pro Val Ser Phe Trp Arg
1               5                   10

<210> SEQ ID NO 141
<211> LENGTH: 10
<212> TYPE: PRT
<213> ORGANISM: Artificial Sequence
<220> FEATURE:
<223> OTHER INFORMATION: ABCB4

<400> SEQUENCE: 141

Ile Ala Thr Glu Ala Ile Glu Asn Ile Arg
1               5                   10

<210> SEQ ID NO 142
<211> LENGTH: 9
<212> TYPE: PRT
<213> ORGANISM: Artificial Sequence
<220> FEATURE:
<223> OTHER INFORMATION: ABCB5

```
<400> SEQUENCE: 142

Ser Ala Asp Leu Ile Val Thr Leu Lys
1               5

<210> SEQ ID NO 143
<211> LENGTH: 9
<212> TYPE: PRT
<213> ORGANISM: Artificial Sequence
<220> FEATURE:
<223> OTHER INFORMATION: ABCB11

<400> SEQUENCE: 143

Ser Thr Ala Leu Gln Leu Ile Gln Arg
1               5

<210> SEQ ID NO 144
<211> LENGTH: 9
<212> TYPE: PRT
<213> ORGANISM: Artificial Sequence
<220> FEATURE:
<223> OTHER INFORMATION: ABCC1

<400> SEQUENCE: 144

Thr Pro Ser Gly Asn Leu Val Asn Arg
1               5

<210> SEQ ID NO 145
<211> LENGTH: 6
<212> TYPE: PRT
<213> ORGANISM: Artificial Sequence
<220> FEATURE:
<223> OTHER INFORMATION: ABCC1

<400> SEQUENCE: 145

Val Val Tyr Ser Ser Lys
1               5

<210> SEQ ID NO 146
<211> LENGTH: 6
<212> TYPE: PRT
<213> ORGANISM: Artificial Sequence
<220> FEATURE:
<223> OTHER INFORMATION: ABCC1

<400> SEQUENCE: 146

Asp Pro Ala Gln Pro Lys
1               5

<210> SEQ ID NO 147
<211> LENGTH: 6
<212> TYPE: PRT
<213> ORGANISM: Artificial Sequence
<220> FEATURE:
<223> OTHER INFORMATION: ABCC1

<400> SEQUENCE: 147

Phe Val Asn Asp Thr Lys
1               5

<210> SEQ ID NO 148
<211> LENGTH: 11
<212> TYPE: PRT
<213> ORGANISM: Artificial Sequence
<220> FEATURE:
<223> OTHER INFORMATION: ABCC1

<400> SEQUENCE: 148
```

-continued

Asp Gly Gly Gly Thr Asn Ser Ile Thr Val Arg
1               5                   10

<210> SEQ ID NO 149
<211> LENGTH: 9
<212> TYPE: PRT
<213> ORGANISM: Artificial Sequence
<220> FEATURE:
<223> OTHER INFORMATION: ABCC1

<400> SEQUENCE: 149

Gly Val Asn Leu Ser Gly Gly Gln Lys
1               5

<210> SEQ ID NO 150
<211> LENGTH: 14
<212> TYPE: PRT
<213> ORGANISM: Artificial Sequence
<220> FEATURE:
<223> OTHER INFORMATION: ABCC1

<400> SEQUENCE: 150

Gln Leu Ser Ser Ser Ser Ser Tyr Ser Gly Asp Ile Ser Arg
1               5                   10

<210> SEQ ID NO 151
<211> LENGTH: 7
<212> TYPE: PRT
<213> ORGANISM: Artificial Sequence
<220> FEATURE:
<223> OTHER INFORMATION: ABCC1

<400> SEQUENCE: 151

Phe Tyr Val Ala Ser Ser Arg
1               5

<210> SEQ ID NO 152
<211> LENGTH: 8
<212> TYPE: PRT
<213> ORGANISM: Artificial Sequence
<220> FEATURE:
<223> OTHER INFORMATION: ABCC1

<400> SEQUENCE: 152

Phe Ile His Gln Ser Asp Leu Lys
1               5

<210> SEQ ID NO 153
<211> LENGTH: 10
<212> TYPE: PRT
<213> ORGANISM: Artificial Sequence
<220> FEATURE:
<223> OTHER INFORMATION: ABCC1

<400> SEQUENCE: 153

Ala Tyr Tyr Pro Ser Ile Val Ala Asn Arg
1               5                   10

<210> SEQ ID NO 154
<211> LENGTH: 9
<212> TYPE: PRT
<213> ORGANISM: Artificial Sequence
<220> FEATURE:
<223> OTHER INFORMATION: ABCC1

<400> SEQUENCE: 154

Ser Ser Leu Thr Leu Gly Leu Phe Arg
1               5

<210> SEQ ID NO 155
<211> LENGTH: 7
<212> TYPE: PRT
<213> ORGANISM: Artificial Sequence
<220> FEATURE:
<223> OTHER INFORMATION: ABCC1

<400> SEQUENCE: 155

Ile Gly Leu His Asp Leu Arg
1               5

<210> SEQ ID NO 156
<211> LENGTH: 16
<212> TYPE: PRT
<213> ORGANISM: Artificial Sequence
<220> FEATURE:
<223> OTHER INFORMATION: ABCC1

<400> SEQUENCE: 156

Ile Thr Ile Ile Pro Gln Asp Pro Val Leu Phe Ser Gly Ser Leu Arg
1               5                   10                  15

<210> SEQ ID NO 157
<211> LENGTH: 9
<212> TYPE: PRT
<213> ORGANISM: Artificial Sequence
<220> FEATURE:
<223> OTHER INFORMATION: ABCC1

<400> SEQUENCE: 157

Asp Phe Val Ser Ala Leu Pro Asp Lys
1               5

<210> SEQ ID NO 158
<211> LENGTH: 6
<212> TYPE: PRT
<213> ORGANISM: Artificial Sequence
<220> FEATURE:
<223> OTHER INFORMATION: ABCC1

<400> SEQUENCE: 158

Val Ile Val Leu Asp Lys
1               5

<210> SEQ ID NO 159
<211> LENGTH: 8
<212> TYPE: PRT
<213> ORGANISM: Artificial Sequence
<220> FEATURE:
<223> OTHER INFORMATION: ABCC2

<400> SEQUENCE: 159

Gln Leu Leu Asn Asn Ile Leu Arg
1               5

<210> SEQ ID NO 160
<211> LENGTH: 9
<212> TYPE: PRT
<213> ORGANISM: Artificial Sequence
<220> FEATURE:
<223> OTHER INFORMATION: ABCC2

<400> SEQUENCE: 160

Ser Ser Gln Gln Asn Ser Gly Ala Arg
1               5

```
<210> SEQ ID NO 161
<211> LENGTH: 6
<212> TYPE: PRT
<213> ORGANISM: Artificial Sequence
<220> FEATURE:
<223> OTHER INFORMATION: ABCC2

<400> SEQUENCE: 161

Leu Pro Gly Leu Asn Lys
1               5

<210> SEQ ID NO 162
<211> LENGTH: 9
<212> TYPE: PRT
<213> ORGANISM: Artificial Sequence
<220> FEATURE:
<223> OTHER INFORMATION: ABCC2

<400> SEQUENCE: 162

Tyr Phe Ala Trp Glu Pro Ser Phe Arg
1               5

<210> SEQ ID NO 163
<211> LENGTH: 13
<212> TYPE: PRT
<213> ORGANISM: Artificial Sequence
<220> FEATURE:
<223> OTHER INFORMATION: ABCC2

<400> SEQUENCE: 163

Tyr Leu Gly Gly Asp Asp Leu Asp Thr Ser Ala Ile Arg
1               5                   10

<210> SEQ ID NO 164
<211> LENGTH: 9
<212> TYPE: PRT
<213> ORGANISM: Artificial Sequence
<220> FEATURE:
<223> OTHER INFORMATION: ABCC2

<400> SEQUENCE: 164

Gly Ile Asn Leu Ser Gly Gly Gln Lys
1               5

<210> SEQ ID NO 165
<211> LENGTH: 9
<212> TYPE: PRT
<213> ORGANISM: Artificial Sequence
<220> FEATURE:
<223> OTHER INFORMATION: ABCC2

<400> SEQUENCE: 165

Val Leu Gly Pro Asn Gly Leu Leu Lys
1               5

<210> SEQ ID NO 166
<211> LENGTH: 6
<212> TYPE: PRT
<213> ORGANISM: Artificial Sequence
<220> FEATURE:
<223> OTHER INFORMATION: ABCC2

<400> SEQUENCE: 166

Asn Val Asn Ser Leu Lys
1               5

<210> SEQ ID NO 167
<211> LENGTH: 7
```

```
<212> TYPE: PRT
<213> ORGANISM: Artificial Sequence
<220> FEATURE:
<223> OTHER INFORMATION: ABCC2

<400> SEQUENCE: 167

Glu Asp Glu Glu Leu Val Lys
1               5

<210> SEQ ID NO 168
<211> LENGTH: 6
<212> TYPE: PRT
<213> ORGANISM: Artificial Sequence
<220> FEATURE:
<223> OTHER INFORMATION: ABCC2

<400> SEQUENCE: 168

Ile Asp Thr Asn Gln Lys
1               5

<210> SEQ ID NO 169
<211> LENGTH: 9
<212> TYPE: PRT
<213> ORGANISM: Artificial Sequence
<220> FEATURE:
<223> OTHER INFORMATION: ABCC2

<400> SEQUENCE: 169

Ile Gln Phe Asn Asn Tyr Gln Val Arg
1               5

<210> SEQ ID NO 170
<211> LENGTH: 8
<212> TYPE: PRT
<213> ORGANISM: Artificial Sequence
<220> FEATURE:
<223> OTHER INFORMATION: ABCC2

<400> SEQUENCE: 170

Pro Glu Leu Asp Leu Val Leu Arg
1               5

<210> SEQ ID NO 171
<211> LENGTH: 6
<212> TYPE: PRT
<213> ORGANISM: Artificial Sequence
<220> FEATURE:
<223> OTHER INFORMATION: ABCC2

<400> SEQUENCE: 171

Ile Gly Val Val Gly Arg
1               5

<210> SEQ ID NO 172
<211> LENGTH: 11
<212> TYPE: PRT
<213> ORGANISM: Artificial Sequence
<220> FEATURE:
<223> OTHER INFORMATION: ABCC2

<400> SEQUENCE: 172

Glu Ala Gly Ile Glu Asn Val Asn Ser Thr Lys
1               5                   10

<210> SEQ ID NO 173
<211> LENGTH: 10
<212> TYPE: PRT
<213> ORGANISM: Artificial Sequence
```

```
<220> FEATURE:
<223> OTHER INFORMATION: ABCC3

<400> SEQUENCE: 173

Ala Glu Gly Glu Ile Ser Asp Pro Phe Arg
1               5                   10

<210> SEQ ID NO 174
<211> LENGTH: 10
<212> TYPE: PRT
<213> ORGANISM: Artificial Sequence
<220> FEATURE:
<223> OTHER INFORMATION: ABCC3

<400> SEQUENCE: 174

Gly Tyr Ile Ile Leu Ser His Leu Ser Lys
1               5                   10

<210> SEQ ID NO 175
<211> LENGTH: 8
<212> TYPE: PRT
<213> ORGANISM: Artificial Sequence
<220> FEATURE:
<223> OTHER INFORMATION: ABCC3

<400> SEQUENCE: 175

Leu Phe Phe Trp Trp Phe Thr Lys
1               5

<210> SEQ ID NO 176
<211> LENGTH: 6
<212> TYPE: PRT
<213> ORGANISM: Artificial Sequence
<220> FEATURE:
<223> OTHER INFORMATION: ABCC3

<400> SEQUENCE: 176

Gln Val Glu Gly Ile Arg
1               5

<210> SEQ ID NO 177
<211> LENGTH: 8
<212> TYPE: PRT
<213> ORGANISM: Artificial Sequence
<220> FEATURE:
<223> OTHER INFORMATION: ABCC3

<400> SEQUENCE: 177

Gln Gly Glu Leu Gln Leu Leu Arg
1               5

<210> SEQ ID NO 178
<211> LENGTH: 7
<212> TYPE: PRT
<213> ORGANISM: Artificial Sequence
<220> FEATURE:
<223> OTHER INFORMATION: ABCC3

<400> SEQUENCE: 178

Val Gln Val Thr Glu Ala Lys
1               5

<210> SEQ ID NO 179
<211> LENGTH: 10
<212> TYPE: PRT
<213> ORGANISM: Artificial Sequence
<220> FEATURE:
<223> OTHER INFORMATION: ABCC3
```

```
<400> SEQUENCE: 179

Ala Asp Gly Ala Leu Thr Gln Glu Glu Lys
1               5                   10

<210> SEQ ID NO 180
<211> LENGTH: 10
<212> TYPE: PRT
<213> ORGANISM: Artificial Sequence
<220> FEATURE:
<223> OTHER INFORMATION: ABCC3

<400> SEQUENCE: 180

Val Leu His Gln Ala Leu Leu His Asn Lys
1               5                   10

<210> SEQ ID NO 181
<211> LENGTH: 13
<212> TYPE: PRT
<213> ORGANISM: Artificial Sequence
<220> FEATURE:
<223> OTHER INFORMATION: ABCC3

<400> SEQUENCE: 181

Ser Pro Gln Ser Phe Phe Asp Thr Thr Pro Ser Gly Arg
1               5                   10

<210> SEQ ID NO 182
<211> LENGTH: 9
<212> TYPE: PRT
<213> ORGANISM: Artificial Sequence
<220> FEATURE:
<223> OTHER INFORMATION: ABCC3

<400> SEQUENCE: 182

Asp Phe Glu Ile Ile Ser Asp Thr Lys
1               5

<210> SEQ ID NO 183
<211> LENGTH: 6
<212> TYPE: PRT
<213> ORGANISM: Artificial Sequence
<220> FEATURE:
<223> OTHER INFORMATION: ABCC3

<400> SEQUENCE: 183

Val Asp Ala Asn Gln Arg
1               5

<210> SEQ ID NO 184
<211> LENGTH: 8
<212> TYPE: PRT
<213> ORGANISM: Artificial Sequence
<220> FEATURE:
<223> OTHER INFORMATION: ABCC3

<400> SEQUENCE: 184

Pro Pro Glu Gly Trp Pro Pro Arg
1               5

<210> SEQ ID NO 185
<211> LENGTH: 6
<212> TYPE: PRT
<213> ORGANISM: Artificial Sequence
<220> FEATURE:
<223> OTHER INFORMATION: ABCC3

<400> SEQUENCE: 185
```

Gly Glu Val Glu Phe Arg
1               5

<210> SEQ ID NO 186
<211> LENGTH: 11
<212> TYPE: PRT
<213> ORGANISM: Artificial Sequence
<220> FEATURE:
<223> OTHER INFORMATION: ABCC3

<400> SEQUENCE: 186

Asp Leu Ser Leu His Val His Gly Gly Glu Lys
1               5                   10

<210> SEQ ID NO 187
<211> LENGTH: 11
<212> TYPE: PRT
<213> ORGANISM: Artificial Sequence
<220> FEATURE:
<223> OTHER INFORMATION: ABCC5

<400> SEQUENCE: 187

Ser Leu Ser Glu Ala Ser Val Ala Val Asp Arg
1               5                   10

<210> SEQ ID NO 188
<211> LENGTH: 9
<212> TYPE: PRT
<213> ORGANISM: Artificial Sequence
<220> FEATURE:
<223> OTHER INFORMATION: ABCC6

<400> SEQUENCE: 188

Ala Pro Glu Thr Glu Pro Phe Leu Arg
1               5

<210> SEQ ID NO 189
<211> LENGTH: 12
<212> TYPE: PRT
<213> ORGANISM: Artificial Sequence
<220> FEATURE:
<223> OTHER INFORMATION: ABCC6

<400> SEQUENCE: 189

Ala Thr Phe Trp Trp Val Ser Gly Leu Val Trp Arg
1               5                   10

<210> SEQ ID NO 190
<211> LENGTH: 7
<212> TYPE: PRT
<213> ORGANISM: Artificial Sequence
<220> FEATURE:
<223> OTHER INFORMATION: ABCC6

<400> SEQUENCE: 190

Asp Leu Trp Ser Leu Gly Arg
1               5

<210> SEQ ID NO 191
<211> LENGTH: 10
<212> TYPE: PRT
<213> ORGANISM: Artificial Sequence
<220> FEATURE:
<223> OTHER INFORMATION: ABCC6

<400> SEQUENCE: 191

Glu Asn Ser Ser Glu Glu Leu Val Ser Arg

```
1               5                   10
```

<210> SEQ ID NO 192
<211> LENGTH: 7
<212> TYPE: PRT
<213> ORGANISM: Artificial Sequence
<220> FEATURE:
<223> OTHER INFORMATION: ABCC6

<400> SEQUENCE: 192

```
Leu Thr Ser Ser Ile Leu Arg
1               5
```

<210> SEQ ID NO 193
<211> LENGTH: 11
<212> TYPE: PRT
<213> ORGANISM: Artificial Sequence
<220> FEATURE:
<223> OTHER INFORMATION: ABCC6

<400> SEQUENCE: 193

```
Phe His Gly Trp Glu Gly Ala Phe Leu Asp Arg
1               5                   10
```

<210> SEQ ID NO 194
<211> LENGTH: 8
<212> TYPE: PRT
<213> ORGANISM: Artificial Sequence
<220> FEATURE:
<223> OTHER INFORMATION: ABCC6

<400> SEQUENCE: 194

```
Gly Gln Glu Leu Gly Ala Leu Arg
1               5
```

<210> SEQ ID NO 195
<211> LENGTH: 12
<212> TYPE: PRT
<213> ORGANISM: Artificial Sequence
<220> FEATURE:
<223> OTHER INFORMATION: ABCC6

<400> SEQUENCE: 195

```
Gly Glu Gly Glu Thr Glu Pro Gly Thr Ser Thr Lys
1               5                   10
```

<210> SEQ ID NO 196
<211> LENGTH: 7
<212> TYPE: PRT
<213> ORGANISM: Artificial Sequence
<220> FEATURE:
<223> OTHER INFORMATION: ABCC6

<400> SEQUENCE: 196

```
Ala Gly Trp Pro Ala Gly Lys
1               5
```

<210> SEQ ID NO 197
<211> LENGTH: 7
<212> TYPE: PRT
<213> ORGANISM: Artificial Sequence
<220> FEATURE:
<223> OTHER INFORMATION: ABCC6

<400> SEQUENCE: 197

```
Asp Ser Ile Gln Tyr Gly Arg
1               5
```

<210> SEQ ID NO 198
<211> LENGTH: 7
<212> TYPE: PRT
<213> ORGANISM: Artificial Sequence
<220> FEATURE:
<223> OTHER INFORMATION: ABCC6

<400> SEQUENCE: 198

Leu Leu Trp Asp Val Val Arg
1               5

<210> SEQ ID NO 199
<211> LENGTH: 9
<212> TYPE: PRT
<213> ORGANISM: Artificial Sequence
<220> FEATURE:
<223> OTHER INFORMATION: ABCC6

<400> SEQUENCE: 199

Thr Pro Ile Gly His Leu Leu Asn Arg
1               5

<210> SEQ ID NO 200
<211> LENGTH: 12
<212> TYPE: PRT
<213> ORGANISM: Artificial Sequence
<220> FEATURE:
<223> OTHER INFORMATION: ABCC6

<400> SEQUENCE: 200

Thr Gln Ala Pro Phe Val Ala Gln Asn Asn Ala Arg
1               5                   10

<210> SEQ ID NO 201
<211> LENGTH: 6
<212> TYPE: PRT
<213> ORGANISM: Artificial Sequence
<220> FEATURE:
<223> OTHER INFORMATION: ABCC6

<400> SEQUENCE: 201

Val Asp Glu Ser Gln Arg
1               5

<210> SEQ ID NO 202
<211> LENGTH: 14
<212> TYPE: PRT
<213> ORGANISM: Artificial Sequence
<220> FEATURE:
<223> OTHER INFORMATION: ABCC6

<400> SEQUENCE: 202

Asn Trp Thr Asp Leu Glu Asn Ser Ile Val Ser Val Glu Arg
1               5                   10

<210> SEQ ID NO 203
<211> LENGTH: 9
<212> TYPE: PRT
<213> ORGANISM: Artificial Sequence
<220> FEATURE:
<223> OTHER INFORMATION: ABCC6

<400> SEQUENCE: 203

Gly Glu Asp Leu Ser Val Gly Gln Lys
1               5

<210> SEQ ID NO 204

```
<211> LENGTH: 8
<212> TYPE: PRT
<213> ORGANISM: Artificial Sequence
<220> FEATURE:
<223> OTHER INFORMATION: ABCC6

<400> SEQUENCE: 204

Leu Ala Gln Glu Ser Gly Leu Val
1               5

<210> SEQ ID NO 205
<211> LENGTH: 13
<212> TYPE: PRT
<213> ORGANISM: Artificial Sequence
<220> FEATURE:
<223> OTHER INFORMATION: ABCC7

<400> SEQUENCE: 205

Gly Leu Pro Leu Val His Thr Leu Ile Thr Val Ser Lys
1               5                   10

<210> SEQ ID NO 206
<211> LENGTH: 7
<212> TYPE: PRT
<213> ORGANISM: Artificial Sequence
<220> FEATURE:
<223> OTHER INFORMATION: ABCC7

<400> SEQUENCE: 206

Ile Gln Asp Phe Leu Gln Lys
1               5

<210> SEQ ID NO 207
<211> LENGTH: 6
<212> TYPE: PRT
<213> ORGANISM: Artificial Sequence
<220> FEATURE:
<223> OTHER INFORMATION: ABCC7

<400> SEQUENCE: 207

Tyr Ile Thr Val His Lys
1               5

<210> SEQ ID NO 208
<211> LENGTH: 7
<212> TYPE: PRT
<213> ORGANISM: Artificial Sequence
<220> FEATURE:
<223> OTHER INFORMATION: ABCC7

<400> SEQUENCE: 208

Ala Gly Gly Ile Leu Asn Arg
1               5

<210> SEQ ID NO 209
<211> LENGTH: 7
<212> TYPE: PRT
<213> ORGANISM: Artificial Sequence
<220> FEATURE:
<223> OTHER INFORMATION: ABCC7

<400> SEQUENCE: 209

Gln Leu Glu Ser Glu Gly Arg
1               5

<210> SEQ ID NO 210
<211> LENGTH: 6
<212> TYPE: PRT
```

```
<213> ORGANISM: Artificial Sequence
<220> FEATURE:
<223> OTHER INFORMATION: ABCC7

<400> SEQUENCE: 210

Asn Gly Gln Leu Ser Lys
1               5

<210> SEQ ID NO 211
<211> LENGTH: 8
<212> TYPE: PRT
<213> ORGANISM: Artificial Sequence
<220> FEATURE:
<223> OTHER INFORMATION: ABCC7

<400> SEQUENCE: 211

Val Ala Asp Glu Val Gly Leu Arg
1               5

<210> SEQ ID NO 212
<211> LENGTH: 9
<212> TYPE: PRT
<213> ORGANISM: Artificial Sequence
<220> FEATURE:
<223> OTHER INFORMATION: ABCC7

<400> SEQUENCE: 212

Ser Val Ile Glu Gln Phe Pro Gly Lys
1               5

<210> SEQ ID NO 213
<211> LENGTH: 7
<212> TYPE: PRT
<213> ORGANISM: Artificial Sequence
<220> FEATURE:
<223> OTHER INFORMATION: ABCC7

<400> SEQUENCE: 213

Gln Tyr Asp Ser Ile Gln Lys
1               5

<210> SEQ ID NO 214
<211> LENGTH: 8
<212> TYPE: PRT
<213> ORGANISM: Artificial Sequence
<220> FEATURE:
<223> OTHER INFORMATION: ABCC7

<400> SEQUENCE: 214

Gln Ala Ile Ser Pro Ser Asp Arg
1               5

<210> SEQ ID NO 215
<211> LENGTH: 8
<212> TYPE: PRT
<213> ORGANISM: Artificial Sequence
<220> FEATURE:
<223> OTHER INFORMATION: ABCC8

<400> SEQUENCE: 215

Thr Val Val Thr Ile Ala His Arg
1               5

<210> SEQ ID NO 216
<211> LENGTH: 7
<212> TYPE: PRT
<213> ORGANISM: Artificial Sequence
<220> FEATURE:
```

```
<223> OTHER INFORMATION: ABCC8

<400> SEQUENCE: 216

Ala Leu Thr Asn Tyr Gln Arg
1               5

<210> SEQ ID NO 217
<211> LENGTH: 6
<212> TYPE: PRT
<213> ORGANISM: Artificial Sequence
<220> FEATURE:
<223> OTHER INFORMATION: ABCC8

<400> SEQUENCE: 217

Gly Ala Ile Gln Thr Lys
1               5

<210> SEQ ID NO 218
<211> LENGTH: 9
<212> TYPE: PRT
<213> ORGANISM: Artificial Sequence
<220> FEATURE:
<223> OTHER INFORMATION: ABCC8

<400> SEQUENCE: 218

Leu Tyr Ala Trp Glu Asn Ile Phe Arg
1               5

<210> SEQ ID NO 219
<211> LENGTH: 11
<212> TYPE: PRT
<213> ORGANISM: Artificial Sequence
<220> FEATURE:
<223> OTHER INFORMATION: ABCC8

<400> SEQUENCE: 219

Leu Ser Glu Phe Leu Ser Ser Ala Glu Ile Arg
1               5                   10

<210> SEQ ID NO 220
<211> LENGTH: 7
<212> TYPE: PRT
<213> ORGANISM: Artificial Sequence
<220> FEATURE:
<223> OTHER INFORMATION: ABCC8

<400> SEQUENCE: 220

Tyr Gln Ala Val Pro Leu Arg
1               5

<210> SEQ ID NO 221
<211> LENGTH: 6
<212> TYPE: PRT
<213> ORGANISM: Artificial Sequence
<220> FEATURE:
<223> OTHER INFORMATION: ABCC8

<400> SEQUENCE: 221

Asp Gly Thr Ile Gln Arg
1               5

<210> SEQ ID NO 222
<211> LENGTH: 6
<212> TYPE: PRT
<213> ORGANISM: Artificial Sequence
<220> FEATURE:
<223> OTHER INFORMATION: ABCC8
```

```
<400> SEQUENCE: 222

Ala Glu Ile Pro Trp Arg
1               5

<210> SEQ ID NO 223
<211> LENGTH: 13
<212> TYPE: PRT
<213> ORGANISM: Artificial Sequence
<220> FEATURE:
<223> OTHER INFORMATION: ABCC8

<400> SEQUENCE: 223

Trp Thr Asp Ser Ala Leu Thr Leu Thr Pro Ala Ala Arg
1               5                   10

<210> SEQ ID NO 224
<211> LENGTH: 13
<212> TYPE: PRT
<213> ORGANISM: Artificial Sequence
<220> FEATURE:
<223> OTHER INFORMATION: ABCC8

<400> SEQUENCE: 224

Phe Phe Glu Thr Thr Pro Leu Gly Ser Ile Leu Asn Arg
1               5                   10

<210> SEQ ID NO 225
<211> LENGTH: 9
<212> TYPE: PRT
<213> ORGANISM: Artificial Sequence
<220> FEATURE:
<223> OTHER INFORMATION: ABCC9

<400> SEQUENCE: 225

Asn Leu His His Asn Leu Leu Asn Lys
1               5

<210> SEQ ID NO 226
<211> LENGTH: 9
<212> TYPE: PRT
<213> ORGANISM: Artificial Sequence
<220> FEATURE:
<223> OTHER INFORMATION: ABCC9

<400> SEQUENCE: 226

Ser Thr Leu Asp Tyr Ser Thr Glu Arg
1               5

<210> SEQ ID NO 227
<211> LENGTH: 7
<212> TYPE: PRT
<213> ORGANISM: Artificial Sequence
<220> FEATURE:
<223> OTHER INFORMATION: ABCC9

<400> SEQUENCE: 227

Ala Ile Ile Ser Val Gln Lys
1               5

<210> SEQ ID NO 228
<211> LENGTH: 9
<212> TYPE: PRT
<213> ORGANISM: Artificial Sequence
<220> FEATURE:
<223> OTHER INFORMATION: ABCC9

<400> SEQUENCE: 228
```

```
Asp Val Glu Leu Tyr Glu His Trp Lys
1               5

<210> SEQ ID NO 229
<211> LENGTH: 7
<212> TYPE: PRT
<213> ORGANISM: Artificial Sequence
<220> FEATURE:
<223> OTHER INFORMATION: ABCC9

<400> SEQUENCE: 229

Ile Ile Leu Gly Pro Ile Arg
1               5

<210> SEQ ID NO 230
<211> LENGTH: 13
<212> TYPE: PRT
<213> ORGANISM: Artificial Sequence
<220> FEATURE:
<223> OTHER INFORMATION: ABCC9

<400> SEQUENCE: 230

Phe Phe Asp Thr Thr Pro Leu Gly Leu Ile Leu Asn Arg
1               5                   10

<210> SEQ ID NO 231
<211> LENGTH: 9
<212> TYPE: PRT
<213> ORGANISM: Artificial Sequence
<220> FEATURE:
<223> OTHER INFORMATION: ABCC9

<400> SEQUENCE: 231

Ser Ser Leu Ser Leu Ala Phe Phe Arg
1               5

<210> SEQ ID NO 232
<211> LENGTH: 10
<212> TYPE: PRT
<213> ORGANISM: Artificial Sequence
<220> FEATURE:
<223> OTHER INFORMATION: ABCC9

<400> SEQUENCE: 232

Ile Val Ile Asp Gly Ile Asp Ile Ser Lys
1               5                   10

<210> SEQ ID NO 233
<211> LENGTH: 9
<212> TYPE: PRT
<213> ORGANISM: Artificial Sequence
<220> FEATURE:
<223> OTHER INFORMATION: ABCC10

<400> SEQUENCE: 233

Val Phe Thr Ala Leu Ala Leu Val Arg
1               5

<210> SEQ ID NO 234
<211> LENGTH: 12
<212> TYPE: PRT
<213> ORGANISM: Artificial Sequence
<220> FEATURE:
<223> OTHER INFORMATION: ABCC10

<400> SEQUENCE: 234

Phe Ser Tyr Ala Trp Leu Ala Pro Leu Leu Ala Arg
1               5                   10
```

<210> SEQ ID NO 235
<211> LENGTH: 8
<212> TYPE: PRT
<213> ORGANISM: Artificial Sequence
<220> FEATURE:
<223> OTHER INFORMATION: ABCC10

<400> SEQUENCE: 235

Leu Gln Pro Thr Tyr Leu Ala Arg
1               5

<210> SEQ ID NO 236
<211> LENGTH: 11
<212> TYPE: PRT
<213> ORGANISM: Artificial Sequence
<220> FEATURE:
<223> OTHER INFORMATION: ABCC10

<400> SEQUENCE: 236

Val Phe Gln Ala His Trp Gln Glu Gly Ala Arg
1               5                   10

<210> SEQ ID NO 237
<211> LENGTH: 6
<212> TYPE: PRT
<213> ORGANISM: Artificial Sequence
<220> FEATURE:
<223> OTHER INFORMATION: ABCC10

<400> SEQUENCE: 237

Val Thr Leu Gln Ala Arg
1               5

<210> SEQ ID NO 238
<211> LENGTH: 10
<212> TYPE: PRT
<213> ORGANISM: Artificial Sequence
<220> FEATURE:
<223> OTHER INFORMATION: ABCC10

<400> SEQUENCE: 238

Leu Val Thr Glu Leu Leu Ser Gly Ile Arg
1               5                   10

<210> SEQ ID NO 239
<211> LENGTH: 6
<212> TYPE: PRT
<213> ORGANISM: Artificial Sequence
<220> FEATURE:
<223> OTHER INFORMATION: ABCC10

<400> SEQUENCE: 239

Gly His Val Ala Val Arg
1               5

<210> SEQ ID NO 240
<211> LENGTH: 8
<212> TYPE: PRT
<213> ORGANISM: Artificial Sequence
<220> FEATURE:
<223> OTHER INFORMATION: ABCC10

<400> SEQUENCE: 240

Thr Phe Asp Ala Gln Leu Tyr Lys
1               5

```
<210> SEQ ID NO 241
<211> LENGTH: 9
<212> TYPE: PRT
<213> ORGANISM: Artificial Sequence
<220> FEATURE:
<223> OTHER INFORMATION: ABCC10

<400> SEQUENCE: 241

Gly Val Thr Leu Ser Gly Gly Gln Arg
1               5

<210> SEQ ID NO 242
<211> LENGTH: 6
<212> TYPE: PRT
<213> ORGANISM: Artificial Sequence
<220> FEATURE:
<223> OTHER INFORMATION: ABCC10

<400> SEQUENCE: 242

Ala Val Tyr Gln Glu Lys
1               5

<210> SEQ ID NO 243
<211> LENGTH: 12
<212> TYPE: PRT
<213> ORGANISM: Artificial Sequence
<220> FEATURE:
<223> OTHER INFORMATION: ABCC10

<400> SEQUENCE: 243

Glu Gly Leu Glu Glu Glu Gln Ser Thr Ser Gly Arg
1               5                   10

<210> SEQ ID NO 244
<211> LENGTH: 15
<212> TYPE: PRT
<213> ORGANISM: Artificial Sequence
<220> FEATURE:
<223> OTHER INFORMATION: ABCC10

<400> SEQUENCE: 244

Asn Ala Ala Asp Trp Trp Leu Ser His Trp Ile Ser Gln Leu Lys
1               5                   10                  15

<210> SEQ ID NO 245
<211> LENGTH: 10
<212> TYPE: PRT
<213> ORGANISM: Artificial Sequence
<220> FEATURE:
<223> OTHER INFORMATION: ABCC10

<400> SEQUENCE: 245

Ala Ala Pro Asn Gly Ser Ser Asp Ile Arg
1               5                   10

<210> SEQ ID NO 246
<211> LENGTH: 6
<212> TYPE: PRT
<213> ORGANISM: Artificial Sequence
<220> FEATURE:
<223> OTHER INFORMATION: ABCC10

<400> SEQUENCE: 246

Leu Gly Ile Val Gly Arg
1               5

<210> SEQ ID NO 247
<211> LENGTH: 9
```

```
<212> TYPE: PRT
<213> ORGANISM: Artificial Sequence
<220> FEATURE:
<223> OTHER INFORMATION: ABCC10

<400> SEQUENCE: 247

Ser Ser Leu Leu Leu Val Leu Phe Arg
1               5

<210> SEQ ID NO 248
<211> LENGTH: 8
<212> TYPE: PRT
<213> ORGANISM: Artificial Sequence
<220> FEATURE:
<223> OTHER INFORMATION: ABCC10

<400> SEQUENCE: 248

Leu Leu Glu Pro Ser Ser Gly Arg
1               5

<210> SEQ ID NO 249
<211> LENGTH: 10
<212> TYPE: PRT
<213> ORGANISM: Artificial Sequence
<220> FEATURE:
<223> OTHER INFORMATION: ABCC10

<400> SEQUENCE: 249

Glu Asn Leu Asp Pro Gln Gly Leu His Lys
1               5                   10

<210> SEQ ID NO 250
<211> LENGTH: 7
<212> TYPE: PRT
<213> ORGANISM: Artificial Sequence
<220> FEATURE:
<223> OTHER INFORMATION: ABCC10

<400> SEQUENCE: 250

Ala Leu Trp Gln Ala Leu Lys
1               5

<210> SEQ ID NO 251
<211> LENGTH: 7
<212> TYPE: PRT
<213> ORGANISM: Artificial Sequence
<220> FEATURE:
<223> OTHER INFORMATION: ABCC10

<400> SEQUENCE: 251

Ser Leu Ser Leu Gly Gln Arg
1               5

<210> SEQ ID NO 252
<211> LENGTH: 7
<212> TYPE: PRT
<213> ORGANISM: Artificial Sequence
<220> FEATURE:
<223> OTHER INFORMATION: ABCC10

<400> SEQUENCE: 252

Ala Leu Leu Thr Asp Ala Lys
1               5

<210> SEQ ID NO 253
<211> LENGTH: 9
<212> TYPE: PRT
<213> ORGANISM: Artificial Sequence
```

```
<220> FEATURE:
<223> OTHER INFORMATION: ABCC10

<400> SEQUENCE: 253

Leu Asn Thr Ile Leu Asn Ser Asp Arg
1               5

<210> SEQ ID NO 254
<211> LENGTH: 8
<212> TYPE: PRT
<213> ORGANISM: Artificial Sequence
<220> FEATURE:
<223> OTHER INFORMATION: ABCC10

<400> SEQUENCE: 254

Val Leu Val Leu Gln Ala Gly Arg
1               5

<210> SEQ ID NO 255
<211> LENGTH: 11
<212> TYPE: PRT
<213> ORGANISM: Artificial Sequence
<220> FEATURE:
<223> OTHER INFORMATION: ABCC10

<400> SEQUENCE: 255

Val Val Glu Leu Asp Ser Pro Ala Thr Leu Arg
1               5                   10

<210> SEQ ID NO 256
<211> LENGTH: 8
<212> TYPE: PRT
<213> ORGANISM: Artificial Sequence
<220> FEATURE:
<223> OTHER INFORMATION: ABCC11

<400> SEQUENCE: 256

Phe Asn Leu Asp Pro Phe Asp Arg
1               5

<210> SEQ ID NO 257
<211> LENGTH: 14
<212> TYPE: PRT
<213> ORGANISM: Artificial Sequence
<220> FEATURE:
<223> OTHER INFORMATION: ABCC11

<400> SEQUENCE: 257

Thr Tyr Thr Leu Gln Asp Gly Pro Trp Ser Gln Gln Glu Arg
1               5                   10

<210> SEQ ID NO 258
<211> LENGTH: 7
<212> TYPE: PRT
<213> ORGANISM: Artificial Sequence
<220> FEATURE:
<223> OTHER INFORMATION: ABCC11

<400> SEQUENCE: 258

Asn Pro Glu Ala Pro Gly Arg
1               5

<210> SEQ ID NO 259
<211> LENGTH: 8
<212> TYPE: PRT
<213> ORGANISM: Artificial Sequence
<220> FEATURE:
<223> OTHER INFORMATION: ABCC11
```

```
<400> SEQUENCE: 259

Ala Ala Val Pro Pro Trp Gly Lys
1               5

<210> SEQ ID NO 260
<211> LENGTH: 13
<212> TYPE: PRT
<213> ORGANISM: Artificial Sequence
<220> FEATURE:
<223> OTHER INFORMATION: ABCC11

<400> SEQUENCE: 260

Ser Leu Ser Phe Ser Ser Ser Trp Ile Ile Asn Gln Arg
1               5                   10

<210> SEQ ID NO 261
<211> LENGTH: 10
<212> TYPE: PRT
<213> ORGANISM: Artificial Sequence
<220> FEATURE:
<223> OTHER INFORMATION: ABCC11

<400> SEQUENCE: 261

Ala Ala Val Ser Ser Phe Ala Phe Glu Lys
1               5                   10

<210> SEQ ID NO 262
<211> LENGTH: 12
<212> TYPE: PRT
<213> ORGANISM: Artificial Sequence
<220> FEATURE:
<223> OTHER INFORMATION: ABCC11

<400> SEQUENCE: 262

Ala Gln His His Thr Ser Glu Val Ser Asp Gln Arg
1               5                   10

<210> SEQ ID NO 263
<211> LENGTH: 7
<212> TYPE: PRT
<213> ORGANISM: Artificial Sequence
<220> FEATURE:
<223> OTHER INFORMATION: ABCC11

<400> SEQUENCE: 263

Ile Asn Leu Val Val Ser Lys
1               5

<210> SEQ ID NO 264
<211> LENGTH: 14
<212> TYPE: PRT
<213> ORGANISM: Artificial Sequence
<220> FEATURE:
<223> OTHER INFORMATION: ABCC11

<400> SEQUENCE: 264

Ile Gly Leu Glu Thr Glu Ala Gln Phe Thr Ala Val Glu Arg
1               5                   10

<210> SEQ ID NO 265
<211> LENGTH: 15
<212> TYPE: PRT
<213> ORGANISM: Artificial Sequence
<220> FEATURE:
<223> OTHER INFORMATION: ABCC11

<400> SEQUENCE: 265
```

```
Asp Asn Thr Pro Thr Val Leu His Gly Ile Asn Leu Thr Ile Arg
1               5                   10                  15

<210> SEQ ID NO 266
<211> LENGTH: 10
<212> TYPE: PRT
<213> ORGANISM: Artificial Sequence
<220> FEATURE:
<223> OTHER INFORMATION: ABCC11

<400> SEQUENCE: 266

Gly His Glu Val Val Gly Ile Val Gly Arg
1               5                   10

<210> SEQ ID NO 267
<211> LENGTH: 12
<212> TYPE: PRT
<213> ORGANISM: Artificial Sequence
<220> FEATURE:
<223> OTHER INFORMATION: ABCC11

<400> SEQUENCE: 267

His Thr Asp Gln Gln Ile Trp Asp Ala Leu Glu Arg
1               5                   10

<210> SEQ ID NO 268
<211> LENGTH: 11
<212> TYPE: PRT
<213> ORGANISM: Artificial Sequence
<220> FEATURE:
<223> OTHER INFORMATION: ABCC12

<400> SEQUENCE: 268

Phe Ser Ile Ala Ile Leu Pro Phe Ser Ile Lys
1               5                   10

<210> SEQ ID NO 269
<211> LENGTH: 8
<212> TYPE: PRT
<213> ORGANISM: Artificial Sequence
<220> FEATURE:
<223> OTHER INFORMATION: ABCC12

<400> SEQUENCE: 269

Glu Asn Ile Leu Phe Gly Glu Lys
1               5

<210> SEQ ID NO 270
<211> LENGTH: 7
<212> TYPE: PRT
<213> ORGANISM: Artificial Sequence
<220> FEATURE:
<223> OTHER INFORMATION: ABCC13

<400> SEQUENCE: 270

Glu Asp Leu Phe Glu Leu Lys
1               5

<210> SEQ ID NO 271
<211> LENGTH: 10
<212> TYPE: PRT
<213> ORGANISM: Artificial Sequence
<220> FEATURE:
<223> OTHER INFORMATION: ABCG1

<400> SEQUENCE: 271

Gly Ala Val Leu Ile Asn Gly Leu Pro Arg
1               5                   10
```

-continued

```
<210> SEQ ID NO 272
<211> LENGTH: 7
<212> TYPE: PRT
<213> ORGANISM: Artificial Sequence
<220> FEATURE:
<223> OTHER INFORMATION: ABCG1

<400> SEQUENCE: 272

Gly Leu Ala Gln Gly Gly Arg
1               5

<210> SEQ ID NO 273
<211> LENGTH: 10
<212> TYPE: PRT
<213> ORGANISM: Artificial Sequence
<220> FEATURE:
<223> OTHER INFORMATION: ABCG1

<400> SEQUENCE: 273

Glu His Leu Asn Tyr Trp Tyr Ser Leu Lys
1               5                   10

<210> SEQ ID NO 274
<211> LENGTH: 15
<212> TYPE: PRT
<213> ORGANISM: Artificial Sequence
<220> FEATURE:
<223> OTHER INFORMATION: ABCG1

<400> SEQUENCE: 274

Tyr Gly Phe Glu Gly Val Ile Leu Ser Ile Tyr Gly Leu Asp Arg
1               5                   10                  15

<210> SEQ ID NO 275
<211> LENGTH: 8
<212> TYPE: PRT
<213> ORGANISM: Artificial Sequence
<220> FEATURE:
<223> OTHER INFORMATION: ABCG1

<400> SEQUENCE: 275

Glu Leu Asp Val Glu Asn Ala Lys
1               5

<210> SEQ ID NO 276
<211> LENGTH: 11
<212> TYPE: PRT
<213> ORGANISM: Artificial Sequence
<220> FEATURE:
<223> OTHER INFORMATION: ABCG4

<400> SEQUENCE: 276

Gly Val Val Thr Asn Leu Ile Pro Tyr Leu Lys
1               5                   10

<210> SEQ ID NO 277
<211> LENGTH: 10
<212> TYPE: PRT
<213> ORGANISM: Artificial Sequence
<220> FEATURE:
<223> OTHER INFORMATION: ABCG4

<400> SEQUENCE: 277

Glu His Leu Asn Tyr Trp Tyr Ser Leu Lys
1               5                   10
```

<210> SEQ ID NO 278
<211> LENGTH: 6
<212> TYPE: PRT
<213> ORGANISM: Artificial Sequence
<220> FEATURE:
<223> OTHER INFORMATION: ABCG4

<400> SEQUENCE: 278

Ala Tyr Tyr Leu Ala Lys
1               5

<210> SEQ ID NO 279
<211> LENGTH: 8
<212> TYPE: PRT
<213> ORGANISM: Artificial Sequence
<220> FEATURE:
<223> OTHER INFORMATION: ABCG5

<400> SEQUENCE: 279

Asp Ser Pro Gly Val Phe Ser Lys
1               5

<210> SEQ ID NO 280
<211> LENGTH: 13
<212> TYPE: PRT
<213> ORGANISM: Artificial Sequence
<220> FEATURE:
<223> OTHER INFORMATION: ABCG5

<400> SEQUENCE: 280

Ala Gly Thr Phe Leu Gly Glu Val Tyr Val Asn Gly Arg
1               5                   10

<210> SEQ ID NO 281
<211> LENGTH: 10
<212> TYPE: PRT
<213> ORGANISM: Artificial Sequence
<220> FEATURE:
<223> OTHER INFORMATION: ABCG5

<400> SEQUENCE: 281

Ile Val Val Leu Thr Ile His Gln Pro Arg
1               5                   10

<210> SEQ ID NO 282
<211> LENGTH: 14
<212> TYPE: PRT
<213> ORGANISM: Artificial Sequence
<220> FEATURE:
<223> OTHER INFORMATION: ABCG5

<400> SEQUENCE: 282

Ala Val Ser Asp Gln Glu Ser Gln Asp Gly Leu Tyr Gln Lys
1               5                   10

<210> SEQ ID NO 283
<211> LENGTH: 9
<212> TYPE: PRT
<213> ORGANISM: Artificial Sequence
<220> FEATURE:
<223> OTHER INFORMATION: ABCG5

<400> SEQUENCE: 283

Ile Ile Ser Tyr Phe Thr Phe Gln Lys
1               5

<210> SEQ ID NO 284

```
<211> LENGTH: 10
<212> TYPE: PRT
<213> ORGANISM: Artificial Sequence
<220> FEATURE:
<223> OTHER INFORMATION: ABCG8

<400> SEQUENCE: 284

Ala Ser Leu Leu Asp Val Ile Thr Gly Arg
1               5                   10

<210> SEQ ID NO 285
<211> LENGTH: 8
<212> TYPE: PRT
<213> ORGANISM: Artificial Sequence
<220> FEATURE:
<223> OTHER INFORMATION: SLC10A1

<400> SEQUENCE: 285

Gly Ile Tyr Asp Gly Asp Leu Lys
1               5

<210> SEQ ID NO 286
<211> LENGTH: 7
<212> TYPE: PRT
<213> ORGANISM: Artificial Sequence
<220> FEATURE:
<223> OTHER INFORMATION: SLC15A1

<400> SEQUENCE: 286

Thr Leu Pro Val Phe Pro Lys
1               5

<210> SEQ ID NO 287
<211> LENGTH: 9
<212> TYPE: PRT
<213> ORGANISM: Artificial Sequence
<220> FEATURE:
<223> OTHER INFORMATION: SLC15A2

<400> SEQUENCE: 287

Ser Gln Asp Phe His Phe His Leu Lys
1               5

<210> SEQ ID NO 288
<211> LENGTH: 7
<212> TYPE: PRT
<213> ORGANISM: Artificial Sequence
<220> FEATURE:
<223> OTHER INFORMATION: SLC16A1

<400> SEQUENCE: 288

Ser Ile Thr Val Phe Phe Lys
1               5

<210> SEQ ID NO 289
<211> LENGTH: 7
<212> TYPE: PRT
<213> ORGANISM: Artificial Sequence
<220> FEATURE:
<223> OTHER INFORMATION: SLC16A7

<400> SEQUENCE: 289

Ala Val Thr Val Phe Phe Lys
1               5

<210> SEQ ID NO 290
<211> LENGTH: 14
<212> TYPE: PRT
```

<213> ORGANISM: Artificial Sequence
<220> FEATURE:
<223> OTHER INFORMATION: SLC21A2

<400> SEQUENCE: 290

Val Asn Thr Ala Ala Val Asn Leu Val Pro Gly Asp Pro Arg
1               5                   10

<210> SEQ ID NO 291
<211> LENGTH: 11
<212> TYPE: PRT
<213> ORGANISM: Artificial Sequence
<220> FEATURE:
<223> OTHER INFORMATION: SLC21A3

<400> SEQUENCE: 291

Glu Gly Leu Glu Thr Asn Ala Asp Ile Ile Lys
1               5                   10

<210> SEQ ID NO 292
<211> LENGTH: 8
<212> TYPE: PRT
<213> ORGANISM: Artificial Sequence
<220> FEATURE:
<223> OTHER INFORMATION: SLC21A6

<400> SEQUENCE: 292

Leu Asn Thr Val Gly Ile Ala Lys
1               5

<210> SEQ ID NO 293
<211> LENGTH: 9
<212> TYPE: PRT
<213> ORGANISM: Artificial Sequence
<220> FEATURE:
<223> OTHER INFORMATION: SLC21A8

<400> SEQUENCE: 293

Ile Tyr Asn Ser Val Phe Phe Gly Arg
1               5

<210> SEQ ID NO 294
<211> LENGTH: 7
<212> TYPE: PRT
<213> ORGANISM: Artificial Sequence
<220> FEATURE:
<223> OTHER INFORMATION: SLC21A9

<400> SEQUENCE: 294

Val Leu Leu Gln Thr Leu Arg
1               5

<210> SEQ ID NO 295
<211> LENGTH: 11
<212> TYPE: PRT
<213> ORGANISM: Artificial Sequence
<220> FEATURE:
<223> OTHER INFORMATION: SLC21A11

<400> SEQUENCE: 295

Ser Gly Glu Leu Gln Gly Asp Glu Ala Gln Arg
1               5                   10

<210> SEQ ID NO 296
<211> LENGTH: 10
<212> TYPE: PRT
<213> ORGANISM: Artificial Sequence
<220> FEATURE:

```
<223> OTHER INFORMATION: SLC21A12

<400> SEQUENCE: 296

Tyr Glu Val Glu Leu Asp Ala Gly Val Arg
1               5                   10

<210> SEQ ID NO 297
<211> LENGTH: 8
<212> TYPE: PRT
<213> ORGANISM: Artificial Sequence
<220> FEATURE:
<223> OTHER INFORMATION: SLC21A14

<400> SEQUENCE: 297

Leu Tyr Asp Ser Asn Val Phe Arg
1               5

<210> SEQ ID NO 298
<211> LENGTH: 11
<212> TYPE: PRT
<213> ORGANISM: Artificial Sequence
<220> FEATURE:
<223> OTHER INFORMATION: SLC21A15

<400> SEQUENCE: 298

Asn Pro Val His Leu Asp Gln Asn Asp Pro Arg
1               5                   10

<210> SEQ ID NO 299
<211> LENGTH: 12
<212> TYPE: PRT
<213> ORGANISM: Artificial Sequence
<220> FEATURE:
<223> OTHER INFORMATION: SLC21A19

<400> SEQUENCE: 299

Ile Phe Gly Thr Ile Pro Gly Pro Ser Ile Phe Lys
1               5                   10

<210> SEQ ID NO 300
<211> LENGTH: 12
<212> TYPE: PRT
<213> ORGANISM: Artificial Sequence
<220> FEATURE:
<223> OTHER INFORMATION: SLC21A20

<400> SEQUENCE: 300

His Leu Pro Gly Thr Ala Glu Ile Gln Ala Gly Lys
1               5                   10

<210> SEQ ID NO 301
<211> LENGTH: 10
<212> TYPE: PRT
<213> ORGANISM: Artificial Sequence
<220> FEATURE:
<223> OTHER INFORMATION: SLC22A1

<400> SEQUENCE: 301

Leu Ser Pro Ser Phe Ala Asp Leu Phe Arg
1               5                   10

<210> SEQ ID NO 302
<211> LENGTH: 8
<212> TYPE: PRT
<213> ORGANISM: Artificial Sequence
<220> FEATURE:
<223> OTHER INFORMATION: SLC22A2
```

```
<400> SEQUENCE: 302

Ser Leu Pro Ala Ser Leu Gln Arg
1               5

<210> SEQ ID NO 303
<211> LENGTH: 8
<212> TYPE: PRT
<213> ORGANISM: Artificial Sequence
<220> FEATURE:
<223> OTHER INFORMATION: SLC22A3

<400> SEQUENCE: 303

Phe Leu Gln Gly Val Phe Gly Lys
1               5

<210> SEQ ID NO 304
<211> LENGTH: 8
<212> TYPE: PRT
<213> ORGANISM: Artificial Sequence
<220> FEATURE:
<223> OTHER INFORMATION: SLC22A4

<400> SEQUENCE: 304

Ala Phe Ile Leu Asp Leu Phe Arg
1               5

<210> SEQ ID NO 305
<211> LENGTH: 30
<212> TYPE: PRT
<213> ORGANISM: Artificial Sequence
<220> FEATURE:
<223> OTHER INFORMATION: SLC22A5

<400> SEQUENCE: 305

Leu Ile Phe Phe Leu Leu Ser Ala Ser Ile Ile Pro Asn Gly Phe Thr
1               5                   10                  15
Gly Leu Ser Ser Val Phe Leu Ile Ala Thr Pro Glu His Arg
            20                  25                  30

<210> SEQ ID NO 306
<211> LENGTH: 8
<212> TYPE: PRT
<213> ORGANISM: Artificial Sequence
<220> FEATURE:
<223> OTHER INFORMATION: SLC22A6

<400> SEQUENCE: 306

Thr Ser Leu Ala Val Leu Gly Lys
1               5

<210> SEQ ID NO 307
<211> LENGTH: 9
<212> TYPE: PRT
<213> ORGANISM: Artificial Sequence
<220> FEATURE:
<223> OTHER INFORMATION: SLC22A7

<400> SEQUENCE: 307

Asn Val Ala Leu Leu Ala Leu Pro Arg
1               5

<210> SEQ ID NO 308
<211> LENGTH: 8
<212> TYPE: PRT
<213> ORGANISM: Artificial Sequence
<220> FEATURE:
<223> OTHER INFORMATION: SLC22A8
```

<400> SEQUENCE: 308

Tyr Thr Ala Ser Asp Leu Phe Arg
1               5

<210> SEQ ID NO 309
<211> LENGTH: 9
<212> TYPE: PRT
<213> ORGANISM: Artificial Sequence
<220> FEATURE:
<223> OTHER INFORMATION: SLC22A9

<400> SEQUENCE: 309

Asp Thr Leu Thr Leu Glu Ile Leu Lys
1               5

<210> SEQ ID NO 310
<211> LENGTH: 9
<212> TYPE: PRT
<213> ORGANISM: Artificial Sequence
<220> FEATURE:
<223> OTHER INFORMATION: SLC22A10

<400> SEQUENCE: 310

Asn Leu Pro Leu Pro Asp Thr Ile Lys
1               5

<210> SEQ ID NO 311
<211> LENGTH: 8
<212> TYPE: PRT
<213> ORGANISM: Artificial Sequence
<220> FEATURE:
<223> OTHER INFORMATION: SLC22A11

<400> SEQUENCE: 311

Val Val Phe Ala Val Leu Gly Lys
1               5

<210> SEQ ID NO 312
<211> LENGTH: 10
<212> TYPE: PRT
<213> ORGANISM: Artificial Sequence
<220> FEATURE:
<223> OTHER INFORMATION: SLC22A12

<400> SEQUENCE: 312

Gly Gly Ala Ile Leu Gly Pro Leu Val Arg
1               5                   10

<210> SEQ ID NO 313
<211> LENGTH: 12
<212> TYPE: PRT
<213> ORGANISM: Artificial Sequence
<220> FEATURE:
<223> OTHER INFORMATION: SLC22A13

<400> SEQUENCE: 313

Thr Gly Pro Ser Gly Asn Ala Leu Asp Leu Phe Arg
1               5                   10

<210> SEQ ID NO 314
<211> LENGTH: 15
<212> TYPE: PRT
<213> ORGANISM: Artificial Sequence
<220> FEATURE:
<223> OTHER INFORMATION: SLC22A14

<400> SEQUENCE: 314

Asp Gln Pro Leu Ser Glu Ser Leu Asn His Ser Ser Gln Ile Arg
1               5                   10                  15

<210> SEQ ID NO 315
<211> LENGTH: 13
<212> TYPE: PRT
<213> ORGANISM: Artificial Sequence
<220> FEATURE:
<223> OTHER INFORMATION: SLC22A15

<400> SEQUENCE: 315

Val Gly Gly Ile Ile Ala Pro Phe Ile Pro Ser Leu Lys
1               5                   10

<210> SEQ ID NO 316
<211> LENGTH: 17
<212> TYPE: PRT
<213> ORGANISM: Artificial Sequence
<220> FEATURE:
<223> OTHER INFORMATION: SLC22A16

<400> SEQUENCE: 316

Asp Tyr Val Thr Val Gln Leu Gln Asn Gly Glu Ile Trp Glu Leu Ser
1               5                   10                  15

Arg

<210> SEQ ID NO 317
<211> LENGTH: 16
<212> TYPE: PRT
<213> ORGANISM: Artificial Sequence
<220> FEATURE:
<223> OTHER INFORMATION: SLC22A17

<400> SEQUENCE: 317

Asn Leu Leu Ile Leu Gly Phe Thr Asn Phe Ile Ala His Ala Ile Arg
1               5                   10                  15

<210> SEQ ID NO 318
<211> LENGTH: 12
<212> TYPE: PRT
<213> ORGANISM: Artificial Sequence
<220> FEATURE:
<223> OTHER INFORMATION: SLC22A18

<400> SEQUENCE: 318

Thr Leu Gly Pro Thr Val Gly Gly Leu Leu Tyr Arg
1               5                   10

<210> SEQ ID NO 319
<211> LENGTH: 9
<212> TYPE: PRT
<213> ORGANISM: Artificial Sequence
<220> FEATURE:
<223> OTHER INFORMATION: SLC29A1

<400> SEQUENCE: 319

Trp Leu Pro Ser Leu Val Leu Ala Arg
1               5

<210> SEQ ID NO 320
<211> LENGTH: 11
<212> TYPE: PRT
<213> ORGANISM: Artificial Sequence
<220> FEATURE:
<223> OTHER INFORMATION: SLC29A2

<400> SEQUENCE: 320

Val Ala Thr Leu Asp Leu Asp Leu Glu Lys
1               5                   10

<210> SEQ ID NO 321
<211> LENGTH: 13
<212> TYPE: PRT
<213> ORGANISM: Artificial Sequence
<220> FEATURE:
<223> OTHER INFORMATION: SLC28A1

<400> SEQUENCE: 321

Ala Gly Ser Ser Phe Val Phe Gly Glu Ala Leu Val Lys
1               5                   10

<210> SEQ ID NO 322
<211> LENGTH: 13
<212> TYPE: PRT
<213> ORGANISM: Artificial Sequence
<220> FEATURE:
<223> OTHER INFORMATION: SLC28A3

<400> SEQUENCE: 322

Thr Asp Pro Gly Phe Ile Ala Phe Asp Trp Leu Gly Arg
1               5                   10

<210> SEQ ID NO 323
<211> LENGTH: 11
<212> TYPE: PRT
<213> ORGANISM: Artificial Sequence
<220> FEATURE:
<223> OTHER INFORMATION: SLC19A1

<400> SEQUENCE: 323

Thr Ile Ile Thr Phe Ile Val Ser Asp Val Arg
1               5                   10

<210> SEQ ID NO 324
<211> LENGTH: 12
<212> TYPE: PRT
<213> ORGANISM: Artificial Sequence
<220> FEATURE:
<223> OTHER INFORMATION: SLC1A1

<400> SEQUENCE: 324

Ser Asp Thr Ile Ser Phe Thr Gln Thr Ser Gln Phe
1               5                   10

<210> SEQ ID NO 325
<211> LENGTH: 11
<212> TYPE: PRT
<213> ORGANISM: Artificial Sequence
<220> FEATURE:
<223> OTHER INFORMATION: SLC1A2

<400> SEQUENCE: 325

Ser Glu Leu Asp Thr Ile Asp Ser Gln His Arg
1               5                   10

<210> SEQ ID NO 326
<211> LENGTH: 12
<212> TYPE: PRT
<213> ORGANISM: Artificial Sequence
<220> FEATURE:
<223> OTHER INFORMATION: SLC1A3

<400> SEQUENCE: 326

Val Thr Ala Ala Asp Ala Phe Leu Asp Leu Ile Arg

<210> SEQ ID NO 327
<211> LENGTH: 11
<212> TYPE: PRT
<213> ORGANISM: Artificial Sequence
<220> FEATURE:
<223> OTHER INFORMATION: SLC1A4

<400> SEQUENCE: 327

Asp Ile Ile Val Leu Val Thr Ser Leu Gly Lys
1               5                   10

<210> SEQ ID NO 328
<211> LENGTH: 13
<212> TYPE: PRT
<213> ORGANISM: Artificial Sequence
<220> FEATURE:
<223> OTHER INFORMATION: SLC1A5

<400> SEQUENCE: 328

Asn Ile Phe Pro Ser Asn Leu Val Ser Ala Ala Phe Arg
1               5                   10

<210> SEQ ID NO 329
<211> LENGTH: 6
<212> TYPE: PRT
<213> ORGANISM: Artificial Sequence
<220> FEATURE:
<223> OTHER INFORMATION: SLC1A6

<400> SEQUENCE: 329

Val Gly Trp Leu Gln Arg
1               5

<210> SEQ ID NO 330
<211> LENGTH: 6
<212> TYPE: PRT
<213> ORGANISM: Artificial Sequence
<220> FEATURE:
<223> OTHER INFORMATION: SLC1A7

<400> SEQUENCE: 330

Thr Thr Pro Val Val Lys
1               5

<210> SEQ ID NO 331
<211> LENGTH: 10
<212> TYPE: PRT
<213> ORGANISM: Artificial Sequence
<220> FEATURE:
<223> OTHER INFORMATION: SLC2A1

<400> SEQUENCE: 331

Thr Phe Asp Glu Ile Ala Ser Gly Phe Arg
1               5                   10

<210> SEQ ID NO 332
<211> LENGTH: 6
<212> TYPE: PRT
<213> ORGANISM: Artificial Sequence
<220> FEATURE:
<223> OTHER INFORMATION: SLC6A12

<400> SEQUENCE: 332

Gly Gln Trp Thr Asn Lys
1               5

```
<210> SEQ ID NO 333
<211> LENGTH: 9
<212> TYPE: PRT
<213> ORGANISM: Artificial Sequence
<220> FEATURE:
<223> OTHER INFORMATION: SLC7A5

<400> SEQUENCE: 333

Val Gln Asp Ala Phe Ala Ala Ala Lys
1               5

<210> SEQ ID NO 334
<211> LENGTH: 15
<212> TYPE: PRT
<213> ORGANISM: Artificial Sequence
<220> FEATURE:
<223> OTHER INFORMATION: SLC17A1

<400> SEQUENCE: 334

Glu Tyr Ile Thr Ser Ser Leu Val Gln Gln Val Ser Ser Ser Arg
1               5                   10                  15

<210> SEQ ID NO 335
<211> LENGTH: 16
<212> TYPE: PRT
<213> ORGANISM: Artificial Sequence
<220> FEATURE:
<223> OTHER INFORMATION: SLC17A2

<400> SEQUENCE: 335

Glu His Ile Leu Ser Ser Leu Ala Gln Gln Pro Ser Ser Pro Gly Arg
1               5                   10                  15

<210> SEQ ID NO 336
<211> LENGTH: 8
<212> TYPE: PRT
<213> ORGANISM: Artificial Sequence
<220> FEATURE:
<223> OTHER INFORMATION: SLC17A3

<400> SEQUENCE: 336

Glu Tyr Ile Ile Ser Ser Leu Lys
1               5

<210> SEQ ID NO 337
<211> LENGTH: 8
<212> TYPE: PRT
<213> ORGANISM: Artificial Sequence
<220> FEATURE:
<223> OTHER INFORMATION: SLC17A4

<400> SEQUENCE: 337

Ala Asp Val Gln Asp Trp Ala Lys
1               5

<210> SEQ ID NO 338
<211> LENGTH: 9
<212> TYPE: PRT
<213> ORGANISM: Artificial Sequence
<220> FEATURE:
<223> OTHER INFORMATION: SLC17A5

<400> SEQUENCE: 338

Thr Pro Leu Leu Pro Gly Ala Pro Arg
1               5

<210> SEQ ID NO 339
```

-continued

```
<211> LENGTH: 6
<212> TYPE: PRT
<213> ORGANISM: Artificial Sequence
<220> FEATURE:
<223> OTHER INFORMATION: SLC17A6

<400> SEQUENCE: 339

Ile Leu Ala Pro Gly Lys
1               5

<210> SEQ ID NO 340
<211> LENGTH: 8
<212> TYPE: PRT
<213> ORGANISM: Artificial Sequence
<220> FEATURE:
<223> OTHER INFORMATION: SLC17A7

<400> SEQUENCE: 340

Gly Gly His Val Val Val Gln Lys
1               5

<210> SEQ ID NO 341
<211> LENGTH: 18
<212> TYPE: PRT
<213> ORGANISM: Artificial Sequence
<220> FEATURE:
<223> OTHER INFORMATION: SLC17A8

<400> SEQUENCE: 341

Thr Tyr Ile Glu Thr Ser Ile Gly Glu Gly Ala Asn Val Val Ser Leu
1               5                   10                  15

Ser Lys

<210> SEQ ID NO 342
<211> LENGTH: 7
<212> TYPE: PRT
<213> ORGANISM: Artificial Sequence
<220> FEATURE:
<223> OTHER INFORMATION: SLC29A4

<400> SEQUENCE: 342

Leu Leu Leu Pro Asp Glu Arg
1               5

<210> SEQ ID NO 343
<211> LENGTH: 14
<212> TYPE: PRT
<213> ORGANISM: Artificial Sequence
<220> FEATURE:
<223> OTHER INFORMATION: SLC44A1

<400> SEQUENCE: 343

Leu Pro Val Pro Ala Ser Ala Pro Ile Pro Phe Phe His Arg
1               5                   10

<210> SEQ ID NO 344
<211> LENGTH: 8
<212> TYPE: PRT
<213> ORGANISM: Artificial Sequence
<220> FEATURE:
<223> OTHER INFORMATION: SLC44A2

<400> SEQUENCE: 344

Tyr Leu Thr Tyr Leu Asn Ala Arg
1               5

<210> SEQ ID NO 345
```

```
<211> LENGTH: 7
<212> TYPE: PRT
<213> ORGANISM: Artificial Sequence
<220> FEATURE:
<223> OTHER INFORMATION: SLC44A3

<400> SEQUENCE: 345

Ser Phe Pro Leu Phe Asn Arg
1               5

<210> SEQ ID NO 346
<211> LENGTH: 8
<212> TYPE: PRT
<213> ORGANISM: Artificial Sequence
<220> FEATURE:
<223> OTHER INFORMATION: SLC44A4

<400> SEQUENCE: 346

Gly Val Gln Asn Pro Val Ala Arg
1               5

<210> SEQ ID NO 347
<211> LENGTH: 10
<212> TYPE: PRT
<213> ORGANISM: Artificial Sequence
<220> FEATURE:
<223> OTHER INFORMATION: SLC44A5

<400> SEQUENCE: 347

Thr Ile Leu Phe Tyr Phe Asn Leu Leu Arg
1               5                   10

<210> SEQ ID NO 348
<211> LENGTH: 11
<212> TYPE: PRT
<213> ORGANISM: Artificial Sequence
<220> FEATURE:
<223> OTHER INFORMATION: MATE1

<400> SEQUENCE: 348

Asp His Val Gly Tyr Ile Phe Thr Thr Asp Arg
1               5                   10

<210> SEQ ID NO 349
<211> LENGTH: 8
<212> TYPE: PRT
<213> ORGANISM: Artificial Sequence
<220> FEATURE:
<223> OTHER INFORMATION: MATE2

<400> SEQUENCE: 349

Ala Ser Phe His Leu Phe Gln Lys
1               5

<210> SEQ ID NO 350
<211> LENGTH: 6
<212> TYPE: PRT
<213> ORGANISM: Artificial Sequence
<220> FEATURE:
<223> OTHER INFORMATION: SLC2A2

<400> SEQUENCE: 350

Leu Asp Glu Glu Val Lys
1               5

<210> SEQ ID NO 351
<211> LENGTH: 8
<212> TYPE: PRT
```

```
<213> ORGANISM: Artificial Sequence
<220> FEATURE:
<223> OTHER INFORMATION: SLC2A2

<400> SEQUENCE: 351

Glu Glu Ala Ser Ser Glu Gln Lys
1               5

<210> SEQ ID NO 352
<211> LENGTH: 7
<212> TYPE: PRT
<213> ORGANISM: Artificial Sequence
<220> FEATURE:
<223> OTHER INFORMATION: SLC2A8

<400> SEQUENCE: 352

Ala Ala Pro Pro Ala Pro Arg
1               5

<210> SEQ ID NO 353
<211> LENGTH: 12
<212> TYPE: PRT
<213> ORGANISM: Artificial Sequence
<220> FEATURE:
<223> OTHER INFORMATION: SLC2A8

<400> SEQUENCE: 353

Thr Leu Glu Gln Ile Thr Ala His Phe Glu Gly Arg
1               5                   10

<210> SEQ ID NO 354
<211> LENGTH: 8
<212> TYPE: PRT
<213> ORGANISM: Artificial Sequence
<220> FEATURE:
<223> OTHER INFORMATION: SLC2A9

<400> SEQUENCE: 354

Ala Phe Gln Thr Phe Leu Gly Lys
1               5

<210> SEQ ID NO 355
<211> LENGTH: 9
<212> TYPE: PRT
<213> ORGANISM: Artificial Sequence
<220> FEATURE:
<223> OTHER INFORMATION: SLC2A9

<400> SEQUENCE: 355

Leu Val Ser Val Leu Glu Leu Leu Arg
1               5

<210> SEQ ID NO 356
<211> LENGTH: 9
<212> TYPE: PRT
<213> ORGANISM: Artificial Sequence
<220> FEATURE:
<223> OTHER INFORMATION: SLC2A9

<400> SEQUENCE: 356

Ile Asp Ser Ala Val Thr Asp Gly Lys
1               5

<210> SEQ ID NO 357
<211> LENGTH: 12
<212> TYPE: PRT
<213> ORGANISM: Artificial Sequence
<220> FEATURE:
```

```
<223> OTHER INFORMATION: SLC2A10

<400> SEQUENCE: 357

Asp Leu Ile Pro Leu Gln Gly Gly Glu Ala Pro Lys
1               5                   10

<210> SEQ ID NO 358
<211> LENGTH: 6
<212> TYPE: PRT
<213> ORGANISM: Artificial Sequence
<220> FEATURE:
<223> OTHER INFORMATION: SLC2A10

<400> SEQUENCE: 358

Thr Asn Glu Asp Gln Arg
1               5

<210> SEQ ID NO 359
<211> LENGTH: 9
<212> TYPE: PRT
<213> ORGANISM: Artificial Sequence
<220> FEATURE:
<223> OTHER INFORMATION: SLC2A10

<400> SEQUENCE: 359

Ser Gly Asp Pro Ser Ala Pro Pro Arg
1               5

<210> SEQ ID NO 360
<211> LENGTH: 15
<212> TYPE: PRT
<213> ORGANISM: Artificial Sequence
<220> FEATURE:
<223> OTHER INFORMATION: SLC2A10

<400> SEQUENCE: 360

Leu Ala Leu Ser Ser Ala Leu Pro Gly Pro Pro Leu Pro Ala Arg
1               5                   10                  15

<210> SEQ ID NO 361
<211> LENGTH: 8
<212> TYPE: PRT
<213> ORGANISM: Artificial Sequence
<220> FEATURE:
<223> OTHER INFORMATION: SLC4A5

<400> SEQUENCE: 361

Gly His Leu Ser Gly Leu Gln Lys
1               5

<210> SEQ ID NO 362
<211> LENGTH: 7
<212> TYPE: PRT
<213> ORGANISM: Artificial Sequence
<220> FEATURE:
<223> OTHER INFORMATION: SLC4A5

<400> SEQUENCE: 362

Val Glu Glu Gly Gly Glu Arg
1               5

<210> SEQ ID NO 363
<211> LENGTH: 7
<212> TYPE: PRT
<213> ORGANISM: Artificial Sequence
<220> FEATURE:
<223> OTHER INFORMATION: SLC4A5
```

```
<400> SEQUENCE: 363

Ser Leu Ala Asp Ile Gly Lys
1               5

<210> SEQ ID NO 364
<211> LENGTH: 7
<212> TYPE: PRT
<213> ORGANISM: Artificial Sequence
<220> FEATURE:
<223> OTHER INFORMATION: SLC4A5

<400> SEQUENCE: 364

Ser Val Ser Thr Thr Asn Arg
1               5

<210> SEQ ID NO 365
<211> LENGTH: 16
<212> TYPE: PRT
<213> ORGANISM: Artificial Sequence
<220> FEATURE:
<223> OTHER INFORMATION: SLC4A5

<400> SEQUENCE: 365

Ser Pro Gly Ala Gly Pro Ser Leu His His Ser Thr Glu Asp Leu Arg
1               5                   10                  15

<210> SEQ ID NO 366
<211> LENGTH: 7
<212> TYPE: PRT
<213> ORGANISM: Artificial Sequence
<220> FEATURE:
<223> OTHER INFORMATION: SLC4A5

<400> SEQUENCE: 366

Gln Ser Ala Asn Tyr Gly Arg
1               5

<210> SEQ ID NO 367
<211> LENGTH: 24
<212> TYPE: PRT
<213> ORGANISM: Artificial Sequence
<220> FEATURE:
<223> OTHER INFORMATION: SLC4A5

<400> SEQUENCE: 367

Asp Ser Glu Ala Ser Asn Val Leu Val Gly Glu Val Asp Phe Leu Asp
1               5                   10                  15

Gln Pro Phe Ile Ala Phe Val Arg
            20

<210> SEQ ID NO 368
<211> LENGTH: 11
<212> TYPE: PRT
<213> ORGANISM: Artificial Sequence
<220> FEATURE:
<223> OTHER INFORMATION: SLC4A5

<400> SEQUENCE: 368

Phe Leu Phe Ile Leu Leu Gly Pro Ser Gly Arg
1               5                   10

<210> SEQ ID NO 369
<211> LENGTH: 27
<212> TYPE: PRT
<213> ORGANISM: Artificial Sequence
<220> FEATURE:
<223> OTHER INFORMATION: SLC4A5
```

<400> SEQUENCE: 369

Glu Asp Leu Ile Ala Gly Ile Asp Glu Phe Leu Asp Glu Val Ile Val
1               5                   10                  15

Leu Pro Pro Gly Glu Trp Asp Pro Asn Ile Arg
            20                  25

<210> SEQ ID NO 370
<211> LENGTH: 7
<212> TYPE: PRT
<213> ORGANISM: Artificial Sequence
<220> FEATURE:
<223> OTHER INFORMATION: SLC4A5

<400> SEQUENCE: 370

Leu Leu Phe Asp Phe Ser Lys
1               5

<210> SEQ ID NO 371
<211> LENGTH: 9
<212> TYPE: PRT
<213> ORGANISM: Artificial Sequence
<220> FEATURE:
<223> OTHER INFORMATION: SLC4A5

<400> SEQUENCE: 371

Gly Trp Phe Val Ala Pro Phe Gly Lys
1               5

<210> SEQ ID NO 372
<211> LENGTH: 21
<212> TYPE: PRT
<213> ORGANISM: Artificial Sequence
<220> FEATURE:
<223> OTHER INFORMATION: SLC4A5

<400> SEQUENCE: 372

Val Thr Gly Ile Ile Val Phe Ile Leu Thr Gly Ile Ser Val Phe Leu
1               5                   10                  15

Ala Pro Ile Leu Lys
            20

<210> SEQ ID NO 373
<211> LENGTH: 9
<212> TYPE: PRT
<213> ORGANISM: Artificial Sequence
<220> FEATURE:
<223> OTHER INFORMATION: SLC4A5

<400> SEQUENCE: 373

His Gln Pro Asp His Ala Phe Leu Arg
1               5

<210> SEQ ID NO 374
<211> LENGTH: 11
<212> TYPE: PRT
<213> ORGANISM: Artificial Sequence
<220> FEATURE:
<223> OTHER INFORMATION: SLC4A7

<400> SEQUENCE: 374

Phe Leu Phe Leu Leu Leu Gly Pro Ala Gly Lys
1               5                   10

<210> SEQ ID NO 375
<211> LENGTH: 9

```
<212> TYPE: PRT
<213> ORGANISM: Artificial Sequence
<220> FEATURE:
<223> OTHER INFORMATION: SLC4A7

<400> SEQUENCE: 375

Ala Pro Gln Tyr His Glu Ile Gly Arg
1               5

<210> SEQ ID NO 376
<211> LENGTH: 12
<212> TYPE: PRT
<213> ORGANISM: Artificial Sequence
<220> FEATURE:
<223> OTHER INFORMATION: SLC4A7

<400> SEQUENCE: 376

Glu Ala Ala His His Ala Gly Pro Glu Leu Gln Arg
1               5                   10

<210> SEQ ID NO 377
<211> LENGTH: 10
<212> TYPE: PRT
<213> ORGANISM: Artificial Sequence
<220> FEATURE:
<223> OTHER INFORMATION: SLC4A7

<400> SEQUENCE: 377

Asp Tyr Gln Leu Ser Tyr Leu Ser Leu Arg
1               5                   10

<210> SEQ ID NO 378
<211> LENGTH: 8
<212> TYPE: PRT
<213> ORGANISM: Artificial Sequence
<220> FEATURE:
<223> OTHER INFORMATION: SLC4A7

<400> SEQUENCE: 378

Phe Glu Pro Thr His Pro Glu Arg
1               5

<210> SEQ ID NO 379
<211> LENGTH: 9
<212> TYPE: PRT
<213> ORGANISM: Artificial Sequence
<220> FEATURE:
<223> OTHER INFORMATION: SLC4A7

<400> SEQUENCE: 379

His Gln Pro Asp Leu Ile Tyr Leu Arg
1               5

<210> SEQ ID NO 380
<211> LENGTH: 12
<212> TYPE: PRT
<213> ORGANISM: Artificial Sequence
<220> FEATURE:
<223> OTHER INFORMATION: SLC5A9

<400> SEQUENCE: 380

Thr Glu Thr Ala Pro His Ile Ala Leu Asp Ser Arg
1               5                   10

<210> SEQ ID NO 381
<211> LENGTH: 11
<212> TYPE: PRT
<213> ORGANISM: Artificial Sequence
```

-continued

```
<220> FEATURE:
<223> OTHER INFORMATION: SLC5A9

<400> SEQUENCE: 381

Leu Thr Ser Ile Glu Glu Pro Leu Trp Arg
1               5                   10

<210> SEQ ID NO 382
<211> LENGTH: 8
<212> TYPE: PRT
<213> ORGANISM: Artificial Sequence
<220> FEATURE:
<223> OTHER INFORMATION: SLC5A11

<400> SEQUENCE: 382

Glu Asp Ala Phe His Ile Phe Arg
1               5

<210> SEQ ID NO 383
<211> LENGTH: 7
<212> TYPE: PRT
<213> ORGANISM: Artificial Sequence
<220> FEATURE:
<223> OTHER INFORMATION: SLC5A11

<400> SEQUENCE: 383

His Asp Pro Val Val Gln Lys
1               5

<210> SEQ ID NO 384
<211> LENGTH: 11
<212> TYPE: PRT
<213> ORGANISM: Artificial Sequence
<220> FEATURE:
<223> OTHER INFORMATION: SLC5A11

<400> SEQUENCE: 384

Leu Val Leu Glu Leu Leu Pro Pro Gly Leu Arg
1               5                   10

<210> SEQ ID NO 385
<211> LENGTH: 15
<212> TYPE: PRT
<213> ORGANISM: Artificial Sequence
<220> FEATURE:
<223> OTHER INFORMATION: SLC5A11

<400> SEQUENCE: 385

Ala Glu Ala Ile Ile Val Ser Leu Glu Glu Asn Pro Leu Val Lys
1               5                   10                  15

<210> SEQ ID NO 386
<211> LENGTH: 9
<212> TYPE: PRT
<213> ORGANISM: Artificial Sequence
<220> FEATURE:
<223> OTHER INFORMATION: SLC6A9

<400> SEQUENCE: 386

Thr Asp Gly Asp Thr Leu Leu Gln Arg
1               5

<210> SEQ ID NO 387
<211> LENGTH: 13
<212> TYPE: PRT
<213> ORGANISM: Artificial Sequence
<220> FEATURE:
<223> OTHER INFORMATION: SLC6A9
```

<400> SEQUENCE: 387

Ala Gln Ile Pro Ile Val Gly Ser Asn Gly Ser Ser Arg
1               5                   10

<210> SEQ ID NO 388
<211> LENGTH: 12
<212> TYPE: PRT
<213> ORGANISM: Artificial Sequence
<220> FEATURE:
<223> OTHER INFORMATION: SLC6A13

<400> SEQUENCE: 388

Ile Ser Asp Gly Ile Gln His Leu Gly Ala Leu Arg
1               5                   10

<210> SEQ ID NO 389
<211> LENGTH: 7
<212> TYPE: PRT
<213> ORGANISM: Artificial Sequence
<220> FEATURE:
<223> OTHER INFORMATION: SLC7A2

<400> SEQUENCE: 389

Ala Ala Leu Thr Phe Ala Arg
1               5

<210> SEQ ID NO 390
<211> LENGTH: 12
<212> TYPE: PRT
<213> ORGANISM: Artificial Sequence
<220> FEATURE:
<223> OTHER INFORMATION: SLC7A2

<400> SEQUENCE: 390

Ala Gly Ser Gly Thr Phe Asp Glu Leu Leu Ser Lys
1               5                   10

<210> SEQ ID NO 391
<211> LENGTH: 7
<212> TYPE: PRT
<213> ORGANISM: Artificial Sequence
<220> FEATURE:
<223> OTHER INFORMATION: SLC7A2

<400> SEQUENCE: 391

Gln Ile Gly Gln Phe Leu Arg
1               5

<210> SEQ ID NO 392
<211> LENGTH: 7
<212> TYPE: PRT
<213> ORGANISM: Artificial Sequence
<220> FEATURE:
<223> OTHER INFORMATION: SLC7A2

<400> SEQUENCE: 392

Glu Ser Ala Trp Val Asn Lys
1               5

<210> SEQ ID NO 393
<211> LENGTH: 7
<212> TYPE: PRT
<213> ORGANISM: Artificial Sequence
<220> FEATURE:
<223> OTHER INFORMATION: SLC7A2

<400> SEQUENCE: 393

Ile Ser Glu Glu Phe Leu Lys
1               5

<210> SEQ ID NO 394
<211> LENGTH: 8
<212> TYPE: PRT
<213> ORGANISM: Artificial Sequence
<220> FEATURE:
<223> OTHER INFORMATION: SLC7A2

<400> SEQUENCE: 394

Asp Gly Leu Gly Ser Ser Pro Arg
1               5

<210> SEQ ID NO 395
<211> LENGTH: 8
<212> TYPE: PRT
<213> ORGANISM: Artificial Sequence
<220> FEATURE:
<223> OTHER INFORMATION: SLC7A2

<400> SEQUENCE: 395

His Ser Leu Glu Gly His Leu Arg
1               5

<210> SEQ ID NO 396
<211> LENGTH: 11
<212> TYPE: PRT
<213> ORGANISM: Artificial Sequence
<220> FEATURE:
<223> OTHER INFORMATION: SLC7A2

<400> SEQUENCE: 396

Ser Ala Ile Gln Ala Asn Asp His His Pro Arg
1               5                   10

<210> SEQ ID NO 397
<211> LENGTH: 11
<212> TYPE: PRT
<213> ORGANISM: Artificial Sequence
<220> FEATURE:
<223> OTHER INFORMATION: SLC7A2

<400> SEQUENCE: 397

Asn Leu Ser Ser Pro Phe Ile Phe His Glu Lys
1               5                   10

<210> SEQ ID NO 398
<211> LENGTH: 9
<212> TYPE: PRT
<213> ORGANISM: Artificial Sequence
<220> FEATURE:
<223> OTHER INFORMATION: SLC7A6

<400> SEQUENCE: 398

Val Gln Asp Thr Phe Thr Tyr Ala Lys
1               5

<210> SEQ ID NO 399
<211> LENGTH: 7
<212> TYPE: PRT
<213> ORGANISM: Artificial Sequence
<220> FEATURE:
<223> OTHER INFORMATION: SLC7A6

<400> SEQUENCE: 399

Leu Phe Phe Val Gly Ser Arg

```
1               5

<210> SEQ ID NO 400
<211> LENGTH: 8
<212> TYPE: PRT
<213> ORGANISM: Artificial Sequence
<220> FEATURE:
<223> OTHER INFORMATION: SLC7A6

<400> SEQUENCE: 400

Asn Val Leu Ala Ala Ile Thr Arg
1               5

<210> SEQ ID NO 401
<211> LENGTH: 8
<212> TYPE: PRT
<213> ORGANISM: Artificial Sequence
<220> FEATURE:
<223> OTHER INFORMATION: SLC7A9

<400> SEQUENCE: 401

Ser Ile Gln Ser Gln Glu Pro Lys
1               5

<210> SEQ ID NO 402
<211> LENGTH: 22
<212> TYPE: PRT
<213> ORGANISM: Artificial Sequence
<220> FEATURE:
<223> OTHER INFORMATION: SLC10A6

<400> SEQUENCE: 402

Ile Gly Ala Val Val Gly Gly Val Leu Leu Val Val Ala Val Ala
1               5                   10                  15

Gly Val Val Leu Ala Lys
            20

<210> SEQ ID NO 403
<211> LENGTH: 37
<212> TYPE: PRT
<213> ORGANISM: Artificial Sequence
<220> FEATURE:
<223> OTHER INFORMATION: SLC10A6

<400> SEQUENCE: 403

Gly Ser Trp Asn Ser Asp Ile Thr Leu Leu Thr Ile Ser Phe Ile Phe
1               5                   10                  15

Pro Leu Ile Gly His Val Thr Gly Phe Leu Leu Ala Leu Phe Thr His
            20                  25                  30

Gln Ser Trp Gln Arg
        35

<210> SEQ ID NO 404
<211> LENGTH: 6
<212> TYPE: PRT
<213> ORGANISM: Artificial Sequence
<220> FEATURE:
<223> OTHER INFORMATION: SLC13A3

<400> SEQUENCE: 404

Ser Leu Phe Gly Gln Lys
1               5

<210> SEQ ID NO 405
<211> LENGTH: 6
<212> TYPE: PRT
```

```
<213> ORGANISM: Artificial Sequence
<220> FEATURE:
<223> OTHER INFORMATION: SLC13A3

<400> SEQUENCE: 405

Thr Asn Ala Glu Asp Arg
1               5

<210> SEQ ID NO 406
<211> LENGTH: 10
<212> TYPE: PRT
<213> ORGANISM: Artificial Sequence
<220> FEATURE:
<223> OTHER INFORMATION: SLC13A3

<400> SEQUENCE: 406

Glu Glu Tyr Gln Asn Leu Gly Pro Ile Lys
1               5                   10

<210> SEQ ID NO 407
<211> LENGTH: 6
<212> TYPE: PRT
<213> ORGANISM: Artificial Sequence
<220> FEATURE:
<223> OTHER INFORMATION: SLC13A3

<400> SEQUENCE: 407

Trp Trp Phe Asp Phe Lys
1               5

<210> SEQ ID NO 408
<211> LENGTH: 8
<212> TYPE: PRT
<213> ORGANISM: Artificial Sequence
<220> FEATURE:
<223> OTHER INFORMATION: SLC13A5

<400> SEQUENCE: 408

Thr Leu Leu Trp Val Gly Ala Lys
1               5

<210> SEQ ID NO 409
<211> LENGTH: 15
<212> TYPE: PRT
<213> ORGANISM: Artificial Sequence
<220> FEATURE:
<223> OTHER INFORMATION: SLC16A2

<400> SEQUENCE: 409

Gly Gly Gly Gly Leu Asp Val Gly Gly Gly Glu Gly Ser Arg
1               5                   10                  15

<210> SEQ ID NO 410
<211> LENGTH: 13
<212> TYPE: PRT
<213> ORGANISM: Artificial Sequence
<220> FEATURE:
<223> OTHER INFORMATION: SLC16A2

<400> SEQUENCE: 410

Val His Glu Pro Glu Pro Thr Pro Thr Val Glu Thr Arg
1               5                   10

<210> SEQ ID NO 411
<211> LENGTH: 10
<212> TYPE: PRT
<213> ORGANISM: Artificial Sequence
<220> FEATURE:
```

<223> OTHER INFORMATION: SLC16A2

<400> SEQUENCE: 411

Tyr Val Glu Glu Glu Phe Ser Glu Ile Lys
1               5                   10

<210> SEQ ID NO 412
<211> LENGTH: 8
<212> TYPE: PRT
<213> ORGANISM: Artificial Sequence
<220> FEATURE:
<223> OTHER INFORMATION: SLC16A4

<400> SEQUENCE: 412

Ser Glu Asn Asn Ser Gly Ile Lys
1               5

<210> SEQ ID NO 413
<211> LENGTH: 7
<212> TYPE: PRT
<213> ORGANISM: Artificial Sequence
<220> FEATURE:
<223> OTHER INFORMATION: SLC16A4

<400> SEQUENCE: 413

Ser Asp Glu Glu Ser Asp Lys
1               5

<210> SEQ ID NO 414
<211> LENGTH: 9
<212> TYPE: PRT
<213> ORGANISM: Artificial Sequence
<220> FEATURE:
<223> OTHER INFORMATION: SLC16A4

<400> SEQUENCE: 414

Gln Leu Phe Asp Ile Ser Leu Phe Arg
1               5

<210> SEQ ID NO 415
<211> LENGTH: 10
<212> TYPE: PRT
<213> ORGANISM: Artificial Sequence
<220> FEATURE:
<223> OTHER INFORMATION: SLC10A2

<400> SEQUENCE: 415

Ala Asn Gly Gly Phe Gln Pro Asp Glu Lys
1               5                   10

<210> SEQ ID NO 416
<211> LENGTH: 12
<212> TYPE: PRT
<213> ORGANISM: Artificial Sequence
<220> FEATURE:
<223> OTHER INFORMATION: SLC10A3

<400> SEQUENCE: 416

Val Thr Ser Leu Asp Thr Glu Val Leu Thr Ile Lys
1               5                   10

<210> SEQ ID NO 417
<211> LENGTH: 14
<212> TYPE: PRT
<213> ORGANISM: Artificial Sequence
<220> FEATURE:
<223> OTHER INFORMATION: SLC10A3

```
<400> SEQUENCE: 417

Leu Leu Ser Ile His Glu Thr Leu His Val Pro Ile Ser Lys
1               5                   10

<210> SEQ ID NO 418
<211> LENGTH: 7
<212> TYPE: PRT
<213> ORGANISM: Artificial Sequence
<220> FEATURE:
<223> OTHER INFORMATION: SLC10A4

<400> SEQUENCE: 418

Val Ala Asp Tyr Ile Val Lys
1               5

<210> SEQ ID NO 419
<211> LENGTH: 8
<212> TYPE: PRT
<213> ORGANISM: Artificial Sequence
<220> FEATURE:
<223> OTHER INFORMATION: SLC10A5

<400> SEQUENCE: 419

Thr Glu Ile Leu Phe Phe Thr Lys
1               5

<210> SEQ ID NO 420
<211> LENGTH: 14
<212> TYPE: PRT
<213> ORGANISM: Artificial Sequence
<220> FEATURE:
<223> OTHER INFORMATION: SLC10A5

<400> SEQUENCE: 420

Ile Leu Gly Leu Ser Gly Thr Phe His Ile Pro Val Ser Lys
1               5                   10

<210> SEQ ID NO 421
<211> LENGTH: 19
<212> TYPE: PRT
<213> ORGANISM: Artificial Sequence
<220> FEATURE:
<223> OTHER INFORMATION: SLC10A5

<400> SEQUENCE: 421

Ile Val Ser Thr Leu Leu Phe Ile Leu Val Pro Val Ser Ile Gly Ile
1               5                   10                  15

Val Ile Lys

<210> SEQ ID NO 422
<211> LENGTH: 7
<212> TYPE: PRT
<213> ORGANISM: Artificial Sequence
<220> FEATURE:
<223> OTHER INFORMATION: SLC11A1

<400> SEQUENCE: 422

Leu Gly Val Val Thr Gly Lys
1               5

<210> SEQ ID NO 423
<211> LENGTH: 17
<212> TYPE: PRT
<213> ORGANISM: Artificial Sequence
<220> FEATURE:
<223> OTHER INFORMATION: SLC11A2
```

```
<400> SEQUENCE: 423

Leu Leu Trp Ile Leu Leu Leu Ala Thr Leu Val Gly Leu Leu Leu Gln
1               5                   10                  15

Arg

<210> SEQ ID NO 424
<211> LENGTH: 9
<212> TYPE: PRT
<213> ORGANISM: Artificial Sequence
<220> FEATURE:
<223> OTHER INFORMATION: SLC12A1

<400> SEQUENCE: 424

Asn Thr Gly Ser Ile Ser Gly Pro Lys
1               5

<210> SEQ ID NO 425
<211> LENGTH: 10
<212> TYPE: PRT
<213> ORGANISM: Artificial Sequence
<220> FEATURE:
<223> OTHER INFORMATION: SLC12A1

<400> SEQUENCE: 425

Ser Leu Leu Gln Ala Ser Gly Leu Gly Arg
1               5                   10

<210> SEQ ID NO 426
<211> LENGTH: 11
<212> TYPE: PRT
<213> ORGANISM: Artificial Sequence
<220> FEATURE:
<223> OTHER INFORMATION: SLC12A1

<400> SEQUENCE: 426

Asn Val Ala Val Thr Pro Ser Ser Ala Asp Arg
1               5                   10

<210> SEQ ID NO 427
<211> LENGTH: 7
<212> TYPE: PRT
<213> ORGANISM: Artificial Sequence
<220> FEATURE:
<223> OTHER INFORMATION: SLC12A1

<400> SEQUENCE: 427

Ala Leu Gln Phe Phe Ala Lys
1               5

<210> SEQ ID NO 428
<211> LENGTH: 12
<212> TYPE: PRT
<213> ORGANISM: Artificial Sequence
<220> FEATURE:
<223> OTHER INFORMATION: SLC12A2

<400> SEQUENCE: 428

Gly Pro Ile Val Pro Leu Asn Val Ala Asp Gln Lys
1               5                   10

<210> SEQ ID NO 429
<211> LENGTH: 8
<212> TYPE: PRT
<213> ORGANISM: Artificial Sequence
<220> FEATURE:
<223> OTHER INFORMATION: SLC12A2
```

```
<400> SEQUENCE: 429

Asp Leu Pro Pro Ile Leu Leu Val
1               5

<210> SEQ ID NO 430
<211> LENGTH: 6
<212> TYPE: PRT
<213> ORGANISM: Artificial Sequence
<220> FEATURE:
<223> OTHER INFORMATION: SLC12A2

<400> SEQUENCE: 430

Asp Gly Gly Gly Val Arg
1               5

<210> SEQ ID NO 431
<211> LENGTH: 10
<212> TYPE: PRT
<213> ORGANISM: Artificial Sequence
<220> FEATURE:
<223> OTHER INFORMATION: SLC12A2

<400> SEQUENCE: 431

Gly Gly Gly Ala Tyr Tyr Leu Ile Ser Arg
1               5                   10

<210> SEQ ID NO 432
<211> LENGTH: 12
<212> TYPE: PRT
<213> ORGANISM: Artificial Sequence
<220> FEATURE:
<223> OTHER INFORMATION: SLC12A2

<400> SEQUENCE: 432

Ala Phe Tyr Ala Pro Val His Ala Asp Leu Arg
1               5                   10

<210> SEQ ID NO 433
<211> LENGTH: 10
<212> TYPE: PRT
<213> ORGANISM: Artificial Sequence
<220> FEATURE:
<223> OTHER INFORMATION: SLC12A3

<400> SEQUENCE: 433

Ser Gly Gly Thr Tyr Phe Leu Ile Ser Arg
1               5                   10

<210> SEQ ID NO 434
<211> LENGTH: 6
<212> TYPE: PRT
<213> ORGANISM: Artificial Sequence
<220> FEATURE:
<223> OTHER INFORMATION: SLC12A3

<400> SEQUENCE: 434

Gly Phe Phe Ser Tyr Arg
1               5

<210> SEQ ID NO 435
<211> LENGTH: 8
<212> TYPE: PRT
<213> ORGANISM: Artificial Sequence
<220> FEATURE:
<223> OTHER INFORMATION: SLC12A3

<400> SEQUENCE: 435
```

```
Asp Pro Ala Ile Ala Ile Pro Lys
1               5

<210> SEQ ID NO 436
<211> LENGTH: 12
<212> TYPE: PRT
<213> ORGANISM: Artificial Sequence
<220> FEATURE:
<223> OTHER INFORMATION: SLC12A4

<400> SEQUENCE: 436

His Gly Leu Pro Ser Ala Asp Ala Pro Ser Leu Lys
1               5                   10

<210> SEQ ID NO 437
<211> LENGTH: 7
<212> TYPE: PRT
<213> ORGANISM: Artificial Sequence
<220> FEATURE:
<223> OTHER INFORMATION: SLC12A4

<400> SEQUENCE: 437

Leu Leu Gln Ala Ile Ala Lys
1               5

<210> SEQ ID NO 438
<211> LENGTH: 8
<212> TYPE: PRT
<213> ORGANISM: Artificial Sequence
<220> FEATURE:
<223> OTHER INFORMATION: SLC12A4

<400> SEQUENCE: 438

Asp Asn Ile Ile Pro Phe Leu Arg
1               5

<210> SEQ ID NO 439
<211> LENGTH: 6
<212> TYPE: PRT
<213> ORGANISM: Artificial Sequence
<220> FEATURE:
<223> OTHER INFORMATION: SLC12A4

<400> SEQUENCE: 439

Val Phe Gly His Gly Lys
1               5

<210> SEQ ID NO 440
<211> LENGTH: 8
<212> TYPE: PRT
<213> ORGANISM: Artificial Sequence
<220> FEATURE:
<223> OTHER INFORMATION: SLC12A4

<400> SEQUENCE: 440

Gly Leu Ser Leu Ser Ala Ala Arg
1               5

<210> SEQ ID NO 441
<211> LENGTH: 9
<212> TYPE: PRT
<213> ORGANISM: Artificial Sequence
<220> FEATURE:
<223> OTHER INFORMATION: SLC12A4

<400> SEQUENCE: 441

Leu Leu Thr Phe Ala Ser Gln Leu Lys
1               5
```

```
<210> SEQ ID NO 442
<211> LENGTH: 7
<212> TYPE: PRT
<213> ORGANISM: Artificial Sequence
<220> FEATURE:
<223> OTHER INFORMATION: SLC12A5

<400> SEQUENCE: 442

Leu Leu Gln Ala Ile Ser Arg
1               5

<210> SEQ ID NO 443
<211> LENGTH: 14
<212> TYPE: PRT
<213> ORGANISM: Artificial Sequence
<220> FEATURE:
<223> OTHER INFORMATION: SLC12A5

<400> SEQUENCE: 443

Asp Gly Ile Val Pro Phe Leu Gln Val Phe Gly His Gly Lys
1               5                   10

<210> SEQ ID NO 444
<211> LENGTH: 8
<212> TYPE: PRT
<213> ORGANISM: Artificial Sequence
<220> FEATURE:
<223> OTHER INFORMATION: SLC12A5

<400> SEQUENCE: 444

Gly Leu Ser Leu Ser Ala Ala Arg
1               5

<210> SEQ ID NO 445
<211> LENGTH: 20
<212> TYPE: PRT
<213> ORGANISM: Artificial Sequence
<220> FEATURE:
<223> OTHER INFORMATION: SLC12A5

<400> SEQUENCE: 445

Val Asp Gln Asp Gln Asn Val Val His Pro Gln Leu Leu Ser Leu Thr
1               5                   10                  15

Ser Gln Leu Lys
            20

<210> SEQ ID NO 446
<211> LENGTH: 7
<212> TYPE: PRT
<213> ORGANISM: Artificial Sequence
<220> FEATURE:
<223> OTHER INFORMATION: SLC12A6

<400> SEQUENCE: 446

Val Ser Ser Leu Leu Asn Arg
1               5

<210> SEQ ID NO 447
<211> LENGTH: 11
<212> TYPE: PRT
<213> ORGANISM: Artificial Sequence
<220> FEATURE:
<223> OTHER INFORMATION: SLC12A6

<400> SEQUENCE: 447

Ala Ala Ile Phe His Ser Asp Asp Ala Leu Lys
```

```
1               5              10
```

<210> SEQ ID NO 448
<211> LENGTH: 8
<212> TYPE: PRT
<213> ORGANISM: Artificial Sequence
<220> FEATURE:
<223> OTHER INFORMATION: SLC12A6

<400> SEQUENCE: 448

Asp Asn Ile Ile Pro Phe Leu Arg
1               5

<210> SEQ ID NO 449
<211> LENGTH: 6
<212> TYPE: PRT
<213> ORGANISM: Artificial Sequence
<220> FEATURE:
<223> OTHER INFORMATION: SLC12A6

<400> SEQUENCE: 449

Val Phe Gly His Ser Lys
1               5

<210> SEQ ID NO 450
<211> LENGTH: 8
<212> TYPE: PRT
<213> ORGANISM: Artificial Sequence
<220> FEATURE:
<223> OTHER INFORMATION: SLC12A6

<400> SEQUENCE: 450

Gly Leu Ser Leu Ser Ala Ala Arg
1               5

<210> SEQ ID NO 451
<211> LENGTH: 9
<212> TYPE: PRT
<213> ORGANISM: Artificial Sequence
<220> FEATURE:
<223> OTHER INFORMATION: SLC12A6

<400> SEQUENCE: 451

Leu Leu Thr Phe Ala Ser Gln Leu Lys
1               5

<210> SEQ ID NO 452
<211> LENGTH: 6
<212> TYPE: PRT
<213> ORGANISM: Artificial Sequence
<220> FEATURE:
<223> OTHER INFORMATION: SLC12A6

<400> SEQUENCE: 452

Gln Ser Glu Asp Ala Arg
1               5

<210> SEQ ID NO 453
<211> LENGTH: 7
<212> TYPE: PRT
<213> ORGANISM: Artificial Sequence
<220> FEATURE:
<223> OTHER INFORMATION: SLC12A6

<400> SEQUENCE: 453

Thr Phe Ile Gly Thr Val Arg
1               5

```
<210> SEQ ID NO 454
<211> LENGTH: 13
<212> TYPE: PRT
<213> ORGANISM: Artificial Sequence
<220> FEATURE:
<223> OTHER INFORMATION: SLC12A6

<400> SEQUENCE: 454

Val Thr Thr Ala Ala His Leu Ala Leu Leu Val Ala Lys
1               5                   10

<210> SEQ ID NO 455
<211> LENGTH: 7
<212> TYPE: PRT
<213> ORGANISM: Artificial Sequence
<220> FEATURE:
<223> OTHER INFORMATION: SLC12A7

<400> SEQUENCE: 455

Leu Leu Gln Ala Ile Ala Arg
1               5

<210> SEQ ID NO 456
<211> LENGTH: 14
<212> TYPE: PRT
<213> ORGANISM: Artificial Sequence
<220> FEATURE:
<223> OTHER INFORMATION: SLC12A7

<400> SEQUENCE: 456

Asp Gly Ile Val Pro Phe Leu Gln Val Phe Gly His Gly Lys
1               5                   10

<210> SEQ ID NO 457
<211> LENGTH: 8
<212> TYPE: PRT
<213> ORGANISM: Artificial Sequence
<220> FEATURE:
<223> OTHER INFORMATION: SLC12A7

<400> SEQUENCE: 457

Gly Leu Ser Leu Asn Ala Ala Arg
1               5

<210> SEQ ID NO 458
<211> LENGTH: 9
<212> TYPE: PRT
<213> ORGANISM: Artificial Sequence
<220> FEATURE:
<223> OTHER INFORMATION: SLC12A7

<400> SEQUENCE: 458

Leu Leu Ser Phe Thr Ser Gln Leu Lys
1               5

<210> SEQ ID NO 459
<211> LENGTH: 7
<212> TYPE: PRT
<213> ORGANISM: Artificial Sequence
<220> FEATURE:
<223> OTHER INFORMATION: SLC12A7

<400> SEQUENCE: 459

Asn Phe Val Asp Thr Val Arg
1               5

<210> SEQ ID NO 460
```

```
<211> LENGTH: 13
<212> TYPE: PRT
<213> ORGANISM: Artificial Sequence
<220> FEATURE:
<223> OTHER INFORMATION: SLC12A7

<400> SEQUENCE: 460

Asp Thr Thr Ala Ala His Gln Ala Leu Leu Val Ala Lys
1               5                   10

<210> SEQ ID NO 461
<211> LENGTH: 11
<212> TYPE: PRT
<213> ORGANISM: Artificial Sequence
<220> FEATURE:
<223> OTHER INFORMATION: SLC12A7

<400> SEQUENCE: 461

Asn Thr Ala Ser His Thr Ala Ala Ala Ala Arg
1               5                   10

<210> SEQ ID NO 462
<211> LENGTH: 9
<212> TYPE: PRT
<213> ORGANISM: Artificial Sequence
<220> FEATURE:
<223> OTHER INFORMATION: SLC12A7

<400> SEQUENCE: 462

Thr Gln Ala Pro Pro Thr Pro Asp Lys
1               5

<210> SEQ ID NO 463
<211> LENGTH: 9
<212> TYPE: PRT
<213> ORGANISM: Artificial Sequence
<220> FEATURE:
<223> OTHER INFORMATION: SLC12A7

<400> SEQUENCE: 463

Arg Asp Thr Ser Leu Ser Gly Phe Lys
1               5

<210> SEQ ID NO 464
<211> LENGTH: 8
<212> TYPE: PRT
<213> ORGANISM: Artificial Sequence
<220> FEATURE:
<223> OTHER INFORMATION: SLC12A7

<400> SEQUENCE: 464

Leu Asn Gly Val Val Leu Asn Lys
1               5

<210> SEQ ID NO 465
<211> LENGTH: 17
<212> TYPE: PRT
<213> ORGANISM: Artificial Sequence
<220> FEATURE:
<223> OTHER INFORMATION: SLC12A8

<400> SEQUENCE: 465

Ala Ser Pro Gly Leu His Leu Gly Ser Ala Ser Asn Phe Ser Phe Phe
1               5                   10                  15

Arg

<210> SEQ ID NO 466
```

```
<211> LENGTH: 9
<212> TYPE: PRT
<213> ORGANISM: Artificial Sequence
<220> FEATURE:
<223> OTHER INFORMATION: SLC12A8

<400> SEQUENCE: 466

Tyr His His Ser Ser Leu Val Asn Arg
1               5

<210> SEQ ID NO 467
<211> LENGTH: 7
<212> TYPE: PRT
<213> ORGANISM: Artificial Sequence
<220> FEATURE:
<223> OTHER INFORMATION: SLC12A9

<400> SEQUENCE: 467

Ile Leu His Ala Leu Ala Arg
1               5

<210> SEQ ID NO 468
<211> LENGTH: 12
<212> TYPE: PRT
<213> ORGANISM: Artificial Sequence
<220> FEATURE:
<223> OTHER INFORMATION: SLC12A9

<400> SEQUENCE: 468

Asp Asp Leu Phe Gly Val Ile Leu Ala Pro Ala Lys
1               5                   10

<210> SEQ ID NO 469
<211> LENGTH: 12
<212> TYPE: PRT
<213> ORGANISM: Artificial Sequence
<220> FEATURE:
<223> OTHER INFORMATION: SLC12A9

<400> SEQUENCE: 469

Ala Phe Val Asp Leu Thr Leu Ser Pro Ser Val Arg
1               5                   10

<210> SEQ ID NO 470
<211> LENGTH: 8
<212> TYPE: PRT
<213> ORGANISM: Artificial Sequence
<220> FEATURE:
<223> OTHER INFORMATION: SLC12A9

<400> SEQUENCE: 470

Gln Gly Ala Gln His Leu Leu Arg
1               5

<210> SEQ ID NO 471
<211> LENGTH: 6
<212> TYPE: PRT
<213> ORGANISM: Artificial Sequence
<220> FEATURE:
<223> OTHER INFORMATION: SLC12A9

<400> SEQUENCE: 471

Ala Pro Gly Ser Pro Arg
1               5

<210> SEQ ID NO 472
<211> LENGTH: 16
<212> TYPE: PRT
```

```
<213> ORGANISM: Artificial Sequence
<220> FEATURE:
<223> OTHER INFORMATION: SLC12A9

<400> SEQUENCE: 472

Ala Leu Asn Pro Gln Asp Tyr Val Ala Thr Val Ala Asp Ala Leu Lys
1               5                   10                  15

<210> SEQ ID NO 473
<211> LENGTH: 6
<212> TYPE: PRT
<213> ORGANISM: Artificial Sequence
<220> FEATURE:
<223> OTHER INFORMATION: SLC12A9

<400> SEQUENCE: 473

Asn Val Val Leu Ala Arg
1               5

<210> SEQ ID NO 474
<211> LENGTH: 7
<212> TYPE: PRT
<213> ORGANISM: Artificial Sequence
<220> FEATURE:
<223> OTHER INFORMATION: SLC12A9

<400> SEQUENCE: 474

Ala Leu Leu Ser Gln Leu Arg
1               5

<210> SEQ ID NO 475
<211> LENGTH: 7
<212> TYPE: PRT
<213> ORGANISM: Artificial Sequence
<220> FEATURE:
<223> OTHER INFORMATION: SLC12A9

<400> SEQUENCE: 475

Ser Ala Asn Ala Leu Val Arg
1               5

<210> SEQ ID NO 476
<211> LENGTH: 10
<212> TYPE: PRT
<213> ORGANISM: Artificial Sequence
<220> FEATURE:
<223> OTHER INFORMATION: SLC12A9

<400> SEQUENCE: 476

Gly Thr Gly Gly Gly Pro Gly Gly Pro Lys
1               5                   10

<210> SEQ ID NO 477
<211> LENGTH: 5
<212> TYPE: PRT
<213> ORGANISM: Artificial Sequence
<220> FEATURE:
<223> OTHER INFORMATION: SLC13A1

<400> SEQUENCE: 477

Leu Gly Pro Ile Arg
1               5

<210> SEQ ID NO 478
<211> LENGTH: 6
<212> TYPE: PRT
<213> ORGANISM: Artificial Sequence
<220> FEATURE:
```

-continued

```
<223> OTHER INFORMATION: SLC13A2

<400> SEQUENCE: 478

Ala His Leu Ser Gln Lys
1               5

<210> SEQ ID NO 479
<211> LENGTH: 5
<212> TYPE: PRT
<213> ORGANISM: Artificial Sequence
<220> FEATURE:
<223> OTHER INFORMATION: SLC13A2

<400> SEQUENCE: 479

Thr Val Asn Gln Lys
1               5

<210> SEQ ID NO 480
<211> LENGTH: 10
<212> TYPE: PRT
<213> ORGANISM: Artificial Sequence
<220> FEATURE:
<223> OTHER INFORMATION: SLC13A4

<400> SEQUENCE: 480

Ser Asn Glu Val Ala Ala Glu Tyr Phe Lys
1               5                   10

<210> SEQ ID NO 481
<211> LENGTH: 15
<212> TYPE: PRT
<213> ORGANISM: Artificial Sequence
<220> FEATURE:
<223> OTHER INFORMATION: SLC13A4

<400> SEQUENCE: 481

Asn Ser Gln Pro Ser Leu Glu Leu Ile Phe Val Asn Glu Asp Arg
1               5                   10                  15

<210> SEQ ID NO 482
<211> LENGTH: 6
<212> TYPE: PRT
<213> ORGANISM: Artificial Sequence
<220> FEATURE:
<223> OTHER INFORMATION: SLC14A1

<400> SEQUENCE: 482

Asn Ser Asn Ile Tyr Lys
1               5

<210> SEQ ID NO 483
<211> LENGTH: 7
<212> TYPE: PRT
<213> ORGANISM: Artificial Sequence
<220> FEATURE:
<223> OTHER INFORMATION: SLC14A2

<400> SEQUENCE: 483

Tyr Gln Ala Tyr Asp Val Ser
1               5

<210> SEQ ID NO 484
<211> LENGTH: 6
<212> TYPE: PRT
<213> ORGANISM: Artificial Sequence
<220> FEATURE:
<223> OTHER INFORMATION: SLC15A3
```

```
<400> SEQUENCE: 484

Gln Pro Leu Leu Pro Arg
1               5

<210> SEQ ID NO 485
<211> LENGTH: 25
<212> TYPE: PRT
<213> ORGANISM: Artificial Sequence
<220> FEATURE:
<223> OTHER INFORMATION: SLC15A3

<400> SEQUENCE: 485

Ala Val Ala Leu Ser Leu Leu Leu Tyr Leu Ala Ala Ser Gly Leu Leu
1               5                   10                  15

Pro Ala Thr Ala Phe Pro Asp Gly Arg
            20                  25

<210> SEQ ID NO 486
<211> LENGTH: 8
<212> TYPE: PRT
<213> ORGANISM: Artificial Sequence
<220> FEATURE:
<223> OTHER INFORMATION: SLC15A3

<400> SEQUENCE: 486

Leu Ile Asp Pro Leu Leu Leu Arg
1               5

<210> SEQ ID NO 487
<211> LENGTH: 8
<212> TYPE: PRT
<213> ORGANISM: Artificial Sequence
<220> FEATURE:
<223> OTHER INFORMATION: SLC15A3

<400> SEQUENCE: 487

Leu Leu Pro Ser Ala Leu Gln Lys
1               5

<210> SEQ ID NO 488
<211> LENGTH: 10
<212> TYPE: PRT
<213> ORGANISM: Artificial Sequence
<220> FEATURE:
<223> OTHER INFORMATION: SLC15A3

<400> SEQUENCE: 488

Ala Ser Gln Gly Pro Ala Ser His Ser Arg
1               5                   10

<210> SEQ ID NO 489
<211> LENGTH: 12
<212> TYPE: PRT
<213> ORGANISM: Artificial Sequence
<220> FEATURE:
<223> OTHER INFORMATION: SLC15A4

<400> SEQUENCE: 489

Ala Asn Ile Thr Pro Phe Gly Ala Asp Gln Val Lys
1               5                   10

<210> SEQ ID NO 490
<211> LENGTH: 6
<212> TYPE: PRT
<213> ORGANISM: Artificial Sequence
<220> FEATURE:
<223> OTHER INFORMATION: SLC15A4
```

<400> SEQUENCE: 490

Thr Leu Asn Ser His Lys
1               5

<210> SEQ ID NO 491
<211> LENGTH: 13
<212> TYPE: PRT
<213> ORGANISM: Artificial Sequence
<220> FEATURE:
<223> OTHER INFORMATION: SLC16A10

<400> SEQUENCE: 491

Val Leu Ile Asp Ser Val Gly Leu Phe Tyr Thr Leu Arg
1               5                   10

<210> SEQ ID NO 492
<211> LENGTH: 15
<212> TYPE: PRT
<213> ORGANISM: Artificial Sequence
<220> FEATURE:
<223> OTHER INFORMATION: SLC16A11

<400> SEQUENCE: 492

Ser Leu Gly Leu Ala Phe Pro Asp Leu Ala Glu His Phe Asp Arg
1               5                   10                  15

<210> SEQ ID NO 493
<211> LENGTH: 29
<212> TYPE: PRT
<213> ORGANISM: Artificial Sequence
<220> FEATURE:
<223> OTHER INFORMATION: SLC16A11

<400> SEQUENCE: 493

Ser Ala Gln Asp Thr Ala Trp Ile Ser Ala Leu Ala Leu Ala Val Gln
1               5                   10                  15

Gln Ala Ala Ser Pro Val Gly Ser Ala Leu Ser Thr Arg
            20                  25

<210> SEQ ID NO 494
<211> LENGTH: 15
<212> TYPE: PRT
<213> ORGANISM: Artificial Sequence
<220> FEATURE:
<223> OTHER INFORMATION: SLC16A12

<400> SEQUENCE: 494

His Gly Glu Pro Val Ala Thr Ala Val Pro Gly Tyr Ser Leu Thr
1               5                   10                  15

<210> SEQ ID NO 495
<211> LENGTH: 14
<212> TYPE: PRT
<213> ORGANISM: Artificial Sequence
<220> FEATURE:
<223> OTHER INFORMATION: SLC16A13

<400> SEQUENCE: 495

Ala Gln Leu Thr Ser Leu Leu His His Gly Pro Phe Leu Arg
1               5                   10

<210> SEQ ID NO 496
<211> LENGTH: 7
<212> TYPE: PRT
<213> ORGANISM: Artificial Sequence
<220> FEATURE:

```
<223> OTHER INFORMATION: SLC16A14

<400> SEQUENCE: 496

Ser Thr Gly Gln Gln Gly Arg
1               5

<210> SEQ ID NO 497
<211> LENGTH: 7
<212> TYPE: PRT
<213> ORGANISM: Artificial Sequence
<220> FEATURE:
<223> OTHER INFORMATION: SLC16A3

<400> SEQUENCE: 497

Ala Val Ser Val Phe Phe Lys
1               5

<210> SEQ ID NO 498
<211> LENGTH: 8
<212> TYPE: PRT
<213> ORGANISM: Artificial Sequence
<220> FEATURE:
<223> OTHER INFORMATION: SLC16A3

<400> SEQUENCE: 498

Asp Leu Gly Val Pro Asp Thr Lys
1               5

<210> SEQ ID NO 499
<211> LENGTH: 6
<212> TYPE: PRT
<213> ORGANISM: Artificial Sequence
<220> FEATURE:
<223> OTHER INFORMATION: SLC16A5

<400> SEQUENCE: 499

Ala Val Leu Gln Ala Lys
1               5

<210> SEQ ID NO 500
<211> LENGTH: 9
<212> TYPE: PRT
<213> ORGANISM: Artificial Sequence
<220> FEATURE:
<223> OTHER INFORMATION: SLC16A6

<400> SEQUENCE: 500

Ile Gly Ala Gly Phe Val Leu Asn Arg
1               5

<210> SEQ ID NO 501
<211> LENGTH: 7
<212> TYPE: PRT
<213> ORGANISM: Artificial Sequence
<220> FEATURE:
<223> OTHER INFORMATION: SLC16A8

<400> SEQUENCE: 501

Ala Val Ser Val Phe Phe Arg
1               5

<210> SEQ ID NO 502
<211> LENGTH: 9
<212> TYPE: PRT
<213> ORGANISM: Artificial Sequence
<220> FEATURE:
<223> OTHER INFORMATION: SLC16A8
```

```
<400> SEQUENCE: 502

Ala Phe Ala Val Tyr Ala Val Thr Lys
1               5

<210> SEQ ID NO 503
<211> LENGTH: 6
<212> TYPE: PRT
<213> ORGANISM: Artificial Sequence
<220> FEATURE:
<223> OTHER INFORMATION: SLC16A8

<400> SEQUENCE: 503

Leu Val Asp Val Leu Lys
1               5

<210> SEQ ID NO 504
<211> LENGTH: 7
<212> TYPE: PRT
<213> ORGANISM: Artificial Sequence
<220> FEATURE:
<223> OTHER INFORMATION: SLC16A9

<400> SEQUENCE: 504

Gln Asp Ser Leu Leu His Lys
1               5

<210> SEQ ID NO 505
<211> LENGTH: 8
<212> TYPE: PRT
<213> ORGANISM: Artificial Sequence
<220> FEATURE:
<223> OTHER INFORMATION: SLC16A9

<400> SEQUENCE: 505

Asn Pro Thr Val Thr His Thr Lys
1               5

<210> SEQ ID NO 506
<211> LENGTH: 10
<212> TYPE: PRT
<213> ORGANISM: Artificial Sequence
<220> FEATURE:
<223> OTHER INFORMATION: SLC16A9

<400> SEQUENCE: 506

Leu Leu Leu Gly Ile Leu Ala Asp Phe Lys
1               5                   10

<210> SEQ ID NO 507
<211> LENGTH: 7
<212> TYPE: PRT
<213> ORGANISM: Artificial Sequence
<220> FEATURE:
<223> OTHER INFORMATION: SLC18A1

<400> SEQUENCE: 507

Val Ser Pro Glu Ser Ala Lys
1               5

<210> SEQ ID NO 508
<211> LENGTH: 16
<212> TYPE: PRT
<213> ORGANISM: Artificial Sequence
<220> FEATURE:
<223> OTHER INFORMATION: SLC18A1

<400> SEQUENCE: 508
```

```
Glu Phe Pro Leu Gly Glu Asp Ser Asp Glu Pro Asp His Glu Glu
1               5                   10                  15

<210> SEQ ID NO 509
<211> LENGTH: 7
<212> TYPE: PRT
<213> ORGANISM: Artificial Sequence
<220> FEATURE:
<223> OTHER INFORMATION: SLC18A2

<400> SEQUENCE: 509

Val Gln Pro Glu Ser Gln Lys
1               5

<210> SEQ ID NO 510
<211> LENGTH: 9
<212> TYPE: PRT
<213> ORGANISM: Artificial Sequence
<220> FEATURE:
<223> OTHER INFORMATION: SLC18A2

<400> SEQUENCE: 510

Gly Thr Pro Leu Thr Thr Leu Leu Lys
1               5

<210> SEQ ID NO 511
<211> LENGTH: 9
<212> TYPE: PRT
<213> ORGANISM: Artificial Sequence
<220> FEATURE:
<223> OTHER INFORMATION: SLC18A3

<400> SEQUENCE: 511

Tyr Pro Thr Glu Ser Glu Asp Val Lys
1               5

<210> SEQ ID NO 512
<211> LENGTH: 7
<212> TYPE: PRT
<213> ORGANISM: Artificial Sequence
<220> FEATURE:
<223> OTHER INFORMATION: SLC18A3

<400> SEQUENCE: 512

Tyr Pro Glu Glu Pro Glu Arg
1               5

<210> SEQ ID NO 513
<211> LENGTH: 11
<212> TYPE: PRT
<213> ORGANISM: Artificial Sequence
<220> FEATURE:
<223> OTHER INFORMATION: SLC18A3

<400> SEQUENCE: 513

Ala Asn Leu Pro Val Gly Thr Pro Ile His Arg
1               5                   10

<210> SEQ ID NO 514
<211> LENGTH: 7
<212> TYPE: PRT
<213> ORGANISM: Artificial Sequence
<220> FEATURE:
<223> OTHER INFORMATION: SLC18A3

<400> SEQUENCE: 514

Asn Val Gly Leu Leu Thr Arg
1               5
```

<210> SEQ ID NO 515
<211> LENGTH: 16
<212> TYPE: PRT
<213> ORGANISM: Artificial Sequence
<220> FEATURE:
<223> OTHER INFORMATION: SLC18A3

<400> SEQUENCE: 515

Asp Val Leu Leu Asp Glu Pro Pro Gln Gly Leu Tyr Asp Ala Val Arg
1               5                   10                  15

<210> SEQ ID NO 516
<211> LENGTH: 5
<212> TYPE: PRT
<213> ORGANISM: Artificial Sequence
<220> FEATURE:
<223> OTHER INFORMATION: SLC19A2

<400> SEQUENCE: 516

Val Asn Gly Ile Lys
1               5

<210> SEQ ID NO 517
<211> LENGTH: 25
<212> TYPE: PRT
<213> ORGANISM: Artificial Sequence
<220> FEATURE:
<223> OTHER INFORMATION: SLC19A2

<400> SEQUENCE: 517

Val Gln Asn Gly Gly Ile Val Thr Asp Thr Pro Ala Ser Asn His Leu
1               5                   10                  15

Pro Gly Trp Glu Asp Ile Glu Ser Lys
            20                  25

<210> SEQ ID NO 518
<211> LENGTH: 34
<212> TYPE: PRT
<213> ORGANISM: Artificial Sequence
<220> FEATURE:
<223> OTHER INFORMATION: SLC19A3

<400> SEQUENCE: 518

Asn Leu Thr Ser Ala Glu Ile Thr Asn Glu Ile Phe Pro Val Trp Thr
1               5                   10                  15

Tyr Ser Tyr Leu Val Leu Leu Leu Pro Val Phe Val Leu Thr Asp Tyr
            20                  25                  30

Val Arg

<210> SEQ ID NO 519
<211> LENGTH: 32
<212> TYPE: PRT
<213> ORGANISM: Artificial Sequence
<220> FEATURE:
<223> OTHER INFORMATION: SLC19A3

<400> SEQUENCE: 519

Ala Pro Ser Gln Asp Ser Ser Ile Tyr Asn Gly Ala Val Glu Ala Ile
1               5                   10                  15

Ala Thr Phe Gly Gly Ala Val Ala Ala Phe Ala Val Gly Tyr Val Lys
            20                  25                  30

<210> SEQ ID NO 520
<211> LENGTH: 6

```
<212> TYPE: PRT
<213> ORGANISM: Artificial Sequence
<220> FEATURE:
<223> OTHER INFORMATION: SLC20A1

<400> SEQUENCE: 520

Gly Gln Glu Gly Val Lys
1               5

<210> SEQ ID NO 521
<211> LENGTH: 6
<212> TYPE: PRT
<213> ORGANISM: Artificial Sequence
<220> FEATURE:
<223> OTHER INFORMATION: SLC20A1

<400> SEQUENCE: 521

Trp Ser Glu Leu Ile Lys
1               5

<210> SEQ ID NO 522
<211> LENGTH: 6
<212> TYPE: PRT
<213> ORGANISM: Artificial Sequence
<220> FEATURE:
<223> OTHER INFORMATION: SLC20A1

<400> SEQUENCE: 522

Ala Phe Ile Leu His Lys
1               5

<210> SEQ ID NO 523
<211> LENGTH: 9
<212> TYPE: PRT
<213> ORGANISM: Artificial Sequence
<220> FEATURE:
<223> OTHER INFORMATION: SLC20A1

<400> SEQUENCE: 523

Ala Asp Pro Val Pro Asn Gly Leu Arg
1               5

<210> SEQ ID NO 524
<211> LENGTH: 9
<212> TYPE: PRT
<213> ORGANISM: Artificial Sequence
<220> FEATURE:
<223> OTHER INFORMATION: SLC20A1

<400> SEQUENCE: 524

Leu Ser Val Gly Asp Ile Glu Asn Lys
1               5

<210> SEQ ID NO 525
<211> LENGTH: 20
<212> TYPE: PRT
<213> ORGANISM: Artificial Sequence
<220> FEATURE:
<223> OTHER INFORMATION: SLC20A1

<400> SEQUENCE: 525

His Pro Val Ser Glu Val Gly Pro Ala Thr Val Pro Leu Gln Ala Val
1               5                   10                  15

Val Glu Glu Arg
            20

<210> SEQ ID NO 526
```

```
<211> LENGTH: 5
<212> TYPE: PRT
<213> ORGANISM: Artificial Sequence
<220> FEATURE:
<223> OTHER INFORMATION: SLC20A1

<400> SEQUENCE: 526

Thr Val Ser Phe Lys
1               5

<210> SEQ ID NO 527
<211> LENGTH: 10
<212> TYPE: PRT
<213> ORGANISM: Artificial Sequence
<220> FEATURE:
<223> OTHER INFORMATION: SLC20A1

<400> SEQUENCE: 527

Leu Gly Asp Leu Glu Glu Ala Pro Glu Arg
1               5                   10

<210> SEQ ID NO 528
<211> LENGTH: 7
<212> TYPE: PRT
<213> ORGANISM: Artificial Sequence
<220> FEATURE:
<223> OTHER INFORMATION: SLC20A1

<400> SEQUENCE: 528

Leu Pro Ser Val Asp Leu Lys
1               5

<210> SEQ ID NO 529
<211> LENGTH: 6
<212> TYPE: PRT
<213> ORGANISM: Artificial Sequence
<220> FEATURE:
<223> OTHER INFORMATION: SLC20A1

<400> SEQUENCE: 529

Asp Ser Gly Leu Tyr Lys
1               5

<210> SEQ ID NO 530
<211> LENGTH: 5
<212> TYPE: PRT
<213> ORGANISM: Artificial Sequence
<220> FEATURE:
<223> OTHER INFORMATION: SLC20A1

<400> SEQUENCE: 530

Glu Leu Leu His Lys
1               5

<210> SEQ ID NO 531
<211> LENGTH: 5
<212> TYPE: PRT
<213> ORGANISM: Artificial Sequence
<220> FEATURE:
<223> OTHER INFORMATION: SLC20A1

<400> SEQUENCE: 531

Leu His Leu Ala Lys
1               5

<210> SEQ ID NO 532
<211> LENGTH: 11
<212> TYPE: PRT
```

<213> ORGANISM: Artificial Sequence
<220> FEATURE:
<223> OTHER INFORMATION: SLC20A1

<400> SEQUENCE: 532

Val Gly Ser Val Val Ser Val Gly Trp Leu Arg
1               5                   10

<210> SEQ ID NO 533
<211> LENGTH: 6
<212> TYPE: PRT
<213> ORGANISM: Artificial Sequence
<220> FEATURE:
<223> OTHER INFORMATION: SLC20A2

<400> SEQUENCE: 533

Glu Gly Ala Leu Ser Arg
1               5

<210> SEQ ID NO 534
<211> LENGTH: 8
<212> TYPE: PRT
<213> ORGANISM: Artificial Sequence
<220> FEATURE:
<223> OTHER INFORMATION: SLC20A2

<400> SEQUENCE: 534

Val Ser Asp Glu Ser Leu Ser Lys
1               5

<210> SEQ ID NO 535
<211> LENGTH: 10
<212> TYPE: PRT
<213> ORGANISM: Artificial Sequence
<220> FEATURE:
<223> OTHER INFORMATION: SLC20A2

<400> SEQUENCE: 535

Val Gln Glu Ala Glu Ser Pro Val Phe Lys
1               5                   10

<210> SEQ ID NO 536
<211> LENGTH: 6
<212> TYPE: PRT
<213> ORGANISM: Artificial Sequence
<220> FEATURE:
<223> OTHER INFORMATION: SLC20A2

<400> SEQUENCE: 536

Glu Leu Pro Gly Ala Lys
1               5

<210> SEQ ID NO 537
<211> LENGTH: 30
<212> TYPE: PRT
<213> ORGANISM: Artificial Sequence
<220> FEATURE:
<223> OTHER INFORMATION: SLC20A2

<400> SEQUENCE: 537

Ala Asn Asp Asp Ser Thr Ile Pro Leu Thr Gly Ala Ala Gly Glu Thr
1               5                   10                  15

Leu Gly Thr Ser Glu Gly Thr Ser Ala Gly Ser His Pro Arg
                20                  25                  30

<210> SEQ ID NO 538
<211> LENGTH: 5

```
<212> TYPE: PRT
<213> ORGANISM: Artificial Sequence
<220> FEATURE:
<223> OTHER INFORMATION: SLC20A2

<400> SEQUENCE: 538

Ala Ala Tyr Gly Arg
1               5

<210> SEQ ID NO 539
<211> LENGTH: 15
<212> TYPE: PRT
<213> ORGANISM: Artificial Sequence
<220> FEATURE:
<223> OTHER INFORMATION: SLC20A2

<400> SEQUENCE: 539

Ser Pro Ile Ser Asn Gly Thr Phe Gly Phe Asp Gly His Thr Arg
1               5                   10                  15

<210> SEQ ID NO 540
<211> LENGTH: 11
<212> TYPE: PRT
<213> ORGANISM: Artificial Sequence
<220> FEATURE:
<223> OTHER INFORMATION: SLC20A2

<400> SEQUENCE: 540

Ser Asp Gly His Val Tyr His Thr Val His Lys
1               5                   10

<210> SEQ ID NO 541
<211> LENGTH: 6
<212> TYPE: PRT
<213> ORGANISM: Artificial Sequence
<220> FEATURE:
<223> OTHER INFORMATION: SLC20A2

<400> SEQUENCE: 541

Asp Ser Gly Leu Tyr Lys
1               5

<210> SEQ ID NO 542
<211> LENGTH: 5
<212> TYPE: PRT
<213> ORGANISM: Artificial Sequence
<220> FEATURE:
<223> OTHER INFORMATION: SLC20A2

<400> SEQUENCE: 542

Asp Leu Leu His Lys
1               5

<210> SEQ ID NO 543
<211> LENGTH: 5
<212> TYPE: PRT
<213> ORGANISM: Artificial Sequence
<220> FEATURE:
<223> OTHER INFORMATION: SLC20A2

<400> SEQUENCE: 543

Ile His Ile Asp Arg
1               5

<210> SEQ ID NO 544
<211> LENGTH: 12
<212> TYPE: PRT
<213> ORGANISM: Artificial Sequence
```

```
<220> FEATURE:
<223> OTHER INFORMATION: SLC20A2

<400> SEQUENCE: 544

Leu Ala Ser Glu Leu Ala Asp Pro Asp Gln Pro Arg
1               5                   10

<210> SEQ ID NO 545
<211> LENGTH: 11
<212> TYPE: PRT
<213> ORGANISM: Artificial Sequence
<220> FEATURE:
<223> OTHER INFORMATION: SLC20A2

<400> SEQUENCE: 545

Val Gly Ser Val Val Ala Val Gly Trp Ile Arg
1               5                   10

<210> SEQ ID NO 546
<211> LENGTH: 5
<212> TYPE: PRT
<213> ORGANISM: Artificial Sequence
<220> FEATURE:
<223> OTHER INFORMATION: SLC20A2

<400> SEQUENCE: 546

Ala Val Asp Trp Arg
1               5

<210> SEQ ID NO 547
<211> LENGTH: 8
<212> TYPE: PRT
<213> ORGANISM: Artificial Sequence
<220> FEATURE:
<223> OTHER INFORMATION: SLC23A1

<400> SEQUENCE: 547

Ala Gln Glu Asp Leu Glu Gly Arg
1               5

<210> SEQ ID NO 548
<211> LENGTH: 11
<212> TYPE: PRT
<213> ORGANISM: Artificial Sequence
<220> FEATURE:
<223> OTHER INFORMATION: SLC23A1

<400> SEQUENCE: 548

Asp Pro Ser Thr Pro Leu Pro Thr Glu Pro Lys
1               5                   10

<210> SEQ ID NO 549
<211> LENGTH: 6
<212> TYPE: PRT
<213> ORGANISM: Artificial Sequence
<220> FEATURE:
<223> OTHER INFORMATION: SLC23A1

<400> SEQUENCE: 549

Gly Leu Ile Gln Trp Lys
1               5

<210> SEQ ID NO 550
<211> LENGTH: 7
<212> TYPE: PRT
<213> ORGANISM: Artificial Sequence
<220> FEATURE:
<223> OTHER INFORMATION: SLC23A1
```

```
<400> SEQUENCE: 550

Gly Phe Ser Ser Ser Ser Lys
1               5

<210> SEQ ID NO 551
<211> LENGTH: 6
<212> TYPE: PRT
<213> ORGANISM: Artificial Sequence
<220> FEATURE:
<223> OTHER INFORMATION: SLC23A2

<400> SEQUENCE: 551

Tyr Glu Asp Glu Ala Lys
1               5

<210> SEQ ID NO 552
<211> LENGTH: 7
<212> TYPE: PRT
<213> ORGANISM: Artificial Sequence
<220> FEATURE:
<223> OTHER INFORMATION: SLC23A2

<400> SEQUENCE: 552

Phe Pro Leu Pro Ile Tyr Lys
1               5

<210> SEQ ID NO 553
<211> LENGTH: 5
<212> TYPE: PRT
<213> ORGANISM: Artificial Sequence
<220> FEATURE:
<223> OTHER INFORMATION: SLC23A2

<400> SEQUENCE: 553

Leu Gln Leu Phe Lys
1               5

<210> SEQ ID NO 554
<211> LENGTH: 6
<212> TYPE: PRT
<213> ORGANISM: Artificial Sequence
<220> FEATURE:
<223> OTHER INFORMATION: SLC23A2

<400> SEQUENCE: 554

Tyr Gly Phe Tyr Ala Arg
1               5

<210> SEQ ID NO 555
<211> LENGTH: 11
<212> TYPE: PRT
<213> ORGANISM: Artificial Sequence
<220> FEATURE:
<223> OTHER INFORMATION: SLC23A2

<400> SEQUENCE: 555

Gln Gly Val Leu Leu Val Ala Pro Trp Phe Lys
1               5                   10

<210> SEQ ID NO 556
<211> LENGTH: 9
<212> TYPE: PRT
<213> ORGANISM: Artificial Sequence
<220> FEATURE:
<223> OTHER INFORMATION: SLC23A3

<400> SEQUENCE: 556
```

```
Ser Pro Leu Asn Pro Ser Gln Leu Arg
1               5

<210> SEQ ID NO 557
<211> LENGTH: 22
<212> TYPE: PRT
<213> ORGANISM: Artificial Sequence
<220> FEATURE:
<223> OTHER INFORMATION: SLC23A3

<400> SEQUENCE: 557

Leu Pro Leu Val Gln Ala Pro Ser Leu Glu Phe Leu Ile Pro Ala Leu
1               5                   10                  15

Val Leu Thr Ser Gln Lys
            20

<210> SEQ ID NO 558
<211> LENGTH: 14
<212> TYPE: PRT
<213> ORGANISM: Artificial Sequence
<220> FEATURE:
<223> OTHER INFORMATION: SLC23A3

<400> SEQUENCE: 558

His Gln Leu Thr Leu Leu Ser Leu Ser Ser Gly Ser Phe Arg
1               5                   10

<210> SEQ ID NO 559
<211> LENGTH: 16
<212> TYPE: PRT
<213> ORGANISM: Artificial Sequence
<220> FEATURE:
<223> OTHER INFORMATION: SLC23A3

<400> SEQUENCE: 559

Gly Leu Gly Gln Gly Leu Pro Ser Pro Phe Thr Ala Gln Glu Ala Arg
1               5                   10                  15

<210> SEQ ID NO 560
<211> LENGTH: 5
<212> TYPE: PRT
<213> ORGANISM: Artificial Sequence
<220> FEATURE:
<223> OTHER INFORMATION: SLC23A3

<400> SEQUENCE: 560

Ala Gln Val Tyr Arg
1               5

<210> SEQ ID NO 561
<211> LENGTH: 16
<212> TYPE: PRT
<213> ORGANISM: Artificial Sequence
<220> FEATURE:
<223> OTHER INFORMATION: SLC24A1

<400> SEQUENCE: 561

Gly Leu Ser Ser Leu Trp Ala Ala Val Ser Ser His Gln Pro Ile Lys
1               5                   10                  15

<210> SEQ ID NO 562
<211> LENGTH: 11
<212> TYPE: PRT
<213> ORGANISM: Artificial Sequence
<220> FEATURE:
<223> OTHER INFORMATION: SLC24A1
```

```
<400> SEQUENCE: 562

Thr Leu Thr Tyr Tyr Thr Ser Thr Ser Ser Arg
1               5                   10

<210> SEQ ID NO 563
<211> LENGTH: 8
<212> TYPE: PRT
<213> ORGANISM: Artificial Sequence
<220> FEATURE:
<223> OTHER INFORMATION: SLC24A1

<400> SEQUENCE: 563

Ser Tyr Ser Pro Thr Gln Val Arg
1               5

<210> SEQ ID NO 564
<211> LENGTH: 6
<212> TYPE: PRT
<213> ORGANISM: Artificial Sequence
<220> FEATURE:
<223> OTHER INFORMATION: SLC24A1

<400> SEQUENCE: 564

Tyr Thr Pro Ser Pro Arg
1               5

<210> SEQ ID NO 565
<211> LENGTH: 9
<212> TYPE: PRT
<213> ORGANISM: Artificial Sequence
<220> FEATURE:
<223> OTHER INFORMATION: SLC24A1

<400> SEQUENCE: 565

Asp Ser Asp Ile Thr Ala Thr Tyr Lys
1               5

<210> SEQ ID NO 566
<211> LENGTH: 9
<212> TYPE: PRT
<213> ORGANISM: Artificial Sequence
<220> FEATURE:
<223> OTHER INFORMATION: SLC24A1

<400> SEQUENCE: 566

Ala Phe Thr Ala Ala Trp Ser Leu Arg
1               5

<210> SEQ ID NO 567
<211> LENGTH: 9
<212> TYPE: PRT
<213> ORGANISM: Artificial Sequence
<220> FEATURE:
<223> OTHER INFORMATION: SLC24A1

<400> SEQUENCE: 567

Thr Ser Val Ser Ala Ile Lys Thr Ala
1               5

<210> SEQ ID NO 568
<211> LENGTH: 6
<212> TYPE: PRT
<213> ORGANISM: Artificial Sequence
<220> FEATURE:
<223> OTHER INFORMATION: SLC24A1

<400> SEQUENCE: 568
```

```
Pro Ala Ile Val Trp Arg
1               5

<210> SEQ ID NO 569
<211> LENGTH: 12
<212> TYPE: PRT
<213> ORGANISM: Artificial Sequence
<220> FEATURE:
<223> OTHER INFORMATION: SLC24A1

<400> SEQUENCE: 569

Glu Ile Leu Asn Leu Thr Trp Trp Pro Leu Phe Arg
1               5                   10

<210> SEQ ID NO 570
<211> LENGTH: 5
<212> TYPE: PRT
<213> ORGANISM: Artificial Sequence
<220> FEATURE:
<223> OTHER INFORMATION: SLC24A1

<400> SEQUENCE: 570

Glu Gln Leu Ser Arg
1               5

<210> SEQ ID NO 571
<211> LENGTH: 10
<212> TYPE: PRT
<213> ORGANISM: Artificial Sequence
<220> FEATURE:
<223> OTHER INFORMATION: SLC24A1

<400> SEQUENCE: 571

Glu Glu Glu Ser Leu Asn Gln Gly Ala Arg
1               5                   10

<210> SEQ ID NO 572
<211> LENGTH: 15
<212> TYPE: PRT
<213> ORGANISM: Artificial Sequence
<220> FEATURE:
<223> OTHER INFORMATION: SLC24A1

<400> SEQUENCE: 572

Leu Pro Ala Val Thr Val Thr Pro Ala Pro Val Pro Asp Ile Lys
1               5                   10                  15

<210> SEQ ID NO 573
<211> LENGTH: 20
<212> TYPE: PRT
<213> ORGANISM: Artificial Sequence
<220> FEATURE:
<223> OTHER INFORMATION: SLC24A1

<400> SEQUENCE: 573

Gly Asn Glu Gly Glu Thr Glu Ser Gln Glu Leu Ser Ala Glu Asn His
1               5                   10                  15

Gly Glu Ala Lys
            20

<210> SEQ ID NO 574
<211> LENGTH: 14
<212> TYPE: PRT
<213> ORGANISM: Artificial Sequence
<220> FEATURE:
<223> OTHER INFORMATION: SLC24A1

<400> SEQUENCE: 574
```

Gly Asn Glu Glu Pro Leu Ser Leu Asp Trp Pro Glu Thr Arg
1               5                   10

<210> SEQ ID NO 575
<211> LENGTH: 8
<212> TYPE: PRT
<213> ORGANISM: Artificial Sequence
<220> FEATURE:
<223> OTHER INFORMATION: SLC24A2

<400> SEQUENCE: 575

Val Ala Gln Gly Tyr His Gln Arg
1               5

<210> SEQ ID NO 576
<211> LENGTH: 8
<212> TYPE: PRT
<213> ORGANISM: Artificial Sequence
<220> FEATURE:
<223> OTHER INFORMATION: SLC24A2

<400> SEQUENCE: 576

Thr Leu Leu Asp Leu Asn Asp Lys
1               5

<210> SEQ ID NO 577
<211> LENGTH: 12
<212> TYPE: PRT
<213> ORGANISM: Artificial Sequence
<220> FEATURE:
<223> OTHER INFORMATION: SLC24A2

<400> SEQUENCE: 577

Ile Leu Asp Tyr Thr Pro Gln Pro Pro Leu Ser Lys
1               5                   10

<210> SEQ ID NO 578
<211> LENGTH: 12
<212> TYPE: PRT
<213> ORGANISM: Artificial Sequence
<220> FEATURE:
<223> OTHER INFORMATION: SLC24A2

<400> SEQUENCE: 578

Glu Ile Leu Asn Leu Thr Trp Trp Pro Leu Phe Arg
1               5                   10

<210> SEQ ID NO 579
<211> LENGTH: 6
<212> TYPE: PRT
<213> ORGANISM: Artificial Sequence
<220> FEATURE:
<223> OTHER INFORMATION: SLC24A2

<400> SEQUENCE: 579

Ala Ser Ile Leu His Lys
1               5

<210> SEQ ID NO 580
<211> LENGTH: 10
<212> TYPE: PRT
<213> ORGANISM: Artificial Sequence
<220> FEATURE:
<223> OTHER INFORMATION: SLC24A2

<400> SEQUENCE: 580

Gln Asn Gly Ala Ala Asn His Val Glu Lys

```
1               5              10
```

<210> SEQ ID NO 581
<211> LENGTH: 5
<212> TYPE: PRT
<213> ORGANISM: Artificial Sequence
<220> FEATURE:
<223> OTHER INFORMATION: SLC24A3

<400> SEQUENCE: 581

```
Leu Ile Asn Ser Arg
1               5
```

<210> SEQ ID NO 582
<211> LENGTH: 12
<212> TYPE: PRT
<213> ORGANISM: Artificial Sequence
<220> FEATURE:
<223> OTHER INFORMATION: SLC24A3

<400> SEQUENCE: 582

```
Ala Tyr Thr Asn Gly Glu Ser Glu Val Ala Ile Lys
1               5                  10
```

<210> SEQ ID NO 583
<211> LENGTH: 15
<212> TYPE: PRT
<213> ORGANISM: Artificial Sequence
<220> FEATURE:
<223> OTHER INFORMATION: SLC24A3

<400> SEQUENCE: 583

```
His Thr Val Glu Asn Gly Thr Gly Pro Ser Ser Ala Pro Asp Arg
1               5                  10                  15
```

<210> SEQ ID NO 584
<211> LENGTH: 5
<212> TYPE: PRT
<213> ORGANISM: Artificial Sequence
<220> FEATURE:
<223> OTHER INFORMATION: SLC24A3

<400> SEQUENCE: 584

```
Leu Glu Thr Val Lys
1               5
```

<210> SEQ ID NO 585
<211> LENGTH: 9
<212> TYPE: PRT
<213> ORGANISM: Artificial Sequence
<220> FEATURE:
<223> OTHER INFORMATION: SLC24A4

<400> SEQUENCE: 585

```
Phe Thr Phe Pro Glu Ala Gly Leu Arg
1               5
```

<210> SEQ ID NO 586
<211> LENGTH: 6
<212> TYPE: PRT
<213> ORGANISM: Artificial Sequence
<220> FEATURE:
<223> OTHER INFORMATION: SLC24A4

<400> SEQUENCE: 586

```
Ile Ile Ile Asn Glu Arg
1               5
```

```
<210> SEQ ID NO 587
<211> LENGTH: 15
<212> TYPE: PRT
<213> ORGANISM: Artificial Sequence
<220> FEATURE:
<223> OTHER INFORMATION: SLC24A5

<400> SEQUENCE: 587

Thr Ala Phe Ile Asn Gly Ser Ala Pro Ala Glu Val Asn Ser Arg
1               5                   10                  15

<210> SEQ ID NO 588
<211> LENGTH: 6
<212> TYPE: PRT
<213> ORGANISM: Artificial Sequence
<220> FEATURE:
<223> OTHER INFORMATION: SLC24A6

<400> SEQUENCE: 588

Asp Asp Gln Asn Trp Lys
1               5

<210> SEQ ID NO 589
<211> LENGTH: 5
<212> TYPE: PRT
<213> ORGANISM: Artificial Sequence
<220> FEATURE:
<223> OTHER INFORMATION: SLC24A6

<400> SEQUENCE: 589

Gln Gly Tyr Pro Arg
1               5

<210> SEQ ID NO 590
<211> LENGTH: 6
<212> TYPE: PRT
<213> ORGANISM: Artificial Sequence
<220> FEATURE:
<223> OTHER INFORMATION: SLC24A6

<400> SEQUENCE: 590

Ser His Thr Glu Val Lys
1               5

<210> SEQ ID NO 591
<211> LENGTH: 11
<212> TYPE: PRT
<213> ORGANISM: Artificial Sequence
<220> FEATURE:
<223> OTHER INFORMATION: SLC25A1

<400> SEQUENCE: 591

Ala Leu Ala Ala Ala Ala Pro Ala Ser Gly Lys
1               5                   10

<210> SEQ ID NO 592
<211> LENGTH: 8
<212> TYPE: PRT
<213> ORGANISM: Artificial Sequence
<220> FEATURE:
<223> OTHER INFORMATION: SLC25A1

<400> SEQUENCE: 592

Thr Gln Leu Gln Leu Asp Glu Arg
1               5

<210> SEQ ID NO 593
```

```
<211> LENGTH: 9
<212> TYPE: PRT
<213> ORGANISM: Artificial Sequence
<220> FEATURE:
<223> OTHER INFORMATION: SLC25A1

<400> SEQUENCE: 593

Ser His Gly Val Leu Gly Leu Tyr Arg
1               5

<210> SEQ ID NO 594
<211> LENGTH: 5
<212> TYPE: PRT
<213> ORGANISM: Artificial Sequence
<220> FEATURE:
<223> OTHER INFORMATION: SLC25A1

<400> SEQUENCE: 594

Leu Asp Ser Thr Arg
1               5

<210> SEQ ID NO 595
<211> LENGTH: 11
<212> TYPE: PRT
<213> ORGANISM: Artificial Sequence
<220> FEATURE:
<223> OTHER INFORMATION: SLC25A1

<400> SEQUENCE: 595

Phe Ile His Asp Gln Thr Ser Pro Asn Pro Lys
1               5                   10

<210> SEQ ID NO 596
<211> LENGTH: 7
<212> TYPE: PRT
<213> ORGANISM: Artificial Sequence
<220> FEATURE:
<223> OTHER INFORMATION: SLC25A1

<400> SEQUENCE: 596

Gly Phe Phe His Gly Val Arg
1               5

<210> SEQ ID NO 597
<211> LENGTH: 5
<212> TYPE: PRT
<213> ORGANISM: Artificial Sequence
<220> FEATURE:
<223> OTHER INFORMATION: SLC25A1

<400> SEQUENCE: 597

Glu Gln Gly Leu Lys
1               5

<210> SEQ ID NO 598
<211> LENGTH: 10
<212> TYPE: PRT
<213> ORGANISM: Artificial Sequence
<220> FEATURE:
<223> OTHER INFORMATION: SLC25A10

<400> SEQUENCE: 598

Val His Leu Gln Thr Gln Gln Glu Val Lys
1               5                   10

<210> SEQ ID NO 599
<211> LENGTH: 8
<212> TYPE: PRT
```

```
<213> ORGANISM: Artificial Sequence
<220> FEATURE:
<223> OTHER INFORMATION: SLC25A10

<400> SEQUENCE: 599

Phe Ala Ile Tyr Glu Thr Val Arg
1               5

<210> SEQ ID NO 600
<211> LENGTH: 11
<212> TYPE: PRT
<213> ORGANISM: Artificial Sequence
<220> FEATURE:
<223> OTHER INFORMATION: SLC25A10

<400> SEQUENCE: 600

Gly Ser Gln Gly Pro Leu Pro Phe His Glu Lys
1               5                   10

<210> SEQ ID NO 601
<211> LENGTH: 8
<212> TYPE: PRT
<213> ORGANISM: Artificial Sequence
<220> FEATURE:
<223> OTHER INFORMATION: SLC25A10

<400> SEQUENCE: 601

Leu Gly Pro Leu Ala Phe Tyr Lys
1               5

<210> SEQ ID NO 602
<211> LENGTH: 11
<212> TYPE: PRT
<213> ORGANISM: Artificial Sequence
<220> FEATURE:
<223> OTHER INFORMATION: SLC25A11

<400> SEQUENCE: 602

Thr Ser Phe His Ala Leu Thr Ser Ile Leu Lys
1               5                   10

<210> SEQ ID NO 603
<211> LENGTH: 5
<212> TYPE: PRT
<213> ORGANISM: Artificial Sequence
<220> FEATURE:
<223> OTHER INFORMATION: SLC25A11

<400> SEQUENCE: 603

Ala Glu Gly Leu Arg
1               5

<210> SEQ ID NO 604
<211> LENGTH: 8
<212> TYPE: PRT
<213> ORGANISM: Artificial Sequence
<220> FEATURE:
<223> OTHER INFORMATION: SLC25A11

<400> SEQUENCE: 604

Asn Val Phe Asn Ala Leu Ile Arg
1               5

<210> SEQ ID NO 605
<211> LENGTH: 9
<212> TYPE: PRT
<213> ORGANISM: Artificial Sequence
<220> FEATURE:
```

```
<223> OTHER INFORMATION: SLC25A11

<400> SEQUENCE: 605

Glu Glu Gly Val Leu Thr Leu Trp Arg
1               5

<210> SEQ ID NO 606
<211> LENGTH: 8
<212> TYPE: PRT
<213> ORGANISM: Artificial Sequence
<220> FEATURE:
<223> OTHER INFORMATION: SLC25A11

<400> SEQUENCE: 606

Asn Gly Leu Asp Val Leu Phe Lys
1               5

<210> SEQ ID NO 607
<211> LENGTH: 9
<212> TYPE: PRT
<213> ORGANISM: Artificial Sequence
<220> FEATURE:
<223> OTHER INFORMATION: SLC25A11

<400> SEQUENCE: 607

Tyr Glu Gly Phe Phe Ser Leu Trp Lys
1               5

<210> SEQ ID NO 608
<211> LENGTH: 15
<212> TYPE: PRT
<213> ORGANISM: Artificial Sequence
<220> FEATURE:
<223> OTHER INFORMATION: SLC25A12

<400> SEQUENCE: 608

Asn Ile Phe Leu Gln Tyr Ala Ser Thr Glu Val Asp Gly Glu Arg
1               5                   10                  15

<210> SEQ ID NO 609
<211> LENGTH: 13
<212> TYPE: PRT
<213> ORGANISM: Artificial Sequence
<220> FEATURE:
<223> OTHER INFORMATION: SLC25A12

<400> SEQUENCE: 609

Tyr Leu Gly Leu Tyr Asn Asp Pro Asn Ser Asn Pro Lys
1               5                   10

<210> SEQ ID NO 610
<211> LENGTH: 13
<212> TYPE: PRT
<213> ORGANISM: Artificial Sequence
<220> FEATURE:
<223> OTHER INFORMATION: SLC25A12

<400> SEQUENCE: 610

Ile Val Gln Leu Leu Ala Gly Val Ala Asp Gln Thr Lys
1               5                   10

<210> SEQ ID NO 611
<211> LENGTH: 12
<212> TYPE: PRT
<213> ORGANISM: Artificial Sequence
<220> FEATURE:
<223> OTHER INFORMATION: SLC25A12
```

```
<400> SEQUENCE: 611

Ser Gly Asn Gly Glu Val Thr Phe Glu Asn Val Lys
1               5                   10

<210> SEQ ID NO 612
<211> LENGTH: 6
<212> TYPE: PRT
<213> ORGANISM: Artificial Sequence
<220> FEATURE:
<223> OTHER INFORMATION: SLC25A12

<400> SEQUENCE: 612

Gln Ala Phe Ala Leu Lys
1               5

<210> SEQ ID NO 613
<211> LENGTH: 9
<212> TYPE: PRT
<213> ORGANISM: Artificial Sequence
<220> FEATURE:
<223> OTHER INFORMATION: SLC25A12

<400> SEQUENCE: 613

Glu Glu Phe Ala Gln Ser Ala Ile Arg
1               5

<210> SEQ ID NO 614
<211> LENGTH: 24
<212> TYPE: PRT
<213> ORGANISM: Artificial Sequence
<220> FEATURE:
<223> OTHER INFORMATION: SLC25A12

<400> SEQUENCE: 614

Tyr Gly Gln Val Thr Pro Leu Glu Ile Asp Ile Leu Tyr Gln Leu Ala
1               5                   10                  15

Asp Leu Tyr Asn Ala Ser Gly Arg
            20

<210> SEQ ID NO 615
<211> LENGTH: 8
<212> TYPE: PRT
<213> ORGANISM: Artificial Sequence
<220> FEATURE:
<223> OTHER INFORMATION: SLC25A12

<400> SEQUENCE: 615

Leu Thr Leu Ala Asp Ile Glu Arg
1               5

<210> SEQ ID NO 616
<211> LENGTH: 18
<212> TYPE: PRT
<213> ORGANISM: Artificial Sequence
<220> FEATURE:
<223> OTHER INFORMATION: SLC25A12

<400> SEQUENCE: 616

Ile Ala Pro Leu Ala Glu Gly Ala Leu Pro Tyr Asn Leu Ala Glu Leu
1               5                   10                  15

Gln Arg

<210> SEQ ID NO 617
<211> LENGTH: 9
<212> TYPE: PRT
<213> ORGANISM: Artificial Sequence
```

-continued

```
<220> FEATURE:
<223> OTHER INFORMATION: SLC25A12

<400> SEQUENCE: 617

Tyr Glu Gly Phe Phe Gly Leu Tyr Arg
1               5

<210> SEQ ID NO 618
<211> LENGTH: 12
<212> TYPE: PRT
<213> ORGANISM: Artificial Sequence
<220> FEATURE:
<223> OTHER INFORMATION: SLC25A12

<400> SEQUENCE: 618

Leu Gln Val Ala Gly Glu Ile Thr Thr Gly Pro Arg
1               5                   10

<210> SEQ ID NO 619
<211> LENGTH: 8
<212> TYPE: PRT
<213> ORGANISM: Artificial Sequence
<220> FEATURE:
<223> OTHER INFORMATION: SLC25A12

<400> SEQUENCE: 619

Val Ser Ala Leu Asn Val Leu Arg
1               5

<210> SEQ ID NO 620
<211> LENGTH: 9
<212> TYPE: PRT
<213> ORGANISM: Artificial Sequence
<220> FEATURE:
<223> OTHER INFORMATION: SLC25A12

<400> SEQUENCE: 620

Asp Leu Gly Ile Phe Gly Leu Tyr Lys
1               5

<210> SEQ ID NO 621
<211> LENGTH: 6
<212> TYPE: PRT
<213> ORGANISM: Artificial Sequence
<220> FEATURE:
<223> OTHER INFORMATION: SLC25A12

<400> SEQUENCE: 621

Leu Gln Val Ala Ala Arg
1               5

<210> SEQ ID NO 622
<211> LENGTH: 9
<212> TYPE: PRT
<213> ORGANISM: Artificial Sequence
<220> FEATURE:
<223> OTHER INFORMATION: SLC25A12

<400> SEQUENCE: 622

Glu Glu Gly Pro Ser Ala Phe Trp Lys
1               5

<210> SEQ ID NO 623
<211> LENGTH: 16
<212> TYPE: PRT
<213> ORGANISM: Artificial Sequence
<220> FEATURE:
<223> OTHER INFORMATION: SLC25A12
```

```
<400> SEQUENCE: 623

Ile Ala Asp Leu Pro Pro Ala Asn Pro Asp His Ile Gly Gly Tyr Arg
1               5                   10                  15

<210> SEQ ID NO 624
<211> LENGTH: 12
<212> TYPE: PRT
<213> ORGANISM: Artificial Sequence
<220> FEATURE:
<223> OTHER INFORMATION: SLC25A12

<400> SEQUENCE: 624

Leu Ala Thr Ala Thr Phe Ala Gly Ile Glu Asn Lys
1               5                   10

<210> SEQ ID NO 625
<211> LENGTH: 7
<212> TYPE: PRT
<213> ORGANISM: Artificial Sequence
<220> FEATURE:
<223> OTHER INFORMATION: SLC25A12

<400> SEQUENCE: 625

Phe Gly Leu Tyr Leu Pro Lys
1               5

<210> SEQ ID NO 626
<211> LENGTH: 10
<212> TYPE: PRT
<213> ORGANISM: Artificial Sequence
<220> FEATURE:
<223> OTHER INFORMATION: SLC25A12

<400> SEQUENCE: 626

Ser Pro Ser Val Ala Val Val Gln Pro Lys
1               5                   10

<210> SEQ ID NO 627
<211> LENGTH: 7
<212> TYPE: PRT
<213> ORGANISM: Artificial Sequence
<220> FEATURE:
<223> OTHER INFORMATION: SLC25A12

<400> SEQUENCE: 627

Ala Ala Val Ala Ala Thr Gln
1               5

<210> SEQ ID NO 628
<211> LENGTH: 5
<212> TYPE: PRT
<213> ORGANISM: Artificial Sequence
<220> FEATURE:
<223> OTHER INFORMATION: SLC25A13

<400> SEQUENCE: 628

Thr Ile Phe Leu Lys
1               5

<210> SEQ ID NO 629
<211> LENGTH: 6
<212> TYPE: PRT
<213> ORGANISM: Artificial Sequence
<220> FEATURE:
<223> OTHER INFORMATION: SLC25A13

<400> SEQUENCE: 629
```

```
Tyr Ala Ser Ile Glu Lys
1               5

<210> SEQ ID NO 630
<211> LENGTH: 13
<212> TYPE: PRT
<213> ORGANISM: Artificial Sequence
<220> FEATURE:
<223> OTHER INFORMATION: SLC25A13

<400> SEQUENCE: 630

Tyr Leu Asn Ile Phe Gly Glu Ser Gln Pro Asn Pro Lys
1               5                   10

<210> SEQ ID NO 631
<211> LENGTH: 13
<212> TYPE: PRT
<213> ORGANISM: Artificial Sequence
<220> FEATURE:
<223> OTHER INFORMATION: SLC25A13

<400> SEQUENCE: 631

Thr Val Glu Leu Leu Ser Gly Val Val Asp Gln Thr Lys
1               5                   10

<210> SEQ ID NO 632
<211> LENGTH: 9
<212> TYPE: PRT
<213> ORGANISM: Artificial Sequence
<220> FEATURE:
<223> OTHER INFORMATION: SLC25A13

<400> SEQUENCE: 632

Gly Glu Val Thr Phe Glu Asp Val Lys
1               5

<210> SEQ ID NO 633
<211> LENGTH: 27
<212> TYPE: PRT
<213> ORGANISM: Artificial Sequence
<220> FEATURE:
<223> OTHER INFORMATION: SLC25A13

<400> SEQUENCE: 633

Gln Val Phe Gly Gln Thr Thr Ile His Gln His Ile Pro Phe Asn Trp
1               5                   10                  15

Asp Ser Glu Phe Val Gln Leu His Phe Gly Lys
            20                  25

<210> SEQ ID NO 634
<211> LENGTH: 6
<212> TYPE: PRT
<213> ORGANISM: Artificial Sequence
<220> FEATURE:
<223> OTHER INFORMATION: SLC25A13

<400> SEQUENCE: 634

Gln Ala Phe Val Gln Arg
1               5

<210> SEQ ID NO 635
<211> LENGTH: 7
<212> TYPE: PRT
<213> ORGANISM: Artificial Sequence
<220> FEATURE:
<223> OTHER INFORMATION: SLC25A13
```

```
<400> SEQUENCE: 635

Val Thr Ala Ile Asp Phe Arg
1               5

<210> SEQ ID NO 636
<211> LENGTH: 9
<212> TYPE: PRT
<213> ORGANISM: Artificial Sequence
<220> FEATURE:
<223> OTHER INFORMATION: SLC25A13

<400> SEQUENCE: 636

Glu Glu Phe Val Leu Ala Ala Gln Lys
1               5

<210> SEQ ID NO 637
<211> LENGTH: 18
<212> TYPE: PRT
<213> ORGANISM: Artificial Sequence
<220> FEATURE:
<223> OTHER INFORMATION: SLC25A13

<400> SEQUENCE: 637

Ile Ala Pro Leu Glu Glu Gly Thr Leu Pro Phe Asn Leu Ala Glu Ala
1               5                   10                  15

Gln Arg

<210> SEQ ID NO 638
<211> LENGTH: 9
<212> TYPE: PRT
<213> ORGANISM: Artificial Sequence
<220> FEATURE:
<223> OTHER INFORMATION: SLC25A13

<400> SEQUENCE: 638

Tyr Glu Gly Phe Phe Gly Leu Tyr Arg
1               5

<210> SEQ ID NO 639
<211> LENGTH: 12
<212> TYPE: PRT
<213> ORGANISM: Artificial Sequence
<220> FEATURE:
<223> OTHER INFORMATION: SLC25A13

<400> SEQUENCE: 639

Leu Gln Val Ala Gly Glu Ile Thr Thr Gly Pro Arg
1               5                   10

<210> SEQ ID NO 640
<211> LENGTH: 8
<212> TYPE: PRT
<213> ORGANISM: Artificial Sequence
<220> FEATURE:
<223> OTHER INFORMATION: SLC25A13

<400> SEQUENCE: 640

Val Ser Ala Leu Ser Val Val Arg
1               5

<210> SEQ ID NO 641
<211> LENGTH: 9
<212> TYPE: PRT
<213> ORGANISM: Artificial Sequence
<220> FEATURE:
<223> OTHER INFORMATION: SLC25A13
```

```
<400> SEQUENCE: 641

Asp Leu Gly Phe Phe Gly Ile Tyr Lys
1               5

<210> SEQ ID NO 642
<211> LENGTH: 6
<212> TYPE: PRT
<213> ORGANISM: Artificial Sequence
<220> FEATURE:
<223> OTHER INFORMATION: SLC25A13

<400> SEQUENCE: 642

Leu Gln Val Ala Ala Arg
1               5

<210> SEQ ID NO 643
<211> LENGTH: 15
<212> TYPE: PRT
<213> ORGANISM: Artificial Sequence
<220> FEATURE:
<223> OTHER INFORMATION: SLC25A13

<400> SEQUENCE: 643

Ile Asn Leu Pro Ala Pro Asn Pro Asp His Val Gly Gly Tyr Lys
1               5                   10                  15

<210> SEQ ID NO 644
<211> LENGTH: 12
<212> TYPE: PRT
<213> ORGANISM: Artificial Sequence
<220> FEATURE:
<223> OTHER INFORMATION: SLC25A13

<400> SEQUENCE: 644

Leu Ala Val Ala Thr Phe Ala Gly Ile Glu Asn Lys
1               5                   10

<210> SEQ ID NO 645
<211> LENGTH: 6
<212> TYPE: PRT
<213> ORGANISM: Artificial Sequence
<220> FEATURE:
<223> OTHER INFORMATION: SLC25A13

<400> SEQUENCE: 645

Ala Ile Gly Gly Gly Pro
1               5

<210> SEQ ID NO 646
<211> LENGTH: 11
<212> TYPE: PRT
<213> ORGANISM: Artificial Sequence
<220> FEATURE:
<223> OTHER INFORMATION: SLC25A14

<400> SEQUENCE: 646

Leu Gln Val Gln Gly Gln Ser Ile Asp Ala Arg
1               5                   10

<210> SEQ ID NO 647
<211> LENGTH: 17
<212> TYPE: PRT
<213> ORGANISM: Artificial Sequence
<220> FEATURE:
<223> OTHER INFORMATION: SLC25A14

<400> SEQUENCE: 647
```

-continued

Glu Glu Gly Val Leu Ala Leu Tyr Ser Gly Ile Ala Pro Ala Leu Leu
1               5                   10                  15

Arg

<210> SEQ ID NO 648
<211> LENGTH: 8
<212> TYPE: PRT
<213> ORGANISM: Artificial Sequence
<220> FEATURE:
<223> OTHER INFORMATION: SLC25A14

<400> SEQUENCE: 648

Gln Ala Ser Tyr Gly Thr Ile Lys
1               5

<210> SEQ ID NO 649
<211> LENGTH: 10
<212> TYPE: PRT
<213> ORGANISM: Artificial Sequence
<220> FEATURE:
<223> OTHER INFORMATION: SLC25A14

<400> SEQUENCE: 649

Ala Ile Val Gly His Val Asp Leu Tyr Lys
1               5                   10

<210> SEQ ID NO 650
<211> LENGTH: 8
<212> TYPE: PRT
<213> ORGANISM: Artificial Sequence
<220> FEATURE:
<223> OTHER INFORMATION: SLC25A14

<400> SEQUENCE: 650

Gly Thr Val Asp Gly Ile Leu Lys
1               5

<210> SEQ ID NO 651
<211> LENGTH: 8
<212> TYPE: PRT
<213> ORGANISM: Artificial Sequence
<220> FEATURE:
<223> OTHER INFORMATION: SLC25A15

<400> SEQUENCE: 651

Thr Tyr Ser Gln Val Gly Phe Arg
1               5

<210> SEQ ID NO 652
<211> LENGTH: 10
<212> TYPE: PRT
<213> ORGANISM: Artificial Sequence
<220> FEATURE:
<223> OTHER INFORMATION: SLC25A15

<400> SEQUENCE: 652

Ser Gln Asn Thr Val Trp Ser Val Ile Lys
1               5                   10

<210> SEQ ID NO 653
<211> LENGTH: 7
<212> TYPE: PRT
<213> ORGANISM: Artificial Sequence
<220> FEATURE:
<223> OTHER INFORMATION: SLC25A15

<400> SEQUENCE: 653

-continued

Ser Phe Ala Ser Gly Arg
1               5

<210> SEQ ID NO 654
<211> LENGTH: 8
<212> TYPE: PRT
<213> ORGANISM: Artificial Sequence
<220> FEATURE:
<223> OTHER INFORMATION: SLC25A16

<400> SEQUENCE: 654

Thr Thr Val Ala Pro Leu Asp Arg
1               5

<210> SEQ ID NO 655
<211> LENGTH: 11
<212> TYPE: PRT
<213> ORGANISM: Artificial Sequence
<220> FEATURE:
<223> OTHER INFORMATION: SLC25A16

<400> SEQUENCE: 655

Val Leu Leu Gln Ala His Asn His His Tyr Lys
1               5                   10

<210> SEQ ID NO 656
<211> LENGTH: 9
<212> TYPE: PRT
<213> ORGANISM: Artificial Sequence
<220> FEATURE:
<223> OTHER INFORMATION: SLC25A16

<400> SEQUENCE: 656

His Leu Gly Val Phe Ser Ala Leu Arg
1               5

<210> SEQ ID NO 657
<211> LENGTH: 5
<212> TYPE: PRT
<213> ORGANISM: Artificial Sequence
<220> FEATURE:
<223> OTHER INFORMATION: SLC25A16

<400> SEQUENCE: 657

Ala Val Pro Gln Lys
1               5

<210> SEQ ID NO 658
<211> LENGTH: 8
<212> TYPE: PRT
<213> ORGANISM: Artificial Sequence
<220> FEATURE:
<223> OTHER INFORMATION: SLC25A16

<400> SEQUENCE: 658

Glu Gly Phe Leu Gly Leu Tyr Lys
1               5

<210> SEQ ID NO 659
<211> LENGTH: 6
<212> TYPE: PRT
<213> ORGANISM: Artificial Sequence
<220> FEATURE:
<223> OTHER INFORMATION: SLC25A16

<400> SEQUENCE: 659

Thr Leu Ile Thr Thr Lys
1               5

-continued

```
<210> SEQ ID NO 660
<211> LENGTH: 9
<212> TYPE: PRT
<213> ORGANISM: Artificial Sequence
<220> FEATURE:
<223> OTHER INFORMATION: SLC25A16

<400> SEQUENCE: 660

Leu Gly Ile Ser Gly His Val His Arg
1               5

<210> SEQ ID NO 661
<211> LENGTH: 6
<212> TYPE: PRT
<213> ORGANISM: Artificial Sequence
<220> FEATURE:
<223> OTHER INFORMATION: SLC25A16

<400> SEQUENCE: 661

Leu Ala Phe Gln Val Lys
1               5

<210> SEQ ID NO 662
<211> LENGTH: 9
<212> TYPE: PRT
<213> ORGANISM: Artificial Sequence
<220> FEATURE:
<223> OTHER INFORMATION: SLC25A16

<400> SEQUENCE: 662

Tyr Thr Gly Ile Ile His Ala Phe Lys
1               5

<210> SEQ ID NO 663
<211> LENGTH: 5
<212> TYPE: PRT
<213> ORGANISM: Artificial Sequence
<220> FEATURE:
<223> OTHER INFORMATION: SLC25A16

<400> SEQUENCE: 663

Thr Ile Tyr Ala Lys
1               5

<210> SEQ ID NO 664
<211> LENGTH: 9
<212> TYPE: PRT
<213> ORGANISM: Artificial Sequence
<220> FEATURE:
<223> OTHER INFORMATION: SLC25A16

<400> SEQUENCE: 664

Glu Gly Gly Phe Phe Gly Phe Tyr Arg
1               5

<210> SEQ ID NO 665
<211> LENGTH: 8
<212> TYPE: PRT
<213> ORGANISM: Artificial Sequence
<220> FEATURE:
<223> OTHER INFORMATION: SLC25A16

<400> SEQUENCE: 665

Gly Leu Ser Leu Asn Tyr Ile Arg
1               5
```

```
<210> SEQ ID NO 666
<211> LENGTH: 6
<212> TYPE: PRT
<213> ORGANISM: Artificial Sequence
<220> FEATURE:
<223> OTHER INFORMATION: SLC25A16

<400> SEQUENCE: 666

Gln Phe Phe His Leu Asn
1               5

<210> SEQ ID NO 667
<211> LENGTH: 9
<212> TYPE: PRT
<213> ORGANISM: Artificial Sequence
<220> FEATURE:
<223> OTHER INFORMATION: SLC25A17

<400> SEQUENCE: 667

Glu Glu Gly Leu Leu Ala Pro Tyr Arg
1               5

<210> SEQ ID NO 668
<211> LENGTH: 5
<212> TYPE: PRT
<213> ORGANISM: Artificial Sequence
<220> FEATURE:
<223> OTHER INFORMATION: SLC25A17

<400> SEQUENCE: 668

Ala Leu Trp Val Lys
1               5

<210> SEQ ID NO 669
<211> LENGTH: 5
<212> TYPE: PRT
<213> ORGANISM: Artificial Sequence
<220> FEATURE:
<223> OTHER INFORMATION: SLC25A17

<400> SEQUENCE: 669

Leu Gln Gly Ala Lys
1               5

<210> SEQ ID NO 670
<211> LENGTH: 10
<212> TYPE: PRT
<213> ORGANISM: Artificial Sequence
<220> FEATURE:
<223> OTHER INFORMATION: SLC25A17

<400> SEQUENCE: 670

Asn Glu Asp Ile Val Pro Thr Asn Tyr Lys
1               5                   10

<210> SEQ ID NO 671
<211> LENGTH: 11
<212> TYPE: PRT
<213> ORGANISM: Artificial Sequence
<220> FEATURE:
<223> OTHER INFORMATION: SLC25A17

<400> SEQUENCE: 671

Gly Ile Ile Asp Ala Phe His Gln Ile Ile Arg
1               5                   10

<210> SEQ ID NO 672
<211> LENGTH: 6
```

```
<212> TYPE: PRT
<213> ORGANISM: Artificial Sequence
<220> FEATURE:
<223> OTHER INFORMATION: SLC25A17

<400> SEQUENCE: 672

Leu Asn Pro Glu Asn Arg
1               5

<210> SEQ ID NO 673
<211> LENGTH: 6
<212> TYPE: PRT
<213> ORGANISM: Artificial Sequence
<220> FEATURE:
<223> OTHER INFORMATION: SLC25A17

<400> SEQUENCE: 673

Thr Leu Gly Ser Leu Arg
1               5

<210> SEQ ID NO 674
<211> LENGTH: 9
<212> TYPE: PRT
<213> ORGANISM: Artificial Sequence
<220> FEATURE:
<223> OTHER INFORMATION: SLC25A17

<400> SEQUENCE: 674

Asn Ile Leu Tyr Leu Leu His Gln Arg
1               5

<210> SEQ ID NO 675
<211> LENGTH: 5
<212> TYPE: PRT
<213> ORGANISM: Artificial Sequence
<220> FEATURE:
<223> OTHER INFORMATION: SLC25A17

<400> SEQUENCE: 675

Gly Leu Glu Ala Lys
1               5

<210> SEQ ID NO 676
<211> LENGTH: 7
<212> TYPE: PRT
<213> ORGANISM: Artificial Sequence
<220> FEATURE:
<223> OTHER INFORMATION: SLC25A18

<400> SEQUENCE: 676

Leu Gln Asn Gln His Gly Lys
1               5

<210> SEQ ID NO 677
<211> LENGTH: 13
<212> TYPE: PRT
<213> ORGANISM: Artificial Sequence
<220> FEATURE:
<223> OTHER INFORMATION: SLC25A18

<400> SEQUENCE: 677

Gly Ala Ala Val Asn Leu Thr Leu Val Thr Pro Glu Lys
1               5                   10

<210> SEQ ID NO 678
<211> LENGTH: 8
<212> TYPE: PRT
<213> ORGANISM: Artificial Sequence
```

```
<220> FEATURE:
<223> OTHER INFORMATION: SLC25A18

<400> SEQUENCE: 678

Ile Gln Leu Gln Asp Ala Gly Arg
1               5

<210> SEQ ID NO 679
<211> LENGTH: 16
<212> TYPE: PRT
<213> ORGANISM: Artificial Sequence
<220> FEATURE:
<223> OTHER INFORMATION: SLC25A18

<400> SEQUENCE: 679

Leu Ala Val His His Gln Gly Ser Ala Ser Ala Pro Ser Thr Ser Arg
1               5                   10                  15

<210> SEQ ID NO 680
<211> LENGTH: 9
<212> TYPE: PRT
<213> ORGANISM: Artificial Sequence
<220> FEATURE:
<223> OTHER INFORMATION: SLC25A18

<400> SEQUENCE: 680

Thr Gln Gly Leu Ala Gly Leu Tyr Arg
1               5

<210> SEQ ID NO 681
<211> LENGTH: 9
<212> TYPE: PRT
<213> ORGANISM: Artificial Sequence
<220> FEATURE:
<223> OTHER INFORMATION: SLC25A19

<400> SEQUENCE: 681

Tyr His Gly Ile Leu Gln Ala Ser Arg
1               5

<210> SEQ ID NO 682
<211> LENGTH: 13
<212> TYPE: PRT
<213> ORGANISM: Artificial Sequence
<220> FEATURE:
<223> OTHER INFORMATION: SLC25A19

<400> SEQUENCE: 682

Gln Ile Leu Gln Glu Glu Gly Pro Thr Ala Phe Trp Lys
1               5                   10

<210> SEQ ID NO 683
<211> LENGTH: 7
<212> TYPE: PRT
<213> ORGANISM: Artificial Sequence
<220> FEATURE:
<223> OTHER INFORMATION: SLC25A19

<400> SEQUENCE: 683

Gly Ser Val Tyr Asp Ala Arg
1               5

<210> SEQ ID NO 684
<211> LENGTH: 6
<212> TYPE: PRT
<213> ORGANISM: Artificial Sequence
<220> FEATURE:
<223> OTHER INFORMATION: SLC25A19
```

```
<400> SEQUENCE: 684

Val Tyr Asn Thr Leu Arg
1               5

<210> SEQ ID NO 685
<211> LENGTH: 9
<212> TYPE: PRT
<213> ORGANISM: Artificial Sequence
<220> FEATURE:
<223> OTHER INFORMATION: SLC25A19

<400> SEQUENCE: 685

Ser Glu Gly Pro Gln Val Phe Tyr Lys
1               5

<210> SEQ ID NO 686
<211> LENGTH: 5
<212> TYPE: PRT
<213> ORGANISM: Artificial Sequence
<220> FEATURE:
<223> OTHER INFORMATION: SLC25A19

<400> SEQUENCE: 686

Gln Val Leu Gln Lys
1               5

<210> SEQ ID NO 687
<211> LENGTH: 8
<212> TYPE: PRT
<213> ORGANISM: Artificial Sequence
<220> FEATURE:
<223> OTHER INFORMATION: SLC25A19

<400> SEQUENCE: 687

Glu Gly Ala Leu Gly Phe Phe Lys
1               5

<210> SEQ ID NO 688
<211> LENGTH: 8
<212> TYPE: PRT
<213> ORGANISM: Artificial Sequence
<220> FEATURE:
<223> OTHER INFORMATION: SLC25A2

<400> SEQUENCE: 688

Thr Tyr Ala Gln Val Gly Leu Arg
1               5

<210> SEQ ID NO 689
<211> LENGTH: 10
<212> TYPE: PRT
<213> ORGANISM: Artificial Sequence
<220> FEATURE:
<223> OTHER INFORMATION: SLC25A2

<400> SEQUENCE: 689

Ser His Asn Thr Ile Trp Ser Val Val Lys
1               5                   10

<210> SEQ ID NO 690
<211> LENGTH: 7
<212> TYPE: PRT
<213> ORGANISM: Artificial Sequence
<220> FEATURE:
<223> OTHER INFORMATION: SLC25A2

<400> SEQUENCE: 690
```

Ser Phe Phe Ala Ser Gly Arg
1               5

<210> SEQ ID NO 691
<211> LENGTH: 12
<212> TYPE: PRT
<213> ORGANISM: Artificial Sequence
<220> FEATURE:
<223> OTHER INFORMATION: SLC25A2

<400> SEQUENCE: 691

Asn Glu Gly Ile Val Ala Leu Tyr Ser Gly Leu Lys
1               5                   10

<210> SEQ ID NO 692
<211> LENGTH: 5
<212> TYPE: PRT
<213> ORGANISM: Artificial Sequence
<220> FEATURE:
<223> OTHER INFORMATION: SLC25A2

<400> SEQUENCE: 692

Gln Leu Glu Ala Tyr
1               5

<210> SEQ ID NO 693
<211> LENGTH: 8
<212> TYPE: PRT
<213> ORGANISM: Artificial Sequence
<220> FEATURE:
<223> OTHER INFORMATION: SLC25A20

<400> SEQUENCE: 693

Glu Gly Ile Thr Gly Leu Tyr Arg
1               5

<210> SEQ ID NO 694
<211> LENGTH: 6
<212> TYPE: PRT
<213> ORGANISM: Artificial Sequence
<220> FEATURE:
<223> OTHER INFORMATION: SLC25A20

<400> SEQUENCE: 694

Tyr Pro Asn Gly Phe Arg
1               5

<210> SEQ ID NO 695
<211> LENGTH: 9
<212> TYPE: PRT
<213> ORGANISM: Artificial Sequence
<220> FEATURE:
<223> OTHER INFORMATION: SLC25A20

<400> SEQUENCE: 695

Asp Glu Gly Val Thr Ser Leu Tyr Lys
1               5

<210> SEQ ID NO 696
<211> LENGTH: 9
<212> TYPE: PRT
<213> ORGANISM: Artificial Sequence
<220> FEATURE:
<223> OTHER INFORMATION: SLC25A20

<400> SEQUENCE: 696

Phe Leu Asn Trp Ala Thr Pro Asn Leu

<210> SEQ ID NO 697
<211> LENGTH: 5
<212> TYPE: PRT
<213> ORGANISM: Artificial Sequence
<220> FEATURE:
<223> OTHER INFORMATION: SLC25A21

<400> SEQUENCE: 697

Phe Gln Ile Gln Arg
1               5

<210> SEQ ID NO 698
<211> LENGTH: 7
<212> TYPE: PRT
<213> ORGANISM: Artificial Sequence
<220> FEATURE:
<223> OTHER INFORMATION: SLC25A21

<400> SEQUENCE: 698

Ser Leu Val Asp Ser Phe Arg
1               5

<210> SEQ ID NO 699
<211> LENGTH: 7
<212> TYPE: PRT
<213> ORGANISM: Artificial Sequence
<220> FEATURE:
<223> OTHER INFORMATION: SLC25A21

<400> SEQUENCE: 699

Val Gly Leu Gln Ala Asn Arg
1               5

<210> SEQ ID NO 700
<211> LENGTH: 14
<212> TYPE: PRT
<213> ORGANISM: Artificial Sequence
<220> FEATURE:
<223> OTHER INFORMATION: SLC25A21

<400> SEQUENCE: 700

Asn Thr Phe Ala Glu Gln Pro Ser Thr Val Gly Tyr Ala Arg
1               5                   10

<210> SEQ ID NO 701
<211> LENGTH: 8
<212> TYPE: PRT
<213> ORGANISM: Artificial Sequence
<220> FEATURE:
<223> OTHER INFORMATION: SLC25A21

<400> SEQUENCE: 701

Gly Leu Thr Ala Thr Leu Gly Arg
1               5

<210> SEQ ID NO 702
<211> LENGTH: 12
<212> TYPE: PRT
<213> ORGANISM: Artificial Sequence
<220> FEATURE:
<223> OTHER INFORMATION: SLC25A21

<400> SEQUENCE: 702

Ile Gln Gly Pro Gln Pro Val Pro Gly Glu Ile Lys
1               5                   10

```
<210> SEQ ID NO 703
<211> LENGTH: 5
<212> TYPE: PRT
<213> ORGANISM: Artificial Sequence
<220> FEATURE:
<223> OTHER INFORMATION: SLC25A21

<400> SEQUENCE: 703

Gly Leu Leu Pro Lys
1               5

<210> SEQ ID NO 704
<211> LENGTH: 7
<212> TYPE: PRT
<213> ORGANISM: Artificial Sequence
<220> FEATURE:
<223> OTHER INFORMATION: SLC25A22

<400> SEQUENCE: 704

Gln Ile Ser Leu Pro Ala Lys
1               5

<210> SEQ ID NO 705
<211> LENGTH: 9
<212> TYPE: PRT
<213> ORGANISM: Artificial Sequence
<220> FEATURE:
<223> OTHER INFORMATION: SLC25A22

<400> SEQUENCE: 705

Leu Gln Asn Gln Gln Asn Gly Gln Arg
1               5

<210> SEQ ID NO 706
<211> LENGTH: 13
<212> TYPE: PRT
<213> ORGANISM: Artificial Sequence
<220> FEATURE:
<223> OTHER INFORMATION: SLC25A22

<400> SEQUENCE: 706

Gly Ala Ala Val Asn Leu Thr Leu Val Thr Pro Glu Lys
1               5                   10

<210> SEQ ID NO 707
<211> LENGTH: 8
<212> TYPE: PRT
<213> ORGANISM: Artificial Sequence
<220> FEATURE:
<223> OTHER INFORMATION: SLC25A22

<400> SEQUENCE: 707

Leu Ala Ala Asn Asp Phe Phe Arg
1               5

<210> SEQ ID NO 708
<211> LENGTH: 5
<212> TYPE: PRT
<213> ORGANISM: Artificial Sequence
<220> FEATURE:
<223> OTHER INFORMATION: SLC25A22

<400> SEQUENCE: 708

His Gln Leu Ser Lys
1               5

<210> SEQ ID NO 709
```

```
<211> LENGTH: 5
<212> TYPE: PRT
<213> ORGANISM: Artificial Sequence
<220> FEATURE:
<223> OTHER INFORMATION: SLC25A22

<400> SEQUENCE: 709

Leu Thr Leu Leu Lys
1               5

<210> SEQ ID NO 710
<211> LENGTH: 8
<212> TYPE: PRT
<213> ORGANISM: Artificial Sequence
<220> FEATURE:
<223> OTHER INFORMATION: SLC25A22

<400> SEQUENCE: 710

Ile Gln Leu Gln Asp Ala Gly Arg
1               5

<210> SEQ ID NO 711
<211> LENGTH: 7
<212> TYPE: PRT
<213> ORGANISM: Artificial Sequence
<220> FEATURE:
<223> OTHER INFORMATION: SLC25A22

<400> SEQUENCE: 711

Gly Ile Ala Gly Leu Tyr Lys
1               5

<210> SEQ ID NO 712
<211> LENGTH: 6
<212> TYPE: PRT
<213> ORGANISM: Artificial Sequence
<220> FEATURE:
<223> OTHER INFORMATION: SLC25A22

<400> SEQUENCE: 712

Leu Gln Ser Leu Gln Arg
1               5

<210> SEQ ID NO 713
<211> LENGTH: 9
<212> TYPE: PRT
<213> ORGANISM: Artificial Sequence
<220> FEATURE:
<223> OTHER INFORMATION: SLC25A22

<400> SEQUENCE: 713

His Glu Gly Pro Ser Ala Phe Leu Lys
1               5

<210> SEQ ID NO 714
<211> LENGTH: 7
<212> TYPE: PRT
<213> ORGANISM: Artificial Sequence
<220> FEATURE:
<223> OTHER INFORMATION: SLC25A23

<400> SEQUENCE: 714

Val Asp Val His Glu Leu Arg
1               5

<210> SEQ ID NO 715
<211> LENGTH: 5
<212> TYPE: PRT
```

```
<213> ORGANISM: Artificial Sequence
<220> FEATURE:
<223> OTHER INFORMATION: SLC25A23

<400> SEQUENCE: 715

Gln Gly Leu Ala Arg
1               5

<210> SEQ ID NO 716
<211> LENGTH: 5
<212> TYPE: PRT
<213> ORGANISM: Artificial Sequence
<220> FEATURE:
<223> OTHER INFORMATION: SLC25A23

<400> SEQUENCE: 716

Tyr Leu Gln Glu Arg
1               5

<210> SEQ ID NO 717
<211> LENGTH: 16
<212> TYPE: PRT
<213> ORGANISM: Artificial Sequence
<220> FEATURE:
<223> OTHER INFORMATION: SLC25A23

<400> SEQUENCE: 717

Asn Gln Asp Gly His Ile Asp Val Ser Glu Ile Gln Gln Ser Phe Arg
1               5                   10                  15

<210> SEQ ID NO 718
<211> LENGTH: 13
<212> TYPE: PRT
<213> ORGANISM: Artificial Sequence
<220> FEATURE:
<223> OTHER INFORMATION: SLC25A23

<400> SEQUENCE: 718

Ala Leu Gly Ile Ser Ile Ser Leu Glu Gln Ala Glu Lys
1               5                   10

<210> SEQ ID NO 719
<211> LENGTH: 19
<212> TYPE: PRT
<213> ORGANISM: Artificial Sequence
<220> FEATURE:
<223> OTHER INFORMATION: SLC25A23

<400> SEQUENCE: 719

Asp His Phe Leu Leu His Ser Leu Glu Asn Val Glu Asp Val Leu Tyr
1               5                   10                  15

Phe Trp Lys

<210> SEQ ID NO 720
<211> LENGTH: 13
<212> TYPE: PRT
<213> ORGANISM: Artificial Sequence
<220> FEATURE:
<223> OTHER INFORMATION: SLC25A23

<400> SEQUENCE: 720

Gln Leu Val Ala Gly Ala Val Ala Gly Ala Val Ser Arg
1               5                   10

<210> SEQ ID NO 721
<211> LENGTH: 8
<212> TYPE: PRT
```

```
<213> ORGANISM: Artificial Sequence
<220> FEATURE:
<223> OTHER INFORMATION: SLC25A23

<400> SEQUENCE: 721

Thr Gly Thr Ala Pro Leu Asp Arg
1               5

<210> SEQ ID NO 722
<211> LENGTH: 8
<212> TYPE: PRT
<213> ORGANISM: Artificial Sequence
<220> FEATURE:
<223> OTHER INFORMATION: SLC25A23

<400> SEQUENCE: 722

Leu Asn Ile Leu Gly Gly Leu Arg
1               5

<210> SEQ ID NO 723
<211> LENGTH: 8
<212> TYPE: PRT
<213> ORGANISM: Artificial Sequence
<220> FEATURE:
<223> OTHER INFORMATION: SLC25A23

<400> SEQUENCE: 723

Gly Asn Gly Ile Asn Val Leu Lys
1               5

<210> SEQ ID NO 724
<211> LENGTH: 8
<212> TYPE: PRT
<213> ORGANISM: Artificial Sequence
<220> FEATURE:
<223> OTHER INFORMATION: SLC25A23

<400> SEQUENCE: 724

Ile Ala Pro Glu Ser Ala Ile Lys
1               5

<210> SEQ ID NO 725
<211> LENGTH: 24
<212> TYPE: PRT
<213> ORGANISM: Artificial Sequence
<220> FEATURE:
<223> OTHER INFORMATION: SLC25A23

<400> SEQUENCE: 725

Gly Tyr Leu Pro Asn Val Leu Gly Ile Ile Pro Tyr Ala Gly Ile Asp
1               5                   10                  15

Leu Ala Val Tyr Glu Thr Leu Lys
            20

<210> SEQ ID NO 726
<211> LENGTH: 8
<212> TYPE: PRT
<213> ORGANISM: Artificial Sequence
<220> FEATURE:
<223> OTHER INFORMATION: SLC25A23

<400> SEQUENCE: 726

Gln Ala Leu Gly Val Thr Ser Arg
1               5

<210> SEQ ID NO 727
<211> LENGTH: 9
```

```
<212> TYPE: PRT
<213> ORGANISM: Artificial Sequence
<220> FEATURE:
<223> OTHER INFORMATION: SLC25A24

<400> SEQUENCE: 727

Ile Phe Thr Thr Gly Asp Val Asn Lys
1               5

<210> SEQ ID NO 728
<211> LENGTH: 16
<212> TYPE: PRT
<213> ORGANISM: Artificial Sequence
<220> FEATURE:
<223> OTHER INFORMATION: SLC25A24

<400> SEQUENCE: 728

Asp Tyr Phe Leu Phe Asn Pro Val Thr Asp Ile Glu Glu Ile Ile Arg
1               5                   10                  15

<210> SEQ ID NO 729
<211> LENGTH: 13
<212> TYPE: PRT
<213> ORGANISM: Artificial Sequence
<220> FEATURE:
<223> OTHER INFORMATION: SLC25A24

<400> SEQUENCE: 729

Gln Leu Leu Ala Gly Gly Ile Ala Gly Ala Val Ser Arg
1               5                   10

<210> SEQ ID NO 730
<211> LENGTH: 8
<212> TYPE: PRT
<213> ORGANISM: Artificial Sequence
<220> FEATURE:
<223> OTHER INFORMATION: SLC25A24

<400> SEQUENCE: 730

Thr Ser Thr Ala Pro Leu Asp Arg
1               5

<210> SEQ ID NO 731
<211> LENGTH: 5
<212> TYPE: PRT
<213> ORGANISM: Artificial Sequence
<220> FEATURE:
<223> OTHER INFORMATION: SLC25A24

<400> SEQUENCE: 731

Glu Gly Gly Ile Arg
1               5

<210> SEQ ID NO 732
<211> LENGTH: 8
<212> TYPE: PRT
<213> ORGANISM: Artificial Sequence
<220> FEATURE:
<223> OTHER INFORMATION: SLC25A24

<400> SEQUENCE: 732

Gly Asn Gly Thr Asn Val Ile Lys
1               5

<210> SEQ ID NO 733
<211> LENGTH: 8
<212> TYPE: PRT
<213> ORGANISM: Artificial Sequence
```

```
<220> FEATURE:
<223> OTHER INFORMATION: SLC25A24

<400> SEQUENCE: 733

Ile Ala Pro Glu Thr Ala Val Lys
1               5

<210> SEQ ID NO 734
<211> LENGTH: 6
<212> TYPE: PRT
<213> ORGANISM: Artificial Sequence
<220> FEATURE:
<223> OTHER INFORMATION: SLC25A24

<400> SEQUENCE: 734

Ile Gly Thr Phe Glu Arg
1               5

<210> SEQ ID NO 735
<211> LENGTH: 5
<212> TYPE: PRT
<213> ORGANISM: Artificial Sequence
<220> FEATURE:
<223> OTHER INFORMATION: SLC25A24

<400> SEQUENCE: 735

Leu Ala Val Gly Lys
1               5

<210> SEQ ID NO 736
<211> LENGTH: 9
<212> TYPE: PRT
<213> ORGANISM: Artificial Sequence
<220> FEATURE:
<223> OTHER INFORMATION: SLC25A24

<400> SEQUENCE: 736

His Glu Gly Leu Gly Ala Phe Tyr Lys
1               5

<210> SEQ ID NO 737
<211> LENGTH: 24
<212> TYPE: PRT
<213> ORGANISM: Artificial Sequence
<220> FEATURE:
<223> OTHER INFORMATION: SLC25A24

<400> SEQUENCE: 737

Gly Tyr Val Pro Asn Leu Leu Gly Ile Ile Pro Tyr Ala Gly Ile Asp
1               5                   10                  15

Leu Ala Val Tyr Glu Leu Leu Lys
            20

<210> SEQ ID NO 738
<211> LENGTH: 9
<212> TYPE: PRT
<213> ORGANISM: Artificial Sequence
<220> FEATURE:
<223> OTHER INFORMATION: SLC25A24

<400> SEQUENCE: 738

Ser Tyr Trp Leu Asp Asn Phe Ala Lys
1               5

<210> SEQ ID NO 739
<211> LENGTH: 8
<212> TYPE: PRT
```

```
<213> ORGANISM: Artificial Sequence
<220> FEATURE:
<223> OTHER INFORMATION: SLC25A24

<400> SEQUENCE: 739

Glu Gly Ile Pro Gly Leu Tyr Arg
1               5

<210> SEQ ID NO 740
<211> LENGTH: 8
<212> TYPE: PRT
<213> ORGANISM: Artificial Sequence
<220> FEATURE:
<223> OTHER INFORMATION: SLC25A24

<400> SEQUENCE: 740

Gln Thr Leu Gly Val Thr Gln Lys
1               5

<210> SEQ ID NO 741
<211> LENGTH: 7
<212> TYPE: PRT
<213> ORGANISM: Artificial Sequence
<220> FEATURE:
<223> OTHER INFORMATION: SLC25A25

<400> SEQUENCE: 741

Ile Val Gln Ala Gly Asp Lys
1               5

<210> SEQ ID NO 742
<211> LENGTH: 5
<212> TYPE: PRT
<213> ORGANISM: Artificial Sequence
<220> FEATURE:
<223> OTHER INFORMATION: SLC25A25

<400> SEQUENCE: 742

Asp Leu Gly Val Lys
1               5

<210> SEQ ID NO 743
<211> LENGTH: 8
<212> TYPE: PRT
<213> ORGANISM: Artificial Sequence
<220> FEATURE:
<223> OTHER INFORMATION: SLC25A25

<400> SEQUENCE: 743

Ile Ser Glu Gln Gln Ala Glu Lys
1               5

<210> SEQ ID NO 744
<211> LENGTH: 19
<212> TYPE: PRT
<213> ORGANISM: Artificial Sequence
<220> FEATURE:
<223> OTHER INFORMATION: SLC25A25

<400> SEQUENCE: 744

Asp Tyr His Leu Leu His Pro Val Glu Asn Ile Pro Glu Ile Ile Leu
1               5                   10                  15

Tyr Trp Lys

<210> SEQ ID NO 745
<211> LENGTH: 22
<212> TYPE: PRT
```

<213> ORGANISM: Artificial Sequence
<220> FEATURE:
<223> OTHER INFORMATION: SLC25A25

<400> SEQUENCE: 745

His Ser Thr Ile Phe Asp Val Gly Glu Asn Leu Thr Val Pro Asp Glu
1               5                   10                  15
Phe Thr Val Glu Glu Arg
            20

<210> SEQ ID NO 746
<211> LENGTH: 13
<212> TYPE: PRT
<213> ORGANISM: Artificial Sequence
<220> FEATURE:
<223> OTHER INFORMATION: SLC25A25

<400> SEQUENCE: 746

His Leu Val Ala Gly Gly Gly Ala Gly Ala Val Ser Arg
1               5                   10

<210> SEQ ID NO 747
<211> LENGTH: 8
<212> TYPE: PRT
<213> ORGANISM: Artificial Sequence
<220> FEATURE:
<223> OTHER INFORMATION: SLC25A25

<400> SEQUENCE: 747

Gly Asn Gly Ile Asn Val Leu Lys
1               5

<210> SEQ ID NO 748
<211> LENGTH: 8
<212> TYPE: PRT
<213> ORGANISM: Artificial Sequence
<220> FEATURE:
<223> OTHER INFORMATION: SLC25A25

<400> SEQUENCE: 748

Ile Ala Pro Glu Ser Ala Ile Lys
1               5

<210> SEQ ID NO 749
<211> LENGTH: 8
<212> TYPE: PRT
<213> ORGANISM: Artificial Sequence
<220> FEATURE:
<223> OTHER INFORMATION: SLC25A25

<400> SEQUENCE: 749

Glu Gly Val Ala Ala Phe Tyr Lys
1               5

<210> SEQ ID NO 750
<211> LENGTH: 9
<212> TYPE: PRT
<213> ORGANISM: Artificial Sequence
<220> FEATURE:
<223> OTHER INFORMATION: SLC25A25

<400> SEQUENCE: 750

Thr Glu Gly Ala Phe Gly Leu Tyr Arg
1               5

<210> SEQ ID NO 751
<211> LENGTH: 16

```
<212> TYPE: PRT
<213> ORGANISM: Artificial Sequence
<220> FEATURE:
<223> OTHER INFORMATION: SLC25A25

<400> SEQUENCE: 751

Val Ile Pro Ala Val Ser Ile Ser Tyr Val Val Tyr Glu Asn Leu Lys
1               5                   10                  15

<210> SEQ ID NO 752
<211> LENGTH: 8
<212> TYPE: PRT
<213> ORGANISM: Artificial Sequence
<220> FEATURE:
<223> OTHER INFORMATION: SLC25A25

<400> SEQUENCE: 752

Ile Thr Leu Gly Val Gln Ser Arg
1               5

<210> SEQ ID NO 753
<211> LENGTH: 7
<212> TYPE: PRT
<213> ORGANISM: Artificial Sequence
<220> FEATURE:
<223> OTHER INFORMATION: SLC25A26

<400> SEQUENCE: 753

Val Pro Ser Glu Val Val Lys
1               5

<210> SEQ ID NO 754
<211> LENGTH: 8
<212> TYPE: PRT
<213> ORGANISM: Artificial Sequence
<220> FEATURE:
<223> OTHER INFORMATION: SLC25A26

<400> SEQUENCE: 754

Ala Gln Val Ser Ala Ser Thr Arg
1               5

<210> SEQ ID NO 755
<211> LENGTH: 19
<212> TYPE: PRT
<213> ORGANISM: Artificial Sequence
<220> FEATURE:
<223> OTHER INFORMATION: SLC25A26

<400> SEQUENCE: 755

Thr Phe Gln Ile Phe Ser Asn Ile Leu Tyr Glu Glu Gly Ile Gln Gly
1               5                   10                  15

Leu Tyr Arg

<210> SEQ ID NO 756
<211> LENGTH: 5
<212> TYPE: PRT
<213> ORGANISM: Artificial Sequence
<220> FEATURE:
<223> OTHER INFORMATION: SLC25A26

<400> SEQUENCE: 756

Ser Thr Val Leu Arg
1               5

<210> SEQ ID NO 757
<211> LENGTH: 7
```

```
<212> TYPE: PRT
<213> ORGANISM: Artificial Sequence
<220> FEATURE:
<223> OTHER INFORMATION: SLC25A27

<400> SEQUENCE: 757

Leu Leu Pro Leu Thr Gln Arg
1               5

<210> SEQ ID NO 758
<211> LENGTH: 6
<212> TYPE: PRT
<213> ORGANISM: Artificial Sequence
<220> FEATURE:
<223> OTHER INFORMATION: SLC25A27

<400> SEQUENCE: 758

Leu Gly Asp Gly Ala Arg
1               5

<210> SEQ ID NO 759
<211> LENGTH: 6
<212> TYPE: PRT
<213> ORGANISM: Artificial Sequence
<220> FEATURE:
<223> OTHER INFORMATION: SLC25A27

<400> SEQUENCE: 759

Glu Ser Ala Pro Tyr Arg
1               5

<210> SEQ ID NO 760
<211> LENGTH: 13
<212> TYPE: PRT
<213> ORGANISM: Artificial Sequence
<220> FEATURE:
<223> OTHER INFORMATION: SLC25A27

<400> SEQUENCE: 760

Thr Ala Leu Gly Ile Ile Glu Glu Gly Phe Leu Lys
1               5                   10

<210> SEQ ID NO 761
<211> LENGTH: 6
<212> TYPE: PRT
<213> ORGANISM: Artificial Sequence
<220> FEATURE:
<223> OTHER INFORMATION: SLC25A27

<400> SEQUENCE: 761

Glu Val Val Phe Gly Lys
1               5

<210> SEQ ID NO 762
<211> LENGTH: 8
<212> TYPE: PRT
<213> ORGANISM: Artificial Sequence
<220> FEATURE:
<223> OTHER INFORMATION: SLC25A27

<400> SEQUENCE: 762

Gly Val His His Ala Phe Ala Lys
1               5

<210> SEQ ID NO 763
<211> LENGTH: 8
<212> TYPE: PRT
<213> ORGANISM: Artificial Sequence
```

```
<220> FEATURE:
<223> OTHER INFORMATION: SLC25A27

<400> SEQUENCE: 763

Ile Leu Ala Glu Gly Gly Ile Arg
1               5

<210> SEQ ID NO 764
<211> LENGTH: 5
<212> TYPE: PRT
<213> ORGANISM: Artificial Sequence
<220> FEATURE:
<223> OTHER INFORMATION: SLC25A27

<400> SEQUENCE: 764

Gly Leu Leu Tyr Lys
1               5

<210> SEQ ID NO 765
<211> LENGTH: 13
<212> TYPE: PRT
<213> ORGANISM: Artificial Sequence
<220> FEATURE:
<223> OTHER INFORMATION: SLC25A28

<400> SEQUENCE: 765

Ala Val Trp Gln Asn Glu Gly Ala Gly Ala Phe Tyr Arg
1               5                   10

<210> SEQ ID NO 766
<211> LENGTH: 13
<212> TYPE: PRT
<213> ORGANISM: Artificial Sequence
<220> FEATURE:
<223> OTHER INFORMATION: SLC25A28

<400> SEQUENCE: 766

Thr Val Tyr Gln Val Gly Gly Val Thr Ala Tyr Phe Arg
1               5                   10

<210> SEQ ID NO 767
<211> LENGTH: 9
<212> TYPE: PRT
<213> ORGANISM: Artificial Sequence
<220> FEATURE:
<223> OTHER INFORMATION: SLC25A29

<400> SEQUENCE: 767

Gln Glu Ser Val Leu Gly Leu Tyr Lys
1               5

<210> SEQ ID NO 768
<211> LENGTH: 10
<212> TYPE: PRT
<213> ORGANISM: Artificial Sequence
<220> FEATURE:
<223> OTHER INFORMATION: SLC25A29

<400> SEQUENCE: 768

Leu Gln Leu Gln Asp Ala Gly Pro Ala Arg
1               5                   10

<210> SEQ ID NO 769
<211> LENGTH: 17
<212> TYPE: PRT
<213> ORGANISM: Artificial Sequence
<220> FEATURE:
<223> OTHER INFORMATION: SLC25A29
```

```
<400> SEQUENCE: 769

Glu Thr Pro Ser Phe Gly Val Tyr Phe Leu Thr Tyr Asp Ala Leu Thr
1               5                   10                  15
Arg

<210> SEQ ID NO 770
<211> LENGTH: 7
<212> TYPE: PRT
<213> ORGANISM: Artificial Sequence
<220> FEATURE:
<223> OTHER INFORMATION: SLC25A29

<400> SEQUENCE: 770

Leu Gln Ala Asp Gly Leu Arg
1               5

<210> SEQ ID NO 771
<211> LENGTH: 5
<212> TYPE: PRT
<213> ORGANISM: Artificial Sequence
<220> FEATURE:
<223> OTHER INFORMATION: SLC25A29

<400> SEQUENCE: 771

Ala Glu Gly Trp Arg
1               5

<210> SEQ ID NO 772
<211> LENGTH: 26
<212> TYPE: PRT
<213> ORGANISM: Artificial Sequence
<220> FEATURE:
<223> OTHER INFORMATION: SLC25A29

<400> SEQUENCE: 772

Gly Glu Glu Ala Gly Pro Glu Gly Glu Ala Val Pro Ala Ala Pro Ala
1               5                   10                  15

Gly Pro Ala Leu Ala Gln Pro Ser Ser Leu
            20                  25

<210> SEQ ID NO 773
<211> LENGTH: 20
<212> TYPE: PRT
<213> ORGANISM: Artificial Sequence
<220> FEATURE:
<223> OTHER INFORMATION: SLC25A3

<400> SEQUENCE: 773

Ala Asn Pro Phe Asn Thr Pro His Leu Gln Leu Val His Asp Gly Leu
1               5                   10                  15

Gly Asp Leu Arg
            20

<210> SEQ ID NO 774
<211> LENGTH: 11
<212> TYPE: PRT
<213> ORGANISM: Artificial Sequence
<220> FEATURE:
<223> OTHER INFORMATION: SLC25A3

<400> SEQUENCE: 774

Gly Ile Phe Asn Gly Phe Ser Val Thr Leu Lys
1               5                   10
```

```
<210> SEQ ID NO 775
<211> LENGTH: 12
<212> TYPE: PRT
<213> ORGANISM: Artificial Sequence
<220> FEATURE:
<223> OTHER INFORMATION: SLC25A3

<400> SEQUENCE: 775

Ile Gln Thr Gln Pro Gly Tyr Ala Asn Thr Leu Arg
1               5                   10

<210> SEQ ID NO 776
<211> LENGTH: 5
<212> TYPE: PRT
<213> ORGANISM: Artificial Sequence
<220> FEATURE:
<223> OTHER INFORMATION: SLC25A3

<400> SEQUENCE: 776

Glu Glu Gly Leu Lys
1               5

<210> SEQ ID NO 777
<211> LENGTH: 7
<212> TYPE: PRT
<213> ORGANISM: Artificial Sequence
<220> FEATURE:
<223> OTHER INFORMATION: SLC25A3

<400> SEQUENCE: 777

Thr Val Glu Ala Leu Tyr Lys
1               5

<210> SEQ ID NO 778
<211> LENGTH: 11
<212> TYPE: PRT
<213> ORGANISM: Artificial Sequence
<220> FEATURE:
<223> OTHER INFORMATION: SLC25A30

<400> SEQUENCE: 778

Leu Gln Ile Gln Gly Gln Thr Asn Asp Ala Lys
1               5                   10

<210> SEQ ID NO 779
<211> LENGTH: 5
<212> TYPE: PRT
<213> ORGANISM: Artificial Sequence
<220> FEATURE:
<223> OTHER INFORMATION: SLC25A30

<400> SEQUENCE: 779

Glu Glu Gly Leu Lys
1               5

<210> SEQ ID NO 780
<211> LENGTH: 8
<212> TYPE: PRT
<213> ORGANISM: Artificial Sequence
<220> FEATURE:
<223> OTHER INFORMATION: SLC25A30

<400> SEQUENCE: 780

Gln Ala Ser Tyr Gly Thr Ile Lys
1               5

<210> SEQ ID NO 781
<211> LENGTH: 8
```

```
<212> TYPE: PRT
<213> ORGANISM: Artificial Sequence
<220> FEATURE:
<223> OTHER INFORMATION: SLC25A30

<400> SEQUENCE: 781

Gly Val Ser Leu Thr Ala Gln Arg
1               5

<210> SEQ ID NO 782
<211> LENGTH: 9
<212> TYPE: PRT
<213> ORGANISM: Artificial Sequence
<220> FEATURE:
<223> OTHER INFORMATION: SLC25A30

<400> SEQUENCE: 782

Asn Glu Gly Phe Phe Ala Leu Tyr Lys
1               5

<210> SEQ ID NO 783
<211> LENGTH: 8
<212> TYPE: PRT
<213> ORGANISM: Artificial Sequence
<220> FEATURE:
<223> OTHER INFORMATION: SLC25A30

<400> SEQUENCE: 783

Gly Phe Trp Pro Asn Trp Leu Arg
1               5

<210> SEQ ID NO 784
<211> LENGTH: 13
<212> TYPE: PRT
<213> ORGANISM: Artificial Sequence
<220> FEATURE:
<223> OTHER INFORMATION: SLC25A31

<400> SEQUENCE: 784

Asp Leu Leu Ala Gly Gly Val Ala Ala Val Ser Lys
1               5                   10

<210> SEQ ID NO 785
<211> LENGTH: 8
<212> TYPE: PRT
<213> ORGANISM: Artificial Sequence
<220> FEATURE:
<223> OTHER INFORMATION: SLC25A31

<400> SEQUENCE: 785

Thr Ala Val Ala Pro Ile Glu Arg
1               5

<210> SEQ ID NO 786
<211> LENGTH: 10
<212> TYPE: PRT
<213> ORGANISM: Artificial Sequence
<220> FEATURE:
<223> OTHER INFORMATION: SLC25A31

<400> SEQUENCE: 786

Leu Leu Leu Gln Val Gln Ala Ser Ser Lys
1               5                   10

<210> SEQ ID NO 787
<211> LENGTH: 7
<212> TYPE: PRT
<213> ORGANISM: Artificial Sequence
```

<220> FEATURE:
<223> OTHER INFORMATION: SLC25A31

<400> SEQUENCE: 787

Gln Ile Ser Pro Glu Ala Arg
1               5

<210> SEQ ID NO 788
<211> LENGTH: 9
<212> TYPE: PRT
<213> ORGANISM: Artificial Sequence
<220> FEATURE:
<223> OTHER INFORMATION: SLC25A31

<400> SEQUENCE: 788

Glu Gln Gly Phe Phe Ser Phe Trp Arg
1               5

<210> SEQ ID NO 789
<211> LENGTH: 8
<212> TYPE: PRT
<213> ORGANISM: Artificial Sequence
<220> FEATURE:
<223> OTHER INFORMATION: SLC25A31

<400> SEQUENCE: 789

Gly Asn Leu Ala Asn Val Ile Arg
1               5

<210> SEQ ID NO 790
<211> LENGTH: 12
<212> TYPE: PRT
<213> ORGANISM: Artificial Sequence
<220> FEATURE:
<223> OTHER INFORMATION: SLC25A31

<400> SEQUENCE: 790

Tyr Phe Pro Thr Gln Ala Leu Asn Phe Ala Phe Lys
1               5                   10

<210> SEQ ID NO 791
<211> LENGTH: 7
<212> TYPE: PRT
<213> ORGANISM: Artificial Sequence
<220> FEATURE:
<223> OTHER INFORMATION: SLC25A31

<400> SEQUENCE: 791

Leu Gly Val Asp Ile Gly Lys
1               5

<210> SEQ ID NO 792
<211> LENGTH: 22
<212> TYPE: PRT
<213> ORGANISM: Artificial Sequence
<220> FEATURE:
<223> OTHER INFORMATION: SLC25A31

<400> SEQUENCE: 792

Ser Asp Gly Ile Ala Gly Leu Tyr Gln Gly Phe Gly Val Ser Val Gln
1               5                   10                  15

Gly Ile Ile Val Tyr Arg
            20

<210> SEQ ID NO 793
<211> LENGTH: 11
<212> TYPE: PRT

<213> ORGANISM: Artificial Sequence
<220> FEATURE:
<223> OTHER INFORMATION: SLC25A31

<400> SEQUENCE: 793

Ala Ser Tyr Phe Gly Ala Tyr Asp Thr Val Lys
1               5                   10

<210> SEQ ID NO 794
<211> LENGTH: 12
<212> TYPE: PRT
<213> ORGANISM: Artificial Sequence
<220> FEATURE:
<223> OTHER INFORMATION: SLC25A31

<400> SEQUENCE: 794

Ile Tyr Gln His Glu Gly Ile Ser Ser Phe Phe Arg
1               5                   10

<210> SEQ ID NO 795
<211> LENGTH: 8
<212> TYPE: PRT
<213> ORGANISM: Artificial Sequence
<220> FEATURE:
<223> OTHER INFORMATION: SLC25A31

<400> SEQUENCE: 795

Gly Ala Phe Ser Asn Val Leu Arg
1               5

<210> SEQ ID NO 796
<211> LENGTH: 13
<212> TYPE: PRT
<213> ORGANISM: Artificial Sequence
<220> FEATURE:
<223> OTHER INFORMATION: SLC25A31

<400> SEQUENCE: 796

Gly Thr Gly Gly Ala Leu Val Leu Val Leu Tyr Asp Lys
1               5                   10

<210> SEQ ID NO 797
<211> LENGTH: 10
<212> TYPE: PRT
<213> ORGANISM: Artificial Sequence
<220> FEATURE:
<223> OTHER INFORMATION: SLC25A31

<400> SEQUENCE: 797

Glu Phe Phe His Ile Asp Ile Gly Gly Arg
1               5                   10

<210> SEQ ID NO 798
<211> LENGTH: 25
<212> TYPE: PRT
<213> ORGANISM: Artificial Sequence
<220> FEATURE:
<223> OTHER INFORMATION: SLC25A32

<400> SEQUENCE: 798

Tyr Glu Asn Leu Ile Ala Gly Val Ser Gly Gly Val Leu Ser Asn Leu
1               5                   10                  15
Ala Leu His Pro Leu Asp Leu Val Lys
            20                  25

<210> SEQ ID NO 799
<211> LENGTH: 5

```
<212> TYPE: PRT
<213> ORGANISM: Artificial Sequence
<220> FEATURE:
<223> OTHER INFORMATION: SLC25A32

<400> SEQUENCE: 799

Leu Asp Gly Leu Arg
1               5

<210> SEQ ID NO 800
<211> LENGTH: 5
<212> TYPE: PRT
<213> ORGANISM: Artificial Sequence
<220> FEATURE:
<223> OTHER INFORMATION: SLC25A32

<400> SEQUENCE: 800

Tyr Glu Gly Val Arg
1               5

<210> SEQ ID NO 801
<211> LENGTH: 7
<212> TYPE: PRT
<213> ORGANISM: Artificial Sequence
<220> FEATURE:
<223> OTHER INFORMATION: SLC25A32

<400> SEQUENCE: 801

Tyr Asn Gln His Ile Asn Arg
1               5

<210> SEQ ID NO 802
<211> LENGTH: 10
<212> TYPE: PRT
<213> ORGANISM: Artificial Sequence
<220> FEATURE:
<223> OTHER INFORMATION: SLC25A34

<400> SEQUENCE: 802

Leu Gln Leu Gln Gly Glu Leu Gln Ala Arg
1               5                   10

<210> SEQ ID NO 803
<211> LENGTH: 9
<212> TYPE: PRT
<213> ORGANISM: Artificial Sequence
<220> FEATURE:
<223> OTHER INFORMATION: SLC25A34

<400> SEQUENCE: 803

Ala Asp Gly Leu Trp Gly Leu Gln Lys
1               5

<210> SEQ ID NO 804
<211> LENGTH: 17
<212> TYPE: PRT
<213> ORGANISM: Artificial Sequence
<220> FEATURE:
<223> OTHER INFORMATION: SLC25A34

<400> SEQUENCE: 804

Gln Gln Gly Leu Leu Gly Leu Trp Gln Gly Val Gly Gly Ala Val Pro
1               5                   10                  15
Arg

<210> SEQ ID NO 805
<211> LENGTH: 5
```

```
<212> TYPE: PRT
<213> ORGANISM: Artificial Sequence
<220> FEATURE:
<223> OTHER INFORMATION: SLC25A34

<400> SEQUENCE: 805

Ala Trp Val Gln Lys
1               5

<210> SEQ ID NO 806
<211> LENGTH: 11
<212> TYPE: PRT
<213> ORGANISM: Artificial Sequence
<220> FEATURE:
<223> OTHER INFORMATION: SLC25A34

<400> SEQUENCE: 806

Leu Tyr Asn Gln Pro Val Asp Thr Ala Gly Arg
1               5                   10

<210> SEQ ID NO 807
<211> LENGTH: 9
<212> TYPE: PRT
<213> ORGANISM: Artificial Sequence
<220> FEATURE:
<223> OTHER INFORMATION: SLC25A34

<400> SEQUENCE: 807

Gln Glu Gly Pro Leu Ala Leu Tyr Lys
1               5

<210> SEQ ID NO 808
<211> LENGTH: 8
<212> TYPE: PRT
<213> ORGANISM: Artificial Sequence
<220> FEATURE:
<223> OTHER INFORMATION: SLC25A34

<400> SEQUENCE: 808

Gly Leu Gly Pro Ala Tyr Leu Arg
1               5

<210> SEQ ID NO 809
<211> LENGTH: 11
<212> TYPE: PRT
<213> ORGANISM: Artificial Sequence
<220> FEATURE:
<223> OTHER INFORMATION: SLC25A35

<400> SEQUENCE: 809

Asn Val Phe His Ala Phe Ile Thr Ile Gly Lys
1               5                   10

<210> SEQ ID NO 810
<211> LENGTH: 9
<212> TYPE: PRT
<213> ORGANISM: Artificial Sequence
<220> FEATURE:
<223> OTHER INFORMATION: SLC25A35

<400> SEQUENCE: 810

Val Asp Gly Leu Ala Ala Leu Gln Lys
1               5

<210> SEQ ID NO 811
<211> LENGTH: 24
<212> TYPE: PRT
<213> ORGANISM: Artificial Sequence
```

```
<220> FEATURE:
<223> OTHER INFORMATION: SLC25A35

<400> SEQUENCE: 811

Leu Gly Thr Tyr Gly Leu Ala Glu Ala Gly Gly Tyr Leu His Thr Ala
1               5                   10                  15
Glu Gly Thr His Ser Pro Ala Arg
            20

<210> SEQ ID NO 812
<211> LENGTH: 18
<212> TYPE: PRT
<213> ORGANISM: Artificial Sequence
<220> FEATURE:
<223> OTHER INFORMATION: SLC25A35

<400> SEQUENCE: 812

Thr His Leu Gln Ala Gln Ala Ala Ser Glu Ile Ala Val Gly His Gln
1               5                   10                  15
Tyr Lys

<210> SEQ ID NO 813
<211> LENGTH: 8
<212> TYPE: PRT
<213> ORGANISM: Artificial Sequence
<220> FEATURE:
<223> OTHER INFORMATION: SLC25A35

<400> SEQUENCE: 813

His Gly Leu Val Gly Leu Trp Arg
1               5

<210> SEQ ID NO 814
<211> LENGTH: 8
<212> TYPE: PRT
<213> ORGANISM: Artificial Sequence
<220> FEATURE:
<223> OTHER INFORMATION: SLC25A35

<400> SEQUENCE: 814

Gly Ala Leu Gly Gly Leu Pro Arg
1               5

<210> SEQ ID NO 815
<211> LENGTH: 15
<212> TYPE: PRT
<213> ORGANISM: Artificial Sequence
<220> FEATURE:
<223> OTHER INFORMATION: SLC25A35

<400> SEQUENCE: 815

Asp Leu Leu Ser Gln Trp Glu Ile Phe Pro Pro Gln Ser Trp Lys
1               5                   10                  15

<210> SEQ ID NO 816
<211> LENGTH: 11
<212> TYPE: PRT
<213> ORGANISM: Artificial Sequence
<220> FEATURE:
<223> OTHER INFORMATION: SLC25A35

<400> SEQUENCE: 816

Leu Tyr Asn Gln Pro Thr Asp Ala Gln Gly Lys
1               5                   10

<210> SEQ ID NO 817
```

```
<211> LENGTH: 5
<212> TYPE: PRT
<213> ORGANISM: Artificial Sequence
<220> FEATURE:
<223> OTHER INFORMATION: SLC25A36

<400> SEQUENCE: 817

Val Ile Leu Glu Lys
1               5

<210> SEQ ID NO 818
<211> LENGTH: 13
<212> TYPE: PRT
<213> ORGANISM: Artificial Sequence
<220> FEATURE:
<223> OTHER INFORMATION: SLC25A36

<400> SEQUENCE: 818

Gly Leu Gly Pro Asn Leu Val Gly Val Ala Pro Ser Arg
1               5                   10

<210> SEQ ID NO 819
<211> LENGTH: 6
<212> TYPE: PRT
<213> ORGANISM: Artificial Sequence
<220> FEATURE:
<223> OTHER INFORMATION: SLC25A36

<400> SEQUENCE: 819

Leu Gln Leu Asp Ala Arg
1               5

<210> SEQ ID NO 820
<211> LENGTH: 5
<212> TYPE: PRT
<213> ORGANISM: Artificial Sequence
<220> FEATURE:
<223> OTHER INFORMATION: SLC25A36

<400> SEQUENCE: 820

Leu Leu Glu Tyr Lys
1               5

<210> SEQ ID NO 821
<211> LENGTH: 20
<212> TYPE: PRT
<213> ORGANISM: Artificial Sequence
<220> FEATURE:
<223> OTHER INFORMATION: SLC25A36

<400> SEQUENCE: 821

Ser Phe Phe Gln Thr Leu Ser Leu Leu Val Gln Glu Glu Gly Tyr Gly
1               5                   10                  15

Ser Leu Tyr Arg
            20

<210> SEQ ID NO 822
<211> LENGTH: 8
<212> TYPE: PRT
<213> ORGANISM: Artificial Sequence
<220> FEATURE:
<223> OTHER INFORMATION: SLC25A36

<400> SEQUENCE: 822

Gly Leu Thr Thr His Leu Val Arg
1               5
```

```
<210> SEQ ID NO 823
<211> LENGTH: 11
<212> TYPE: PRT
<213> ORGANISM: Artificial Sequence
<220> FEATURE:
<223> OTHER INFORMATION: SLC25A37

<400> SEQUENCE: 823

Ser Gly Ser Val Gly Ser Gln Ala Val Ala Arg
1               5                   10

<210> SEQ ID NO 824
<211> LENGTH: 11
<212> TYPE: PRT
<213> ORGANISM: Artificial Sequence
<220> FEATURE:
<223> OTHER INFORMATION: SLC25A37

<400> SEQUENCE: 824

Ala Gln Tyr Thr Ser Ile Tyr Gly Ala Leu Lys
1               5                   10

<210> SEQ ID NO 825
<211> LENGTH: 9
<212> TYPE: PRT
<213> ORGANISM: Artificial Sequence
<220> FEATURE:
<223> OTHER INFORMATION: SLC25A37

<400> SEQUENCE: 825

Thr Glu Gly Leu Gly Ala Phe Tyr Arg
1               5

<210> SEQ ID NO 826
<211> LENGTH: 13
<212> TYPE: PRT
<213> ORGANISM: Artificial Sequence
<220> FEATURE:
<223> OTHER INFORMATION: SLC25A37

<400> SEQUENCE: 826

Thr Val Tyr Gln Leu Asn Gly Leu Pro Ala Thr Ser Lys
1               5                   10

<210> SEQ ID NO 827
<211> LENGTH: 6
<212> TYPE: PRT
<213> ORGANISM: Artificial Sequence
<220> FEATURE:
<223> OTHER INFORMATION: SLC25A4

<400> SEQUENCE: 827

Gln Ile Ser Ala Glu Lys
1               5

<210> SEQ ID NO 828
<211> LENGTH: 9
<212> TYPE: PRT
<213> ORGANISM: Artificial Sequence
<220> FEATURE:
<223> OTHER INFORMATION: SLC25A4

<400> SEQUENCE: 828

Glu Gln Gly Phe Leu Ser Phe Trp Arg
1               5

<210> SEQ ID NO 829
<211> LENGTH: 5
```

```
<212> TYPE: PRT
<213> ORGANISM: Artificial Sequence
<220> FEATURE:
<223> OTHER INFORMATION: SLC25A4

<400> SEQUENCE: 829

Ser Asp Gly Leu Arg
1               5

<210> SEQ ID NO 830
<211> LENGTH: 6
<212> TYPE: PRT
<213> ORGANISM: Artificial Sequence
<220> FEATURE:
<223> OTHER INFORMATION: SLC25A5

<400> SEQUENCE: 830

Gln Ile Thr Ala Asp Lys
1               5

<210> SEQ ID NO 831
<211> LENGTH: 5
<212> TYPE: PRT
<213> ORGANISM: Artificial Sequence
<220> FEATURE:
<223> OTHER INFORMATION: SLC25A5

<400> SEQUENCE: 831

Ser Asp Gly Ile Lys
1               5

<210> SEQ ID NO 832
<211> LENGTH: 6
<212> TYPE: PRT
<213> ORGANISM: Artificial Sequence
<220> FEATURE:
<223> OTHER INFORMATION: SLC25A6

<400> SEQUENCE: 832

Gln Ile Ala Ala Asp Lys
1               5

<210> SEQ ID NO 833
<211> LENGTH: 9
<212> TYPE: PRT
<213> ORGANISM: Artificial Sequence
<220> FEATURE:
<223> OTHER INFORMATION: SLC25A6

<400> SEQUENCE: 833

Glu Gln Gly Val Leu Ser Phe Trp Arg
1               5

<210> SEQ ID NO 834
<211> LENGTH: 5
<212> TYPE: PRT
<213> ORGANISM: Artificial Sequence
<220> FEATURE:
<223> OTHER INFORMATION: SLC25A6

<400> SEQUENCE: 834

Ser Asp Gly Ile Arg
1               5

<210> SEQ ID NO 835
<211> LENGTH: 9
<212> TYPE: PRT
<213> ORGANISM: Artificial Sequence
```

```
<220> FEATURE:
<223> OTHER INFORMATION: SLC25A7

<400> SEQUENCE: 835

Glu Thr Ala Pro Ser Leu Gly Ser Lys
1               5

<210> SEQ ID NO 836
<211> LENGTH: 9
<212> TYPE: PRT
<213> ORGANISM: Artificial Sequence
<220> FEATURE:
<223> OTHER INFORMATION: SLC25A7

<400> SEQUENCE: 836

Tyr Thr Gly Thr Tyr Asn Ala Tyr Arg
1               5

<210> SEQ ID NO 837
<211> LENGTH: 13
<212> TYPE: PRT
<213> ORGANISM: Artificial Sequence
<220> FEATURE:
<223> OTHER INFORMATION: SLC25A7

<400> SEQUENCE: 837

Ile Ile Ala Thr Thr Glu Gly Leu Thr Gly Leu Trp Lys
1               5                   10

<210> SEQ ID NO 838
<211> LENGTH: 5
<212> TYPE: PRT
<213> ORGANISM: Artificial Sequence
<220> FEATURE:
<223> OTHER INFORMATION: SLC25A7

<400> SEQUENCE: 838

Glu Ala Phe Val Lys
1               5

<210> SEQ ID NO 839
<211> LENGTH: 10
<212> TYPE: PRT
<213> ORGANISM: Artificial Sequence
<220> FEATURE:
<223> OTHER INFORMATION: SLC25A7

<400> SEQUENCE: 839

Phe Ile Asn Ser Pro Pro Gly Gln Tyr Lys
1               5                   10

<210> SEQ ID NO 840
<211> LENGTH: 12
<212> TYPE: PRT
<213> ORGANISM: Artificial Sequence
<220> FEATURE:
<223> OTHER INFORMATION: SLC25A8

<400> SEQUENCE: 840

Leu Gln Ile Gln Gly Glu Ser Gln Gly Pro Val Arg
1               5                   10

<210> SEQ ID NO 841
<211> LENGTH: 5
<212> TYPE: PRT
<213> ORGANISM: Artificial Sequence
<220> FEATURE:
<223> OTHER INFORMATION: SLC25A8
```

```
<400> SEQUENCE: 841

Gln Phe Tyr Thr Lys
1               5

<210> SEQ ID NO 842
<211> LENGTH: 10
<212> TYPE: PRT
<213> ORGANISM: Artificial Sequence
<220> FEATURE:
<223> OTHER INFORMATION: SLC25A8

<400> SEQUENCE: 842

Gly Ser Glu His Ala Ser Ile Gly Ser Arg
1               5                   10

<210> SEQ ID NO 843
<211> LENGTH: 6
<212> TYPE: PRT
<213> ORGANISM: Artificial Sequence
<220> FEATURE:
<223> OTHER INFORMATION: SLC25A8

<400> SEQUENCE: 843

Phe Gln Ala Gln Ala Arg
1               5

<210> SEQ ID NO 844
<211> LENGTH: 5
<212> TYPE: PRT
<213> ORGANISM: Artificial Sequence
<220> FEATURE:
<223> OTHER INFORMATION: SLC25A8

<400> SEQUENCE: 844

Glu Glu Gly Phe Arg
1               5

<210> SEQ ID NO 845
<211> LENGTH: 5
<212> TYPE: PRT
<213> ORGANISM: Artificial Sequence
<220> FEATURE:
<223> OTHER INFORMATION: SLC25A8

<400> SEQUENCE: 845

Asp Ala Leu Leu Lys
1               5

<210> SEQ ID NO 846
<211> LENGTH: 14
<212> TYPE: PRT
<213> ORGANISM: Artificial Sequence
<220> FEATURE:
<223> OTHER INFORMATION: SLC25A9

<400> SEQUENCE: 846

Leu Gln Ile Gln Gly Glu Asn Gln Ala Val Gln Thr Ala Arg
1               5                   10

<210> SEQ ID NO 847
<211> LENGTH: 5
<212> TYPE: PRT
<213> ORGANISM: Artificial Sequence
<220> FEATURE:
<223> OTHER INFORMATION: SLC25A9

<400> SEQUENCE: 847
```

```
Leu Val Gln Tyr Arg
1               5

<210> SEQ ID NO 848
<211> LENGTH: 6
<212> TYPE: PRT
<213> ORGANISM: Artificial Sequence
<220> FEATURE:
<223> OTHER INFORMATION: SLC25A9

<400> SEQUENCE: 848

Gln Val Tyr Thr Pro Lys
1               5

<210> SEQ ID NO 849
<211> LENGTH: 11
<212> TYPE: PRT
<213> ORGANISM: Artificial Sequence
<220> FEATURE:
<223> OTHER INFORMATION: SLC26A1

<400> SEQUENCE: 849

Ala Leu Val Gln Asp Leu Leu Pro Ala Thr Arg
1               5                   10

<210> SEQ ID NO 850
<211> LENGTH: 6
<212> TYPE: PRT
<213> ORGANISM: Artificial Sequence
<220> FEATURE:
<223> OTHER INFORMATION: SLC26A1

<400> SEQUENCE: 850

His Leu Leu Gly Val Arg
1               5

<210> SEQ ID NO 851
<211> LENGTH: 5
<212> TYPE: PRT
<213> ORGANISM: Artificial Sequence
<220> FEATURE:
<223> OTHER INFORMATION: SLC26A1

<400> SEQUENCE: 851

Glu Leu Ser Asp Arg
1               5

<210> SEQ ID NO 852
<211> LENGTH: 7
<212> TYPE: PRT
<213> ORGANISM: Artificial Sequence
<220> FEATURE:
<223> OTHER INFORMATION: SLC26A1

<400> SEQUENCE: 852

Ser His Gly Tyr Ser Val Arg
1               5

<210> SEQ ID NO 853
<211> LENGTH: 6
<212> TYPE: PRT
<213> ORGANISM: Artificial Sequence
<220> FEATURE:
<223> OTHER INFORMATION: SLC26A1

<400> SEQUENCE: 853

Thr Ala Leu Leu Ala Arg
```

```
<210> SEQ ID NO 854
<211> LENGTH: 23
<212> TYPE: PRT
<213> ORGANISM: Artificial Sequence
<220> FEATURE:
<223> OTHER INFORMATION: SLC26A1

<400> SEQUENCE: 854

Ile Gly Asp Thr Ala Phe Tyr Glu Asp Ala Thr Glu Phe Glu Gly Leu
1               5                   10                  15

Val Pro Glu Pro Gly Val Arg
            20

<210> SEQ ID NO 855
<211> LENGTH: 10
<212> TYPE: PRT
<213> ORGANISM: Artificial Sequence
<220> FEATURE:
<223> OTHER INFORMATION: SLC26A1

<400> SEQUENCE: 855

Phe Gly Gly Pro Leu Tyr Tyr Ala Asn Lys
1               5                   10

<210> SEQ ID NO 856
<211> LENGTH: 5
<212> TYPE: PRT
<213> ORGANISM: Artificial Sequence
<220> FEATURE:
<223> OTHER INFORMATION: SLC26A1

<400> SEQUENCE: 856

Asp Ile Leu Ser Arg
1               5

<210> SEQ ID NO 857
<211> LENGTH: 29
<212> TYPE: PRT
<213> ORGANISM: Artificial Sequence
<220> FEATURE:
<223> OTHER INFORMATION: SLC26A1

<400> SEQUENCE: 857

Gly Gly Phe Leu Gly Glu Gly Pro Gly Asp Thr Ala Glu Glu Glu Gln
1               5                   10                  15

Leu Phe Leu Ser Val His Asp Ala Val Gln Thr Ala Arg
            20                  25

<210> SEQ ID NO 858
<211> LENGTH: 9
<212> TYPE: PRT
<213> ORGANISM: Artificial Sequence
<220> FEATURE:
<223> OTHER INFORMATION: SLC26A1

<400> SEQUENCE: 858

Glu Leu Glu Ala Thr Asp Ala His Leu
1               5

<210> SEQ ID NO 859
<211> LENGTH: 7
<212> TYPE: PRT
<213> ORGANISM: Artificial Sequence
<220> FEATURE:
<223> OTHER INFORMATION: SLC26A10
```

```
<400> SEQUENCE: 859

Ser Leu Gly Ser Ala Phe Lys
1               5

<210> SEQ ID NO 860
<211> LENGTH: 15
<212> TYPE: PRT
<213> ORGANISM: Artificial Sequence
<220> FEATURE:
<223> OTHER INFORMATION: SLC26A10

<400> SEQUENCE: 860

Leu Val Pro Glu Pro Leu Val Gly Asn Leu Ser Gly Ile Glu Lys
1               5                   10                  15

<210> SEQ ID NO 861
<211> LENGTH: 7
<212> TYPE: PRT
<213> ORGANISM: Artificial Sequence
<220> FEATURE:
<223> OTHER INFORMATION: SLC26A10

<400> SEQUENCE: 861

Glu Gln Leu Asp Ala Gln Arg
1               5

<210> SEQ ID NO 862
<211> LENGTH: 25
<212> TYPE: PRT
<213> ORGANISM: Artificial Sequence
<220> FEATURE:
<223> OTHER INFORMATION: SLC26A10

<400> SEQUENCE: 862

Ala Leu Thr Ser Gly Ala Ala Leu His Val Leu Leu Ser Gln Leu Pro
1               5                   10                  15

Ser Leu Leu Gly Leu Ser Leu Pro Arg
            20                  25

<210> SEQ ID NO 863
<211> LENGTH: 11
<212> TYPE: PRT
<213> ORGANISM: Artificial Sequence
<220> FEATURE:
<223> OTHER INFORMATION: SLC26A10

<400> SEQUENCE: 863

Thr Leu Ala Ser Leu Leu Thr Ala Leu Pro Arg
1               5                   10

<210> SEQ ID NO 864
<211> LENGTH: 20
<212> TYPE: PRT
<213> ORGANISM: Artificial Sequence
<220> FEATURE:
<223> OTHER INFORMATION: SLC26A10

<400> SEQUENCE: 864

Ser Ser Pro Ala Glu Leu Thr Ile Ser Ala Leu Ser Leu Ala Leu Leu
1               5                   10                  15

Val Pro Val Lys
            20

<210> SEQ ID NO 865
<211> LENGTH: 5
```

<212> TYPE: PRT
<213> ORGANISM: Artificial Sequence
<220> FEATURE:
<223> OTHER INFORMATION: SLC26A10

<400> SEQUENCE: 865

Glu Leu Asn Val Arg
1               5

<210> SEQ ID NO 866
<211> LENGTH: 26
<212> TYPE: PRT
<213> ORGANISM: Artificial Sequence
<220> FEATURE:
<223> OTHER INFORMATION: SLC26A10

<400> SEQUENCE: 866

Tyr Gln Val Gln Ile Val Gly Leu Leu Pro Gly Gly Phe Pro Gln Pro
1               5                   10                  15
Leu Leu Pro Asn Leu Ala Glu Leu Pro Arg
            20                  25

<210> SEQ ID NO 867
<211> LENGTH: 26
<212> TYPE: PRT
<213> ORGANISM: Artificial Sequence
<220> FEATURE:
<223> OTHER INFORMATION: SLC26A10

<400> SEQUENCE: 867

Ile Leu Ala Asp Ser Leu Pro Ile Ala Leu Val Ser Phe Ala Val Ser
1               5                   10                  15
Ala Ser Leu Ala Ser Ile His Ala Asp Lys
            20                  25

<210> SEQ ID NO 868
<211> LENGTH: 18
<212> TYPE: PRT
<213> ORGANISM: Artificial Sequence
<220> FEATURE:
<223> OTHER INFORMATION: SLC26A10

<400> SEQUENCE: 868

Val Val Val Leu Asp Phe Ser Gly Val Thr Phe Ala Asp Ala Ala Gly
1               5                   10                  15
Ala Arg

<210> SEQ ID NO 869
<211> LENGTH: 6
<212> TYPE: PRT
<213> ORGANISM: Artificial Sequence
<220> FEATURE:
<223> OTHER INFORMATION: SLC26A10

<400> SEQUENCE: 869

Glu Val Val Gln Val Arg
1               5

<210> SEQ ID NO 870
<211> LENGTH: 6
<212> TYPE: PRT
<213> ORGANISM: Artificial Sequence
<220> FEATURE:
<223> OTHER INFORMATION: SLC26A10

<400> SEQUENCE: 870

```
Val Gly Leu Leu Asp Arg
1               5

<210> SEQ ID NO 871
<211> LENGTH: 23
<212> TYPE: PRT
<213> ORGANISM: Artificial Sequence
<220> FEATURE:
<223> OTHER INFORMATION: SLC26A10

<400> SEQUENCE: 871

Val Thr Pro Asp Gln Leu Phe Val Ser Val Gln Asp Ala Ala Ala Tyr
1               5                   10                  15

Ala Leu Gly Ser Leu Leu Arg
            20

<210> SEQ ID NO 872
<211> LENGTH: 14
<212> TYPE: PRT
<213> ORGANISM: Artificial Sequence
<220> FEATURE:
<223> OTHER INFORMATION: SLC26A11

<400> SEQUENCE: 872

Leu Gly Phe Leu Leu Asp Phe Ile Ser Tyr Pro Val Ile Lys
1               5                   10

<210> SEQ ID NO 873
<211> LENGTH: 16
<212> TYPE: PRT
<213> ORGANISM: Artificial Sequence
<220> FEATURE:
<223> OTHER INFORMATION: SLC26A11

<400> SEQUENCE: 873

Gly Phe Thr Ser Ala Ala Ala Val Thr Ile Gly Phe Gly Gln Ile Lys
1               5                   10                  15

<210> SEQ ID NO 874
<211> LENGTH: 5
<212> TYPE: PRT
<213> ORGANISM: Artificial Sequence
<220> FEATURE:
<223> OTHER INFORMATION: SLC26A11

<400> SEQUENCE: 874

Ile Ala Glu Thr Arg
1               5

<210> SEQ ID NO 875
<211> LENGTH: 10
<212> TYPE: PRT
<213> ORGANISM: Artificial Sequence
<220> FEATURE:
<223> OTHER INFORMATION: SLC26A11

<400> SEQUENCE: 875

Gly Leu Val Trp Ala Ala Thr Thr Ala Arg
1               5                   10

<210> SEQ ID NO 876
<211> LENGTH: 6
<212> TYPE: PRT
<213> ORGANISM: Artificial Sequence
<220> FEATURE:
<223> OTHER INFORMATION: SLC26A11

<400> SEQUENCE: 876
```

Glu Glu Ile Leu Ser Arg
1               5

<210> SEQ ID NO 877
<211> LENGTH: 8
<212> TYPE: PRT
<213> ORGANISM: Artificial Sequence
<220> FEATURE:
<223> OTHER INFORMATION: SLC26A11

<400> SEQUENCE: 877

Ala Leu Glu Val Ser Pro Pro Arg
1               5

<210> SEQ ID NO 878
<211> LENGTH: 16
<212> TYPE: PRT
<213> ORGANISM: Artificial Sequence
<220> FEATURE:
<223> OTHER INFORMATION: SLC26A11

<400> SEQUENCE: 878

Gln Gly Val Ala Leu Ala Phe Val Gly Leu Gln Val Pro Val Leu Arg
1               5                   10                  15

<210> SEQ ID NO 879
<211> LENGTH: 8
<212> TYPE: PRT
<213> ORGANISM: Artificial Sequence
<220> FEATURE:
<223> OTHER INFORMATION: SLC26A11

<400> SEQUENCE: 879

Val Leu Leu Ser Ala Asp Leu Lys
1               5

<210> SEQ ID NO 880
<211> LENGTH: 8
<212> TYPE: PRT
<213> ORGANISM: Artificial Sequence
<220> FEATURE:
<223> OTHER INFORMATION: SLC26A11

<400> SEQUENCE: 880

Glu Asp Ser Ile Leu Asp Gln Lys
1               5

<210> SEQ ID NO 881
<211> LENGTH: 5
<212> TYPE: PRT
<213> ORGANISM: Artificial Sequence
<220> FEATURE:
<223> OTHER INFORMATION: SLC26A11

<400> SEQUENCE: 881

Val Ala Leu Leu Lys
1               5

<210> SEQ ID NO 882
<211> LENGTH: 8
<212> TYPE: PRT
<213> ORGANISM: Artificial Sequence
<220> FEATURE:
<223> OTHER INFORMATION: SLC26A2

<400> SEQUENCE: 882

Glu Gln His Asn Val Ser Pro Arg

-continued

```
1               5

<210> SEQ ID NO 883
<211> LENGTH: 19
<212> TYPE: PRT
<213> ORGANISM: Artificial Sequence
<220> FEATURE:
<223> OTHER INFORMATION: SLC26A2

<400> SEQUENCE: 883

Asp Ser Ala Glu Gly Asn Asp Ser Tyr Pro Ser Gly Ile His Leu Glu
1               5                   10                  15

Leu Gln Arg

<210> SEQ ID NO 884
<211> LENGTH: 7
<212> TYPE: PRT
<213> ORGANISM: Artificial Sequence
<220> FEATURE:
<223> OTHER INFORMATION: SLC26A2

<400> SEQUENCE: 884

Glu Ser Ser Thr Asp Phe Lys
1               5

<210> SEQ ID NO 885
<211> LENGTH: 5
<212> TYPE: PRT
<213> ORGANISM: Artificial Sequence
<220> FEATURE:
<223> OTHER INFORMATION: SLC26A2

<400> SEQUENCE: 885

Ile Leu Ile Glu Arg
1               5

<210> SEQ ID NO 886
<211> LENGTH: 6
<212> TYPE: PRT
<213> ORGANISM: Artificial Sequence
<220> FEATURE:
<223> OTHER INFORMATION: SLC26A2

<400> SEQUENCE: 886

Ser Asp Thr Asn Phe Lys
1               5

<210> SEQ ID NO 887
<211> LENGTH: 7
<212> TYPE: PRT
<213> ORGANISM: Artificial Sequence
<220> FEATURE:
<223> OTHER INFORMATION: SLC26A2

<400> SEQUENCE: 887

Glu Leu Asn Glu His Phe Lys
1               5

<210> SEQ ID NO 888
<211> LENGTH: 12
<212> TYPE: PRT
<213> ORGANISM: Artificial Sequence
<220> FEATURE:
<223> OTHER INFORMATION: SLC26A2

<400> SEQUENCE: 888

Ser Val Leu Gly Val Ile Thr Ile Val Asn Leu Arg
```

-continued

```
1               5                  10

<210> SEQ ID NO 889
<211> LENGTH: 20
<212> TYPE: PRT
<213> ORGANISM: Artificial Sequence
<220> FEATURE:
<223> OTHER INFORMATION: SLC26A2

<400> SEQUENCE: 889

Ser Ser Leu Leu Gly Leu Val Glu Glu Ser Glu Val Phe Glu Ser Val
1               5                   10                  15

Ser Ala Tyr Lys
            20

<210> SEQ ID NO 890
<211> LENGTH: 10
<212> TYPE: PRT
<213> ORGANISM: Artificial Sequence
<220> FEATURE:
<223> OTHER INFORMATION: SLC26A2

<400> SEQUENCE: 890

Phe Val Ala Pro Leu Tyr Tyr Ile Asn Lys
1               5                   10

<210> SEQ ID NO 891
<211> LENGTH: 5
<212> TYPE: PRT
<213> ORGANISM: Artificial Sequence
<220> FEATURE:
<223> OTHER INFORMATION: SLC26A2

<400> SEQUENCE: 891

Ser Ala Leu Tyr Lys
1               5

<210> SEQ ID NO 892
<211> LENGTH: 9
<212> TYPE: PRT
<213> ORGANISM: Artificial Sequence
<220> FEATURE:
<223> OTHER INFORMATION: SLC26A2

<400> SEQUENCE: 892

Gln Thr Val Asn Pro Ile Leu Ile Lys
1               5

<210> SEQ ID NO 893
<211> LENGTH: 7
<212> TYPE: PRT
<213> ORGANISM: Artificial Sequence
<220> FEATURE:
<223> OTHER INFORMATION: SLC26A3

<400> SEQUENCE: 893

Thr Phe Leu Asp His Leu Lys
1               5

<210> SEQ ID NO 894
<211> LENGTH: 5
<212> TYPE: PRT
<213> ORGANISM: Artificial Sequence
<220> FEATURE:
<223> OTHER INFORMATION: SLC26A3

<400> SEQUENCE: 894
```

```
Ala Val Pro Asp Arg
1               5

<210> SEQ ID NO 895
<211> LENGTH: 21
<212> TYPE: PRT
<213> ORGANISM: Artificial Sequence
<220> FEATURE:
<223> OTHER INFORMATION: SLC26A3

<400> SEQUENCE: 895

Asn Ala Thr Thr Leu Gly Leu Pro Asn Asn Ser Asn Asn Ser Ser Leu
1               5                   10                  15

Leu Asp Asp Glu Arg
            20

<210> SEQ ID NO 896
<211> LENGTH: 18
<212> TYPE: PRT
<213> ORGANISM: Artificial Sequence
<220> FEATURE:
<223> OTHER INFORMATION: SLC26A3

<400> SEQUENCE: 896

Phe Ile Phe Gln Leu Thr Val Pro Ser His Thr Asp Pro Val Ser Ile
1               5                   10                  15

Phe Lys

<210> SEQ ID NO 897
<211> LENGTH: 11
<212> TYPE: PRT
<213> ORGANISM: Artificial Sequence
<220> FEATURE:
<223> OTHER INFORMATION: SLC26A3

<400> SEQUENCE: 897

Val Leu Tyr Ser Val Phe Ser Gln Ile Glu Lys
1               5                   10

<210> SEQ ID NO 898
<211> LENGTH: 10
<212> TYPE: PRT
<213> ORGANISM: Artificial Sequence
<220> FEATURE:
<223> OTHER INFORMATION: SLC26A3

<400> SEQUENCE: 898

Ser Ala Val Gln Glu Ser Thr Gly Gly Lys
1               5                   10

<210> SEQ ID NO 899
<211> LENGTH: 5
<212> TYPE: PRT
<213> ORGANISM: Artificial Sequence
<220> FEATURE:
<223> OTHER INFORMATION: SLC26A3

<400> SEQUENCE: 899

Thr Gln Phe Pro Lys
1               5

<210> SEQ ID NO 900
<211> LENGTH: 5
<212> TYPE: PRT
<213> ORGANISM: Artificial Sequence
<220> FEATURE:
<223> OTHER INFORMATION: SLC26A3
```

```
<400> SEQUENCE: 900

Thr Asn Ile Tyr Lys
1               5

<210> SEQ ID NO 901
<211> LENGTH: 9
<212> TYPE: PRT
<213> ORGANISM: Artificial Sequence
<220> FEATURE:
<223> OTHER INFORMATION: SLC26A3

<400> SEQUENCE: 901

Gln Gly Leu Leu Gln Val Thr Pro Lys
1               5

<210> SEQ ID NO 902
<211> LENGTH: 8
<212> TYPE: PRT
<213> ORGANISM: Artificial Sequence
<220> FEATURE:
<223> OTHER INFORMATION: SLC26A3

<400> SEQUENCE: 902

Ser Ile Leu Gln Glu Phe Ile Arg
1               5

<210> SEQ ID NO 903
<211> LENGTH: 15
<212> TYPE: PRT
<213> ORGANISM: Artificial Sequence
<220> FEATURE:
<223> OTHER INFORMATION: SLC26A3

<400> SEQUENCE: 903

Val Asp Val Tyr Ile Val Gly Thr Asp Asp Phe Ile Glu Lys
1               5                   10                  15

<210> SEQ ID NO 904
<211> LENGTH: 7
<212> TYPE: PRT
<213> ORGANISM: Artificial Sequence
<220> FEATURE:
<223> OTHER INFORMATION: SLC26A3

<400> SEQUENCE: 904

Phe Asn Pro Ser Gln Glu Lys
1               5

<210> SEQ ID NO 905
<211> LENGTH: 12
<212> TYPE: PRT
<213> ORGANISM: Artificial Sequence
<220> FEATURE:
<223> OTHER INFORMATION: SLC26A3

<400> SEQUENCE: 905

Ile Asp Phe Thr Ile Asn Thr Asn Gly Gly Leu Arg
1               5                   10

<210> SEQ ID NO 906
<211> LENGTH: 9
<212> TYPE: PRT
<213> ORGANISM: Artificial Sequence
<220> FEATURE:
<223> OTHER INFORMATION: SLC26A3

<400> SEQUENCE: 906
```

Val Tyr Glu Val Pro Val Glu Thr Lys
1               5

<210> SEQ ID NO 907
<211> LENGTH: 5
<212> TYPE: PRT
<213> ORGANISM: Artificial Sequence
<220> FEATURE:
<223> OTHER INFORMATION: SLC26A4

<400> SEQUENCE: 907

Glu Ser Leu Ala Lys
1               5

<210> SEQ ID NO 908
<211> LENGTH: 11
<212> TYPE: PRT
<213> ORGANISM: Artificial Sequence
<220> FEATURE:
<223> OTHER INFORMATION: SLC26A4

<400> SEQUENCE: 908

Thr Leu Val Pro Ile Leu Glu Trp Leu Pro Lys
1               5                   10

<210> SEQ ID NO 909
<211> LENGTH: 5
<212> TYPE: PRT
<213> ORGANISM: Artificial Sequence
<220> FEATURE:
<223> OTHER INFORMATION: SLC26A4

<400> SEQUENCE: 909

Glu Leu Asn Asp Arg
1               5

<210> SEQ ID NO 910
<211> LENGTH: 8
<212> TYPE: PRT
<213> ORGANISM: Artificial Sequence
<220> FEATURE:
<223> OTHER INFORMATION: SLC26A4

<400> SEQUENCE: 910

Asn Tyr Asn Ala Gly Ile Val Lys
1               5

<210> SEQ ID NO 911
<211> LENGTH: 9
<212> TYPE: PRT
<213> ORGANISM: Artificial Sequence
<220> FEATURE:
<223> OTHER INFORMATION: SLC26A4

<400> SEQUENCE: 911

Asn Ile Glu Glu Pro Gln Gly Val Lys
1               5

<210> SEQ ID NO 912
<211> LENGTH: 9
<212> TYPE: PRT
<213> ORGANISM: Artificial Sequence
<220> FEATURE:
<223> OTHER INFORMATION: SLC26A4

<400> SEQUENCE: 912

Ser Thr Val Gly Phe Asp Ala Ile Arg

```
1               5
```

<210> SEQ ID NO 913
<211> LENGTH: 15
<212> TYPE: PRT
<213> ORGANISM: Artificial Sequence
<220> FEATURE:
<223> OTHER INFORMATION: SLC26A4

<400> SEQUENCE: 913

```
Glu Ile Glu Ile Gln Val Asp Trp Asn Ser Glu Leu Pro Val Lys
1               5                  10                  15
```

<210> SEQ ID NO 914
<211> LENGTH: 5
<212> TYPE: PRT
<213> ORGANISM: Artificial Sequence
<220> FEATURE:
<223> OTHER INFORMATION: SLC26A4

<400> SEQUENCE: 914

```
Val Asn Val Pro Lys
1               5
```

<210> SEQ ID NO 915
<211> LENGTH: 8
<212> TYPE: PRT
<213> ORGANISM: Artificial Sequence
<220> FEATURE:
<223> OTHER INFORMATION: SLC26A5

<400> SEQUENCE: 915

```
Val Pro Asp Ser Ile Ala Asp Lys
1               5
```

<210> SEQ ID NO 916
<211> LENGTH: 6
<212> TYPE: PRT
<213> ORGANISM: Artificial Sequence
<220> FEATURE:
<223> OTHER INFORMATION: SLC26A5

<400> SEQUENCE: 916

```
Trp Leu Pro Ala Tyr Lys
1               5
```

<210> SEQ ID NO 917
<211> LENGTH: 5
<212> TYPE: PRT
<213> ORGANISM: Artificial Sequence
<220> FEATURE:
<223> OTHER INFORMATION: SLC26A5

<400> SEQUENCE: 917

```
Glu Phe Asn Glu Arg
1               5
```

<210> SEQ ID NO 918
<211> LENGTH: 6
<212> TYPE: PRT
<213> ORGANISM: Artificial Sequence
<220> FEATURE:
<223> OTHER INFORMATION: SLC26A6

<400> SEQUENCE: 918

```
Trp Gly Ser Ala Pro Arg
1               5
```

```
<210> SEQ ID NO 919
<211> LENGTH: 5
<212> TYPE: PRT
<213> ORGANISM: Artificial Sequence
<220> FEATURE:
<223> OTHER INFORMATION: SLC26A6

<400> SEQUENCE: 919

Thr His Gln Trp Arg
1               5

<210> SEQ ID NO 920
<211> LENGTH: 17
<212> TYPE: PRT
<213> ORGANISM: Artificial Sequence
<220> FEATURE:
<223> OTHER INFORMATION: SLC26A6

<400> SEQUENCE: 920

Ala Tyr Ala Leu Leu Leu Gln His Leu Pro Val Leu Val Trp Leu Pro
1               5                   10                  15

Arg

<210> SEQ ID NO 921
<211> LENGTH: 16
<212> TYPE: PRT
<213> ORGANISM: Artificial Sequence
<220> FEATURE:
<223> OTHER INFORMATION: SLC26A6

<400> SEQUENCE: 921

Gly Tyr Thr Thr Ala Ala Ala Val Gln Val Phe Val Ser Gln Leu Lys
1               5                   10                  15

<210> SEQ ID NO 922
<211> LENGTH: 5
<212> TYPE: PRT
<213> ORGANISM: Artificial Sequence
<220> FEATURE:
<223> OTHER INFORMATION: SLC26A6

<400> SEQUENCE: 922

Leu Pro Gln Ser Lys
1               5

<210> SEQ ID NO 923
<211> LENGTH: 26
<212> TYPE: PRT
<213> ORGANISM: Artificial Sequence
<220> FEATURE:
<223> OTHER INFORMATION: SLC26A6

<400> SEQUENCE: 923

Phe Glu Val Asp Val Val Gly Asn Ile Pro Ala Gly Leu Val Pro Pro
1               5                   10                  15

Val Ala Pro Asn Thr Gln Leu Phe Ser Lys
            20                  25

<210> SEQ ID NO 924
<211> LENGTH: 9
<212> TYPE: PRT
<213> ORGANISM: Artificial Sequence
<220> FEATURE:
<223> OTHER INFORMATION: SLC26A6

<400> SEQUENCE: 924
```

Asp Val Ala Glu Tyr Ser Glu Ala Lys
1               5

<210> SEQ ID NO 925
<211> LENGTH: 18
<212> TYPE: PRT
<213> ORGANISM: Artificial Sequence
<220> FEATURE:
<223> OTHER INFORMATION: SLCA26A6

<400> SEQUENCE: 925

Ser Ser Ala Thr Val Tyr Phe Ala Asn Ala Glu Phe Tyr Ser Asp Ala
1               5                   10                  15

Leu Lys

<210> SEQ ID NO 926
<211> LENGTH: 8
<212> TYPE: PRT
<213> ORGANISM: Artificial Sequence
<220> FEATURE:
<223> OTHER INFORMATION: SLC26A6

<400> SEQUENCE: 926

Ala Pro Asp Gly Ser Thr Leu Lys
1               5

<210> SEQ ID NO 927
<211> LENGTH: 7
<212> TYPE: PRT
<213> ORGANISM: Artificial Sequence
<220> FEATURE:
<223> OTHER INFORMATION: SLC26A6

<400> SEQUENCE: 927

Asn Ile Phe His Asp Phe Arg
1               5

<210> SEQ ID NO 928
<211> LENGTH: 18
<212> TYPE: PRT
<213> ORGANISM: Artificial Sequence
<220> FEATURE:
<223> OTHER INFORMATION: SLC26A7

<400> SEQUENCE: 928

Leu Glu Ala Leu Leu Leu Ser Leu Leu Ser Ile Val Val Leu Val Leu
1               5                   10                  15

Val Lys

<210> SEQ ID NO 929
<211> LENGTH: 10
<212> TYPE: PRT
<213> ORGANISM: Artificial Sequence
<220> FEATURE:
<223> OTHER INFORMATION: SLC26A7

<400> SEQUENCE: 929

Thr Ala Gly Leu Tyr Ser Thr Gly Ala Lys
1               5                   10

<210> SEQ ID NO 930
<211> LENGTH: 14
<212> TYPE: PRT
<213> ORGANISM: Artificial Sequence
<220> FEATURE:
<223> OTHER INFORMATION: SLC26A8

```
<400> SEQUENCE: 930

Ile Leu Leu Leu Gly Gln Ile Pro Asn Thr Asn Ile Tyr Arg
1               5                   10

<210> SEQ ID NO 931
<211> LENGTH: 9
<212> TYPE: PRT
<213> ORGANISM: Artificial Sequence
<220> FEATURE:
<223> OTHER INFORMATION: SLC26A8

<400> SEQUENCE: 931

Glu Ile Ile Thr Ile Pro Gly Val Lys
1               5

<210> SEQ ID NO 932
<211> LENGTH: 6
<212> TYPE: PRT
<213> ORGANISM: Artificial Sequence
<220> FEATURE:
<223> OTHER INFORMATION: SLC26A8

<400> SEQUENCE: 932

Ile Leu Tyr Thr Glu Arg
1               5

<210> SEQ ID NO 933
<211> LENGTH: 5
<212> TYPE: PRT
<213> ORGANISM: Artificial Sequence
<220> FEATURE:
<223> OTHER INFORMATION: SLC26A9

<400> SEQUENCE: 933

Tyr Val Val Asp Arg
1               5

<210> SEQ ID NO 934
<211> LENGTH: 7
<212> TYPE: PRT
<213> ORGANISM: Artificial Sequence
<220> FEATURE:
<223> OTHER INFORMATION: SLC26A9

<400> SEQUENCE: 934

Thr Tyr Pro Val Gly Glu Lys
1               5

<210> SEQ ID NO 935
<211> LENGTH: 15
<212> TYPE: PRT
<213> ORGANISM: Artificial Sequence
<220> FEATURE:
<223> OTHER INFORMATION: SLC26A9

<400> SEQUENCE: 935

Ala Val Val Phe Gly Leu Leu Pro Val Leu Ser Trp Leu Pro Lys
1               5                   10                  15

<210> SEQ ID NO 936
<211> LENGTH: 24
<212> TYPE: PRT
<213> ORGANISM: Artificial Sequence
<220> FEATURE:
<223> OTHER INFORMATION: SLC26A9

<400> SEQUENCE: 936
```

Asn Leu Pro His Thr Asn Ile Ala Ser Leu Ile Phe Ala Leu Ile Ser
1               5                   10                  15

Gly Ala Phe Leu Val Leu Val Lys
            20

<210> SEQ ID NO 937
<211> LENGTH: 5
<212> TYPE: PRT
<213> ORGANISM: Artificial Sequence
<220> FEATURE:
<223> OTHER INFORMATION: SLC26A9

<400> SEQUENCE: 937

Glu Leu Asn Ala Arg
1               5

<210> SEQ ID NO 938
<211> LENGTH: 14
<212> TYPE: PRT
<213> ORGANISM: Artificial Sequence
<220> FEATURE:
<223> OTHER INFORMATION: SLC26A9

<400> SEQUENCE: 938

Gly Phe Pro Thr Pro Val Ser Pro Val Val Ser Gln Trp Lys
1               5                   10

<210> SEQ ID NO 939
<211> LENGTH: 5
<212> TYPE: PRT
<213> ORGANISM: Artificial Sequence
<220> FEATURE:
<223> OTHER INFORMATION: SLC26A9

<400> SEQUENCE: 939

Thr Leu Ala Asn Lys
1               5

<210> SEQ ID NO 940
<211> LENGTH: 12
<212> TYPE: PRT
<213> ORGANISM: Artificial Sequence
<220> FEATURE:
<223> OTHER INFORMATION: SLC26A9

<400> SEQUENCE: 940

Ser Val Leu Gly Ala Leu Ile Ala Val Asn Leu Lys
1               5                   10

<210> SEQ ID NO 941
<211> LENGTH: 8
<212> TYPE: PRT
<213> ORGANISM: Artificial Sequence
<220> FEATURE:
<223> OTHER INFORMATION: SLC26A9

<400> SEQUENCE: 941

Ala Gln Asp Ile Gln Gly Ile Lys
1               5

<210> SEQ ID NO 942
<211> LENGTH: 5
<212> TYPE: PRT
<213> ORGANISM: Artificial Sequence
<220> FEATURE:
<223> OTHER INFORMATION: SLC26A9

<400> SEQUENCE: 942

Val Leu Leu Ala Lys
1               5

<210> SEQ ID NO 943
<211> LENGTH: 7
<212> TYPE: PRT
<213> ORGANISM: Artificial Sequence
<220> FEATURE:
<223> OTHER INFORMATION: SLC26A9

<400> SEQUENCE: 943

Leu Ser Ser Thr Tyr Gly Lys
1               5

<210> SEQ ID NO 944
<211> LENGTH: 18
<212> TYPE: PRT
<213> ORGANISM: Artificial Sequence
<220> FEATURE:
<223> OTHER INFORMATION: SLC26A9

<400> SEQUENCE: 944

His Val Phe Pro Ser Ile His Asp Ala Val Leu Phe Ala Gln Ala Asn
1               5                   10                  15

Ala Arg

<210> SEQ ID NO 945
<211> LENGTH: 27
<212> TYPE: PRT
<213> ORGANISM: Artificial Sequence
<220> FEATURE:
<223> OTHER INFORMATION: SLC26A9

<400> SEQUENCE: 945

Asp Val Thr Pro Gly His Asn Phe Gln Gly Ala Pro Gly Asp Ala Glu
1               5                   10                  15

Leu Ser Leu Tyr Asp Ser Glu Glu Asp Ile Arg
            20                  25

<210> SEQ ID NO 946
<211> LENGTH: 8
<212> TYPE: PRT
<213> ORGANISM: Artificial Sequence
<220> FEATURE:
<223> OTHER INFORMATION: SLC27A1

<400> SEQUENCE: 946

Ile Phe Gln Ala Val Val Gln Arg
1               5

<210> SEQ ID NO 947
<211> LENGTH: 12
<212> TYPE: PRT
<213> ORGANISM: Artificial Sequence
<220> FEATURE:
<223> OTHER INFORMATION: SLC27A1

<400> SEQUENCE: 947

Leu Leu Pro Gln Val Asp Thr Thr Gly Thr Phe Lys
1               5                   10

<210> SEQ ID NO 948
<211> LENGTH: 15
<212> TYPE: PRT
<213> ORGANISM: Artificial Sequence
<220> FEATURE:

<223> OTHER INFORMATION: SLC27A1

<400> SEQUENCE: 948

Gly Glu Asn Val Ser Thr Thr Glu Val Glu Gly Val Leu Ser Arg
1               5                   10                  15

<210> SEQ ID NO 949
<211> LENGTH: 13
<212> TYPE: PRT
<213> ORGANISM: Artificial Sequence
<220> FEATURE:
<223> OTHER INFORMATION: SLC27A2

<400> SEQUENCE: 949

Thr Ser Asn Thr Asp Gly Ile Asp Ser Phe Leu Asp Lys
1               5                   10

<210> SEQ ID NO 950
<211> LENGTH: 9
<212> TYPE: PRT
<213> ORGANISM: Artificial Sequence
<220> FEATURE:
<223> OTHER INFORMATION: SLC27A2

<400> SEQUENCE: 950

Ala Leu His Asp His Leu Gly Leu Arg
1               5

<210> SEQ ID NO 951
<211> LENGTH: 14
<212> TYPE: PRT
<213> ORGANISM: Artificial Sequence
<220> FEATURE:
<223> OTHER INFORMATION: SLC27A2

<400> SEQUENCE: 951

Val Asp Glu Val Ser Thr Glu Pro Ile Pro Glu Ser Trp Arg
1               5                   10

<210> SEQ ID NO 952
<211> LENGTH: 12
<212> TYPE: PRT
<213> ORGANISM: Artificial Sequence
<220> FEATURE:
<223> OTHER INFORMATION: SLC27A2

<400> SEQUENCE: 952

Ile Gln Asp Thr Ile Glu Ile Thr Gly Thr Phe Lys
1               5                   10

<210> SEQ ID NO 953
<211> LENGTH: 8
<212> TYPE: PRT
<213> ORGANISM: Artificial Sequence
<220> FEATURE:
<223> OTHER INFORMATION: SLC27A2

<400> SEQUENCE: 953

Leu Ala Leu Gly Asn Gly Leu Arg
1               5

<210> SEQ ID NO 954
<211> LENGTH: 14
<212> TYPE: PRT
<213> ORGANISM: Artificial Sequence
<220> FEATURE:
<223> OTHER INFORMATION: SLC27A3

-continued

```
<400> SEQUENCE: 954

Leu Ala Val Gly Ser Gly Leu Arg Pro Asp Thr Trp Glu Arg
1               5                   10

<210> SEQ ID NO 955
<211> LENGTH: 12
<212> TYPE: PRT
<213> ORGANISM: Artificial Sequence
<220> FEATURE:
<223> OTHER INFORMATION: SLC27A3

<400> SEQUENCE: 955

Leu Gln Glu Ser Leu Ala Thr Thr Glu Thr Phe Lys
1               5                   10

<210> SEQ ID NO 956
<211> LENGTH: 9
<212> TYPE: PRT
<213> ORGANISM: Artificial Sequence
<220> FEATURE:
<223> OTHER INFORMATION: SLC27A3

<400> SEQUENCE: 956

His Ile Phe Pro Phe Ser Leu Ile Arg
1               5

<210> SEQ ID NO 957
<211> LENGTH: 8
<212> TYPE: PRT
<213> ORGANISM: Artificial Sequence
<220> FEATURE:
<223> OTHER INFORMATION: SLC27A3

<400> SEQUENCE: 957

Leu Ala Glu Leu Ala Gln Gln Arg
1               5

<210> SEQ ID NO 958
<211> LENGTH: 15
<212> TYPE: PRT
<213> ORGANISM: Artificial Sequence
<220> FEATURE:
<223> OTHER INFORMATION: SLC27A4

<400> SEQUENCE: 958

Thr Ala Leu Ile Phe Glu Gly Thr Asp Thr His Trp Thr Phe Arg
1               5                   10                  15

<210> SEQ ID NO 959
<211> LENGTH: 8
<212> TYPE: PRT
<213> ORGANISM: Artificial Sequence
<220> FEATURE:
<223> OTHER INFORMATION: SLC27A4

<400> SEQUENCE: 959

Ala Ala Ile Val Val His Ser Arg
1               5

<210> SEQ ID NO 960
<211> LENGTH: 15
<212> TYPE: PRT
<213> ORGANISM: Artificial Sequence
<220> FEATURE:
<223> OTHER INFORMATION: SLC27A4

<400> SEQUENCE: 960
```

```
Gly Glu Asn Val Ser Thr Thr Glu Val Glu Gly Thr Leu Ser Arg
1               5                   10                  15
```

<210> SEQ ID NO 961
<211> LENGTH: 10
<212> TYPE: PRT
<213> ORGANISM: Artificial Sequence
<220> FEATURE:
<223> OTHER INFORMATION: SLC27A4

<400> SEQUENCE: 961

```
Gln Ser Ile Trp Thr Asn Phe Ser Ser Arg
1               5                   10
```

<210> SEQ ID NO 962
<211> LENGTH: 7
<212> TYPE: PRT
<213> ORGANISM: Artificial Sequence
<220> FEATURE:
<223> OTHER INFORMATION: SLC27A4

<400> SEQUENCE: 962

```
Leu Leu Pro Glu Leu His Lys
1               5
```

<210> SEQ ID NO 963
<211> LENGTH: 12
<212> TYPE: PRT
<213> ORGANISM: Artificial Sequence
<220> FEATURE:
<223> OTHER INFORMATION: SLC27A5

<400> SEQUENCE: 963

```
Gln Pro Pro Asp Thr Phe Val Asp Ala Phe Glu Arg
1               5                   10
```

<210> SEQ ID NO 964
<211> LENGTH: 10
<212> TYPE: PRT
<213> ORGANISM: Artificial Sequence
<220> FEATURE:
<223> OTHER INFORMATION: SLC27A5

<400> SEQUENCE: 964

```
Ala Asp Val Trp Glu Thr Phe Gln Gln Arg
1               5                   10
```

<210> SEQ ID NO 965
<211> LENGTH: 11
<212> TYPE: PRT
<213> ORGANISM: Artificial Sequence
<220> FEATURE:
<223> OTHER INFORMATION: SLC27A5

<400> SEQUENCE: 965

```
Trp Leu Pro Ala Asp Val Ile Phe Leu Ala Lys
1               5                   10
```

<210> SEQ ID NO 966
<211> LENGTH: 11
<212> TYPE: PRT
<213> ORGANISM: Artificial Sequence
<220> FEATURE:
<223> OTHER INFORMATION: SLC27A6

<400> SEQUENCE: 966

```
Ala Ala Val Ile Ser Gln Leu Gln Val Leu Arg
1               5                   10
```

<210> SEQ ID NO 967
<211> LENGTH: 8
<212> TYPE: PRT
<213> ORGANISM: Artificial Sequence
<220> FEATURE:
<223> OTHER INFORMATION: SLC27A6

<400> SEQUENCE: 967

Leu Ala Ile Gly Asn Gly Ile Arg
1               5

<210> SEQ ID NO 968
<211> LENGTH: 12
<212> TYPE: PRT
<213> ORGANISM: Artificial Sequence
<220> FEATURE:
<223> OTHER INFORMATION: SLC27A6

<400> SEQUENCE: 968

His Gln Leu Val Glu Asp Gly Phe Asn Pro Leu Lys
1               5                   10

<210> SEQ ID NO 969
<211> LENGTH: 9
<212> TYPE: PRT
<213> ORGANISM: Artificial Sequence
<220> FEATURE:
<223> OTHER INFORMATION: SLC27A6

<400> SEQUENCE: 969

Leu Leu Ser Thr Phe Asp Leu Ile Lys
1               5

<210> SEQ ID NO 970
<211> LENGTH: 6
<212> TYPE: PRT
<213> ORGANISM: Artificial Sequence
<220> FEATURE:
<223> OTHER INFORMATION: SLC28A2

<400> SEQUENCE: 970

Gln Trp Ile Ser Val Arg
1               5

<210> SEQ ID NO 971
<211> LENGTH: 6
<212> TYPE: PRT
<213> ORGANISM: Artificial Sequence
<220> FEATURE:
<223> OTHER INFORMATION: SLC28A2

<400> SEQUENCE: 971

Ser Glu Glu Gly Val Lys
1               5

<210> SEQ ID NO 972
<211> LENGTH: 16
<212> TYPE: PRT
<213> ORGANISM: Artificial Sequence
<220> FEATURE:
<223> OTHER INFORMATION: SLC28A2

<400> SEQUENCE: 972

Phe Phe Ile Asn Glu Phe Val Ala Tyr Gln Gln Leu Ser Gln Tyr Lys
1               5                   10                  15

<210> SEQ ID NO 973
<211> LENGTH: 9
<212> TYPE: PRT
<213> ORGANISM: Artificial Sequence
<220> FEATURE:
<223> OTHER INFORMATION: SLC29A3

<400> SEQUENCE: 973

Ala Asp Gln Glu Ala Leu Leu Glu Lys
1               5

<210> SEQ ID NO 974
<211> LENGTH: 9
<212> TYPE: PRT
<213> ORGANISM: Artificial Sequence
<220> FEATURE:
<223> OTHER INFORMATION: SLC29A3

<400> SEQUENCE: 974

Gly Ser Gly Ser Leu Trp Thr Thr Lys
1               5

<210> SEQ ID NO 975
<211> LENGTH: 14
<212> TYPE: PRT
<213> ORGANISM: Artificial Sequence
<220> FEATURE:
<223> OTHER INFORMATION: SLC29A3

<400> SEQUENCE: 975

Gln Leu Thr Ala Trp Ile Gln Val Pro Gly Pro Asn Ser Lys
1               5                   10

<210> SEQ ID NO 976
<211> LENGTH: 9
<212> TYPE: PRT
<213> ORGANISM: Artificial Sequence
<220> FEATURE:
<223> OTHER INFORMATION: SLC29A3

<400> SEQUENCE: 976

Ala Leu Pro Gly Phe Val Leu Leu Arg
1               5

<210> SEQ ID NO 977
<211> LENGTH: 6
<212> TYPE: PRT
<213> ORGANISM: Artificial Sequence
<220> FEATURE:
<223> OTHER INFORMATION: SLC2A11

<400> SEQUENCE: 977

Thr Gln Ile Gln Gly Arg
1               5

<210> SEQ ID NO 978
<211> LENGTH: 7
<212> TYPE: PRT
<213> ORGANISM: Artificial Sequence
<220> FEATURE:
<223> OTHER INFORMATION: SLC2A11

<400> SEQUENCE: 978

Ala Gly Val Pro Glu Ala Lys
1               5

<210> SEQ ID NO 979
<211> LENGTH: 7

```
<212> TYPE: PRT
<213> ORGANISM: Artificial Sequence
<220> FEATURE:
<223> OTHER INFORMATION: SLC2A11

<400> SEQUENCE: 979

Thr Phe Gln Glu Ile Ser Lys
1               5

<210> SEQ ID NO 980
<211> LENGTH: 7
<212> TYPE: PRT
<213> ORGANISM: Artificial Sequence
<220> FEATURE:
<223> OTHER INFORMATION: SLC2A11

<400> SEQUENCE: 980

Ala Gln Gly Pro Thr Trp Arg
1               5

<210> SEQ ID NO 981
<211> LENGTH: 7
<212> TYPE: PRT
<213> ORGANISM: Artificial Sequence
<220> FEATURE:
<223> OTHER INFORMATION: SLC2A12

<400> SEQUENCE: 981

Gly Ile Ser Ser His Ser Arg
1               5

<210> SEQ ID NO 982
<211> LENGTH: 17
<212> TYPE: PRT
<213> ORGANISM: Artificial Sequence
<220> FEATURE:
<223> OTHER INFORMATION: SLC2A12

<400> SEQUENCE: 982

Val Ile Ser Thr Ile Pro Ala Thr Leu Leu Val Asp His Val Gly Ser
1               5                   10                  15

Lys

<210> SEQ ID NO 983
<211> LENGTH: 5
<212> TYPE: PRT
<213> ORGANISM: Artificial Sequence
<220> FEATURE:
<223> OTHER INFORMATION: SLC2A13

<400> SEQUENCE: 983

Gly Gln Thr Gln Lys
1               5

<210> SEQ ID NO 984
<211> LENGTH: 5
<212> TYPE: PRT
<213> ORGANISM: Artificial Sequence
<220> FEATURE:
<223> OTHER INFORMATION: SLC2A13

<400> SEQUENCE: 984

Trp Leu Ile Gln Lys
1               5

<210> SEQ ID NO 985
<211> LENGTH: 7
```

```
<212> TYPE: PRT
<213> ORGANISM: Artificial Sequence
<220> FEATURE:
<223> OTHER INFORMATION: SLC2A13

<400> SEQUENCE: 985

Glu Thr Leu Leu Ala Gly Arg
1               5

<210> SEQ ID NO 986
<211> LENGTH: 6
<212> TYPE: PRT
<213> ORGANISM: Artificial Sequence
<220> FEATURE:
<223> OTHER INFORMATION: SLC2A13

<400> SEQUENCE: 986

Tyr Ile Glu Tyr Ile Arg
1               5

<210> SEQ ID NO 987
<211> LENGTH: 11
<212> TYPE: PRT
<213> ORGANISM: Artificial Sequence
<220> FEATURE:
<223> OTHER INFORMATION: SLC2A13

<400> SEQUENCE: 987

Glu Val Gly Ser Ala Gly Pro Val Ile Cys Arg
1               5                   10

<210> SEQ ID NO 988
<211> LENGTH: 15
<212> TYPE: PRT
<213> ORGANISM: Artificial Sequence
<220> FEATURE:
<223> OTHER INFORMATION: SLC2A13

<400> SEQUENCE: 988

Gly Ser Asn Tyr His Leu Ser Asp Asn Asp Ala Ser Asp Val Glu
1               5                   10                  15

<210> SEQ ID NO 989
<211> LENGTH: 6
<212> TYPE: PRT
<213> ORGANISM: Artificial Sequence
<220> FEATURE:
<223> OTHER INFORMATION: SLC2A14

<400> SEQUENCE: 989

Phe Leu Leu Ile Asn Arg
1               5

<210> SEQ ID NO 990
<211> LENGTH: 7
<212> TYPE: PRT
<213> ORGANISM: Artificial Sequence
<220> FEATURE:
<223> OTHER INFORMATION: SLC2A14

<400> SEQUENCE: 990

Thr Phe Glu Asp Ile Thr Arg
1               5

<210> SEQ ID NO 991
<211> LENGTH: 11
<212> TYPE: PRT
<213> ORGANISM: Artificial Sequence
```

```
<220> FEATURE:
<223> OTHER INFORMATION: SLC2A14

<400> SEQUENCE: 991

Ala Phe Glu Gly Gln Ala His Gly Ala Asp Arg
1               5                   10

<210> SEQ ID NO 992
<211> LENGTH: 10
<212> TYPE: PRT
<213> ORGANISM: Artificial Sequence
<220> FEATURE:
<223> OTHER INFORMATION: SLC2A3

<400> SEQUENCE: 992

Ala Phe Glu Gly Gln Ala His Ser Gly Lys
1               5                   10

<210> SEQ ID NO 993
<211> LENGTH: 11
<212> TYPE: PRT
<213> ORGANISM: Artificial Sequence
<220> FEATURE:
<223> OTHER INFORMATION: SLC2A3

<400> SEQUENCE: 993

Glu Glu Asp Gln Ala Thr Glu Ile Leu Gln Arg
1               5                   10

<210> SEQ ID NO 994
<211> LENGTH: 7
<212> TYPE: PRT
<213> ORGANISM: Artificial Sequence
<220> FEATURE:
<223> OTHER INFORMATION: SLC2A3

<400> SEQUENCE: 994

Thr Phe Glu Asp Ile Ala Arg
1               5

<210> SEQ ID NO 995
<211> LENGTH: 6
<212> TYPE: PRT
<213> ORGANISM: Artificial Sequence
<220> FEATURE:
<223> OTHER INFORMATION: SLC2A3

<400> SEQUENCE: 995

Glu Thr Pro Gly Asn Ala
1               5

<210> SEQ ID NO 996
<211> LENGTH: 15
<212> TYPE: PRT
<213> ORGANISM: Artificial Sequence
<220> FEATURE:
<223> OTHER INFORMATION: SLC2A4

<400> SEQUENCE: 996

Leu Thr Gly Trp Ala Asp Val Ser Gly Val Leu Ala Glu Leu Lys
1               5                   10                  15

<210> SEQ ID NO 997
<211> LENGTH: 11
<212> TYPE: PRT
<213> ORGANISM: Artificial Sequence
<220> FEATURE:
<223> OTHER INFORMATION: SLC2A4
```

```
<400> SEQUENCE: 997

Thr Phe Asp Gln Ile Ser Ala Ala Phe His Arg
1               5                   10

<210> SEQ ID NO 998
<211> LENGTH: 7
<212> TYPE: PRT
<213> ORGANISM: Artificial Sequence
<220> FEATURE:
<223> OTHER INFORMATION: SLC2A5

<400> SEQUENCE: 998

Gly Trp Asp Ser Val Asp Arg
1               5

<210> SEQ ID NO 999
<211> LENGTH: 11
<212> TYPE: PRT
<213> ORGANISM: Artificial Sequence
<220> FEATURE:
<223> OTHER INFORMATION: SLC2A5

<400> SEQUENCE: 999

Thr Phe Ile Glu Ile Asn Gln Ile Phe Thr Lys
1               5                   10

<210> SEQ ID NO 1000
<211> LENGTH: 7
<212> TYPE: PRT
<213> ORGANISM: Artificial Sequence
<220> FEATURE:
<223> OTHER INFORMATION: SLC2A6

<400> SEQUENCE: 1000

Val Gly Thr Leu Gln Asn Lys
1               5

<210> SEQ ID NO 1001
<211> LENGTH: 10
<212> TYPE: PRT
<213> ORGANISM: Artificial Sequence
<220> FEATURE:
<223> OTHER INFORMATION: SLC2A6

<400> SEQUENCE: 1001

Ser Leu Asp Pro Asp Leu His Leu Thr Lys
1               5                   10

<210> SEQ ID NO 1002
<211> LENGTH: 6
<212> TYPE: PRT
<213> ORGANISM: Artificial Sequence
<220> FEATURE:
<223> OTHER INFORMATION: SLC2A7

<400> SEQUENCE: 1002

Tyr Ser Leu Ile Gln Lys
1               5

<210> SEQ ID NO 1003
<211> LENGTH: 10
<212> TYPE: PRT
<213> ORGANISM: Artificial Sequence
<220> FEATURE:
<223> OTHER INFORMATION: SLC30A1

<400> SEQUENCE: 1003
```

```
Leu Asp Pro Ala Asp Pro Glu Asn Pro Arg
1               5                   10

<210> SEQ ID NO 1004
<211> LENGTH: 7
<212> TYPE: PRT
<213> ORGANISM: Artificial Sequence
<220> FEATURE:
<223> OTHER INFORMATION: SLC30A1

<400> SEQUENCE: 1004

Asn Thr Phe Gly Trp Ile Arg
1               5

<210> SEQ ID NO 1005
<211> LENGTH: 8
<212> TYPE: PRT
<213> ORGANISM: Artificial Sequence
<220> FEATURE:
<223> OTHER INFORMATION: SLC30A1

<400> SEQUENCE: 1005

Ile Ile Ala Thr Val His Ile Lys
1               5

<210> SEQ ID NO 1006
<211> LENGTH: 16
<212> TYPE: PRT
<213> ORGANISM: Artificial Sequence
<220> FEATURE:
<223> OTHER INFORMATION: SLC30A10

<400> SEQUENCE: 1006

Gly Ala Thr Val Phe Ala Asn Val Ala Glu Leu Ile His Asn Thr Arg
1               5                   10                  15

<210> SEQ ID NO 1007
<211> LENGTH: 6
<212> TYPE: PRT
<213> ORGANISM: Artificial Sequence
<220> FEATURE:
<223> OTHER INFORMATION: SLC30A10

<400> SEQUENCE: 1007

Leu Ala Arg Pro Glu Arg
1               5

<210> SEQ ID NO 1008
<211> LENGTH: 6
<212> TYPE: PRT
<213> ORGANISM: Artificial Sequence
<220> FEATURE:
<223> OTHER INFORMATION: SLC30A11

<400> SEQUENCE: 1008

Thr Gln Ile Gln Gly Arg
1               5

<210> SEQ ID NO 1009
<211> LENGTH: 20
<212> TYPE: PRT
<213> ORGANISM: Artificial Sequence
<220> FEATURE:
<223> OTHER INFORMATION: SLC30A11

<400> SEQUENCE: 1009

Ser Leu Leu Val Asn Asn Ile Phe Val Val Ser Ala Ala Ile Leu Phe
```

```
                1               5                  10                  15

Gly Phe Ser Arg
            20

<210> SEQ ID NO 1010
<211> LENGTH: 7
<212> TYPE: PRT
<213> ORGANISM: Artificial Sequence
<220> FEATURE:
<223> OTHER INFORMATION: SLC30A11

<400> SEQUENCE: 1010

Ala Gln Gly Pro Thr Trp Arg
1               5

<210> SEQ ID NO 1011
<211> LENGTH: 11
<212> TYPE: PRT
<213> ORGANISM: Artificial Sequence
<220> FEATURE:
<223> OTHER INFORMATION: SLC30A2

<400> SEQUENCE: 1011

Gln His Leu Leu Asp Ala Arg Pro Ala Ile Arg
1               5                   10

<210> SEQ ID NO 1012
<211> LENGTH: 8
<212> TYPE: PRT
<213> ORGANISM: Artificial Sequence
<220> FEATURE:
<223> OTHER INFORMATION: SLC30A2

<400> SEQUENCE: 1012

Gly Val Asp Phe Thr Ala Val Arg
1               5

<210> SEQ ID NO 1013
<211> LENGTH: 8
<212> TYPE: PRT
<213> ORGANISM: Artificial Sequence
<220> FEATURE:
<223> OTHER INFORMATION: SLC30A3

<400> SEQUENCE: 1013

Gly Gly Ala Gly Gly Ser Leu Arg
1               5

<210> SEQ ID NO 1014
<211> LENGTH: 10
<212> TYPE: PRT
<213> ORGANISM: Artificial Sequence
<220> FEATURE:
<223> OTHER INFORMATION: SLC30A3

<400> SEQUENCE: 1014

Asp Thr Leu Leu Ser Val Pro Gly Val Arg
1               5                   10

<210> SEQ ID NO 1015
<211> LENGTH: 8
<212> TYPE: PRT
<213> ORGANISM: Artificial Sequence
<220> FEATURE:
<223> OTHER INFORMATION: SLC30A3

<400> SEQUENCE: 1015
```

```
Asn Val Gly Phe Glu Pro Val Arg
1               5

<210> SEQ ID NO 1016
<211> LENGTH: 12
<212> TYPE: PRT
<213> ORGANISM: Artificial Sequence
<220> FEATURE:
<223> OTHER INFORMATION: SLC30A3

<400> SEQUENCE: 1016

Asp Pro Leu Pro Pro Pro Gly Leu Thr Pro Glu Arg
1               5                   10

<210> SEQ ID NO 1017
<211> LENGTH: 7
<212> TYPE: PRT
<213> ORGANISM: Artificial Sequence
<220> FEATURE:
<223> OTHER INFORMATION: SLC30A4

<400> SEQUENCE: 1017

Phe Thr Phe Gly Phe His Arg
1               5

<210> SEQ ID NO 1018
<211> LENGTH: 10
<212> TYPE: PRT
<213> ORGANISM: Artificial Sequence
<220> FEATURE:
<223> OTHER INFORMATION: SLC30A4

<400> SEQUENCE: 1018

Asn His Gly Gln Asp Ser Leu Ala Val Arg
1               5                   10

<210> SEQ ID NO 1019
<211> LENGTH: 16
<212> TYPE: PRT
<213> ORGANISM: Artificial Sequence
<220> FEATURE:
<223> OTHER INFORMATION: SLC30A4

<400> SEQUENCE: 1019

Ser Thr Ala Ile Val His Ile Gln Leu Ile Pro Gly Ser Ser Ser Lys
1               5                   10                  15

<210> SEQ ID NO 1020
<211> LENGTH: 14
<212> TYPE: PRT
<213> ORGANISM: Artificial Sequence
<220> FEATURE:
<223> OTHER INFORMATION: SLC30A4

<400> SEQUENCE: 1020

His Ser His Ser His Ser Leu Pro Ser Asn Ser Pro Thr Arg
1               5                   10

<210> SEQ ID NO 1021
<211> LENGTH: 7
<212> TYPE: PRT
<213> ORGANISM: Artificial Sequence
<220> FEATURE:
<223> OTHER INFORMATION: SLC30A4

<400> SEQUENCE: 1021

Trp Glu Glu Val Gln Ser Lys
1               5
```

<210> SEQ ID NO 1022
<211> LENGTH: 8
<212> TYPE: PRT
<213> ORGANISM: Artificial Sequence
<220> FEATURE:
<223> OTHER INFORMATION: SLC30A5

<400> SEQUENCE: 1022

His Gln Ile Ile Gly Ser Leu Lys
1               5

<210> SEQ ID NO 1023
<211> LENGTH: 8
<212> TYPE: PRT
<213> ORGANISM: Artificial Sequence
<220> FEATURE:
<223> OTHER INFORMATION: SLC30A5

<400> SEQUENCE: 1023

Val Gly Phe His Thr Ala Ser Arg
1               5

<210> SEQ ID NO 1024
<211> LENGTH: 6
<212> TYPE: PRT
<213> ORGANISM: Artificial Sequence
<220> FEATURE:
<223> OTHER INFORMATION: SLC30A6

<400> SEQUENCE: 1024

Leu Leu Gln Glu Phe Arg
1               5

<210> SEQ ID NO 1025
<211> LENGTH: 11
<212> TYPE: PRT
<213> ORGANISM: Artificial Sequence
<220> FEATURE:
<223> OTHER INFORMATION: SLC30A6

<400> SEQUENCE: 1025

Phe Leu Glu Gln Pro Glu Ile His Thr Gly Arg
1               5                   10

<210> SEQ ID NO 1026
<211> LENGTH: 16
<212> TYPE: PRT
<213> ORGANISM: Artificial Sequence
<220> FEATURE:
<223> OTHER INFORMATION: SLC30A6

<400> SEQUENCE: 1026

Val Leu Leu Gln Thr Thr Pro Pro His Val Ile Gly Gln Leu Asp Lys
1               5                   10                  15

<210> SEQ ID NO 1027
<211> LENGTH: 10
<212> TYPE: PRT
<213> ORGANISM: Artificial Sequence
<220> FEATURE:
<223> OTHER INFORMATION: SLC30A7

<400> SEQUENCE: 1027

Leu Ile Val Ala Pro Asp Ala Asp Ala Arg
1               5                   10

```
<210> SEQ ID NO 1028
<211> LENGTH: 11
<212> TYPE: PRT
<213> ORGANISM: Artificial Sequence
<220> FEATURE:
<223> OTHER INFORMATION: SLC30A7

<400> SEQUENCE: 1028

Ala Leu Ala Pro Pro Asp Val His His Glu Arg
1               5                   10

<210> SEQ ID NO 1029
<211> LENGTH: 16
<212> TYPE: PRT
<213> ORGANISM: Artificial Sequence
<220> FEATURE:
<223> OTHER INFORMATION: SLC30A7

<400> SEQUENCE: 1029

Trp Ile Leu Ser Gln Thr His Asn Ile Phe Thr Gln Ala Gly Val Arg
1               5                   10                  15

<210> SEQ ID NO 1030
<211> LENGTH: 7
<212> TYPE: PRT
<213> ORGANISM: Artificial Sequence
<220> FEATURE:
<223> OTHER INFORMATION: SLC30A8

<400> SEQUENCE: 1030

Leu Thr Phe Gly Trp His Arg
1               5

<210> SEQ ID NO 1031
<211> LENGTH: 9
<212> TYPE: PRT
<213> ORGANISM: Artificial Sequence
<220> FEATURE:
<223> OTHER INFORMATION: SLC30A8

<400> SEQUENCE: 1031

Gly Ala Asn Glu Tyr Ala Tyr Ala Lys
1               5

<210> SEQ ID NO 1032
<211> LENGTH: 9
<212> TYPE: PRT
<213> ORGANISM: Artificial Sequence
<220> FEATURE:
<223> OTHER INFORMATION: SLC30A8

<400> SEQUENCE: 1032

Glu Val Gln Ala Asn Ala Ser Val Arg
1               5

<210> SEQ ID NO 1033
<211> LENGTH: 8
<212> TYPE: PRT
<213> ORGANISM: Artificial Sequence
<220> FEATURE:
<223> OTHER INFORMATION: SLC30A8

<400> SEQUENCE: 1033

Ser Leu Asn Tyr Ser Gly Val Lys
1               5

<210> SEQ ID NO 1034
<211> LENGTH: 7
```

```
-continued

<212> TYPE: PRT
<213> ORGANISM: Artificial Sequence
<220> FEATURE:
<223> OTHER INFORMATION: SLC30A8

<400> SEQUENCE: 1034

Thr Tyr Leu Val Asn Asp Lys
1               5

<210> SEQ ID NO 1035
<211> LENGTH: 15
<212> TYPE: PRT
<213> ORGANISM: Artificial Sequence
<220> FEATURE:
<223> OTHER INFORMATION: SLC30A9

<400> SEQUENCE: 1035

His Gly Glu Asn Ile Ile Asp Thr Leu Gly Ala Glu Val Asp Arg
1               5                   10                  15

<210> SEQ ID NO 1036
<211> LENGTH: 12
<212> TYPE: PRT
<213> ORGANISM: Artificial Sequence
<220> FEATURE:
<223> OTHER INFORMATION: SLC30A9

<400> SEQUENCE: 1036

Leu Thr Glu Leu Leu Glu Asn Asp Pro Ser Val Arg
1               5                   10

<210> SEQ ID NO 1037
<211> LENGTH: 8
<212> TYPE: PRT
<213> ORGANISM: Artificial Sequence
<220> FEATURE:
<223> OTHER INFORMATION: SLC30A9

<400> SEQUENCE: 1037

Ala Glu Val Asp Phe Asp Gly Arg
1               5

<210> SEQ ID NO 1038
<211> LENGTH: 8
<212> TYPE: PRT
<213> ORGANISM: Artificial Sequence
<220> FEATURE:
<223> OTHER INFORMATION: SLC30A9

<400> SEQUENCE: 1038

Ala Thr Asp Leu Gly Leu Gly Lys
1               5

<210> SEQ ID NO 1039
<211> LENGTH: 9
<212> TYPE: PRT
<213> ORGANISM: Artificial Sequence
<220> FEATURE:
<223> OTHER INFORMATION: SLC30A9

<400> SEQUENCE: 1039

Ser Ile Gln Pro Glu Gln Val Gln Arg
1               5

<210> SEQ ID NO 1040
<211> LENGTH: 15
<212> TYPE: PRT
<213> ORGANISM: Artificial Sequence
```

```
<220> FEATURE:
<223> OTHER INFORMATION: SLC30A9

<400> SEQUENCE: 1040

Val Pro Ser Phe Glu Thr Ala Glu Gly Ile Gly Ala Glu Leu Lys
1               5                   10                  15

<210> SEQ ID NO 1041
<211> LENGTH: 5
<212> TYPE: PRT
<213> ORGANISM: Artificial Sequence
<220> FEATURE:
<223> OTHER INFORMATION: SLC31A1

<400> SEQUENCE: 1041

Glu Ser Leu Leu Arg
1               5

<210> SEQ ID NO 1042
<211> LENGTH: 6
<212> TYPE: PRT
<213> ORGANISM: Artificial Sequence
<220> FEATURE:
<223> OTHER INFORMATION: SLC31A1

<400> SEQUENCE: 1042

Ser Gln Val Ser Ile Arg
1               5

<210> SEQ ID NO 1043
<211> LENGTH: 4
<212> TYPE: PRT
<213> ORGANISM: Artificial Sequence
<220> FEATURE:
<223> OTHER INFORMATION: SLC31A2

<400> SEQUENCE: 1043

Thr His His Arg
1

<210> SEQ ID NO 1044
<211> LENGTH: 11
<212> TYPE: PRT
<213> ORGANISM: Artificial Sequence
<220> FEATURE:
<223> OTHER INFORMATION: SLC32A1

<400> SEQUENCE: 1044

Leu Ser Asn Val Ala Thr Ser Val Ser Asn Lys
1               5                   10

<210> SEQ ID NO 1045
<211> LENGTH: 8
<212> TYPE: PRT
<213> ORGANISM: Artificial Sequence
<220> FEATURE:
<223> OTHER INFORMATION: SLC32A1

<400> SEQUENCE: 1045

Ser Leu Phe Gln Glu Gly Ser Arg
1               5

<210> SEQ ID NO 1046
<211> LENGTH: 7
<212> TYPE: PRT
<213> ORGANISM: Artificial Sequence
<220> FEATURE:
<223> OTHER INFORMATION: SLC32A1
```

```
<400> SEQUENCE: 1046

Ser Trp Gly Leu Thr Leu Arg
1               5

<210> SEQ ID NO 1047
<211> LENGTH: 13
<212> TYPE: PRT
<213> ORGANISM: Artificial Sequence
<220> FEATURE:
<223> OTHER INFORMATION: SLC33A1

<400> SEQUENCE: 1047

Ile Gly Phe Ser Ala Ala Asp Ala Val Thr Gly Leu Lys
1               5                   10

<210> SEQ ID NO 1048
<211> LENGTH: 8
<212> TYPE: PRT
<213> ORGANISM: Artificial Sequence
<220> FEATURE:
<223> OTHER INFORMATION: SLC33A1

<400> SEQUENCE: 1048

Leu Leu Gly Asn Thr Asp Asp Arg
1               5

<210> SEQ ID NO 1049
<211> LENGTH: 8
<212> TYPE: PRT
<213> ORGANISM: Artificial Sequence
<220> FEATURE:
<223> OTHER INFORMATION: SLC34A1

<400> SEQUENCE: 1049

Ile Ile Thr Glu Pro Phe Thr Lys
1               5

<210> SEQ ID NO 1050
<211> LENGTH: 12
<212> TYPE: PRT
<213> ORGANISM: Artificial Sequence
<220> FEATURE:
<223> OTHER INFORMATION: SLC34A1

<400> SEQUENCE: 1050

Leu Gly Ser Pro Ala Val Ser Pro Leu Pro Val Arg
1               5                   10

<210> SEQ ID NO 1051
<211> LENGTH: 10
<212> TYPE: PRT
<213> ORGANISM: Artificial Sequence
<220> FEATURE:
<223> OTHER INFORMATION: SLC34A1

<400> SEQUENCE: 1051

Trp Leu Gln Thr Trp Asp Phe Leu Pro Arg
1               5                   10

<210> SEQ ID NO 1052
<211> LENGTH: 14
<212> TYPE: PRT
<213> ORGANISM: Artificial Sequence
<220> FEATURE:
<223> OTHER INFORMATION: SLC34A1

<400> SEQUENCE: 1052
```

Val Phe Leu Glu Glu Leu Pro Pro Ala Thr Pro Ser Pro Arg
1               5                   10

<210> SEQ ID NO 1053
<211> LENGTH: 12
<212> TYPE: PRT
<213> ORGANISM: Artificial Sequence
<220> FEATURE:
<223> OTHER INFORMATION: SLC34A1

<400> SEQUENCE: 1053

Leu Ala Leu Glu Glu Glu Gln Lys Pro Glu Ser Arg
1               5                   10

<210> SEQ ID NO 1054
<211> LENGTH: 8
<212> TYPE: PRT
<213> ORGANISM: Artificial Sequence
<220> FEATURE:
<223> OTHER INFORMATION: SLC34A2

<400> SEQUENCE: 1054

Val Ile Thr Asp Pro Phe Thr Lys
1               5

<210> SEQ ID NO 1055
<211> LENGTH: 10
<212> TYPE: PRT
<213> ORGANISM: Artificial Sequence
<220> FEATURE:
<223> OTHER INFORMATION: SLC34A2

<400> SEQUENCE: 1055

Thr Asn Asp Asn Gly Thr Pro Val Ala Lys
1               5                   10

<210> SEQ ID NO 1056
<211> LENGTH: 12
<212> TYPE: PRT
<213> ORGANISM: Artificial Sequence
<220> FEATURE:
<223> OTHER INFORMATION: SLC34A2

<400> SEQUENCE: 1056

Phe Gln Asn Gly Glu Asp Ala Pro Asp Ile Leu Lys
1               5                   10

<210> SEQ ID NO 1057
<211> LENGTH: 8
<212> TYPE: PRT
<213> ORGANISM: Artificial Sequence
<220> FEATURE:
<223> OTHER INFORMATION: SLC34A3

<400> SEQUENCE: 1057

Asn Ser Thr Ala Pro Ala Asp Arg
1               5

<210> SEQ ID NO 1058
<211> LENGTH: 14
<212> TYPE: PRT
<213> ORGANISM: Artificial Sequence
<220> FEATURE:
<223> OTHER INFORMATION: SLC34A3

<400> SEQUENCE: 1058

Leu Ser Glu Leu Ala Leu Gly Ala Ala Ser Leu Thr Pro Arg

<210> SEQ ID NO 1059
<211> LENGTH: 7
<212> TYPE: PRT
<213> ORGANISM: Artificial Sequence
<220> FEATURE:
<223> OTHER INFORMATION: SLC34A3

<400> SEQUENCE: 1059

Asp Thr Ser Gln Pro Trp Lys
1               5

<210> SEQ ID NO 1060
<211> LENGTH: 8
<212> TYPE: PRT
<213> ORGANISM: Artificial Sequence
<220> FEATURE:
<223> OTHER INFORMATION: SLC34A3

<400> SEQUENCE: 1060

His Phe Gly Val Val Thr Ala Arg
1               5

<210> SEQ ID NO 1061
<211> LENGTH: 8
<212> TYPE: PRT
<213> ORGANISM: Artificial Sequence
<220> FEATURE:
<223> OTHER INFORMATION: SLC34A3

<400> SEQUENCE: 1061

Arg Pro Ala Trp Leu Pro Val Arg
1               5

<210> SEQ ID NO 1062
<211> LENGTH: 9
<212> TYPE: PRT
<213> ORGANISM: Artificial Sequence
<220> FEATURE:
<223> OTHER INFORMATION: SLC35A1

<400> SEQUENCE: 1062

Ser Ser Asp Thr Ser Leu Trp Val Arg
1               5

<210> SEQ ID NO 1063
<211> LENGTH: 9
<212> TYPE: PRT
<213> ORGANISM: Artificial Sequence
<220> FEATURE:
<223> OTHER INFORMATION: SLC35A2

<400> SEQUENCE: 1063

Gly Ser Ser Gly Ser Val Trp Leu Arg
1               5

<210> SEQ ID NO 1064
<211> LENGTH: 11
<212> TYPE: PRT
<213> ORGANISM: Artificial Sequence
<220> FEATURE:
<223> OTHER INFORMATION: SLC35A2

<400> SEQUENCE: 1064

Gly Asp Leu Ile Thr Glu Pro Phe Leu Pro Lys
1               5                   10

```
<210> SEQ ID NO 1065
<211> LENGTH: 17
<212> TYPE: PRT
<213> ORGANISM: Artificial Sequence
<220> FEATURE:
<223> OTHER INFORMATION: SLC35A2

<400> SEQUENCE: 1065

Gly Phe Ala Thr Ser Leu Ser Ile Val Leu Ser Thr Val Ala Ser Ile
1               5                   10                  15

Arg

<210> SEQ ID NO 1066
<211> LENGTH: 6
<212> TYPE: PRT
<213> ORGANISM: Artificial Sequence
<220> FEATURE:
<223> OTHER INFORMATION: SLC35A3

<400> SEQUENCE: 1066

Gln Ser Val Trp Ile Arg
1               5

<210> SEQ ID NO 1067
<211> LENGTH: 9
<212> TYPE: PRT
<213> ORGANISM: Artificial Sequence
<220> FEATURE:
<223> OTHER INFORMATION: SLC35A3

<400> SEQUENCE: 1067

Asn Gly Phe Phe Gln Gly Tyr Asn Arg
1               5

<210> SEQ ID NO 1068
<211> LENGTH: 16
<212> TYPE: PRT
<213> ORGANISM: Artificial Sequence
<220> FEATURE:
<223> OTHER INFORMATION: SLC35A4

<400> SEQUENCE: 1068

Val Pro Phe Arg Pro Ser Ser Ala Val Leu Leu Thr Glu Leu Thr Lys
1               5                   10                  15

<210> SEQ ID NO 1069
<211> LENGTH: 7
<212> TYPE: PRT
<213> ORGANISM: Artificial Sequence
<220> FEATURE:
<223> OTHER INFORMATION: SLC35A4

<400> SEQUENCE: 1069

His Gly Ser Ser Ile Thr Arg
1               5

<210> SEQ ID NO 1070
<211> LENGTH: 9
<212> TYPE: PRT
<213> ORGANISM: Artificial Sequence
<220> FEATURE:
<223> OTHER INFORMATION: SLC35A5

<400> SEQUENCE: 1070

Thr Leu Gln His Asn Leu Ala Gly Arg
1               5
```

<210> SEQ ID NO 1071
<211> LENGTH: 9
<212> TYPE: PRT
<213> ORGANISM: Artificial Sequence
<220> FEATURE:
<223> OTHER INFORMATION: SLC35A5

<400> SEQUENCE: 1071

Ser Asp Glu Ser Asp Glu Asp Thr Phe
1               5

<210> SEQ ID NO 1072
<211> LENGTH: 10
<212> TYPE: PRT
<213> ORGANISM: Artificial Sequence
<220> FEATURE:
<223> OTHER INFORMATION: SLC35A5

<400> SEQUENCE: 1072

Ser Ser Gly Asp Gly Glu Glu Leu Glu Arg
1               5                   10

<210> SEQ ID NO 1073
<211> LENGTH: 6
<212> TYPE: PRT
<213> ORGANISM: Artificial Sequence
<220> FEATURE:
<223> OTHER INFORMATION: SLC35B1

<400> SEQUENCE: 1073

Tyr Gly Glu Gly Ala Lys
1               5

<210> SEQ ID NO 1074
<211> LENGTH: 10
<212> TYPE: PRT
<213> ORGANISM: Artificial Sequence
<220> FEATURE:
<223> OTHER INFORMATION: SLC35B2

<400> SEQUENCE: 1074

Ala Val Pro Val Glu Ser Pro Val Gln Lys
1               5                   10

<210> SEQ ID NO 1075
<211> LENGTH: 10
<212> TYPE: PRT
<213> ORGANISM: Artificial Sequence
<220> FEATURE:
<223> OTHER INFORMATION: SLC35B2

<400> SEQUENCE: 1075

Ala Ser Asp Glu Val Pro Leu Ala Pro Arg
1               5                   10

<210> SEQ ID NO 1076
<211> LENGTH: 12
<212> TYPE: PRT
<213> ORGANISM: Artificial Sequence
<220> FEATURE:
<223> OTHER INFORMATION: SLC35B2

<400> SEQUENCE: 1076

Ser Tyr Gly Ala Thr Ala Thr Ser Pro Gly Glu Arg
1               5                   10

<210> SEQ ID NO 1077

```
<211> LENGTH: 11
<212> TYPE: PRT
<213> ORGANISM: Artificial Sequence
<220> FEATURE:
<223> OTHER INFORMATION: SLC35B2

<400> SEQUENCE: 1077

Phe Val Ser Phe Pro Thr Gln Val Leu Ala Lys
1               5                   10

<210> SEQ ID NO 1078
<211> LENGTH: 6
<212> TYPE: PRT
<213> ORGANISM: Artificial Sequence
<220> FEATURE:
<223> OTHER INFORMATION: SLC35B3

<400> SEQUENCE: 1078

Thr Leu Ala Gln Thr Val
1               5

<210> SEQ ID NO 1079
<211> LENGTH: 9
<212> TYPE: PRT
<213> ORGANISM: Artificial Sequence
<220> FEATURE:
<223> OTHER INFORMATION: SLC35B3

<400> SEQUENCE: 1079

Tyr Ile Ser Ile Thr Val Pro Ser Lys
1               5

<210> SEQ ID NO 1080
<211> LENGTH: 10
<212> TYPE: PRT
<213> ORGANISM: Artificial Sequence
<220> FEATURE:
<223> OTHER INFORMATION: SLC35B3

<400> SEQUENCE: 1080

Leu Pro Ser Leu Tyr Asp Leu Ile Asn Lys
1               5                   10

<210> SEQ ID NO 1081
<211> LENGTH: 5
<212> TYPE: PRT
<213> ORGANISM: Artificial Sequence
<220> FEATURE:
<223> OTHER INFORMATION: SLC35B4

<400> SEQUENCE: 1081

Ser Glu Pro Gln Lys
1               5

<210> SEQ ID NO 1082
<211> LENGTH: 4
<212> TYPE: PRT
<213> ORGANISM: Artificial Sequence
<220> FEATURE:
<223> OTHER INFORMATION: SLC35B4

<400> SEQUENCE: 1082

Gln Phe Gly Lys
1

<210> SEQ ID NO 1083
<211> LENGTH: 9
<212> TYPE: PRT
```

```
<213> ORGANISM: Artificial Sequence
<220> FEATURE:
<223> OTHER INFORMATION: SLC35C1

<400> SEQUENCE: 1083

Tyr Leu Leu Asp Ser Pro Ser Leu Arg
1               5

<210> SEQ ID NO 1084
<211> LENGTH: 14
<212> TYPE: PRT
<213> ORGANISM: Artificial Sequence
<220> FEATURE:
<223> OTHER INFORMATION: SLC35C1

<400> SEQUENCE: 1084

Phe Thr Ser Pro Leu Thr His Asn Val Ser Gly Thr Ala Lys
1               5                   10

<210> SEQ ID NO 1085
<211> LENGTH: 10
<212> TYPE: PRT
<213> ORGANISM: Artificial Sequence
<220> FEATURE:
<223> OTHER INFORMATION: SLC35C2

<400> SEQUENCE: 1085

Trp Ala Leu Asp Val Ala Phe Leu Trp Lys
1               5                   10

<210> SEQ ID NO 1086
<211> LENGTH: 13
<212> TYPE: PRT
<213> ORGANISM: Artificial Sequence
<220> FEATURE:
<223> OTHER INFORMATION: SLC35C2

<400> SEQUENCE: 1086

Gly Leu Gly Ser Ser Pro Asp Leu Glu Leu Leu Leu Arg
1               5                   10

<210> SEQ ID NO 1087
<211> LENGTH: 9
<212> TYPE: PRT
<213> ORGANISM: Artificial Sequence
<220> FEATURE:
<223> OTHER INFORMATION: SLC35C2

<400> SEQUENCE: 1087

Phe Gln Asp Thr Gly Leu Leu Leu Arg
1               5

<210> SEQ ID NO 1088
<211> LENGTH: 7
<212> TYPE: PRT
<213> ORGANISM: Artificial Sequence
<220> FEATURE:
<223> OTHER INFORMATION: SLC35D1

<400> SEQUENCE: 1088

Gln Ser Glu Ala Asn Asn Lys
1               5

<210> SEQ ID NO 1089
<211> LENGTH: 7
<212> TYPE: PRT
<213> ORGANISM: Artificial Sequence
<220> FEATURE:
```

<223> OTHER INFORMATION: SLC35D1

<400> SEQUENCE: 1089

Ser Val Leu Thr Asn Tyr Arg
1               5

<210> SEQ ID NO 1090
<211> LENGTH: 21
<212> TYPE: PRT
<213> ORGANISM: Artificial Sequence
<220> FEATURE:
<223> OTHER INFORMATION: SLC35D2

<400> SEQUENCE: 1090

Leu Phe Pro Leu Pro Leu Leu Tyr Val Gly Asn His Ile Ser Gly Leu
1               5                   10                  15

Ser Ser Thr Ser Lys
            20

<210> SEQ ID NO 1091
<211> LENGTH: 4
<212> TYPE: PRT
<213> ORGANISM: Artificial Sequence
<220> FEATURE:
<223> OTHER INFORMATION: SLC35D2

<400> SEQUENCE: 1091

Glu Leu Gly Lys
1

<210> SEQ ID NO 1092
<211> LENGTH: 4
<212> TYPE: PRT
<213> ORGANISM: Artificial Sequence
<220> FEATURE:
<223> OTHER INFORMATION: SLC35D2

<400> SEQUENCE: 1092

Leu Pro Ser Arg
1

<210> SEQ ID NO 1093
<211> LENGTH: 15
<212> TYPE: PRT
<213> ORGANISM: Artificial Sequence
<220> FEATURE:
<223> OTHER INFORMATION: SLC35D3

<400> SEQUENCE: 1093

Leu Gly Leu Ile Ala Val Pro Pro Phe Gly Leu Ser Leu Ala Arg
1               5                   10                  15

<210> SEQ ID NO 1094
<211> LENGTH: 15
<212> TYPE: PRT
<213> ORGANISM: Artificial Sequence
<220> FEATURE:
<223> OTHER INFORMATION: SLC35D3

<400> SEQUENCE: 1094

Ser Glu Gly Gly Glu Ala Ala Gly Gly Pro Ala Gln Glu Ser Arg
1               5                   10                  15

<210> SEQ ID NO 1095
<211> LENGTH: 21
<212> TYPE: PRT
<213> ORGANISM: Artificial Sequence

<220> FEATURE:
<223> OTHER INFORMATION: SLC35D3

<400> SEQUENCE: 1095

Ser Phe Ala Gly Val Ala Val Leu Ser Thr Leu Gln Ser Ser Leu Thr
1               5                   10                  15

Leu Trp Ser Leu Arg
            20

<210> SEQ ID NO 1096
<211> LENGTH: 13
<212> TYPE: PRT
<213> ORGANISM: Artificial Sequence
<220> FEATURE:
<223> OTHER INFORMATION: SLC35E1

<400> SEQUENCE: 1096

His Leu Leu Pro Val Thr Thr Ala Asp Leu Ser Ser Lys
1               5                   10

<210> SEQ ID NO 1097
<211> LENGTH: 12
<212> TYPE: PRT
<213> ORGANISM: Artificial Sequence
<220> FEATURE:
<223> OTHER INFORMATION: SLC35E1

<400> SEQUENCE: 1097

Ile Met Val Ile Thr Val Ser Leu Ile Met Leu Arg
1               5                   10

<210> SEQ ID NO 1098
<211> LENGTH: 12
<212> TYPE: PRT
<213> ORGANISM: Artificial Sequence
<220> FEATURE:
<223> OTHER INFORMATION: SLC35E1

<400> SEQUENCE: 1098

Asn Asn Ile Leu Thr Asp His Phe Gln Tyr Ser Arg
1               5                   10

<210> SEQ ID NO 1099
<211> LENGTH: 11
<212> TYPE: PRT
<213> ORGANISM: Artificial Sequence
<220> FEATURE:
<223> OTHER INFORMATION: SLC35E2

<400> SEQUENCE: 1099

Asn Val Ala Val Ser Phe Ala Glu Thr Val Lys
1               5                   10

<210> SEQ ID NO 1100
<211> LENGTH: 12
<212> TYPE: PRT
<213> ORGANISM: Artificial Sequence
<220> FEATURE:
<223> OTHER INFORMATION: SLC35E2

<400> SEQUENCE: 1100

Phe Ala Thr Val Val Leu Gly Leu Val Ser Leu Lys
1               5                   10

<210> SEQ ID NO 1101
<211> LENGTH: 11
<212> TYPE: PRT

```
<213> ORGANISM: Artificial Sequence
<220> FEATURE:
<223> OTHER INFORMATION: SLC35E2

<400> SEQUENCE: 1101

Val Phe Phe Thr Asp Val Pro Val Ile Gly Arg
1               5                   10

<210> SEQ ID NO 1102
<211> LENGTH: 13
<212> TYPE: PRT
<213> ORGANISM: Artificial Sequence
<220> FEATURE:
<223> OTHER INFORMATION: SLC35E2

<400> SEQUENCE: 1102

Ile Ser Pro Val Thr Phe Ser Val Ala Ser Thr Val Lys
1               5                   10

<210> SEQ ID NO 1103
<211> LENGTH: 12
<212> TYPE: PRT
<213> ORGANISM: Artificial Sequence
<220> FEATURE:
<223> OTHER INFORMATION: SLC35E2

<400> SEQUENCE: 1103

Ser Pro Leu Ser Trp Gly Ser Leu Phe Gly His Arg
1               5                   10

<210> SEQ ID NO 1104
<211> LENGTH: 15
<212> TYPE: PRT
<213> ORGANISM: Artificial Sequence
<220> FEATURE:
<223> OTHER INFORMATION: SLC35E2

<400> SEQUENCE: 1104

Ala Pro Asp Asp Thr Val Glu Pro Leu Leu Pro Gln Asp Pro Arg
1               5                   10                  15

<210> SEQ ID NO 1105
<211> LENGTH: 15
<212> TYPE: PRT
<213> ORGANISM: Artificial Sequence
<220> FEATURE:
<223> OTHER INFORMATION: SLC35E2

<400> SEQUENCE: 1105

His Ala Leu Ser Ile Trp Leu Ser Val Ile Val Phe Gly Asn Lys
1               5                   10                  15

<210> SEQ ID NO 1106
<211> LENGTH: 16
<212> TYPE: PRT
<213> ORGANISM: Artificial Sequence
<220> FEATURE:
<223> OTHER INFORMATION: SLC35E2

<400> SEQUENCE: 1106

Thr Pro Ala Leu Glu Glu Leu Val Pro Gly Ser Glu Glu Lys Pro Lys
1               5                   10                  15

<210> SEQ ID NO 1107
<211> LENGTH: 16
<212> TYPE: PRT
<213> ORGANISM: Artificial Sequence
<220> FEATURE:
```

```
<223> OTHER INFORMATION: SLC35E2

<400> SEQUENCE: 1107

Gln His Gln Gln Glu Ala Leu Gln Ser Leu Ala Ala Ala Thr Gly Arg
1               5                   10                  15

<210> SEQ ID NO 1108
<211> LENGTH: 7
<212> TYPE: PRT
<213> ORGANISM: Artificial Sequence
<220> FEATURE:
<223> OTHER INFORMATION: SLC35E3

<400> SEQUENCE: 1108

Leu Asp Ile Phe Ala Pro Lys
1               5

<210> SEQ ID NO 1109
<211> LENGTH: 8
<212> TYPE: PRT
<213> ORGANISM: Artificial Sequence
<220> FEATURE:
<223> OTHER INFORMATION: SLC35E3

<400> SEQUENCE: 1109

Leu Ser Glu Gln Glu Gly Ser Arg
1               5

<210> SEQ ID NO 1110
<211> LENGTH: 9
<212> TYPE: PRT
<213> ORGANISM: Artificial Sequence
<220> FEATURE:
<223> OTHER INFORMATION: SLC35E3

<400> SEQUENCE: 1110

Gly Asp His Gly Ile Val Val Asp Arg
1               5

<210> SEQ ID NO 1111
<211> LENGTH: 12
<212> TYPE: PRT
<213> ORGANISM: Artificial Sequence
<220> FEATURE:
<223> OTHER INFORMATION: SLC35E4

<400> SEQUENCE: 1111

Ser Val Gln Gln Ser Ala Leu Leu Gln Glu Glu Arg
1               5                   10

<210> SEQ ID NO 1112
<211> LENGTH: 6
<212> TYPE: PRT
<213> ORGANISM: Artificial Sequence
<220> FEATURE:
<223> OTHER INFORMATION: SLC35E4

<400> SEQUENCE: 1112

Leu Leu Phe Gly Ser Arg
1               5

<210> SEQ ID NO 1113
<211> LENGTH: 8
<212> TYPE: PRT
<213> ORGANISM: Artificial Sequence
<220> FEATURE:
<223> OTHER INFORMATION: SLC35F1
```

```
<400> SEQUENCE: 1113

His Gln Gly Ala Gly Glu Asn Lys
1               5

<210> SEQ ID NO 1114
<211> LENGTH: 13
<212> TYPE: PRT
<213> ORGANISM: Artificial Sequence
<220> FEATURE:
<223> OTHER INFORMATION: SLC35F2

<400> SEQUENCE: 1114

Leu Glu Glu Asn Leu Gln Glu Thr His Ser Ala Val Leu
1               5                   10

<210> SEQ ID NO 1115
<211> LENGTH: 8
<212> TYPE: PRT
<213> ORGANISM: Artificial Sequence
<220> FEATURE:
<223> OTHER INFORMATION: SLC35F2

<400> SEQUENCE: 1115

Leu Phe Thr Trp Asn Ile Leu Lys
1               5

<210> SEQ ID NO 1116
<211> LENGTH: 10
<212> TYPE: PRT
<213> ORGANISM: Artificial Sequence
<220> FEATURE:
<223> OTHER INFORMATION: SLC35F3

<400> SEQUENCE: 1116

Phe Phe Gly Asp Asn Gly Leu Thr Leu Lys
1               5                   10

<210> SEQ ID NO 1117
<211> LENGTH: 7
<212> TYPE: PRT
<213> ORGANISM: Artificial Sequence
<220> FEATURE:
<223> OTHER INFORMATION: SLC35F3

<400> SEQUENCE: 1117

Leu Leu Leu Gly Ser Ala Lys
1               5

<210> SEQ ID NO 1118
<211> LENGTH: 11
<212> TYPE: PRT
<213> ORGANISM: Artificial Sequence
<220> FEATURE:
<223> OTHER INFORMATION: SLC35F5

<400> SEQUENCE: 1118

Gln Leu Pro Ser Ser His Ala Leu Glu Ala Lys
1               5                   10

<210> SEQ ID NO 1119
<211> LENGTH: 8
<212> TYPE: PRT
<213> ORGANISM: Artificial Sequence
<220> FEATURE:
<223> OTHER INFORMATION: SLC35F5

<400> SEQUENCE: 1119
```

```
Leu Thr Ala Thr Gln Val Ala Lys
1               5

<210> SEQ ID NO 1120
<211> LENGTH: 14
<212> TYPE: PRT
<213> ORGANISM: Artificial Sequence
<220> FEATURE:
<223> OTHER INFORMATION: SLC36A1

<400> SEQUENCE: 1120

Ile Pro Asp Pro Ser His Leu Pro Leu Val Ala Pro Trp Lys
1               5                   10

<210> SEQ ID NO 1121
<211> LENGTH: 8
<212> TYPE: PRT
<213> ORGANISM: Artificial Sequence
<220> FEATURE:
<223> OTHER INFORMATION: SLC36A2

<400> SEQUENCE: 1121

Leu Pro Leu Val Ala Ser Trp Lys
1               5

<210> SEQ ID NO 1122
<211> LENGTH: 13
<212> TYPE: PRT
<213> ORGANISM: Artificial Sequence
<220> FEATURE:
<223> OTHER INFORMATION: SLC36A2

<400> SEQUENCE: 1122

Gly Ile Thr Val Phe Gln Ala Leu Ile His Leu Val Lys
1               5                   10

<210> SEQ ID NO 1123
<211> LENGTH: 10
<212> TYPE: PRT
<213> ORGANISM: Artificial Sequence
<220> FEATURE:
<223> OTHER INFORMATION: SLC36A2

<400> SEQUENCE: 1123

Trp Ala Leu Pro Leu Asp Leu Ser Ile Arg
1               5                   10

<210> SEQ ID NO 1124
<211> LENGTH: 8
<212> TYPE: PRT
<213> ORGANISM: Artificial Sequence
<220> FEATURE:
<223> OTHER INFORMATION: SLC36A3

<400> SEQUENCE: 1124

Trp Asn Leu Ala Leu Ser Pro Arg
1               5

<210> SEQ ID NO 1125
<211> LENGTH: 7
<212> TYPE: PRT
<213> ORGANISM: Artificial Sequence
<220> FEATURE:
<223> OTHER INFORMATION: SLC36A3

<400> SEQUENCE: 1125

Ala His Ala Val Trp Gly Arg
1               5
```

<210> SEQ ID NO 1126
<211> LENGTH: 6
<212> TYPE: PRT
<213> ORGANISM: Artificial Sequence
<220> FEATURE:
<223> OTHER INFORMATION: SLC36A4

<400> SEQUENCE: 1126

Gln Ala Ala Trp Gly Arg
1               5

<210> SEQ ID NO 1127
<211> LENGTH: 10
<212> TYPE: PRT
<213> ORGANISM: Artificial Sequence
<220> FEATURE:
<223> OTHER INFORMATION: SLC36A4

<400> SEQUENCE: 1127

Gln Val His Glu Gly Phe Leu Glu Ser Lys
1               5                   10

<210> SEQ ID NO 1128
<211> LENGTH: 15
<212> TYPE: PRT
<213> ORGANISM: Artificial Sequence
<220> FEATURE:
<223> OTHER INFORMATION: SLC36A4

<400> SEQUENCE: 1128

Gly Asn Ile Gly Thr Gly Leu Leu Gly Leu Pro Leu Ala Ile Lys
1               5                   10                  15

<210> SEQ ID NO 1129
<211> LENGTH: 18
<212> TYPE: PRT
<213> ORGANISM: Artificial Sequence
<220> FEATURE:
<223> OTHER INFORMATION: SLC36A4

<400> SEQUENCE: 1129

Gly Ser Ile Thr Leu Asn Leu Pro Gln Asp Val Trp Leu Tyr Gln Ser
1               5                   10                  15

Val Lys

<210> SEQ ID NO 1130
<211> LENGTH: 7
<212> TYPE: PRT
<213> ORGANISM: Artificial Sequence
<220> FEATURE:
<223> OTHER INFORMATION: SLC37A1

<400> SEQUENCE: 1130

Phe Ile Ile Ser Phe Ser Arg
1               5

<210> SEQ ID NO 1131
<211> LENGTH: 6
<212> TYPE: PRT
<213> ORGANISM: Artificial Sequence
<220> FEATURE:
<223> OTHER INFORMATION: SLC37A1

<400> SEQUENCE: 1131

Leu Pro Ala Gly Ile Arg
1               5

```
<210> SEQ ID NO 1132
<211> LENGTH: 5
<212> TYPE: PRT
<213> ORGANISM: Artificial Sequence
<220> FEATURE:
<223> OTHER INFORMATION: SLC37A1

<400> SEQUENCE: 1132

Gly Glu Leu His Lys
1               5

<210> SEQ ID NO 1133
<211> LENGTH: 11
<212> TYPE: PRT
<213> ORGANISM: Artificial Sequence
<220> FEATURE:
<223> OTHER INFORMATION: SLC37A2

<400> SEQUENCE: 1133

Ser Ser Leu Ala Pro Gly Val Trp Phe Phe Arg
1               5                   10

<210> SEQ ID NO 1134
<211> LENGTH: 9
<212> TYPE: PRT
<213> ORGANISM: Artificial Sequence
<220> FEATURE:
<223> OTHER INFORMATION: SLC37A2

<400> SEQUENCE: 1134

Glu Ser Gly Leu Glu Thr Val Ala Lys
1               5

<210> SEQ ID NO 1135
<211> LENGTH: 6
<212> TYPE: PRT
<213> ORGANISM: Artificial Sequence
<220> FEATURE:
<223> OTHER INFORMATION: SLC37A3

<400> SEQUENCE: 1135

Gln Glu Leu Ile Gln Arg
1               5

<210> SEQ ID NO 1136
<211> LENGTH: 6
<212> TYPE: PRT
<213> ORGANISM: Artificial Sequence
<220> FEATURE:
<223> OTHER INFORMATION: SLC37A3

<400> SEQUENCE: 1136

Glu Ala Glu Ala Asp Lys
1               5

<210> SEQ ID NO 1137
<211> LENGTH: 5
<212> TYPE: PRT
<213> ORGANISM: Artificial Sequence
<220> FEATURE:
<223> OTHER INFORMATION: SLC37A3

<400> SEQUENCE: 1137

Ser Pro Asn Asp Lys
1               5
```

<210> SEQ ID NO 1138
<211> LENGTH: 10
<212> TYPE: PRT
<213> ORGANISM: Artificial Sequence
<220> FEATURE:
<223> OTHER INFORMATION: SLC37A4

<400> SEQUENCE: 1138

Met Ala Ala Gln Gly Tyr Gly Tyr Tyr Arg
1               5                   10

<210> SEQ ID NO 1139
<211> LENGTH: 15
<212> TYPE: PRT
<213> ORGANISM: Artificial Sequence
<220> FEATURE:
<223> OTHER INFORMATION: SLC37A4

<400> SEQUENCE: 1139

Thr Cys Cys Thr Asp Trp Gly Gln Phe Phe Leu Ile Gln Glu Lys
1               5                   10                  15

<210> SEQ ID NO 1140
<211> LENGTH: 9
<212> TYPE: PRT
<213> ORGANISM: Artificial Sequence
<220> FEATURE:
<223> OTHER INFORMATION: SLC38A1

<400> SEQUENCE: 1140

Asp Asp Ile Leu Ile Leu Thr Val Arg
1               5

<210> SEQ ID NO 1141
<211> LENGTH: 8
<212> TYPE: PRT
<213> ORGANISM: Artificial Sequence
<220> FEATURE:
<223> OTHER INFORMATION: SLC38A1

<400> SEQUENCE: 1141

Ile Thr Asp Gln Asp Gly Asp Lys
1               5

<210> SEQ ID NO 1142
<211> LENGTH: 7
<212> TYPE: PRT
<213> ORGANISM: Artificial Sequence
<220> FEATURE:
<223> OTHER INFORMATION: SLC38A2

<400> SEQUENCE: 1142

Ala Phe Gly Leu Val Gly Lys
1               5

<210> SEQ ID NO 1143
<211> LENGTH: 16
<212> TYPE: PRT
<213> ORGANISM: Artificial Sequence
<220> FEATURE:
<223> OTHER INFORMATION: SLC38A2

<400> SEQUENCE: 1143

Thr Ala Asn Glu Gly Gly Ser Leu Leu Tyr Glu Gln Leu Gly Tyr Lys
1               5                   10                  15

<210> SEQ ID NO 1144
<211> LENGTH: 16

```
<212> TYPE: PRT
<213> ORGANISM: Artificial Sequence
<220> FEATURE:
<223> OTHER INFORMATION: SLC38A2

<400> SEQUENCE: 1144

Tyr Glu Leu Pro Leu Val Ile Gln Ala Leu Thr Asn Ile Glu Asp Lys
1               5                   10                  15

<210> SEQ ID NO 1145
<211> LENGTH: 7
<212> TYPE: PRT
<213> ORGANISM: Artificial Sequence
<220> FEATURE:
<223> OTHER INFORMATION: SLC38A3

<400> SEQUENCE: 1145

Ala Phe Gly Thr Pro Gly Lys
1               5

<210> SEQ ID NO 1146
<211> LENGTH: 16
<212> TYPE: PRT
<213> ORGANISM: Artificial Sequence
<220> FEATURE:
<223> OTHER INFORMATION: SLC38A3

<400> SEQUENCE: 1146

Ser Glu Leu Pro Leu Val Ile Gln Thr Phe Leu Asn Leu Glu Glu Lys
1               5                   10                  15

<210> SEQ ID NO 1147
<211> LENGTH: 8
<212> TYPE: PRT
<213> ORGANISM: Artificial Sequence
<220> FEATURE:
<223> OTHER INFORMATION: SLC38A3

<400> SEQUENCE: 1147

Ala Tyr Glu Gln Leu Gly Tyr Arg
1               5

<210> SEQ ID NO 1148
<211> LENGTH: 7
<212> TYPE: PRT
<213> ORGANISM: Artificial Sequence
<220> FEATURE:
<223> OTHER INFORMATION: SLC38A4

<400> SEQUENCE: 1148

Tyr Phe Val Phe Asn Ser Arg
1               5

<210> SEQ ID NO 1149
<211> LENGTH: 10
<212> TYPE: PRT
<213> ORGANISM: Artificial Sequence
<220> FEATURE:
<223> OTHER INFORMATION: SLC38A4

<400> SEQUENCE: 1149

Thr Ser Val Ile Thr Leu Leu Gly Pro Lys
1               5                   10

<210> SEQ ID NO 1150
<211> LENGTH: 7
<212> TYPE: PRT
<213> ORGANISM: Artificial Sequence
```

```
<220> FEATURE:
<223> OTHER INFORMATION: SLC38A5

<400> SEQUENCE: 1150

Ala Phe Gly Pro Ala Gly Lys
1               5

<210> SEQ ID NO 1151
<211> LENGTH: 8
<212> TYPE: PRT
<213> ORGANISM: Artificial Sequence
<220> FEATURE:
<223> OTHER INFORMATION: SLC38A5

<400> SEQUENCE: 1151

Ala Tyr Glu Gln Leu Gly Gln Arg
1               5

<210> SEQ ID NO 1152
<211> LENGTH: 6
<212> TYPE: PRT
<213> ORGANISM: Artificial Sequence
<220> FEATURE:
<223> OTHER INFORMATION: SLC38A5

<400> SEQUENCE: 1152

Ala Phe Ser Trp Pro Arg
1               5

<210> SEQ ID NO 1153
<211> LENGTH: 14
<212> TYPE: PRT
<213> ORGANISM: Artificial Sequence
<220> FEATURE:
<223> OTHER INFORMATION: SLC38A5

<400> SEQUENCE: 1153

Ile Val Pro Ser Glu Val Glu Pro Phe Leu Ser Trp Pro Lys
1               5                   10

<210> SEQ ID NO 1154
<211> LENGTH: 7
<212> TYPE: PRT
<213> ORGANISM: Artificial Sequence
<220> FEATURE:
<223> OTHER INFORMATION: SLC38A5

<400> SEQUENCE: 1154

Glu Gly Phe Leu Pro Ser Arg
1               5

<210> SEQ ID NO 1155
<211> LENGTH: 6
<212> TYPE: PRT
<213> ORGANISM: Artificial Sequence
<220> FEATURE:
<223> OTHER INFORMATION: SLC38A6

<400> SEQUENCE: 1155

Leu Phe His Phe Ser Lys
1               5

<210> SEQ ID NO 1156
<211> LENGTH: 17
<212> TYPE: PRT
<213> ORGANISM: Artificial Sequence
<220> FEATURE:
<223> OTHER INFORMATION: SLC38A6
```

```
<400> SEQUENCE: 1156

Thr Glu Leu Pro Ala Ala Ile Ala Glu Phe Leu Thr Gly Asp Tyr Ser
1               5                   10                  15
Arg

<210> SEQ ID NO 1157
<211> LENGTH: 7
<212> TYPE: PRT
<213> ORGANISM: Artificial Sequence
<220> FEATURE:
<223> OTHER INFORMATION: SLC38A6

<400> SEQUENCE: 1157

Val Glu Ser Glu Leu Leu Lys
1               5

<210> SEQ ID NO 1158
<211> LENGTH: 7
<212> TYPE: PRT
<213> ORGANISM: Artificial Sequence
<220> FEATURE:
<223> OTHER INFORMATION: SLC39A1

<400> SEQUENCE: 1158

Leu Leu Gln Ser His Leu Arg
1               5

<210> SEQ ID NO 1159
<211> LENGTH: 12
<212> TYPE: PRT
<213> ORGANISM: Artificial Sequence
<220> FEATURE:
<223> OTHER INFORMATION: SLC39A1

<400> SEQUENCE: 1159

Glu Gln Ser Gly Pro Ser Pro Leu Glu Glu Thr Arg
1               5                   10

<210> SEQ ID NO 1160
<211> LENGTH: 7
<212> TYPE: PRT
<213> ORGANISM: Artificial Sequence
<220> FEATURE:
<223> OTHER INFORMATION: SLC39A10

<400> SEQUENCE: 1160

Asn Gly His Asp Pro Gly Arg
1               5

<210> SEQ ID NO 1161
<211> LENGTH: 6
<212> TYPE: PRT
<213> ORGANISM: Artificial Sequence
<220> FEATURE:
<223> OTHER INFORMATION: SLC39A10

<400> SEQUENCE: 1161

Val His Lys Pro Asp Arg
1               5

<210> SEQ ID NO 1162
<211> LENGTH: 7
<212> TYPE: PRT
<213> ORGANISM: Artificial Sequence
<220> FEATURE:
<223> OTHER INFORMATION: SLC39A10
```

<400> SEQUENCE: 1162

Ile Val Phe Asp Ile Gln Phe
1               5

<210> SEQ ID NO 1163
<211> LENGTH: 10
<212> TYPE: PRT
<213> ORGANISM: Artificial Sequence
<220> FEATURE:
<223> OTHER INFORMATION: SLC39A11

<400> SEQUENCE: 1163

Thr Ala Ser Ala Thr Phe Glu Ser Ala Arg
1               5                   10

<210> SEQ ID NO 1164
<211> LENGTH: 8
<212> TYPE: PRT
<213> ORGANISM: Artificial Sequence
<220> FEATURE:
<223> OTHER INFORMATION: SLC39A11

<400> SEQUENCE: 1164

Gly Ala Gly Phe Ser Thr Trp Arg
1               5

<210> SEQ ID NO 1165
<211> LENGTH: 10
<212> TYPE: PRT
<213> ORGANISM: Artificial Sequence
<220> FEATURE:
<223> OTHER INFORMATION: SLC39A12

<400> SEQUENCE: 1165

Phe Tyr Leu His Ser Leu Leu Ser Leu Arg
1               5                   10

<210> SEQ ID NO 1166
<211> LENGTH: 7
<212> TYPE: PRT
<213> ORGANISM: Artificial Sequence
<220> FEATURE:
<223> OTHER INFORMATION: SLC39A12

<400> SEQUENCE: 1166

Gly Leu Ser Leu Ile Ser Lys
1               5

<210> SEQ ID NO 1167
<211> LENGTH: 9
<212> TYPE: PRT
<213> ORGANISM: Artificial Sequence
<220> FEATURE:
<223> OTHER INFORMATION: SLC39A13

<400> SEQUENCE: 1167

Ala Gly Gly Ser Gln Pro Ala Leu Arg
1               5

<210> SEQ ID NO 1168
<211> LENGTH: 5
<212> TYPE: PRT
<213> ORGANISM: Artificial Sequence
<220> FEATURE:
<223> OTHER INFORMATION: SLC39A13

<400> SEQUENCE: 1168

Ala Gly Phe Asp Arg
1               5

<210> SEQ ID NO 1169
<211> LENGTH: 4
<212> TYPE: PRT
<213> ORGANISM: Artificial Sequence
<220> FEATURE:
<223> OTHER INFORMATION: SLC39A13

<400> SEQUENCE: 1169

Leu Asp Asn Lys
1

<210> SEQ ID NO 1170
<211> LENGTH: 12
<212> TYPE: PRT
<213> ORGANISM: Artificial Sequence
<220> FEATURE:
<223> OTHER INFORMATION: SLC39A14

<400> SEQUENCE: 1170

Ala Leu Leu Asn His Leu Asp Val Gly Val Gly Arg
1               5                   10

<210> SEQ ID NO 1171
<211> LENGTH: 13
<212> TYPE: PRT
<213> ORGANISM: Artificial Sequence
<220> FEATURE:
<223> OTHER INFORMATION: SLC39A14

<400> SEQUENCE: 1171

Tyr Gly Glu Gly Asp Ser Leu Thr Leu Gln Gln Leu Lys
1               5                   10

<210> SEQ ID NO 1172
<211> LENGTH: 9
<212> TYPE: PRT
<213> ORGANISM: Artificial Sequence
<220> FEATURE:
<223> OTHER INFORMATION: SLC39A2

<400> SEQUENCE: 1172

Leu Val His Leu Gly Thr Ser Ser Arg
1               5

<210> SEQ ID NO 1173
<211> LENGTH: 4
<212> TYPE: PRT
<213> ORGANISM: Artificial Sequence
<220> FEATURE:
<223> OTHER INFORMATION: SLC39A2

<400> SEQUENCE: 1173

Gly Pro Leu Arg
1

<210> SEQ ID NO 1174
<211> LENGTH: 8
<212> TYPE: PRT
<213> ORGANISM: Artificial Sequence
<220> FEATURE:
<223> OTHER INFORMATION: SLC39A2

<400> SEQUENCE: 1174

Trp Phe Gln Ile Asp Ala Ala Arg

<210> SEQ ID NO 1175
<211> LENGTH: 5
<212> TYPE: PRT
<213> ORGANISM: Artificial Sequence
<220> FEATURE:
<223> OTHER INFORMATION: SLC39A2

<400> SEQUENCE: 1175

Ser Ala Ser Glu Arg
1               5

<210> SEQ ID NO 1176
<211> LENGTH: 5
<212> TYPE: PRT
<213> ORGANISM: Artificial Sequence
<220> FEATURE:
<223> OTHER INFORMATION: SLC39A3

<400> SEQUENCE: 1176

Ala Ser Pro Val Arg
1               5

<210> SEQ ID NO 1177
<211> LENGTH: 4
<212> TYPE: PRT
<213> ORGANISM: Artificial Sequence
<220> FEATURE:
<223> OTHER INFORMATION: SLC39A3

<400> SEQUENCE: 1177

Asp Ala Ala Lys
1

<210> SEQ ID NO 1178
<211> LENGTH: 7
<212> TYPE: PRT
<213> ORGANISM: Artificial Sequence
<220> FEATURE:
<223> OTHER INFORMATION: SLC39A3

<400> SEQUENCE: 1178

Ile Ile Glu Thr Asp Phe Glu
1               5

<210> SEQ ID NO 1179
<211> LENGTH: 5
<212> TYPE: PRT
<213> ORGANISM: Artificial Sequence
<220> FEATURE:
<223> OTHER INFORMATION: SLC39A3

<400> SEQUENCE: 1179

Leu Leu Val Ala Lys
1               5

<210> SEQ ID NO 1180
<211> LENGTH: 7
<212> TYPE: PRT
<213> ORGANISM: Artificial Sequence
<220> FEATURE:
<223> OTHER INFORMATION: SLC39A4

<400> SEQUENCE: 1180

Ala Ala Gly Gln Thr Pro Lys
1               5

```
<210> SEQ ID NO 1181
<211> LENGTH: 5
<212> TYPE: PRT
<213> ORGANISM: Artificial Sequence
<220> FEATURE:
<223> OTHER INFORMATION: SLC39A4

<400> SEQUENCE: 1181

Leu Gly Val Gly Arg
1               5

<210> SEQ ID NO 1182
<211> LENGTH: 19
<212> TYPE: PRT
<213> ORGANISM: Artificial Sequence
<220> FEATURE:
<223> OTHER INFORMATION: SLC39A4

<400> SEQUENCE: 1182

Ala Gly Leu Trp Ala Ser His Ala Asp His Leu Leu Ala Leu Leu Glu
1               5                   10                  15

Ser Pro Lys

<210> SEQ ID NO 1183
<211> LENGTH: 12
<212> TYPE: PRT
<213> ORGANISM: Artificial Sequence
<220> FEATURE:
<223> OTHER INFORMATION: SLC39A4

<400> SEQUENCE: 1183

Ala Leu Thr Pro Gly Leu Ser Trp Leu Leu Gln Arg
1               5                   10

<210> SEQ ID NO 1184
<211> LENGTH: 10
<212> TYPE: PRT
<213> ORGANISM: Artificial Sequence
<220> FEATURE:
<223> OTHER INFORMATION: SLC39A5

<400> SEQUENCE: 1184

Leu Gly Gln His Gly Pro Leu Thr Gly Arg
1               5                   10

<210> SEQ ID NO 1185
<211> LENGTH: 12
<212> TYPE: PRT
<213> ORGANISM: Artificial Sequence
<220> FEATURE:
<223> OTHER INFORMATION: SLC39A5

<400> SEQUENCE: 1185

Gly Pro Ala Pro Ser Gly Leu Asp Leu Leu His Arg
1               5                   10

<210> SEQ ID NO 1186
<211> LENGTH: 9
<212> TYPE: PRT
<213> ORGANISM: Artificial Sequence
<220> FEATURE:
<223> OTHER INFORMATION: SLC39A5

<400> SEQUENCE: 1186

Leu Leu His Ser Leu Gly Leu Gly Arg
1               5
```

<210> SEQ ID NO 1187
<211> LENGTH: 6
<212> TYPE: PRT
<213> ORGANISM: Artificial Sequence
<220> FEATURE:
<223> OTHER INFORMATION: SLC39A6

<400> SEQUENCE: 1187

Val Asp Thr Asp Asp Arg
1               5

<210> SEQ ID NO 1188
<211> LENGTH: 11
<212> TYPE: PRT
<213> ORGANISM: Artificial Sequence
<220> FEATURE:
<223> OTHER INFORMATION: SLC39A6

<400> SEQUENCE: 1188

Tyr Glu Ser Gln Leu Ser Thr Asn Glu Glu Lys
1               5                   10

<210> SEQ ID NO 1189
<211> LENGTH: 6
<212> TYPE: PRT
<213> ORGANISM: Artificial Sequence
<220> FEATURE:
<223> OTHER INFORMATION: SLC39A6

<400> SEQUENCE: 1189

Thr Glu Gly Tyr Leu Arg
1               5

<210> SEQ ID NO 1190
<211> LENGTH: 7
<212> TYPE: PRT
<213> ORGANISM: Artificial Sequence
<220> FEATURE:
<223> OTHER INFORMATION: SLC39A7

<400> SEQUENCE: 1190

Gly Ser His Gly His Gly Arg
1               5

<210> SEQ ID NO 1191
<211> LENGTH: 17
<212> TYPE: PRT
<213> ORGANISM: Artificial Sequence
<220> FEATURE:
<223> OTHER INFORMATION: SLC39A7

<400> SEQUENCE: 1191

Gly Gly His Gly His Ser His Gly His Gly His Ala His Ser His Thr
1               5                   10                  15

Arg

<210> SEQ ID NO 1192
<211> LENGTH: 22
<212> TYPE: PRT
<213> ORGANISM: Artificial Sequence
<220> FEATURE:
<223> OTHER INFORMATION: SLC39A7

<400> SEQUENCE: 1192

Gly His Gly His Asp His Glu His Ser His Gly Gly Tyr Gly Glu Ser
1               5                   10                  15

Gly Ala Pro Gly Ile Lys
            20

<210> SEQ ID NO 1193
<211> LENGTH: 5
<212> TYPE: PRT
<213> ORGANISM: Artificial Sequence
<220> FEATURE:
<223> OTHER INFORMATION: SLC39A8

<400> SEQUENCE: 1193

Thr His Gln Pro Lys
1               5

<210> SEQ ID NO 1194
<211> LENGTH: 7
<212> TYPE: PRT
<213> ORGANISM: Artificial Sequence
<220> FEATURE:
<223> OTHER INFORMATION: SLC39A8

<400> SEQUENCE: 1194

Val Asp Ser Tyr Val Glu Lys
1               5

<210> SEQ ID NO 1195
<211> LENGTH: 16
<212> TYPE: PRT
<213> ORGANISM: Artificial Sequence
<220> FEATURE:
<223> OTHER INFORMATION: SLC39A8

<400> SEQUENCE: 1195

Ala Val Ala Val Phe Gly Gly Phe Tyr Leu Leu Phe Phe Phe Glu Arg
1               5                   10                  15

<210> SEQ ID NO 1196
<211> LENGTH: 4
<212> TYPE: PRT
<213> ORGANISM: Artificial Sequence
<220> FEATURE:
<223> OTHER INFORMATION: SLC39A9

<400> SEQUENCE: 1196

Gly Leu Ser Arg
1

<210> SEQ ID NO 1197
<211> LENGTH: 4
<212> TYPE: PRT
<213> ORGANISM: Artificial Sequence
<220> FEATURE:
<223> OTHER INFORMATION: SLC39A9

<400> SEQUENCE: 1197

Ala Ala Glu Lys
1

<210> SEQ ID NO 1198
<211> LENGTH: 15
<212> TYPE: PRT
<213> ORGANISM: Artificial Sequence
<220> FEATURE:
<223> OTHER INFORMATION: SLC39A9

<400> SEQUENCE: 1198

His His Gln Ala Ser Glu Thr His Asn Val Ile Ala Ser Asp Lys
1               5                   10                  15

-continued

<210> SEQ ID NO 1199
<211> LENGTH: 7
<212> TYPE: PRT
<213> ORGANISM: Artificial Sequence
<220> FEATURE:
<223> OTHER INFORMATION: SLC3A1

<400> SEQUENCE: 1199

Asp Gly Asn Gly Asp Leu Lys
1               5

<210> SEQ ID NO 1200
<211> LENGTH: 8
<212> TYPE: PRT
<213> ORGANISM: Artificial Sequence
<220> FEATURE:
<223> OTHER INFORMATION: SLC3A1

<400> SEQUENCE: 1200

Leu Ser Thr Asn Ser Ala Asp Lys
1               5

<210> SEQ ID NO 1201
<211> LENGTH: 10
<212> TYPE: PRT
<213> ORGANISM: Artificial Sequence
<220> FEATURE:
<223> OTHER INFORMATION: SLC3A1

<400> SEQUENCE: 1201

Val Asp Thr Ser Gly Ile Phe Leu Asp Lys
1               5                   10

<210> SEQ ID NO 1202
<211> LENGTH: 11
<212> TYPE: PRT
<213> ORGANISM: Artificial Sequence
<220> FEATURE:
<223> OTHER INFORMATION: SLC3A1

<400> SEQUENCE: 1202

Gly Val Asp Gly Phe Ser Leu Asp Ala Val Lys
1               5                   10

<210> SEQ ID NO 1203
<211> LENGTH: 10
<212> TYPE: PRT
<213> ORGANISM: Artificial Sequence
<220> FEATURE:
<223> OTHER INFORMATION: SLC3A1

<400> SEQUENCE: 1203

Leu Asp Tyr Ile Thr Ala Leu Asn Ile Lys
1               5                   10

<210> SEQ ID NO 1204
<211> LENGTH: 12
<212> TYPE: PRT
<213> ORGANISM: Artificial Sequence
<220> FEATURE:
<223> OTHER INFORMATION: SLC3A2

<400> SEQUENCE: 1204

Leu Leu Thr Ser Phe Leu Pro Ala Gln Leu Leu Arg
1               5                   10

```
<210> SEQ ID NO 1205
<211> LENGTH: 10
<212> TYPE: PRT
<213> ORGANISM: Artificial Sequence
<220> FEATURE:
<223> OTHER INFORMATION: SLC3A2

<400> SEQUENCE: 1205

Val Ile Leu Asp Leu Thr Pro Asn Tyr Arg
1               5                   10

<210> SEQ ID NO 1206
<211> LENGTH: 5
<212> TYPE: PRT
<213> ORGANISM: Artificial Sequence
<220> FEATURE:
<223> OTHER INFORMATION: SLC3A2

<400> SEQUENCE: 1206

Leu Ser Asp Gln Arg
1               5

<210> SEQ ID NO 1207
<211> LENGTH: 6
<212> TYPE: PRT
<213> ORGANISM: Artificial Sequence
<220> FEATURE:
<223> OTHER INFORMATION: SLC3A2

<400> SEQUENCE: 1207

Phe Thr Gly Leu Ser Lys
1               5

<210> SEQ ID NO 1208
<211> LENGTH: 11
<212> TYPE: PRT
<213> ORGANISM: Artificial Sequence
<220> FEATURE:
<223> OTHER INFORMATION: SLC3A2

<400> SEQUENCE: 1208

Ala Asp Leu Leu Leu Ser Thr Gln Pro Gly Arg
1               5                   10

<210> SEQ ID NO 1209
<211> LENGTH: 7
<212> TYPE: PRT
<213> ORGANISM: Artificial Sequence
<220> FEATURE:
<223> OTHER INFORMATION: SLC40A1

<400> SEQUENCE: 1209

Thr Pro Ala Leu Ala Val Lys
1               5

<210> SEQ ID NO 1210
<211> LENGTH: 6
<212> TYPE: PRT
<213> ORGANISM: Artificial Sequence
<220> FEATURE:
<223> OTHER INFORMATION: SLC40A1

<400> SEQUENCE: 1210

Ala Gly Asp His Asn Arg
1               5

<210> SEQ ID NO 1211
<211> LENGTH: 11
```

```
<212> TYPE: PRT
<213> ORGANISM: Artificial Sequence
<220> FEATURE:
<223> OTHER INFORMATION: SLC40A1

<400> SEQUENCE: 1211

Phe Ile Gln Gly Glu Ser Ile Thr Pro Thr Lys
1               5                   10

<210> SEQ ID NO 1212
<211> LENGTH: 9
<212> TYPE: PRT
<213> ORGANISM: Artificial Sequence
<220> FEATURE:
<223> OTHER INFORMATION: SLC41A1

<400> SEQUENCE: 1212

Gly Pro Ala Pro Pro Ser Pro Leu Lys
1               5

<210> SEQ ID NO 1213
<211> LENGTH: 15
<212> TYPE: PRT
<213> ORGANISM: Artificial Sequence
<220> FEATURE:
<223> OTHER INFORMATION: SLC41A1

<400> SEQUENCE: 1213

Val Thr Glu Val Phe Ile Leu Val Pro Ala Leu Leu Gly Leu Lys
1               5                   10                  15

<210> SEQ ID NO 1214
<211> LENGTH: 6
<212> TYPE: PRT
<213> ORGANISM: Artificial Sequence
<220> FEATURE:
<223> OTHER INFORMATION: SLC41A1

<400> SEQUENCE: 1214

Asp Thr Asp Val Gly Asp
1               5

<210> SEQ ID NO 1215
<211> LENGTH: 9
<212> TYPE: PRT
<213> ORGANISM: Artificial Sequence
<220> FEATURE:
<223> OTHER INFORMATION: SLC41A2

<400> SEQUENCE: 1215

Leu Ser Thr Ala Val Asn Ile Gly Lys
1               5

<210> SEQ ID NO 1216
<211> LENGTH: 8
<212> TYPE: PRT
<213> ORGANISM: Artificial Sequence
<220> FEATURE:
<223> OTHER INFORMATION: SLC41A2

<400> SEQUENCE: 1216

Leu Asn Thr Ile Gln Ser Asp Lys
1               5

<210> SEQ ID NO 1217
<211> LENGTH: 10
<212> TYPE: PRT
<213> ORGANISM: Artificial Sequence
```

```
<220> FEATURE:
<223> OTHER INFORMATION: SLC41A2

<400> SEQUENCE: 1217

Thr Phe Phe Gly Pro Gly Val Asn Asn Lys
1               5                   10

<210> SEQ ID NO 1218
<211> LENGTH: 13
<212> TYPE: PRT
<213> ORGANISM: Artificial Sequence
<220> FEATURE:
<223> OTHER INFORMATION: SLC41A3

<400> SEQUENCE: 1218

Asp Leu Leu Thr Leu Val Pro Pro Leu Val Gly Leu Lys
1               5                   10

<210> SEQ ID NO 1219
<211> LENGTH: 7
<212> TYPE: PRT
<213> ORGANISM: Artificial Sequence
<220> FEATURE:
<223> OTHER INFORMATION: SLC41A3

<400> SEQUENCE: 1219

Gln Ser Pro Pro Ile Val Lys
1               5

<210> SEQ ID NO 1220
<211> LENGTH: 9
<212> TYPE: PRT
<213> ORGANISM: Artificial Sequence
<220> FEATURE:
<223> OTHER INFORMATION: SLC42A1

<400> SEQUENCE: 1220

Phe Leu Thr Pro Leu Phe Thr Thr Lys
1               5

<210> SEQ ID NO 1221
<211> LENGTH: 6
<212> TYPE: PRT
<213> ORGANISM: Artificial Sequence
<220> FEATURE:
<223> OTHER INFORMATION: SLC42A1

<400> SEQUENCE: 1221

Phe Asn Ile Gly Ile Lys
1               5

<210> SEQ ID NO 1222
<211> LENGTH: 9
<212> TYPE: PRT
<213> ORGANISM: Artificial Sequence
<220> FEATURE:
<223> OTHER INFORMATION: SLC42A2

<400> SEQUENCE: 1222

Val Leu Tyr Arg Pro Gln Leu Glu Lys
1               5

<210> SEQ ID NO 1223
<211> LENGTH: 9
<212> TYPE: PRT
<213> ORGANISM: Artificial Sequence
<220> FEATURE:
<223> OTHER INFORMATION: SLC42A2
```

<400> SEQUENCE: 1223

Phe Phe Thr Pro Ile Leu Glu Ser Lys
1               5

<210> SEQ ID NO 1224
<211> LENGTH: 13
<212> TYPE: PRT
<213> ORGANISM: Artificial Sequence
<220> FEATURE:
<223> OTHER INFORMATION: SLC42A3

<400> SEQUENCE: 1224

Tyr Asp Phe Glu Ala Asp Ala His Trp Trp Ser Glu Arg
1               5                   10

<210> SEQ ID NO 1225
<211> LENGTH: 6
<212> TYPE: PRT
<213> ORGANISM: Artificial Sequence
<220> FEATURE:
<223> OTHER INFORMATION: SLC42A3

<400> SEQUENCE: 1225

Gly Asp Ser Gln His Arg
1               5

<210> SEQ ID NO 1226
<211> LENGTH: 4
<212> TYPE: PRT
<213> ORGANISM: Artificial Sequence
<220> FEATURE:
<223> OTHER INFORMATION: SLC42A3

<400> SEQUENCE: 1226

Thr Gln Gly Lys
1

<210> SEQ ID NO 1227
<211> LENGTH: 19
<212> TYPE: PRT
<213> ORGANISM: Artificial Sequence
<220> FEATURE:
<223> OTHER INFORMATION: SLC42A3

<400> SEQUENCE: 1227

Glu Gly Leu Val His Ser Phe Asp Phe Gln Cys Phe Asn Gly Asp Trp
1               5                   10                  15

Thr Ala Arg

<210> SEQ ID NO 1228
<211> LENGTH: 9
<212> TYPE: PRT
<213> ORGANISM: Artificial Sequence
<220> FEATURE:
<223> OTHER INFORMATION: SLC43A1

<400> SEQUENCE: 1228

Leu Ser Gly Leu Ala Leu Asp His Lys
1               5

<210> SEQ ID NO 1229
<211> LENGTH: 9
<212> TYPE: PRT
<213> ORGANISM: Artificial Sequence
<220> FEATURE:
<223> OTHER INFORMATION: SLC43A1

<400> SEQUENCE: 1229

Gly Thr Ser Glu Asn Leu Pro Glu Arg
1               5

<210> SEQ ID NO 1230
<211> LENGTH: 6
<212> TYPE: PRT
<213> ORGANISM: Artificial Sequence
<220> FEATURE:
<223> OTHER INFORMATION: SLC43A1

<400> SEQUENCE: 1230

Asp Gly Val Ala Thr Lys
1               5

<210> SEQ ID NO 1231
<211> LENGTH: 8
<212> TYPE: PRT
<213> ORGANISM: Artificial Sequence
<220> FEATURE:
<223> OTHER INFORMATION: SLC43A2

<400> SEQUENCE: 1231

Phe Leu Val Ser Gly Asp Gln Lys
1               5

<210> SEQ ID NO 1232
<211> LENGTH: 10
<212> TYPE: PRT
<213> ORGANISM: Artificial Sequence
<220> FEATURE:
<223> OTHER INFORMATION: SLC43A2

<400> SEQUENCE: 1232

Glu Gln Val Ala Leu Gln Glu Gly His Lys
1               5                   10

<210> SEQ ID NO 1233
<211> LENGTH: 9
<212> TYPE: PRT
<213> ORGANISM: Artificial Sequence
<220> FEATURE:
<223> OTHER INFORMATION: SLC43A2

<400> SEQUENCE: 1233

Phe Ser Trp Leu Gly Phe Asp His Lys
1               5

<210> SEQ ID NO 1234
<211> LENGTH: 9
<212> TYPE: PRT
<213> ORGANISM: Artificial Sequence
<220> FEATURE:
<223> OTHER INFORMATION: SLC43A3

<400> SEQUENCE: 1234

Glu Glu Thr Pro Gly Ala Gly Gln Lys
1               5

<210> SEQ ID NO 1235
<211> LENGTH: 8
<212> TYPE: PRT
<213> ORGANISM: Artificial Sequence
<220> FEATURE:
<223> OTHER INFORMATION: SLC43A3

<400> SEQUENCE: 1235

```
Glu Thr Ala Glu His Glu Asn Arg
1               5
```

<210> SEQ ID NO 1236
<211> LENGTH: 7
<212> TYPE: PRT
<213> ORGANISM: Artificial Sequence
<220> FEATURE:
<223> OTHER INFORMATION: SLC43A3

<400> SEQUENCE: 1236

```
Glu Ser Pro Ser Ala Ile Ala
1               5
```

<210> SEQ ID NO 1237
<211> LENGTH: 12
<212> TYPE: PRT
<213> ORGANISM: Artificial Sequence
<220> FEATURE:
<223> OTHER INFORMATION: SLC45A1

<400> SEQUENCE: 1237

```
Ser Gln Val Thr Gly Tyr Ser Gly Ser Val Thr Arg
1               5                   10
```

<210> SEQ ID NO 1238
<211> LENGTH: 19
<212> TYPE: PRT
<213> ORGANISM: Artificial Sequence
<220> FEATURE:
<223> OTHER INFORMATION: SLC45A1

<400> SEQUENCE: 1238

```
His Leu Ser His Arg Asp Ile Gly Ile Ala Leu Ala Asp Val Thr Gly
1               5                   10                  15

Asn His Lys
```

<210> SEQ ID NO 1239
<211> LENGTH: 10
<212> TYPE: PRT
<213> ORGANISM: Artificial Sequence
<220> FEATURE:
<223> OTHER INFORMATION: SLC45A1

<400> SEQUENCE: 1239

```
Val Gly Ser Leu Asp Thr Ser Lys Pro Arg
1               5                   10
```

<210> SEQ ID NO 1240
<211> LENGTH: 7
<212> TYPE: PRT
<213> ORGANISM: Artificial Sequence
<220> FEATURE:
<223> OTHER INFORMATION: SLC45A1

<400> SEQUENCE: 1240

```
Ala Pro Asp Gly Phe Tyr Arg
1               5
```

<210> SEQ ID NO 1241
<211> LENGTH: 11
<212> TYPE: PRT
<213> ORGANISM: Artificial Sequence
<220> FEATURE:
<223> OTHER INFORMATION: SLC45A2

<400> SEQUENCE: 1241

Leu Ile Met His Ser Met Ala Met Phe Gly Arg
1               5                   10

<210> SEQ ID NO 1242
<211> LENGTH: 10
<212> TYPE: PRT
<213> ORGANISM: Artificial Sequence
<220> FEATURE:
<223> OTHER INFORMATION: SLC45A2

<400> SEQUENCE: 1242

Met Gly Ser Asn Ser Gly Gln Ala Gly Arg
1               5                   10

<210> SEQ ID NO 1243
<211> LENGTH: 4
<212> TYPE: PRT
<213> ORGANISM: Artificial Sequence
<220> FEATURE:
<223> OTHER INFORMATION: SLC45A2

<400> SEQUENCE: 1243

His Ile Tyr Lys
1

<210> SEQ ID NO 1244
<211> LENGTH: 8
<212> TYPE: PRT
<213> ORGANISM: Artificial Sequence
<220> FEATURE:
<223> OTHER INFORMATION: SLC45A3

<400> SEQUENCE: 1244

Asn Leu Gly Ala Leu Leu Pro Arg
1               5

<210> SEQ ID NO 1245
<211> LENGTH: 10
<212> TYPE: PRT
<213> ORGANISM: Artificial Sequence
<220> FEATURE:
<223> OTHER INFORMATION: SLC45A3

<400> SEQUENCE: 1245

Val Val Val Gly Glu Pro Thr Glu Ala Arg
1               5                   10

<210> SEQ ID NO 1246
<211> LENGTH: 6
<212> TYPE: PRT
<213> ORGANISM: Artificial Sequence
<220> FEATURE:
<223> OTHER INFORMATION: SLC45A3

<400> SEQUENCE: 1246

Gln Val Phe Leu Pro Lys
1               5

<210> SEQ ID NO 1247
<211> LENGTH: 5
<212> TYPE: PRT
<213> ORGANISM: Artificial Sequence
<220> FEATURE:
<223> OTHER INFORMATION: SLC45A3

<400> SEQUENCE: 1247

Val Val Pro Gly Arg

-continued

```
<210> SEQ ID NO 1248
<211> LENGTH: 5
<212> TYPE: PRT
<213> ORGANISM: Artificial Sequence
<220> FEATURE:
<223> OTHER INFORMATION: SLC45A3

<400> SEQUENCE: 1248

Ser Asp Leu Ala Lys
1               5

<210> SEQ ID NO 1249
<211> LENGTH: 8
<212> TYPE: PRT
<213> ORGANISM: Artificial Sequence
<220> FEATURE:
<223> OTHER INFORMATION: SLC45A4

<400> SEQUENCE: 1249

Ala Ser His His Pro Pro Ala Arg
1               5

<210> SEQ ID NO 1250
<211> LENGTH: 9
<212> TYPE: PRT
<213> ORGANISM: Artificial Sequence
<220> FEATURE:
<223> OTHER INFORMATION: SLC45A4

<400> SEQUENCE: 1250

Gly Leu Arg Pro Ser Pro Gly Asp Arg
1               5

<210> SEQ ID NO 1251
<211> LENGTH: 6
<212> TYPE: PRT
<213> ORGANISM: Artificial Sequence
<220> FEATURE:
<223> OTHER INFORMATION: SLC45A4

<400> SEQUENCE: 1251

Asn Tyr Leu Val Pro Leu
1               5

<210> SEQ ID NO 1252
<211> LENGTH: 14
<212> TYPE: PRT
<213> ORGANISM: Artificial Sequence
<220> FEATURE:
<223> OTHER INFORMATION: SLC4A1

<400> SEQUENCE: 1252

Ile Pro Pro Asp Ser Glu Ala Thr Leu Val Leu Val Gly Arg
1               5                   10

<210> SEQ ID NO 1253
<211> LENGTH: 13
<212> TYPE: PRT
<213> ORGANISM: Artificial Sequence
<220> FEATURE:
<223> OTHER INFORMATION: SLC4A1

<400> SEQUENCE: 1253

Ala Asp Phe Leu Glu Gln Pro Val Leu Gly Phe Val Arg
1               5                   10
```

<210> SEQ ID NO 1254
<211> LENGTH: 8
<212> TYPE: PRT
<213> ORGANISM: Artificial Sequence
<220> FEATURE:
<223> OTHER INFORMATION: SLC4A1

<400> SEQUENCE: 1254

Leu Ser Val Pro Asp Gly Phe Lys
1               5

<210> SEQ ID NO 1255
<211> LENGTH: 10
<212> TYPE: PRT
<213> ORGANISM: Artificial Sequence
<220> FEATURE:
<223> OTHER INFORMATION: SLC4A1

<400> SEQUENCE: 1255

Gly Trp Val Ile His Pro Leu Gly Leu Arg
1               5                   10

<210> SEQ ID NO 1256
<211> LENGTH: 14
<212> TYPE: PRT
<213> ORGANISM: Artificial Sequence
<220> FEATURE:
<223> OTHER INFORMATION: SLC4A1

<400> SEQUENCE: 1256

Ala Ser Thr Pro Gly Ala Ala Ala Gln Ile Gln Glu Val Lys
1               5                   10

<210> SEQ ID NO 1257
<211> LENGTH: 9
<212> TYPE: PRT
<213> ORGANISM: Artificial Sequence
<220> FEATURE:
<223> OTHER INFORMATION: SLC4A1

<400> SEQUENCE: 1257

Tyr His Pro Asp Val Pro Tyr Val Lys
1               5

<210> SEQ ID NO 1258
<211> LENGTH: 8
<212> TYPE: PRT
<213> ORGANISM: Artificial Sequence
<220> FEATURE:
<223> OTHER INFORMATION: SLC4A1

<400> SEQUENCE: 1258

Val Leu Leu Pro Leu Ile Phe Arg
1               5

<210> SEQ ID NO 1259
<211> LENGTH: 10
<212> TYPE: PRT
<213> ORGANISM: Artificial Sequence
<220> FEATURE:
<223> OTHER INFORMATION: SLC4A10

<400> SEQUENCE: 1259

Asn Leu Leu Ile Thr Ala Asp Asn Ser Lys
1               5                   10

<210> SEQ ID NO 1260

```
<211> LENGTH: 10
<212> TYPE: PRT
<213> ORGANISM: Artificial Sequence
<220> FEATURE:
<223> OTHER INFORMATION: SLC4A10

<400> SEQUENCE: 1260

Ile Phe Gly Gly Leu Ile Leu Asp Ile Lys
1               5                   10

<210> SEQ ID NO 1261
<211> LENGTH: 11
<212> TYPE: PRT
<213> ORGANISM: Artificial Sequence
<220> FEATURE:
<223> OTHER INFORMATION: SLC4A10

<400> SEQUENCE: 1261

Phe Leu Phe Ile Leu Leu Gly Pro Leu Gly Lys
1               5                   10

<210> SEQ ID NO 1262
<211> LENGTH: 7
<212> TYPE: PRT
<213> ORGANISM: Artificial Sequence
<220> FEATURE:
<223> OTHER INFORMATION: SLC4A10

<400> SEQUENCE: 1262

Thr Val Val Ala Phe Val Arg
1               5

<210> SEQ ID NO 1263
<211> LENGTH: 7
<212> TYPE: PRT
<213> ORGANISM: Artificial Sequence
<220> FEATURE:
<223> OTHER INFORMATION: SLC4A10

<400> SEQUENCE: 1263

Gly Leu Gly Gly Gln Gln Lys
1               5

<210> SEQ ID NO 1264
<211> LENGTH: 7
<212> TYPE: PRT
<213> ORGANISM: Artificial Sequence
<220> FEATURE:
<223> OTHER INFORMATION: SLC4A10

<400> SEQUENCE: 1264

Ser Phe Ala Asp Ile Gly Lys
1               5

<210> SEQ ID NO 1265
<211> LENGTH: 13
<212> TYPE: PRT
<213> ORGANISM: Artificial Sequence
<220> FEATURE:
<223> OTHER INFORMATION: SLC4A10

<400> SEQUENCE: 1265

Thr Leu Phe Ile Gly Val His Val Pro Leu Gly Gly Arg
1               5                   10

<210> SEQ ID NO 1266
<211> LENGTH: 12
<212> TYPE: PRT
```

-continued

```
<213> ORGANISM: Artificial Sequence
<220> FEATURE:
<223> OTHER INFORMATION: SLC4A11

<400> SEQUENCE: 1266

Glu Gln Thr Ala Tyr Pro Pro Thr His Tyr Ile Arg
1               5                   10

<210> SEQ ID NO 1267
<211> LENGTH: 14
<212> TYPE: PRT
<213> ORGANISM: Artificial Sequence
<220> FEATURE:
<223> OTHER INFORMATION: SLC4A11

<400> SEQUENCE: 1267

Val Glu Asn Gly His Ile Tyr Asp Thr Ile Val Asn Val Lys
1               5                   10

<210> SEQ ID NO 1268
<211> LENGTH: 13
<212> TYPE: PRT
<213> ORGANISM: Artificial Sequence
<220> FEATURE:
<223> OTHER INFORMATION: SLC4A11

<400> SEQUENCE: 1268

Tyr Tyr Tyr Gly His Tyr Leu Asp Asp Tyr His Thr Lys
1               5                   10

<210> SEQ ID NO 1269
<211> LENGTH: 15
<212> TYPE: PRT
<213> ORGANISM: Artificial Sequence
<220> FEATURE:
<223> OTHER INFORMATION: SLC4A11

<400> SEQUENCE: 1269

Phe Pro Leu Tyr Pro Leu Asp Phe Thr Asp Gly Ile Ile Gly Lys
1               5                   10                  15

<210> SEQ ID NO 1270
<211> LENGTH: 7
<212> TYPE: PRT
<213> ORGANISM: Artificial Sequence
<220> FEATURE:
<223> OTHER INFORMATION: SLC4A11

<400> SEQUENCE: 1270

Asp Phe Val Pro Phe Gly Lys
1               5

<210> SEQ ID NO 1271
<211> LENGTH: 7
<212> TYPE: PRT
<213> ORGANISM: Artificial Sequence
<220> FEATURE:
<223> OTHER INFORMATION: SLC4A11

<400> SEQUENCE: 1271

Glu Ala Leu Val His Gln Arg
1               5

<210> SEQ ID NO 1272
<211> LENGTH: 10
<212> TYPE: PRT
<213> ORGANISM: Artificial Sequence
<220> FEATURE:
```

<223> OTHER INFORMATION: SLC4A11

<400> SEQUENCE: 1272

Phe Val Ile Leu Val Leu Ala Pro Pro Lys
1               5                   10

<210> SEQ ID NO 1273
<211> LENGTH: 19
<212> TYPE: PRT
<213> ORGANISM: Artificial Sequence
<220> FEATURE:
<223> OTHER INFORMATION: SLC4A11

<400> SEQUENCE: 1273

Val His Leu Leu Ser Asp Thr Ile Gln Gly Val Thr Ala Thr Val Thr
1               5                   10                  15

Gly Val Arg

<210> SEQ ID NO 1274
<211> LENGTH: 5
<212> TYPE: PRT
<213> ORGANISM: Artificial Sequence
<220> FEATURE:
<223> OTHER INFORMATION: SLC4A2

<400> SEQUENCE: 1274

Asn Gln Glu Leu Arg
1               5

<210> SEQ ID NO 1275
<211> LENGTH: 5
<212> TYPE: PRT
<213> ORGANISM: Artificial Sequence
<220> FEATURE:
<223> OTHER INFORMATION: SLC4A2

<400> SEQUENCE: 1275

Ala Leu Leu Leu Lys
1               5

<210> SEQ ID NO 1276
<211> LENGTH: 14
<212> TYPE: PRT
<213> ORGANISM: Artificial Sequence
<220> FEATURE:
<223> OTHER INFORMATION: SLC4A2

<400> SEQUENCE: 1276

Ile Pro Pro Asp Ser Glu Ala Thr Leu Val Leu Val Gly Arg
1               5                   10

<210> SEQ ID NO 1277
<211> LENGTH: 13
<212> TYPE: PRT
<213> ORGANISM: Artificial Sequence
<220> FEATURE:
<223> OTHER INFORMATION: SLC4A2

<400> SEQUENCE: 1277

Ala Asp Phe Leu Glu Gln Pro Val Leu Gly Phe Val Arg
1               5                   10

<210> SEQ ID NO 1278
<211> LENGTH: 8
<212> TYPE: PRT
<213> ORGANISM: Artificial Sequence
<220> FEATURE:

<223> OTHER INFORMATION: SLC4A2

<400> SEQUENCE: 1278

Leu Ser Val Pro Asp Gly Phe Lys
1               5

<210> SEQ ID NO 1279
<211> LENGTH: 10
<212> TYPE: PRT
<213> ORGANISM: Artificial Sequence
<220> FEATURE:
<223> OTHER INFORMATION: SLC4A2

<400> SEQUENCE: 1279

Gly Trp Val Ile His Pro Leu Gly Leu Arg
1               5                   10

<210> SEQ ID NO 1280
<211> LENGTH: 14
<212> TYPE: PRT
<213> ORGANISM: Artificial Sequence
<220> FEATURE:
<223> OTHER INFORMATION: SLC4A2

<400> SEQUENCE: 1280

Ala Ser Thr Pro Gly Ala Ala Ala Gln Ile Gln Glu Val Lys
1               5                   10

<210> SEQ ID NO 1281
<211> LENGTH: 9
<212> TYPE: PRT
<213> ORGANISM: Artificial Sequence
<220> FEATURE:
<223> OTHER INFORMATION: SLC4A2

<400> SEQUENCE: 1281

Tyr His Pro Asp Val Pro Tyr Val Lys
1               5

<210> SEQ ID NO 1282
<211> LENGTH: 8
<212> TYPE: PRT
<213> ORGANISM: Artificial Sequence
<220> FEATURE:
<223> OTHER INFORMATION: SLC4A2

<400> SEQUENCE: 1282

Val Leu Leu Pro Leu Ile Phe Arg
1               5

<210> SEQ ID NO 1283
<211> LENGTH: 14
<212> TYPE: PRT
<213> ORGANISM: Artificial Sequence
<220> FEATURE:
<223> OTHER INFORMATION: SLC4A3

<400> SEQUENCE: 1283

Leu Thr Val Pro Thr Gly Leu Ser Val Thr Ser Pro Asp Lys
1               5                   10

<210> SEQ ID NO 1284
<211> LENGTH: 9
<212> TYPE: PRT
<213> ORGANISM: Artificial Sequence
<220> FEATURE:
<223> OTHER INFORMATION: SLC4A3

-continued

```
<400> SEQUENCE: 1284

Tyr Pro His Tyr Pro Ser Asp Leu Arg
1               5

<210> SEQ ID NO 1285
<211> LENGTH: 10
<212> TYPE: PRT
<213> ORGANISM: Artificial Sequence
<220> FEATURE:
<223> OTHER INFORMATION: SLC4A3

<400> SEQUENCE: 1285

Thr Gly Ser Val Phe Gly Gly Leu Val Arg
1               5                   10

<210> SEQ ID NO 1286
<211> LENGTH: 8
<212> TYPE: PRT
<213> ORGANISM: Artificial Sequence
<220> FEATURE:
<223> OTHER INFORMATION: SLC4A3

<400> SEQUENCE: 1286

Gly Gly Tyr Thr Ala Pro Gly Lys
1               5

<210> SEQ ID NO 1287
<211> LENGTH: 7
<212> TYPE: PRT
<213> ORGANISM: Artificial Sequence
<220> FEATURE:
<223> OTHER INFORMATION: SLC4A3

<400> SEQUENCE: 1287

Ser Val Ala Ala Phe Gln Arg
1               5

<210> SEQ ID NO 1288
<211> LENGTH: 7
<212> TYPE: PRT
<213> ORGANISM: Artificial Sequence
<220> FEATURE:
<223> OTHER INFORMATION: SLC4A3

<400> SEQUENCE: 1288

Asp Ser Gly Phe Phe Pro Arg
1               5

<210> SEQ ID NO 1289
<211> LENGTH: 8
<212> TYPE: PRT
<213> ORGANISM: Artificial Sequence
<220> FEATURE:
<223> OTHER INFORMATION: SLC4A3

<400> SEQUENCE: 1289

His Ser His Pro Asn Asp Asp Lys
1               5

<210> SEQ ID NO 1290
<211> LENGTH: 11
<212> TYPE: PRT
<213> ORGANISM: Artificial Sequence
<220> FEATURE:
<223> OTHER INFORMATION: SLC4A3

<400> SEQUENCE: 1290
```

```
<210> SEQ ID NO 1291
<211> LENGTH: 14
<212> TYPE: PRT
<213> ORGANISM: Artificial Sequence
<220> FEATURE:
<223> OTHER INFORMATION: SLC4A3

<400> SEQUENCE: 1291

Gly Ser Pro Ser Gly Leu Ala Pro Ile Leu Arg
1               5                   10

<210> SEQ ID NO 1291
<211> LENGTH: 14
<212> TYPE: PRT
<213> ORGANISM: Artificial Sequence
<220> FEATURE:
<223> OTHER INFORMATION: SLC4A3

<400> SEQUENCE: 1291

Asp Gly Asp Gly Thr Thr Asp Leu Ala Leu Ser Ser Pro Arg
1               5                   10

<210> SEQ ID NO 1292
<211> LENGTH: 7
<212> TYPE: PRT
<213> ORGANISM: Artificial Sequence
<220> FEATURE:
<223> OTHER INFORMATION: SLC4A3

<400> SEQUENCE: 1292

Leu Pro Pro Thr Ser Ala Arg
1               5

<210> SEQ ID NO 1293
<211> LENGTH: 6
<212> TYPE: PRT
<213> ORGANISM: Artificial Sequence
<220> FEATURE:
<223> OTHER INFORMATION: SLC4A3

<400> SEQUENCE: 1293

Leu Pro Pro Pro His Lys
1               5

<210> SEQ ID NO 1294
<211> LENGTH: 9
<212> TYPE: PRT
<213> ORGANISM: Artificial Sequence
<220> FEATURE:
<223> OTHER INFORMATION: SLC4A4

<400> SEQUENCE: 1294

His Gln Pro Asp Phe Ile Tyr Leu Arg
1               5

<210> SEQ ID NO 1295
<211> LENGTH: 12
<212> TYPE: PRT
<213> ORGANISM: Artificial Sequence
<220> FEATURE:
<223> OTHER INFORMATION: SLC4A4

<400> SEQUENCE: 1295

Leu Ala Asp Tyr Tyr Pro Ile Asn Ser Asn Phe Lys
1               5                   10

<210> SEQ ID NO 1296
<211> LENGTH: 7
<212> TYPE: PRT
<213> ORGANISM: Artificial Sequence
<220> FEATURE:
<223> OTHER INFORMATION: SLC4A4

<400> SEQUENCE: 1296

Leu Leu Phe Asn Phe Ser Lys
1               5
```

```
<210> SEQ ID NO 1297
<211> LENGTH: 7
<212> TYPE: PRT
<213> ORGANISM: Artificial Sequence
<220> FEATURE:
<223> OTHER INFORMATION: SLC4A4

<400> SEQUENCE: 1297

Ser Leu Pro Ser Ser Asp Lys
1               5

<210> SEQ ID NO 1298
<211> LENGTH: 9
<212> TYPE: PRT
<213> ORGANISM: Artificial Sequence
<220> FEATURE:
<223> OTHER INFORMATION: SLC4A4

<400> SEQUENCE: 1298

Phe Leu Phe Ile Leu Leu Gly Pro Lys
1               5

<210> SEQ ID NO 1299
<211> LENGTH: 7
<212> TYPE: PRT
<213> ORGANISM: Artificial Sequence
<220> FEATURE:
<223> OTHER INFORMATION: SLC4A4

<400> SEQUENCE: 1299

Ser Leu Ala Asp Ile Gly Lys
1               5

<210> SEQ ID NO 1300
<211> LENGTH: 4
<212> TYPE: PRT
<213> ORGANISM: Artificial Sequence
<220> FEATURE:
<223> OTHER INFORMATION: SLC4A4

<400> SEQUENCE: 1300

Ser Asn Leu Arg
1

<210> SEQ ID NO 1301
<211> LENGTH: 7
<212> TYPE: PRT
<213> ORGANISM: Artificial Sequence
<220> FEATURE:
<223> OTHER INFORMATION: SLC4A8

<400> SEQUENCE: 1301

Leu Leu Ser Ser Pro Gly Lys
1               5

<210> SEQ ID NO 1302
<211> LENGTH: 5
<212> TYPE: PRT
<213> ORGANISM: Artificial Sequence
<220> FEATURE:
<223> OTHER INFORMATION: SLC4A8

<400> SEQUENCE: 1302

Tyr Phe Pro Thr Arg
1               5
```

```
<210> SEQ ID NO 1303
<211> LENGTH: 10
<212> TYPE: PRT
<213> ORGANISM: Artificial Sequence
<220> FEATURE:
<223> OTHER INFORMATION: SLC4A8

<400> SEQUENCE: 1303

Leu Phe Gly Gly Leu Val Leu Asp Ile Lys
1               5                   10

<210> SEQ ID NO 1304
<211> LENGTH: 11
<212> TYPE: PRT
<213> ORGANISM: Artificial Sequence
<220> FEATURE:
<223> OTHER INFORMATION: SLC4A8

<400> SEQUENCE: 1304

Phe Leu Phe Ile Leu Leu Gly Pro Val Gly Lys
1               5                   10

<210> SEQ ID NO 1305
<211> LENGTH: 8
<212> TYPE: PRT
<213> ORGANISM: Artificial Sequence
<220> FEATURE:
<223> OTHER INFORMATION: SLC4A8

<400> SEQUENCE: 1305

Asn Asn Leu Ile Pro Ile Val Arg
1               5

<210> SEQ ID NO 1306
<211> LENGTH: 5
<212> TYPE: PRT
<213> ORGANISM: Artificial Sequence
<220> FEATURE:
<223> OTHER INFORMATION: SLC4A8

<400> SEQUENCE: 1306

Thr His Gly Gln Lys
1               5

<210> SEQ ID NO 1307
<211> LENGTH: 7
<212> TYPE: PRT
<213> ORGANISM: Artificial Sequence
<220> FEATURE:
<223> OTHER INFORMATION: SLC4A8

<400> SEQUENCE: 1307

Thr Leu Tyr Val Gly Val Arg
1               5

<210> SEQ ID NO 1308
<211> LENGTH: 9
<212> TYPE: PRT
<213> ORGANISM: Artificial Sequence
<220> FEATURE:
<223> OTHER INFORMATION: SLC4A9

<400> SEQUENCE: 1308

His Gln Pro Asp Leu Leu Leu Leu Arg
1               5

<210> SEQ ID NO 1309
<211> LENGTH: 7
```

```
<212> TYPE: PRT
<213> ORGANISM: Artificial Sequence
<220> FEATURE:
<223> OTHER INFORMATION: SLC4A9

<400> SEQUENCE: 1309

Phe Phe Pro Ser Val Val Arg
1               5

<210> SEQ ID NO 1310
<211> LENGTH: 10
<212> TYPE: PRT
<213> ORGANISM: Artificial Sequence
<220> FEATURE:
<223> OTHER INFORMATION: SLC4A9

<400> SEQUENCE: 1310

Asp Tyr Ser Leu Asp Tyr Leu Pro Phe Arg
1               5                   10

<210> SEQ ID NO 1311
<211> LENGTH: 10
<212> TYPE: PRT
<213> ORGANISM: Artificial Sequence
<220> FEATURE:
<223> OTHER INFORMATION: SLC4A9

<400> SEQUENCE: 1311

Leu Phe Gly Gly Leu Ile Gln Asp Val Arg
1               5                   10

<210> SEQ ID NO 1312
<211> LENGTH: 11
<212> TYPE: PRT
<213> ORGANISM: Artificial Sequence
<220> FEATURE:
<223> OTHER INFORMATION: SLC5A1

<400> SEQUENCE: 1312

Gly Thr Val Gly Gly Phe Phe Leu Ala Gly Arg
1               5                   10

<210> SEQ ID NO 1313
<211> LENGTH: 12
<212> TYPE: PRT
<213> ORGANISM: Artificial Sequence
<220> FEATURE:
<223> OTHER INFORMATION: SLC5A12

<400> SEQUENCE: 1313

Leu His Ile Phe Asp Phe Asp Val Asp Pro Leu Arg
1               5                   10

<210> SEQ ID NO 1314
<211> LENGTH: 11
<212> TYPE: PRT
<213> ORGANISM: Artificial Sequence
<220> FEATURE:
<223> OTHER INFORMATION: SLC5A2

<400> SEQUENCE: 1314

Gly Thr Val Gly Gly Tyr Phe Leu Ala Gly Arg
1               5                   10

<210> SEQ ID NO 1315
<211> LENGTH: 15
<212> TYPE: PRT
<213> ORGANISM: Artificial Sequence
```

-continued

```
<220> FEATURE:
<223> OTHER INFORMATION: SLC5A2

<400> SEQUENCE: 1315

Leu Tyr Leu Ser Val Leu Ser Leu Phe Leu Tyr Ile Phe Thr Lys
1               5                   10                  15

<210> SEQ ID NO 1316
<211> LENGTH: 6
<212> TYPE: PRT
<213> ORGANISM: Artificial Sequence
<220> FEATURE:
<223> OTHER INFORMATION: SLC5A2

<400> SEQUENCE: 1316

Ser Leu Thr His Ile Lys
1               5

<210> SEQ ID NO 1317
<211> LENGTH: 6
<212> TYPE: PRT
<213> ORGANISM: Artificial Sequence
<220> FEATURE:
<223> OTHER INFORMATION: SLC5A2

<400> SEQUENCE: 1317

Leu Val Phe Ser Leu Arg
1               5

<210> SEQ ID NO 1318
<211> LENGTH: 6
<212> TYPE: PRT
<213> ORGANISM: Artificial Sequence
<220> FEATURE:
<223> OTHER INFORMATION: SLC5A3

<400> SEQUENCE: 1318

Asn Ile Ala His Ala Lys
1               5

<210> SEQ ID NO 1319
<211> LENGTH: 8
<212> TYPE: PRT
<213> ORGANISM: Artificial Sequence
<220> FEATURE:
<223> OTHER INFORMATION: SLC5A3

<400> SEQUENCE: 1319

Leu Ile Leu Ala Phe Ala Tyr Arg
1               5

<210> SEQ ID NO 1320
<211> LENGTH: 11
<212> TYPE: PRT
<213> ORGANISM: Artificial Sequence
<220> FEATURE:
<223> OTHER INFORMATION: SLC5A4

<400> SEQUENCE: 1320

Gly Thr Ile Gly Gly Phe Phe Leu Ala Gly Arg
1               5                   10

<210> SEQ ID NO 1321
<211> LENGTH: 8
<212> TYPE: PRT
<213> ORGANISM: Artificial Sequence
<220> FEATURE:
<223> OTHER INFORMATION: SLC5A4
```

```
<400> SEQUENCE: 1321

Ala Asp Ser Phe His Ile Phe Arg
1               5

<210> SEQ ID NO 1322
<211> LENGTH: 6
<212> TYPE: PRT
<213> ORGANISM: Artificial Sequence
<220> FEATURE:
<223> OTHER INFORMATION: SLC5A5

<400> SEQUENCE: 1322

Leu Val Ile Ile Ser Lys
1               5

<210> SEQ ID NO 1323
<211> LENGTH: 8
<212> TYPE: PRT
<213> ORGANISM: Artificial Sequence
<220> FEATURE:
<223> OTHER INFORMATION: SLC5A5

<400> SEQUENCE: 1323

Val Leu Pro Ser Ser Ala Ala Arg
1               5

<210> SEQ ID NO 1324
<211> LENGTH: 7
<212> TYPE: PRT
<213> ORGANISM: Artificial Sequence
<220> FEATURE:
<223> OTHER INFORMATION: SLC5A5

<400> SEQUENCE: 1324

Leu Phe Phe Leu Gly Gln Lys
1               5

<210> SEQ ID NO 1325
<211> LENGTH: 7
<212> TYPE: PRT
<213> ORGANISM: Artificial Sequence
<220> FEATURE:
<223> OTHER INFORMATION: SLC6A1

<400> SEQUENCE: 1325

Ala Ala Asp Leu Pro Asp Arg
1               5

<210> SEQ ID NO 1326
<211> LENGTH: 8
<212> TYPE: PRT
<213> ORGANISM: Artificial Sequence
<220> FEATURE:
<223> OTHER INFORMATION: SLC6A1

<400> SEQUENCE: 1326

Gly Val Thr Leu Pro Gly Ala Lys
1               5

<210> SEQ ID NO 1327
<211> LENGTH: 8
<212> TYPE: PRT
<213> ORGANISM: Artificial Sequence
<220> FEATURE:
<223> OTHER INFORMATION: SLC6A11

<400> SEQUENCE: 1327
```

```
Ala Leu Pro Leu Gly Asn Gly Lys
1               5
```

<210> SEQ ID NO 1328
<211> LENGTH: 9
<212> TYPE: PRT
<213> ORGANISM: Artificial Sequence
<220> FEATURE:
<223> OTHER INFORMATION: SLC6A11

<400> SEQUENCE: 1328

```
Phe Tyr Leu Tyr Pro Asp Leu Ser Arg
1               5
```

<210> SEQ ID NO 1329
<211> LENGTH: 9
<212> TYPE: PRT
<213> ORGANISM: Artificial Sequence
<220> FEATURE:
<223> OTHER INFORMATION: SLC6A11

<400> SEQUENCE: 1329

```
Leu Thr Thr Pro Ser Thr Asp Leu Lys
1               5
```

<210> SEQ ID NO 1330
<211> LENGTH: 9
<212> TYPE: PRT
<213> ORGANISM: Artificial Sequence
<220> FEATURE:
<223> OTHER INFORMATION: SLC6A14

<400> SEQUENCE: 1330

```
Gly Ala Thr Leu Glu Gly Ala Ser Lys
1               5
```

<210> SEQ ID NO 1331
<211> LENGTH: 7
<212> TYPE: PRT
<213> ORGANISM: Artificial Sequence
<220> FEATURE:
<223> OTHER INFORMATION: SLC6A15

<400> SEQUENCE: 1331

```
Gly Ile Gln Ser Ser Gly Lys
1               5
```

<210> SEQ ID NO 1332
<211> LENGTH: 12
<212> TYPE: PRT
<213> ORGANISM: Artificial Sequence
<220> FEATURE:
<223> OTHER INFORMATION: SLC6A15

<400> SEQUENCE: 1332

```
Ala Phe Leu Leu Asn Gly Ser Ile Asp Gly Ile Arg
1               5                   10
```

<210> SEQ ID NO 1333
<211> LENGTH: 10
<212> TYPE: PRT
<213> ORGANISM: Artificial Sequence
<220> FEATURE:
<223> OTHER INFORMATION: SLC6A16

<400> SEQUENCE: 1333

```
Phe Gly Leu Gln Gln Leu Val Val Ala Lys
```

-continued

```
<210> SEQ ID NO 1334
<211> LENGTH: 12
<212> TYPE: PRT
<213> ORGANISM: Artificial Sequence
<220> FEATURE:
<223> OTHER INFORMATION: SLC6A17

<400> SEQUENCE: 1334

Ile Leu Gly Tyr Leu Asn Thr Asn Val Leu Ser Arg
1               5                   10

<210> SEQ ID NO 1335
<211> LENGTH: 17
<212> TYPE: PRT
<213> ORGANISM: Artificial Sequence
<220> FEATURE:
<223> OTHER INFORMATION: SLC6A17

<400> SEQUENCE: 1335

His Phe His Leu Leu Ser Asp Gly Ser Asn Thr Leu Ser Val Ser Tyr
1               5                   10                  15

Lys

<210> SEQ ID NO 1336
<211> LENGTH: 7
<212> TYPE: PRT
<213> ORGANISM: Artificial Sequence
<220> FEATURE:
<223> OTHER INFORMATION: SLC6A18

<400> SEQUENCE: 1336

Val Ala Gln Leu Pro Leu Lys
1               5

<210> SEQ ID NO 1337
<211> LENGTH: 11
<212> TYPE: PRT
<213> ORGANISM: Artificial Sequence
<220> FEATURE:
<223> OTHER INFORMATION: SLC6A19

<400> SEQUENCE: 1337

Leu Val Leu Pro Asn Pro Gly Leu Asp Ala Arg
1               5                   10

<210> SEQ ID NO 1338
<211> LENGTH: 7
<212> TYPE: PRT
<213> ORGANISM: Artificial Sequence
<220> FEATURE:
<223> OTHER INFORMATION: SLC6A2

<400> SEQUENCE: 1338

Asp Gly Asp Ala Gln Pro Arg
1               5

<210> SEQ ID NO 1339
<211> LENGTH: 10
<212> TYPE: PRT
<213> ORGANISM: Artificial Sequence
<220> FEATURE:
<223> OTHER INFORMATION: SLC6A20

<400> SEQUENCE: 1339

Gly Tyr Leu Ala Ser Ala Tyr Pro Ser Lys
```

1               5                  10

<210> SEQ ID NO 1340
<211> LENGTH: 8
<212> TYPE: PRT
<213> ORGANISM: Artificial Sequence
<220> FEATURE:
<223> OTHER INFORMATION: SLC6A20

<400> SEQUENCE: 1340

Ile Ile Ser Ser His Leu Pro Lys
1               5

<210> SEQ ID NO 1341
<211> LENGTH: 7
<212> TYPE: PRT
<213> ORGANISM: Artificial Sequence
<220> FEATURE:
<223> OTHER INFORMATION: SLC6A20

<400> SEQUENCE: 1341

Gly Asp Ala Asp Pro Val Ala
1               5

<210> SEQ ID NO 1342
<211> LENGTH: 12
<212> TYPE: PRT
<213> ORGANISM: Artificial Sequence
<220> FEATURE:
<223> OTHER INFORMATION: SLC6A3

<400> SEQUENCE: 1342

Gly Val Thr Leu Pro Gly Ala Ile Asp Gly Ile Arg
1               5                  10

<210> SEQ ID NO 1343
<211> LENGTH: 9
<212> TYPE: PRT
<213> ORGANISM: Artificial Sequence
<220> FEATURE:
<223> OTHER INFORMATION: SLC6A3

<400> SEQUENCE: 1343

Ala Tyr Leu Ser Val Asp Phe Tyr Arg
1               5

<210> SEQ ID NO 1344
<211> LENGTH: 10
<212> TYPE: PRT
<213> ORGANISM: Artificial Sequence
<220> FEATURE:
<223> OTHER INFORMATION: SLC6A3

<400> SEQUENCE: 1344

His Ser Val Pro Ile Gly Asp Val Ala Lys
1               5                  10

<210> SEQ ID NO 1345
<211> LENGTH: 8
<212> TYPE: PRT
<213> ORGANISM: Artificial Sequence
<220> FEATURE:
<223> OTHER INFORMATION: SLC6A4

<400> SEQUENCE: 1345

Val Val Pro Thr Pro Gly Asp Lys
1               5

<210> SEQ ID NO 1346
<211> LENGTH: 7
<212> TYPE: PRT
<213> ORGANISM: Artificial Sequence
<220> FEATURE:
<223> OTHER INFORMATION: SLC6A4

<400> SEQUENCE: 1346

His Val Leu Gln Ile His Arg
1               5

<210> SEQ ID NO 1347
<211> LENGTH: 9
<212> TYPE: PRT
<213> ORGANISM: Artificial Sequence
<220> FEATURE:
<223> OTHER INFORMATION: SLC6A4

<400> SEQUENCE: 1347

Leu Ile Ile Thr Pro Gly Thr Phe Lys
1               5

<210> SEQ ID NO 1348
<211> LENGTH: 15
<212> TYPE: PRT
<213> ORGANISM: Artificial Sequence
<220> FEATURE:
<223> OTHER INFORMATION: SLC6A5

<400> SEQUENCE: 1348

Ser Ala Ser Thr Gly Ala Gln Thr Phe Gln Ser Ala Asp Ala Arg
1               5                   10                  15

<210> SEQ ID NO 1349
<211> LENGTH: 9
<212> TYPE: PRT
<213> ORGANISM: Artificial Sequence
<220> FEATURE:
<223> OTHER INFORMATION: SLC6A5

<400> SEQUENCE: 1349

Ala Gln Ala Ala Ser Ala Ala Leu Arg
1               5

<210> SEQ ID NO 1350
<211> LENGTH: 16
<212> TYPE: PRT
<213> ORGANISM: Artificial Sequence
<220> FEATURE:
<223> OTHER INFORMATION: SLC6A6

<400> SEQUENCE: 1350

Asn Val Leu Ser Leu Ser Pro Gly Ile Asp His Pro Gly Ser Leu Lys
1               5                   10                  15

<210> SEQ ID NO 1351
<211> LENGTH: 12
<212> TYPE: PRT
<213> ORGANISM: Artificial Sequence
<220> FEATURE:
<223> OTHER INFORMATION: SLC6A6

<400> SEQUENCE: 1351

Gly Leu Thr Leu Pro Gly Ala Gly Ala Gly Ile Lys
1               5                   10

<210> SEQ ID NO 1352

```
<211> LENGTH: 9
<212> TYPE: PRT
<213> ORGANISM: Artificial Sequence
<220> FEATURE:
<223> OTHER INFORMATION: SLC6A6

<400> SEQUENCE: 1352

Phe Tyr Leu Tyr Pro Asp Ile Thr Arg
1               5

<210> SEQ ID NO 1353
<211> LENGTH: 8
<212> TYPE: PRT
<213> ORGANISM: Artificial Sequence
<220> FEATURE:
<223> OTHER INFORMATION: SLC6A6

<400> SEQUENCE: 1353

Tyr Val Pro Leu Thr Tyr Asn Lys
1               5

<210> SEQ ID NO 1354
<211> LENGTH: 6
<212> TYPE: PRT
<213> ORGANISM: Artificial Sequence
<220> FEATURE:
<223> OTHER INFORMATION: SLC6A6

<400> SEQUENCE: 1354

Tyr Leu Leu Thr Pro Arg
1               5

<210> SEQ ID NO 1355
<211> LENGTH: 7
<212> TYPE: PRT
<213> ORGANISM: Artificial Sequence
<220> FEATURE:
<223> OTHER INFORMATION: SLC6A7

<400> SEQUENCE: 1355

Leu Gln Gly Ala His Leu Arg
1               5

<210> SEQ ID NO 1356
<211> LENGTH: 6
<212> TYPE: PRT
<213> ORGANISM: Artificial Sequence
<220> FEATURE:
<223> OTHER INFORMATION: SLC6A7

<400> SEQUENCE: 1356

Ile Ser Pro Leu Phe Lys
1               5

<210> SEQ ID NO 1357
<211> LENGTH: 17
<212> TYPE: PRT
<213> ORGANISM: Artificial Sequence
<220> FEATURE:
<223> OTHER INFORMATION: SLC6A7

<400> SEQUENCE: 1357

Gly Ile Gln Phe Tyr Leu Thr Pro Gln Phe His His Leu Leu Ser Ser
1               5                   10                  15

Lys

<210> SEQ ID NO 1358
```

<210> SEQ ID NO 1358
<211> LENGTH: 14
<212> TYPE: PRT
<213> ORGANISM: Artificial Sequence
<220> FEATURE:
<223> OTHER INFORMATION: SLC6A8

<400> SEQUENCE: 1358

Gly Pro Leu Ile Ala Pro Gly Pro Asp Gly Ala Pro Ala Lys
1               5                   10

<210> SEQ ID NO 1359
<211> LENGTH: 13
<212> TYPE: PRT
<213> ORGANISM: Artificial Sequence
<220> FEATURE:
<223> OTHER INFORMATION: SLC6A8

<400> SEQUENCE: 1359

Gly Asp Gly Pro Val Gly Leu Gly Thr Pro Gly Gly Arg
1               5                   10

<210> SEQ ID NO 1360
<211> LENGTH: 6
<212> TYPE: PRT
<213> ORGANISM: Artificial Sequence
<220> FEATURE:
<223> OTHER INFORMATION: SLC6A8

<400> SEQUENCE: 1360

Leu Ala Val Pro Pro Arg
1               5

<210> SEQ ID NO 1361
<211> LENGTH: 8
<212> TYPE: PRT
<213> ORGANISM: Artificial Sequence
<220> FEATURE:
<223> OTHER INFORMATION: SLC7A1

<400> SEQUENCE: 1361

Phe Leu Ala Asn Val Asn Asp Arg
1               5

<210> SEQ ID NO 1362
<211> LENGTH: 9
<212> TYPE: PRT
<213> ORGANISM: Artificial Sequence
<220> FEATURE:
<223> OTHER INFORMATION: SLC7A10

<400> SEQUENCE: 1362

Ile Gln Asp Met Phe Thr Gly Gly Lys
1               5

<210> SEQ ID NO 1363
<211> LENGTH: 11
<212> TYPE: PRT
<213> ORGANISM: Artificial Sequence
<220> FEATURE:
<223> OTHER INFORMATION: SLC7A11

<400> SEQUENCE: 1363

Gly Gly Tyr Leu Gln Gly Asn Val Asn Gly Arg
1               5                   10

<210> SEQ ID NO 1364
<211> LENGTH: 7
<212> TYPE: PRT

-continued

```
<213> ORGANISM: Artificial Sequence
<220> FEATURE:
<223> OTHER INFORMATION: SLC7A11

<400> SEQUENCE: 1364

Leu Pro Ser Leu Gly Asn Lys
1               5

<210> SEQ ID NO 1365
<211> LENGTH: 7
<212> TYPE: PRT
<213> ORGANISM: Artificial Sequence
<220> FEATURE:
<223> OTHER INFORMATION: SLC7A11

<400> SEQUENCE: 1365

Gly Gln Thr Gln Asn Phe Lys
1               5

<210> SEQ ID NO 1366
<211> LENGTH: 6
<212> TYPE: PRT
<213> ORGANISM: Artificial Sequence
<220> FEATURE:
<223> OTHER INFORMATION: SLC7A11

<400> SEQUENCE: 1366

Asp Ala Phe Ser Gly Arg
1               5

<210> SEQ ID NO 1367
<211> LENGTH: 6
<212> TYPE: PRT
<213> ORGANISM: Artificial Sequence
<220> FEATURE:
<223> OTHER INFORMATION: SLC7A11

<400> SEQUENCE: 1367

Asp Ser Ser Ile Thr Arg
1               5

<210> SEQ ID NO 1368
<211> LENGTH: 7
<212> TYPE: PRT
<213> ORGANISM: Artificial Sequence
<220> FEATURE:
<223> OTHER INFORMATION: SLC7A11

<400> SEQUENCE: 1368

Leu Phe Tyr Val Ala Ser Arg
1               5

<210> SEQ ID NO 1369
<211> LENGTH: 17
<212> TYPE: PRT
<213> ORGANISM: Artificial Sequence
<220> FEATURE:
<223> OTHER INFORMATION: SLC7A13

<400> SEQUENCE: 1369

Val Ser Ile Leu Ser Phe Ile Ser Leu Thr Gly Val Val Phe Leu Ile
1               5                   10                  15

Arg

<210> SEQ ID NO 1370
<211> LENGTH: 23
<212> TYPE: PRT
```

```
<213> ORGANISM: Artificial Sequence
<220> FEATURE:
<223> OTHER INFORMATION: SLC7A13

<400> SEQUENCE: 1370

Val Phe Leu Ser Phe Pro Leu Ala Thr Ile Val Ile Asp Val Gly Leu
1               5                   10                  15

Val Val Ile Pro Leu Val Lys
            20

<210> SEQ ID NO 1371
<211> LENGTH: 8
<212> TYPE: PRT
<213> ORGANISM: Artificial Sequence
<220> FEATURE:
<223> OTHER INFORMATION: SLC7A14

<400> SEQUENCE: 1371

Leu Ser Thr Ile Thr Trp Ile Arg
1               5

<210> SEQ ID NO 1372
<211> LENGTH: 6
<212> TYPE: PRT
<213> ORGANISM: Artificial Sequence
<220> FEATURE:
<223> OTHER INFORMATION: SLC7A3

<400> SEQUENCE: 1372

Ser Asn Gln Pro Ser Arg
1               5

<210> SEQ ID NO 1373
<211> LENGTH: 14
<212> TYPE: PRT
<213> ORGANISM: Artificial Sequence
<220> FEATURE:
<223> OTHER INFORMATION: SLC7A3

<400> SEQUENCE: 1373

Thr Val Asp Leu Asp Pro Gly Thr Leu Tyr Val His Ser Val
1               5                   10

<210> SEQ ID NO 1374
<211> LENGTH: 10
<212> TYPE: PRT
<213> ORGANISM: Artificial Sequence
<220> FEATURE:
<223> OTHER INFORMATION: SLC7A4

<400> SEQUENCE: 1374

Gly Leu Pro Thr Ile Ala Ser Leu Ala Arg
1               5                   10

<210> SEQ ID NO 1375
<211> LENGTH: 17
<212> TYPE: PRT
<213> ORGANISM: Artificial Sequence
<220> FEATURE:
<223> OTHER INFORMATION: SLC7A4

<400> SEQUENCE: 1375

Ser Ser Pro Pro Ser Ser Pro Gly Pro Ala Ser Pro Gly Pro Leu Thr
1               5                   10                  15

Lys
```

```
<210> SEQ ID NO 1376
<211> LENGTH: 7
<212> TYPE: PRT
<213> ORGANISM: Artificial Sequence
<220> FEATURE:
<223> OTHER INFORMATION: SLC7A7

<400> SEQUENCE: 1376

Ile Val Gly Ser Ala Thr Arg
1               5

<210> SEQ ID NO 1377
<211> LENGTH: 9
<212> TYPE: PRT
<213> ORGANISM: Artificial Sequence
<220> FEATURE:
<223> OTHER INFORMATION: SLC7A8

<400> SEQUENCE: 1377

Ser Gly Gly Asp Tyr Ser Tyr Val Lys
1               5

<210> SEQ ID NO 1378
<211> LENGTH: 7
<212> TYPE: PRT
<213> ORGANISM: Artificial Sequence
<220> FEATURE:
<223> OTHER INFORMATION: SLC7A8

<400> SEQUENCE: 1378

Leu Phe Phe Ala Gly Ala Arg
1               5

<210> SEQ ID NO 1379
<211> LENGTH: 8
<212> TYPE: PRT
<213> ORGANISM: Artificial Sequence
<220> FEATURE:
<223> OTHER INFORMATION: SLC7A8

<400> SEQUENCE: 1379

Asp Val Ala Gly Gln Pro Gln Pro
1               5

<210> SEQ ID NO 1380
<211> LENGTH: 8
<212> TYPE: PRT
<213> ORGANISM: Artificial Sequence
<220> FEATURE:
<223> OTHER INFORMATION: SLC8A1

<400> SEQUENCE: 1380

Gly Asn Val Ile Val Pro Tyr Lys
1               5

<210> SEQ ID NO 1381
<211> LENGTH: 22
<212> TYPE: PRT
<213> ORGANISM: Artificial Sequence
<220> FEATURE:
<223> OTHER INFORMATION: SLC8A1

<400> SEQUENCE: 1381

Asp Ser Val Thr Ala Val Val Phe Val Ala Leu Gly Thr Ser Val Pro
1               5                   10                  15

Asp Thr Phe Ala Ser Lys
            20
```

```
<210> SEQ ID NO 1382
<211> LENGTH: 6
<212> TYPE: PRT
<213> ORGANISM: Artificial Sequence
<220> FEATURE:
<223> OTHER INFORMATION: SLC8A1

<400> SEQUENCE: 1382

Gln Pro Leu Thr Ser Lys
1               5

<210> SEQ ID NO 1383
<211> LENGTH: 7
<212> TYPE: PRT
<213> ORGANISM: Artificial Sequence
<220> FEATURE:
<223> OTHER INFORMATION: SLC8A2

<400> SEQUENCE: 1383

Thr Val Asp Gly Thr Ala Arg
1               5

<210> SEQ ID NO 1384
<211> LENGTH: 21
<212> TYPE: PRT
<213> ORGANISM: Artificial Sequence
<220> FEATURE:
<223> OTHER INFORMATION: SLC8A2

<400> SEQUENCE: 1384

Asp Ser Val Asn Ala Val Val Phe Val Ala Leu Gly Thr Ser Ile Pro
1               5                   10                  15

Asp Thr Phe Ala Ser
            20

<210> SEQ ID NO 1385
<211> LENGTH: 8
<212> TYPE: PRT
<213> ORGANISM: Artificial Sequence
<220> FEATURE:
<223> OTHER INFORMATION: SLC8A3

<400> SEQUENCE: 1385

Gly Thr Val Ile Val Pro Phe Arg
1               5

<210> SEQ ID NO 1386
<211> LENGTH: 24
<212> TYPE: PRT
<213> ORGANISM: Artificial Sequence
<220> FEATURE:
<223> OTHER INFORMATION: SLC8A3

<400> SEQUENCE: 1386

Leu Gln Pro Leu Thr Ser Ala Phe Leu His Phe Gly Leu Val Thr Phe
1               5                   10                  15

Val Leu Phe Leu Asn Gly Leu Arg
            20

<210> SEQ ID NO 1387
<211> LENGTH: 11
<212> TYPE: PRT
<213> ORGANISM: Artificial Sequence
<220> FEATURE:
<223> OTHER INFORMATION: SLC9A1

<400> SEQUENCE: 1387
```

Ile Asn Asn Tyr Leu Thr Val Pro Ala His Lys
1               5                   10

<210> SEQ ID NO 1388
<211> LENGTH: 14
<212> TYPE: PRT
<213> ORGANISM: Artificial Sequence
<220> FEATURE:
<223> OTHER INFORMATION: SLC9A1

<400> SEQUENCE: 1388

Ser His Gly Leu Gln Leu Ser Pro Thr Ala Ser Thr Ile Arg
1               5                   10

<210> SEQ ID NO 1389
<211> LENGTH: 6
<212> TYPE: PRT
<213> ORGANISM: Artificial Sequence
<220> FEATURE:
<223> OTHER INFORMATION: SLC9A1

<400> SEQUENCE: 1389

Phe Thr Ser His Ile Arg
1               5

<210> SEQ ID NO 1390
<211> LENGTH: 6
<212> TYPE: PRT
<213> ORGANISM: Artificial Sequence
<220> FEATURE:
<223> OTHER INFORMATION: SLC9A1

<400> SEQUENCE: 1390

Ser His Thr Thr Ile Lys
1               5

<210> SEQ ID NO 1391
<211> LENGTH: 11
<212> TYPE: PRT
<213> ORGANISM: Artificial Sequence
<220> FEATURE:
<223> OTHER INFORMATION: SLC9A1

<400> SEQUENCE: 1391

Asp Gln Phe Ile Ile Ala Tyr Gly Gly Leu Arg
1               5                   10

<210> SEQ ID NO 1392
<211> LENGTH: 7
<212> TYPE: PRT
<213> ORGANISM: Artificial Sequence
<220> FEATURE:
<223> OTHER INFORMATION: SLC9A1

<400> SEQUENCE: 1392

Ile Leu Pro Ala Leu Ser Lys
1               5

<210> SEQ ID NO 1393
<211> LENGTH: 6
<212> TYPE: PRT
<213> ORGANISM: Artificial Sequence
<220> FEATURE:
<223> OTHER INFORMATION: SLC9A1

<400> SEQUENCE: 1393

Val Leu Gly Leu Ser Arg

```
1               5
```

<210> SEQ ID NO 1394
<211> LENGTH: 11
<212> TYPE: PRT
<213> ORGANISM: Artificial Sequence
<220> FEATURE:
<223> OTHER INFORMATION: SLC9A2

<400> SEQUENCE: 1394

```
Asp Gln Phe Ile Ile Ala Tyr Gly Gly Leu Arg
1               5                   10
```

<210> SEQ ID NO 1395
<211> LENGTH: 6
<212> TYPE: PRT
<213> ORGANISM: Artificial Sequence
<220> FEATURE:
<223> OTHER INFORMATION: SLC9A2

<400> SEQUENCE: 1395

```
Phe Thr His Asn Ile Arg
1               5
```

<210> SEQ ID NO 1396
<211> LENGTH: 6
<212> TYPE: PRT
<213> ORGANISM: Artificial Sequence
<220> FEATURE:
<223> OTHER INFORMATION: SLC9A2

<400> SEQUENCE: 1396

```
Ser Tyr Thr Thr Ile Lys
1               5
```

<210> SEQ ID NO 1397
<211> LENGTH: 13
<212> TYPE: PRT
<213> ORGANISM: Artificial Sequence
<220> FEATURE:
<223> OTHER INFORMATION: SLC9A2

<400> SEQUENCE: 1397

```
Ala Leu Gly Val Phe Val Leu Thr Gln Val Ile Asn Arg
1               5                   10
```

<210> SEQ ID NO 1398
<211> LENGTH: 7
<212> TYPE: PRT
<213> ORGANISM: Artificial Sequence
<220> FEATURE:
<223> OTHER INFORMATION: SLC9A2

<400> SEQUENCE: 1398

```
Thr Ile Pro Leu Thr Phe Lys
1               5
```

<210> SEQ ID NO 1399
<211> LENGTH: 6
<212> TYPE: PRT
<213> ORGANISM: Artificial Sequence
<220> FEATURE:
<223> OTHER INFORMATION: SLC9A2

<400> SEQUENCE: 1399

```
Leu Phe Asp His Val Lys
1               5
```

```
<210> SEQ ID NO 1400
<211> LENGTH: 6
<212> TYPE: PRT
<213> ORGANISM: Artificial Sequence
<220> FEATURE:
<223> OTHER INFORMATION: SLC9A2

<400> SEQUENCE: 1400

Asn Leu Tyr Gln Ile Arg
1               5

<210> SEQ ID NO 1401
<211> LENGTH: 6
<212> TYPE: PRT
<213> ORGANISM: Artificial Sequence
<220> FEATURE:
<223> OTHER INFORMATION: SLC9A2

<400> SEQUENCE: 1401

Thr Leu Ser Tyr Asn Arg
1               5

<210> SEQ ID NO 1402
<211> LENGTH: 7
<212> TYPE: PRT
<213> ORGANISM: Artificial Sequence
<220> FEATURE:
<223> OTHER INFORMATION: SLC9A2

<400> SEQUENCE: 1402

Ala Ser Thr Ser Thr Ser Arg
1               5

<210> SEQ ID NO 1403
<211> LENGTH: 6
<212> TYPE: PRT
<213> ORGANISM: Artificial Sequence
<220> FEATURE:
<223> OTHER INFORMATION: SLC9A2

<400> SEQUENCE: 1403

Tyr Leu Ser Leu Pro Lys
1               5

<210> SEQ ID NO 1404
<211> LENGTH: 15
<212> TYPE: PRT
<213> ORGANISM: Artificial Sequence
<220> FEATURE:
<223> OTHER INFORMATION: SLC9A2

<400> SEQUENCE: 1404

Gly Thr Gln Thr Ser Gly Leu Leu Gln Gln Pro Leu Leu Ser Lys
1               5                   10                  15

<210> SEQ ID NO 1405
<211> LENGTH: 8
<212> TYPE: PRT
<213> ORGANISM: Artificial Sequence
<220> FEATURE:
<223> OTHER INFORMATION: SLC9A3

<400> SEQUENCE: 1405

Ile Gly Phe His Leu Ser His Lys
1               5

<210> SEQ ID NO 1406
```

```
<211> LENGTH: 15
<212> TYPE: PRT
<213> ORGANISM: Artificial Sequence
<220> FEATURE:
<223> OTHER INFORMATION: SLC9A3

<400> SEQUENCE: 1406

Ser Pro Ser Thr Asp Asn Val Val Asn Val Asp Phe Thr Pro Arg
1               5                   10                  15

<210> SEQ ID NO 1407
<211> LENGTH: 28
<212> TYPE: PRT
<213> ORGANISM: Artificial Sequence
<220> FEATURE:
<223> OTHER INFORMATION: SLC9A3

<400> SEQUENCE: 1407

Gly Ile Val Ser Phe Phe Val Val Ser Leu Gly Gly Thr Leu Val Gly
1               5                   10                  15

Val Val Phe Ala Phe Leu Leu Ser Leu Val Thr Arg
            20                  25

<210> SEQ ID NO 1408
<211> LENGTH: 8
<212> TYPE: PRT
<213> ORGANISM: Artificial Sequence
<220> FEATURE:
<223> OTHER INFORMATION: SLC9A4

<400> SEQUENCE: 1408

Ile Gly Phe His Leu Tyr His Arg
1               5

<210> SEQ ID NO 1409
<211> LENGTH: 15
<212> TYPE: PRT
<213> ORGANISM: Artificial Sequence
<220> FEATURE:
<223> OTHER INFORMATION: SLC9A4

<400> SEQUENCE: 1409

Ala Ile Ser Val Phe Ala Leu Phe Tyr Ile Ser Asn Gln Phe Arg
1               5                   10                  15

<210> SEQ ID NO 1410
<211> LENGTH: 7
<212> TYPE: PRT
<213> ORGANISM: Artificial Sequence
<220> FEATURE:
<223> OTHER INFORMATION: SLC9A4

<400> SEQUENCE: 1410

Thr Phe Pro Phe Ser Ile Lys
1               5

<210> SEQ ID NO 1411
<211> LENGTH: 14
<212> TYPE: PRT
<213> ORGANISM: Artificial Sequence
<220> FEATURE:
<223> OTHER INFORMATION: SLC9A4

<400> SEQUENCE: 1411

Tyr Leu Ser Tyr Pro Tyr Gly Asn Pro Gln Ser Ala Gly Arg
1               5                   10
```

```
<210> SEQ ID NO 1412
<211> LENGTH: 11
<212> TYPE: PRT
<213> ORGANISM: Artificial Sequence
<220> FEATURE:
<223> OTHER INFORMATION: SLC9A5

<400> SEQUENCE: 1412

Ser Ser Phe Ala Phe Pro Pro Ser Leu Ala Lys
1               5                   10

<210> SEQ ID NO 1413
<211> LENGTH: 6
<212> TYPE: PRT
<213> ORGANISM: Artificial Sequence
<220> FEATURE:
<223> OTHER INFORMATION: SLC9A5

<400> SEQUENCE: 1413

Leu Val Pro Leu Asp Lys
1               5

<210> SEQ ID NO 1414
<211> LENGTH: 7
<212> TYPE: PRT
<213> ORGANISM: Artificial Sequence
<220> FEATURE:
<223> OTHER INFORMATION: SLC9A6

<400> SEQUENCE: 1414

Asp Thr Ala Thr Tyr Ala Arg
1               5

<210> SEQ ID NO 1415
<211> LENGTH: 8
<212> TYPE: PRT
<213> ORGANISM: Artificial Sequence
<220> FEATURE:
<223> OTHER INFORMATION: SLC9A7

<400> SEQUENCE: 1415

Ala Thr Gly Ala Pro Pro Arg
1               5

<210> SEQ ID NO 1416
<211> LENGTH: 7
<212> TYPE: PRT
<213> ORGANISM: Artificial Sequence
<220> FEATURE:
<223> OTHER INFORMATION: SLC9A7

<400> SEQUENCE: 1416

Asp Thr Ala Ser Tyr Ala Arg
1               5

<210> SEQ ID NO 1417
<211> LENGTH: 19
<212> TYPE: PRT
<213> ORGANISM: Artificial Sequence
<220> FEATURE:
<223> OTHER INFORMATION: SLC9A7

<400> SEQUENCE: 1417

His Val Phe Ser Pro Ile Phe Ile Ile Gly Ala Phe Val Ala Ile Phe
1               5                   10                  15

Leu Gly Arg
```

```
<210> SEQ ID NO 1418
<211> LENGTH: 15
<212> TYPE: PRT
<213> ORGANISM: Artificial Sequence
<220> FEATURE:
<223> OTHER INFORMATION: SLC9A8

<400> SEQUENCE: 1418

Ala Val Asn Ile Phe Pro Leu Ser Tyr Leu Leu Asn Phe Phe Arg
1               5                   10                  15

<210> SEQ ID NO 1419
<211> LENGTH: 6
<212> TYPE: PRT
<213> ORGANISM: Artificial Sequence
<220> FEATURE:
<223> OTHER INFORMATION: SLC9A9

<400> SEQUENCE: 1419

Leu Gly Leu Asp Gln Lys
1               5

<210> SEQ ID NO 1420
<211> LENGTH: 8
<212> TYPE: PRT
<213> ORGANISM: Artificial Sequence
<220> FEATURE:
<223> OTHER INFORMATION: SLC9A9

<400> SEQUENCE: 1420

Ala Ser Pro Gln Thr Pro Gly Lys
1               5
```

METHOD OF QUANTIFYING MEMBRANE PROTEIN BY MASS SPECTROMETRY USING PEPTIDE SELECTION CRITERIA

The present invention relates to a method for measuring quantitatively a plasma membrane protein, specifically to a method for measuring quantitatively a membrane protein present in a plasma membrane, by using a stable-isotope labeled peptide as a probe, by a mass spectrometry using liquid chromatography-tandem mass spectrometry (LS/MS/MS).

BACKGROUND ART

Plasma membrane protein (sometimes referred to as membrane protein) is present as a protein constituting a biological membrane. A plasma membrane protein has a function as a receptor of an enzyme, peptide hormone, growth factor, autacoid, etc.; transporter of sugar, etc.; ion channel, or plasma membrane antigen, and is associated with dynamic functions of a cell such as penetration/transportation of a substance, by receiving a signal from the surface of a cell. A plasma membrane protein is a protein or a glycoprotein incorporated in a plasma membrane lipid bilayer, which is present in various forms, for example, penetrating all layers of a plasma membrane (transmembrane protein), located on the surface layer (cell surface protein), or undercoating a plasma membrane. In either case, it is a high molecular protein.

As one of plasma membrane protein, ABCG2 (ATP binding cassette transporter G2) is known. ABCG2 is known as a member of human ATP binding cassette (ABC) transporter, and it is reported that ABC transporter is associated with causes of diseases or drug transport. ABC transporter is one of the biggest superfamily of protein which is found in any cell of from bacterium to higher animal such as human, and about 250 members (about 50 in human) are known. Almost all ABC proteins function as a transporter, while some function as an ion channel. ABCG2 gene has been first isolated by Allikmets et al (Humann Mol. Genet. 5(10), 1649-1655, 1996). This protein is a transporter being the cause of drug resistance, and has been revealed to have a function to discharge anticancer agents to the outside of the cell (Proc. Natl. Acad. Sci., 95, 15665-15670, 1998; Clin. Cancer. Res. 7, 935-941, 2001).

Further, also as one of plasma membrane proteins, P-glycoprotein (PGP; also known as multidrug transporter MDR1) is known (Medicine, Stanford University School of Medicine, Stanford, Calif. 94306, USA; Nature 323(6090), 728-731, 1986; Biochem. Biophys. Res. Commun. 162(1), 224-231, 1989). P-glycoprotein is a member of the ABC transporter superfamily, and is expressed in human intestines, liver or other tissues. The enzyme is incorporated in the plasma membrane and acts, as an efflux pump transporting small molecules. It has been known these last several years that expression of a high-level P-glycoprotein is a mechanism of tumor resistance against chemotherapy of cancer. Further, expression of P-glycoprotein in intestines, affects oral bioavailability of an agent molecule which is a substrate of this transporter, enables effective discharge of drug in intestine lumen, thus reducing the drug amount to circulate.

Further, ABCC4 is known as one of plasma membrane proteins (Genetics, 123(1), 45-54, 1989). ABCC4 is known as a member of ATP binding domain (ABC) transporter. ABC transporter superfamily is one of the biggest gene families, which encodes membrane protein groups having various functions related to energy-dependent transportation of a wide variety of substances passing through the membrane (Curr. Opin. Genet. Dev., 5, 779-85, 1995). ABC proteins are associated with extracellular and intracellular membrane transport of various substances, including ion, amino acid, peptide, sugar, vitamin, and steroid hormone. Human ABCC subfamily has at present 10 identified members (ABCC 1-10), among which 7 are derived from multidrug resistance-like (MRP) subgroup, 2 are derived from sulfonyaurea receptor (SUR) subgroup, and 1 is CFTR gene. MRP-like protein is an organic anion transporter. ABCC4 and ABCC5 proteins are known to impart resistance against nucleotide analog including PMEA and purine base analog.

As for biogenic proteins such as the above-mentioned plasma membrane protein, it is necessary to detect proteins contained in the cells or the like, and measure them quantitatively in order to elucidate the function of the protein, or when testing or screening for the protein, or to use the protein. Particularly, when developing a novel drug, it is significant to quantify absolutely proteins such as membrane proteins to test a novel drug candidate, with a simple and accurate method.

For example, more than 90% of substances: as novel drug candidates, which pharmaceuticals companies have developed by spending much time and cost, are dropped out (halt development). Most of the reasons are drug kinetics (absorption, distribution, metabolism, excretion) such as low-absorption to digestive tracts, or drug transfer into inappropriate organs, and side effects. As drug kinetics are considered by using animals conventionally, it cannot be considered at an early phase of the development as high throughput screening. Further, as there are species differences of drug kinetics, some data obtained from animal experiments are not reproduced in human. In other words, the problem of drug kinetics is often revealed in clinical experiments at a late stage of the development, which cause significant losses for pharmaceutical companies. Due to such problems, it is awaited that human drug kinetics can be estimated at an early phase of development by using a system that enables high throughput screening in vitro.

Performance of the above system is actualized for metabolisms of drug kinetics. In other words, the absolute amount of each metabolic enzyme in human liver is revealed. Further, the metabolic velocity per molecule by each metabolic enzyme of the subject drug in vitro is calculated by using a recombinant protein. From the information from each metabolic enzyme functioning mainly in liver, the metabolic velocity of the subject drug can be estimated by calculation. In other words, a means for obtaining the absolute amount of enzyme protein in organs and in vitro is indispensable.

On the other hand, a membrane protein associated with drug kinetics (drug transporter, receptor), which transports drugs is playing a crucial role for absorption, distribution and excretion among the drug kinetics. Therefore, if the absolute amount of the membrane protein associated with drug kinetics in organs, and the transportation ability or the binding ability of the drug per molecule can be measured, it would be possible to estimate the metabolic velocity from the obtained information by calculation, similarly with metabolism. Presently, there is a system to estimate in vitro the transportation or binding by using a membrane protein forcibly expressing cell or an expressed membrane vesicle, while it is very difficult to quantify the absolute amount of membrane protein. Therefore, if a more general method for quantifying the absolute amount of membrane protein with a high sensitivity is established, it becomes possible to estimate drug kinetics from an experiment system in vitro. Thus, it would be possible to estimate drug kinetics in human at an early stage of drug development, and reduce significantly time and cost necessary for drug development. The development of a method for absolutely quantifying membrane protein is awaited also even in the field of drug development.

Conventionally, a method using electrophoresis such as two-dimensional electrophoresis was conducted for quantifying biogenic proteins. With this method, detection and quantification were performed by staining the protein to be quantified, or by autoradiography, or by using an antibody specific to a particular protein (western blot). Particularly, a method using an antibody was conducted for quantifying a plasma membrane protein. For a method for quantifying a plasma membrane protein using an antibody, it is necessary to prepare an antibody against the protein, and it cannot be applied to a membrane protein against which an antibody cannot be prepared. Further, the method for quantifying comprises solubilizing the membrane protein when preparing a sample, and then electrophoresing to stain the antibody. However, as solubilizing conditions vary upon membrane proteins, conditions must be considered individually, which takes time. Further, as it is not possible to electrophorese insoluble proteins or high-molecular proteins, it was difficult to apply these methods for quantifying a plasma membrane protein.

On the other hand, mass spectrometry is making a significant progress recently, and the method is considered and used for detecting or measuring various biological materials. Mass spectrometers having various function have been developed including: a mass spectrometer having an electrospray ionization (ESI) source, a mass spectrometer having a liquid chromatography spectrometry (LC-MS), a MS/MS spectrum or tandem mass spectrum (tandemu MS) mass spectrometer wherein two mass spectrometers are bound. They are used for detecting or measuring biological materials (Japanese Laid-Open Patent Application No. 2004-28993; Japanese Laid-Open Patent Application No. 2004-77276; Published Japanese translation of PCT international publication No. 2004-533610).

Recently, a mass spectrometry using a stable-isotope label has been developed, and is used for detecting or measuring biological materials. This method quantifies proteins or peptides in a sample by mass spectrometry, by using proteins or peptides labeled with a stable-isotope. Examples of using the method for quantifying C-reactive protein (CRP) which is a diagnostic marker in the serum of a patient with rheumatism, and -amyloid in a sample from mammalian tissues or in body fluid have been reported. However, no example of using such mass spectrometry for quantifying a plasma membrane protein which is insoluble and high-molecular is known.

Conventionally, LS/MS/MS is used for detecting or measuring biological materials by using mass spectrometry. Quantification by using LS/MS/MS is performed by using channel in which MS spectrum of the intended compound, and a particular MSMS spectrum peak are combined. For a low-molecular weight compound, usually the method is performed by using a single channel. However, in case of a peptide, which is high molecular, it was estimated that quantification using a single channel would cause some problems, and quantification using a single channel in fact caused some problems.

In other words, when there is a peptide with a different sequence from that of the selected peptide detected in the same channel, plural peaks are detected in the selected channel. It is possible to synthesize an internal standard peptide, and to identify the peak of the elution time identical with the internal standard peptide, as a peak of the intended peptide. However, when plural channels are prepared for various membrane proteins, it is very difficult to synthesize internal standard peptides for all of them, from the view points of time and cost. Therefore, a means for identifying the peak of the intended peptide without an internal standard peptide is necessary. Further, it is possible that a peptide with a different sequence detected in the same channel is detected within the same elution time as the intended peptide, which lowers quantification accuracy.

Patent reference 1: Japanese Laid-Open Patent Application No. 2004-28993
Patent reference 2: Japanese Laid-Open Patent Application. No. 2004-77276
Patent reference 3: Japanese; Laid-Open Patent Application No. 2004-157124
Patent reference 4: Published Japanese translation of PCT International Publication NO. 2004-533610
Non-patent reference 1: Humann Mol. Genet. 5(10), 1649-1655, 1996
Non-patent reference 2: Proc. Natl. Acad. Sci., 95, 15665-15670, 1998
Non-patent reference 3: Clin. Cancer. Res. 7, 935-941, 2001
Non-patent reference 4: Medicine, Stanford University School of Medicine, Stanford, Calif. 94306, USA
Non-patent reference 5: Nature 323(6090), 728-731, 1986
Non-patent reference 6: Biochem. Biophys. Res. Commun. 162(1), 224-231,
Non-patent reference 7: Genetics, 123(1), 45-54, 1989
Non-patent reference 8: Curr. Opin. Genet. Dev., 5, 779-85, 1995
Non-patent reference 9: Proteomics 4, 1175-1186, 2004

DISCLOSURE OF THE INVENTION

Object to be Solved by the Invention

A plasma membrane protein constituting a biological membrane has important functions including receptor against factors acting on organisms, transporter of biological substances, ion channel, and plasma membrane antigen. Elucidation of functions of the protein, screening of active substances using the protein, and test or diagnosis using expression of the protein have been performed. When elucidating functions of the protein, screening of active substances, or testing/diagnosis utilizing expression of the protein, it is necessary to detect the protein contained in cells and to measure it quantitatively. Particularly, when developing a novel drug, it is significantly important to quantify absolutely the plasma protein with a simple and accurate method for testing a material being a novel drug candidate.

Conventionally, when detecting and quantifying biological proteins, methods such as staining method, autoradiography, or electrophoresis using an antibody were used. However, as a plasma membrane protein is high molecular and insoluble, it is difficult to conduct electrophoresis, and thus difficult to quantify with these conventional methods. For a method for quantifying a plasma membrane protein using an antibody, it is necessary to prepare an antibody against the protein, and it cannot be applied to a membrane protein against which an antibody cannot be prepared. Further, the method for quantifying comprises solubilizing the plasma membrane protein when preparing a sample, and then electrophoresing to stain the antibody. However, as solubilizing conditions vary upon plasma membrane proteins, conditions must be considered individually, which takes time. Further, a lot of time, technique, and cost are necessary to prepare an antibody.

Thus, the object of the present invention is to provide a method for measuring accurately and quantitatively a high molecular and insoluble plasma membrane protein with a simple method, more specifically a method for measuring quantitatively and accurately a membrane protein which is present in a cell membrane by using a stable-isotope labeled peptide as a probe, by mass spectrometry in a simple and accurate manner, with a simple means. Further, the present invention is to provide a method for measuring a plasma membrane protein accurately and easily by improving selection of measuring samples or measuring means, when quantifying a plasma membrane protein by mass spectrometry.

Means to Solve the Object

The present inventors made a keen study to resolve the above object, and found out that a high molecular and insoluble plasma membrane protein can be quantified simply and quickly, and accurately by the following steps: fragmentizing a separated plasma membrane protein to be quantified with a protease to prepare an oligopeptide fragment, identifying it by LS/MS/MS; setting as essential criteria that it is a peptide obtained by fragmentizing with a protease, and that it is a peptide sequence specific to the target molecule, and by establishing selective criteria with scores for content of hydrophobic amino acid, sequence conditions, amino acid residue numbers, specific amino acid sequence conditions, etc.; selecting the peptide fragment that can be ionized by ESI, according to a selective criterion by which a peptide with a high score is preferentially selected; selecting the peptide fragment as a subject peptide for quantification; on the other hand, by preparing a stable-isotope labeled peptide having the same sequence as the subject peptide for quantification, and labeled with a stable-isotope element; preparing in advance a calibration curve with the subject peptide for quantification and a stable-isotope labeled peptide from a mass spectrometry by LS/MS/MS by using a sample of a certain concentration; and calculating from the calibration curve from the results of LS/MS/MS mass spectrometry of an oligopeptide fragment of a sample of a plasma membrane protein to be quantified, and the stable-isotope labeled peptide.

One of the features of the method for quantifying a plasma membrane protein by using LS/MS/MS mass spectrometry of the present invention, is to select the oligopeptide fragment enabling ionization by ESI method, and to select a subject peptide for quantification, using the selective criteria for a subject peptide for quantification, established for at least, a protease to use, hydrophobic amino acid content and sequence conditions, amino acid residue numbers, and specific amino acid sequence conditions. In other words, when quantifying a plasma membrane protein by mass spectrometry, it is effective to quantify by using LS/MS/MS method. As a problem of a conventional method, for quantifying a protein by using LS/MS/MS method, it is necessary to select a peptide that can be separated by liquid chromatography, and has a superior ionization efficiency. For this, it is necessary to measure a sample containing a large amount of the protein by LS/MS/MS, and to confirm peptide that ionizes. When there is a little amount of the plasma membrane protein, a very long time and burden are required for pre-treatment of separation/concentration. The determination of a subject peptide for quantification is a rate-controlling step of the conventional LS/MS/MS method, and it was difficult to apply the method for quantifying of a large amount of membrane proteins (example: 48 ABC transporters, and 319 SCL transporters in human). To resolve this problem, in the present invention, the above criteria for selecting peptide (selective standard) were established to select a subject peptide for quantification, and by selecting a peptide having an excellent ionization efficiency, it became possible to quantify a plasma membrane protein by LS/MS/MS mass spectrometry accurately and effectively. The selection of a peptide having an excellent ionization efficiency by using the criteria for selecting peptide can be performed at a high speed with a computer, and it is possible to select an appropriate peptide.

In other words, the present invention relates to: ("1") a method for quantifying a plasma membrane protein by liquid chromatograph-tandem mass spectrometer (LS/MS/MS) using a stable-isotope labeled peptide, comprising the following steps (a) to (e):

(a) a step of preparing and identifying an oligopeptide fragment by fragmentizing a separated plasma membrane protein to be quantified; selecting a subject peptide for quantification that can be ionized by ESI method, according to a criteria for selecting a subject peptide for quantification including essential criteria consisting of at least as: 1) that it is a peptide obtained from a protease comprising trypsin, endoproteinase, and pepsin; and 2) that it is a peptide sequence specific to the target molecule;

b) a step of preparing a stable-isotope labeled peptide having the same sequence as the subject peptide for quantification, and labeled with a stable-isotope element by a peptide synthesis-method;

c) a step of preparing a calibration curve by using the subject peptide for quantification and the stable-isotope labeled peptide, and performing mass spectrometry using LS/MS/MS for each predetermined concentration level;

(d) a step of performing mass spectrometry by using LS/MS/MS by adding a stable-isotope labeled peptide to the peptide fragment obtained by fragmentizing the plasma membrane protein to be quantified in a sample with the protease, and calculating the mass spectrum area ratio of a plasma membrane protein peptide to be quantified to the stable-isotope labeled peptide;

(e) a step of calculating the quantitative level from the area ratio by using the calibration curve.

In other words, the present invention relates to: ("1") a method for quantifying a plasma membrane protein by liquid chromatograph-tandem mass spectrometer (LC-MSMS) using a stable-isotope labeled peptide, comprising the following steps (a) to (e):

(a) a step of preparing and identifying an oligopeptide fragment by fragmentizing a separated plasma membrane protein to be quantified; selecting a subject peptide for quantification that can be ionized by ESI method, according to a criteria for selecting a subject peptide for quantification including essential criteria consisting of at least as: 1) that it is a peptide obtained from a protease comprising trypsin, endoproteinase, and pepsin; and 2) that it is a peptide sequence specific to the target molecule;

b) a step of preparing a stable-isotope labeled peptide having the same sequence as the subject peptide for quantification, and labeled with a stable-isotope element by a peptide synthesis-method;

c) a step of preparing a calibration curve by using the subject peptide for quantification and the stable-isotope labeled peptide, and performing mass spectrometry using LC-MSMS for each predetermined concentration level;

(d) a step of performing mass spectrometry by using LC-MSMS by adding a stable-isotope labeled peptide to the peptide fragment obtained by fragmentizing the plasma membrane protein to be quantified in a sample with the protease, and calculating the mass spectrum area ratio of a plasma membrane protein peptide to be quantified/stable-isotope labeled peptide;

(e) a step of calculating the quantitative level from the area ratio by using the calibration curve.

Further, the present invention relates to ("2") the method for quantifying a plasma membrane protein according to ("1"), wherein the criteria for selecting the subject peptide for quantification are criteria for selecting preferentially a peptide with a high score by setting as selective criteria with score, further to the above essential criteria (1) and (2), the followings:

3) that it is a peptide wherein the content of hydrophobic amino acids is 80% or less, and that not more than 10 hydrophobic amino acids are consecutive, as for the content of hydrophobic amino acids consisting of tryptophan, tyrosine, valine, leucine, isoleucine, phenylalanine, and for sequence conditions [score 2];

4) that it is a peptide wherein the number of amino acid residues is 4-30 [score 3];

5) that it is a peptide that does not contain the sequence of asparagine-X (wherein X represents amino acids other than proline)-serine or -threonine, -cysteine, as specific amino acid sequence conditions [score 2];

6) that it is a peptide that does not contain a post-translation modified site (it is not limited to this when quantifying a post-translation modified protein) [score 3];

7) that it is a peptide that does not contain a single nucleotide polymorphism (SNP) site [score 4];

8) that it is a peptide wherein the protease cleavage site is not arginine-arginine, arginine-lysine, lysine-arginine, lysine-lysine [score 5];

9) that it is a peptide that does not contain a transmembrane domain when the protein structure is determined or estimated [score 2];

10) that it is a peptide that does not contain methionine and cysteine [score 3];

11) that it is a peptide that does not contain tryptophan and glutamic acid [score 1].

Further, the present invention relates to: ("3") the method for quantifying a plasma membrane protein according to ("2"), wherein the hydrophobic amino acid content is 50% or less, and the number of amino acid residues is 8-12; ("4") the method for quantifying a plasma membrane protein according to any one of ("1") to ("3"), wherein an additional criterion that it is the same amino acid sequence in plural animal species is added to the criteria for selecting a subject peptide for quantification; ("5") the method for quantifying a plasma membrane protein according to any one of ("1") to ("4"), wherein plural specific measurement channels are prepared by combining parent ion (m/z) and peptide fragment ion (m/z) of candidate peptides selected according to the criteria for selecting subject peptide for quantification, and measured; ("6") the method for quantifying a plasma membrane protein according to ("5"), wherein the plural specific channels are prepared for plural candidate peptides of the same protein and for a candidate peptide for plural proteins, and measured at the same time; ("7") the method for quantifying a plasma membrane protein according to any one of ("1") to ("6"), wherein the stable-isotope labeled peptide is labeled with an amino acid containing any one of $^{15}$N, $^{13}$C, $^{18}$O, or $^{2}$H, ("8") the method for quantifying a plasma membrane protein according to any one of ("1") to ("7") by a mass spectrometry using a stable-isotope labeled peptide, wherein a source of plasma membrane protein is a plasma membrane protein obtained from a tissue sample.

Further, the present invention relates to ("9") the method for quantifying a plasma membrane protein according to any one of ("1") to ("8"), wherein the plasma membrane protein is 1 or more proteins selected from the group consisting of human ABCA1, human ABCA2, human ABCA3, human ABCA4, human ABCA5, human ABCA6, human ABCA7, human ABCA8, human ABCA9, human ABCA10, human ABCA12, human ABCA13, human ABCB1, human ABCB4, human ABCB5, human ABCB11, human ABCC1, human ABCC2, human ABCC3, human ABCC4, human ABCC5, human ABCC6, human ABCC7, human ABCC8, human ABCC9, human ABCC10, human ABCC11, human ABCC12, human ABCC13, human ABCG1, human ABCG2, human ABCG4, human ABCG5, human ABCG8, and human P-glycoprotein [hereinafter referred to as "the present ABC transporter"].

Further, the present invention relates to ("10") the method for quantifying a plasma membrane protein according to any one of ("1") to ("8"), wherein the plasma protein is 1 or more proteins selected from the group consisting of human SLC10A1, human SLC10A2, human SLC15A1, human SLC15A2, human SLC16A1, human SLC16A7, human SLC19A11, human SLC19A2, human SLC19A3', human SLC21A1, human SLC21A10, human SLC21A11, human SLC21A12, human SLC21A13, human SLC21A14, human SLC21A15, human SLC21A19, human SLC21A2, human SLC21A20, human SLC21A3, human SLC21A4, human SLC21A5, human SLC21A6, human SLC21A7, human SLC21A8, human SLC21A9, human SLC22A1, human SLC22A10, human SLC22A11, human SLC22A12, human SLC22A13, human SLC22A14, human SLC22A15, human SLC22A16, human SLC22A17, human SLC22A18, human SLC22A2, human SLC22A3, human SLC22A4, human SLC22A5, human SLC22A6, human SLC22A7, human SLC22A8, human SLC22A9, human SLC23A1, human SLC23A2, human SLC28A1, human SLC28A2, human SLC28A3, human SLC29A1, human SLC29A2, human SLC29A3, human SLC29A4, human SLC31A1, human SLC3A2, human SLC43A1, human SLC43A2, human SLC43A3, human SLC7A5, human SLC7A6, and human SLC7A8 [hereinafter referred to as "the present SLC transporter (group A)"].

Further, the present invention relates to ("11") the method for quantifying a plasma membrane, protein according to any one of ("1") to ("8"), wherein the plasma protein is 1 or more proteins selected from the group consisting of human SLC10A3, human SLC10A4, human SLC10A5, human SLC10A6, human SLC11A1, human SLC11A2, human SLC12A1, human SLC12A2, human SLC12A3, human SLC12A4, human SLC12A5, human SLC12A6, human SLC12A7, human SLC12A8, human SLC12 A9, human SLC13A1, human SLC13A2, human SLC13A3, human SLC13A4, human SLC13A5, human SLC14A1, human SLC14A2, human SLC15A3, human SLC15A4, human SLC16A10, human SLC16A11, human SLC16A12, human SLC16A13, human SLC16A14, human SLC16A2, human SLC16A3, human SLC16A4, human SLC16A5, human SLC16A6, human SLC16A8, human SLC16A9, human SLC17A1, human SLC17A2, human SLC17A3, human SLC17A4, human SLC17A5, human SLC17A6, human SLC17A7, human SLC17A8, human SLC18A1, human SLC18A2, human SLC18A3, human SLC1A1, human SLC1A2, human SLC1A3, human SLC1A4, human SLC1A5, human SLC1A6, human SLC1A7, human SLC20A1, human SLC20A2, human SLC23A3, human SLC24A1, human SLC24A2, human SLC24A3, human SLC24A4, human SLC24A5, human SLC24A6, human SLC25A1, human SLC25A10, human SLC25A11, human SLC25A12, human SLC25A13, human SLC25A14, human SLC25A15, human SLC25A16, human SLC25A17, human SLC25A18, human SLC25A19, human SLC25A2, human SLC25A20, human SLC25A21, human SLC25A22, human SLC25A23, human SLC25A24, human SLC25A25, human SLC25A26, human SLC25A27, human SLC25A28, human SLC25A29, human SLC25A3, human SLC25A30, human SLC25A31, human SLC25A32, human SLC25A33, human SLC25A34, human SLC25A35, human SLC25A36, human SLC25A37, human SLC25A4, human SLC25A5, human SLC25A6, human SLC25A7, human SLC25A8, human SLC25A9, human SLC26A1, human SLC26A10, human SLC26A11, human SLC26A2, human SLC26A3, human SLC26A4, human SLC26A5, human SLC26A6, human SLC26A7, human SLC26A8, human SLC26A9, human SLC27A1, human SLC27A2, human SLC27A3, human SLC27A4, human SLC27A5, human SLC27A6, human SLC2A1, human SLC2A10, human SLC2A11, human SLC2A12, human SLC2A13, human SLC2A14, human SLC2A2, human SLC2A3, human SLC2A4, human SLC2A5, human SLC2A6, human SLC2A7, human SLC2A8, human SLC2A9, human SLC30A1, human SLC30A10, human SLC30A11, human SLC30A2, human SLC30A3, human SLC30A4, human SLC30A5, human SLC30A6, human SLC30A7, human SLC30A8, human SLC30A9, human SLC31A2, human SLC32A1, human SLC33A1, human SLC34A1, human SLC34A2, human SLC34A3, human SLC35B1, human SLC35B2, human SLC35B3, human SLC35B4, human SLC35C1, human SLC35C2, human SLC35D1, human SLC35D2, human SLC35D3, human SLC36A1, human SLC36A2, human SLC36A3, human SLC36A4, human SLC37A1, human SLC37A2, human SLC37A3, human SLC37A4, human SLC38A1, human SLC38A2, human SLC38A3, human SLC38A4, human SLC38A5, human SLC38A6, human SLC3A1, human SLC40A1, human SLC41A1, human SLC41A2, human SLC41A3, human SLC44A1, human SLC44A2, human SLC44A3, human SLC44A4, human SLC44A5, human SLC45A1, human SLC45A2, human SLC45A3, human SLC45A4, human SLC4A1, human SLC4A10, human SLC4A11, human SLC4A2, human SLC4A3, human SLC4A4, human SLC4A5, human SLC4A7, human SLC4A8, human SLC4A9, human SLC5A10, human SLC5A11, human SLC5A12, human SLC5A2, human SLC5A3, human SLC5A4, human SLC5A5, human SLC5A9, human SLC6A1, human SLC6A10, human SLC6A1, human SLC6A12, human SLC6A13, human SLC6A14, human SLC6A15, human SLC6A16, human SLC6A17, human SLC6A18, human SLC6A19, human SLC6A2, human SLC6A20, human SLC6A3, human SLC6A4, human SLC6A5, human SLC6A6, human SLC6A7, human SLC6A8, human SLC6A9, human SLC7A1, human SLC7A10, human SLC7A11, human SLC7A13, human SLC7A14, human SLC7A2, human SLC7A3, human SLC7A4, human SLC7A7, human SLC7A9, human SLC8A1, human SLC8A2, human SLC8A3, human SLC9A1, human SLC9A2, human SLC9A3, human SLC9A4, human SLC9A5, human SLC9A6, human SLC9A7, human SLC9A8, and human SLC9A9 [hereinafter referred to as "the present SLC transporter (group B)"].

Further, the present invention relates to ("12") the method for quantifying a plasma membrane protein according to any one of ("1") to ("8"), wherein the plasma protein is 1 or more proteins selected from the group consisting of human SLC35A1, human SLC35A2, human SLC35A3, human SLC35A4, human SLC35A5, human SLC35E1, human SLC35E2, human SLC35E3, human SLC35E4, human SLC35F1, human SLC35F2, human SLC35F3, human SLC35F5, human SLC39A1, human SLC39A10, human SLC39A11, human SLC39A12, human SLC39A13, human SLC39A14, human SLC39A2, human SLC39A3, human SLC39A4, human SLC39A5, human SLC39A6, human SLC39A7, human SLC39A8, human SLC39A9, human SLC42A1, human SLC42A2, and human SLC42A3 [hereinafter referred to as "the present SLC transporter (group C)"].

Further, the present invention relates to ("13") the method for quantifying a plasma membrane protein according to any one of ("1") to ("8"), wherein the plasma membrane protein is human MATE1 and/or human MATE2 [hereinafter referred to as "the present MATE transporter"].

Further, the present invention relates to ("14") the method for quantifying a plasma membrane protein according to any one of ("1") to ("8"), wherein the plasma membrane protein is 1 or more proteins selected from the group consisting of human ABCA1, human ABCA2, human ABCA3, human ABCA4, human ABCA5, human ABCA6, human ABCA7, human ABCA8, human ABCA9, human ABCA10, human ABCA12, human ABCA13, human ABCB1, human ABCB4, human ABCB5, human ABCB11, human ABCC1, human ABCC2, human ABCC3, human ABCC4, human ABCC5, human ABCC6, human ABCC10, human ABCC11, human ABCC12, human ABCC13, human ABCC1, human ABCG2, human ABCG4, human ABCG5, human ABCG8, human MATE1, human MATE2, human SLC3A2, human SLC7A5, human SLC7A6, human SLC10A1, human SLC10A2, human SLC15A1, human SLC15A2, human SLC16A1, human SLC16A7, human SLC19A1, human SLC21A2, human SLC21A3, human SLC21A4, human SLC21A5, human SLC21A6, human SLC21A7, human SLC21A8, human SLC21A9, human SLC21A11, human SLC21A12, human SLC21A13, human SLC21A14, human SLC21A15, human SLC21A19, human SLC21A20, human SLC22A1, human SLC22A2, human SLC22A3, human SLC22A4, human SLC22A5, human SLC22A6, human SLC22A7, human SLC22A8, human SLC22A9, human SLC22A10, human SLC22A11, human SLC22A12, human SLC22A13, human SLC22A14, human SLC22A15, human SLC22A16, human SLC22A17, human SLC23A1, human SLC23A2, human SLC28A1, human SLC28A2, human SLC28A3, human SLC29A1, human SLC29A2, and human SLC31A1 [hereinafter referred to as "the suitable transporter of the present invention"].

BRIEF DESCRIPTION OF DRAWINGS

The patent or application file contains at least one drawing executed in color. Copies of this patent or patent application publication with color drawing(s) will be provided by the Office upon request and payment of the necessary fee.

FIG. 3*a* It is a figure showing the results of mass spectrometry by human ABCG2 peptide in an Example of the present invention. A) shows the MS spectrum of 5 fmol standard peptide and 50 fmol, $^{13}C_6$—, $^{15}N$-labeled peptide.

FIG. 6 It is a figure showing the results of mass spectrometry, in an experiment measuring content of ABCB1, ABCB4, ABCB5, ABCB11, ABCC1, ABCC2, ABCC3, ABCC4, ABCC5, ABCC6, ABCC7, ABCC8, ABCC9, ABCC10, ABCC11, ABCC12, ABCC13, ABCG1, ABCG4, ABCG5, and ABCG8 at the same time, in 50 µg of a plasma membrane peptide sample of leukemia cells, in Example 2 of the present invention.

Figure 1:
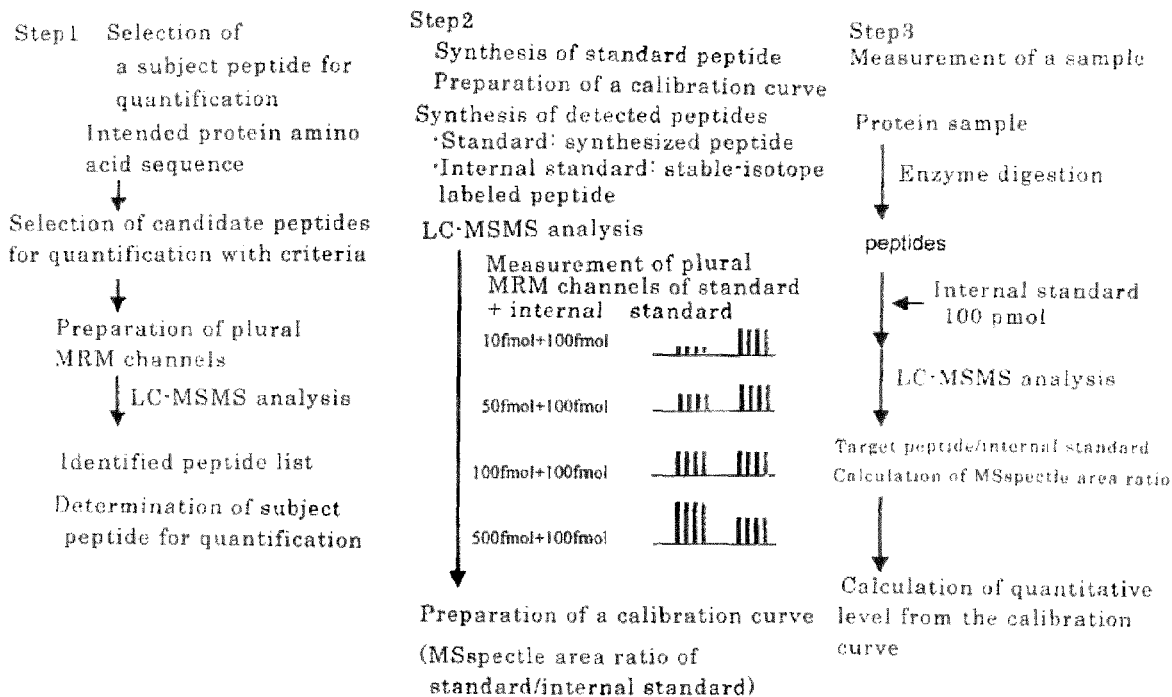
FIG. 1 It is a figure showing the flow of the method for quantifying a plasma membrane protein by mass spectrometry of the present invention.

A method for quantifying a plasma membrane protein by LS/MS/MS using a stable-isotope labeled peptide of the present invention is not particularly limited as long as it is a method comprising the following steps:
(a) a step of fragmentizing a separated plasma membrane protein for quantification and preparing and identifying an oligopeptide fragment, and selecting a subject peptide for quantification that can be ionized by ESI, according to criteria for selecting a subject peptide for quantification including essential criteria set from at least: (1) that it is a peptide obtained by fragmentizing with a protease consisting of trypsin, endoproteinase, or pepsine, (2) that it is a peptide sequence specific to a target molecule;
(b) a step of preparing a stable-isotope labeled peptide having the same sequence as the subject peptide for quantification, and labeled with a stable-isotope element by a peptide synthesis method;
(c) a step of preparing a calibration curve by using a subject peptide for quantification and the stable-isotope labeled peptide, and performing mass spectrometry using LS/MS/MS for each predetermined concentration level;
(d) a step of calculating the mass spectrum area ratio of subject plasma membrane protein peptide for quantification/stable-isotope labeled peptide, by adding a stable-isotope labeled peptide to the peptide fragment obtained by fragmentizing a plasma membrane protein for quantification of a sample with the protease and performing mass spectrometry using LS/MS/MS;
(e) a step of calculating the quantitative level from the area ratio by using the calibration curve. A plasma membrane protein obtained from a tissue sample or cultured cell can be suitably exemplified as a source for the above plasma membrane protein.

BEST MODE OF CARRYING OUT THE INVENTION

A method for quantifying a plasma membrane protein by LC-MSMS using a stable-isotope labeled peptide of the present invention is not particularly limited as long as it is a method comprising the following steps:
(a) a step of fragmentizing a separated plasma membrane protein for quantification and preparing and identifying an oligopeptide fragment, and selecting a subject peptide for quantification that can be ionized by ESI, according to criteria for selecting a subject peptide for quantification including essential criteria set from at least: (1) that it is a peptide obtained by fragmentizing with a protease consisting of trypsin, endoproteinase, or pepsine, (2) that it is a peptide sequence specific to a target molecule;
(b) a step of preparing a stable-isotope labeled peptide having the same sequence as the subject peptide for quantification, and labeled with a stable-isotope element by a peptide synthesis method;
(c) a step of preparing a calibration curve by using a subject peptide for quantification and the stable-isotope labeled peptide, and performing mass spectrometry using LC-MSMS for each predetermined concentration level;
(d) a step of calculating the mass spectrum area ratio of subject plasma membrane protein peptide for quantification/stable-isotope labeled peptide, by adding a stable-isotope labeled peptide to the peptide fragment obtained by fragmentizing a plasma membrane protein for quantification of a sample with the protease and performing mass spectrometry using LC-MSMS;
(e) a step of calculating the quantitative level from the area ratio by using the calibration curve. A plasma membrane protein obtained from a tissue sample or cultured cell can be suitably exemplified as a source for the above plasma membrane protein.

It is preferable to add to the above essential criteria set as (1) that it is a peptide obtained from a protease consisting of trypsin, endoproteinase, or pepsine, (2) that it is a peptide sequence specific to a target molecule, the following selective criteria with score, in order to apply criteria for preferentially selecting a peptide with high total score 3) that it is a peptide wherein the content of hydrophobic amino acids is 80% or less, preferably 50% or less and that not more than 10 hydrophobic amino acids are consecutive, as for the content of hydrophobic amino acids consisting of tryptophan, tyrosine, valine, leucine, isoleucine, phenylalanine, and sequence conditions [score 2];
4) that it is a peptide wherein the number of amino acid residues is 4-30, preferably 8-12 [score 3]
5) that it is a peptide that does not contain the sequence of asparagine-X (wherein X represents amino acids other than proline)-serine or -threonine, -cysteine, as a specific amino acid sequence condition [score 2];
6) that it is a peptide that does not contain a post-translation modified site (it is not limited to this when quantifying a post-translation modified protein) [score 3];
7) that it is a peptide that does not contain a single nucleotide polymorphism (SNP) site [score 4];
8) that it is a peptide wherein the protease cleavage site is not arginine-arginine, arginine-lysine, lysine-arginine, lysine-lysine [score 5];
9) that it is a peptide that does not contain a transmembrane domain when the protein structure is determined or estimated [score 2];
10) that it is a peptide that does not contain methionine and cysteine [score 3];
11) that it is a peptide that does not contain tryptophan and glutamic acid [score 1]. Further, an additional criterion that it is the same amino acid sequence in plural animal species (for example, human, mouse, rat) can be added, and by adding this criterion, it would be possible to quantify plasma membrane proteins of plural animal species with a single peptide.

In the present invention, when the membrane protein level contained in the source (sample) of a protein to be a measuring subject is less than measuring threshold limit of mass spectrometry using LS/MS/MS, it is preferred to use a plasma membrane separated by high pressure nitrogen gas filling method, etc. In the present invention, an oligopeptide fragment is prepared by enzymatically digesting a plasma membrane protein with a protease consisting of trypsin, endoproteinase, and/or pepsine. For example, a peptide sample can be prepared by isolating a plasma membrane by high pressure nitrogen gas filling method, etc. from a cell in which the plasma membrane protein is expressed, followed by an enzymatic digestion. As for the fragmentizing level, it is preferred to clarify the separation by increasing the mass difference between a stable-isotope labeled peptide and a non-labeled peptide that can be separated by mass spectrometry, as well as to lower molecules so that the number of amino acid residues becomes 4-30, in order to retain the specificity of the sequence.

It is preferred to identify the fragmented oligopeptide fragment sample with LS/MS/MS and to select a subject peptide for quantification. Thus, it is preferred that a peptide being the subject for quantification can be separated by liquid chromatography, ionized by ESI method, and detected by LS/MS/MS. Then, by using the above criteria for selecting the subject peptide for quantification, a subject peptide for quantification that can be separated by liquid chromatography, and ionized by ESI method can be selected.

Based on the selected subject peptide for quantification, a stable-isotope labeled peptide which is labeled with a stable-isotope is prepared. The peptide labeled with a stable-isotope and added as an internal standard has the same amino acid sequence as the subject peptide for quantification, and is labeled with at least one stable-isotope selected from $^{15}N$, $^{13}C$, $^{18}O$, and $^{2}H$. As the internal standard is separated from the subject peptide according to the mass, a mass difference that can be separated with LS/MS/MS is necessary. For example, it is preferred to use a peptide containing leucine wherein 6 sites are labeled with $^{13}C$.

As for a stable-isotope labeled peptide, it is necessary that at least one amino acid is labeled with a stable-isotope element. The peptide can be prepared by any method known to a person skilled in the art. For example, the intended stable-isotope labeled peptide can be chemically synthesized with a suitable means such as F-moc method (Amblard M, Fehrentz J A, Martinez J, Subra G. Methods Mol Biol. 298:3-24 (2005)). A stable-isotope labeled peptide thus obtained is chemically identical with a subject peptide for quantification except for that the mass of the labeled amino acid is different, exert the same behavior in the measurement with LS/MS/MS, and the loss levels of the analyte and standard are equal.

In the present invention, the selected subject peptides for quantification and prepared stable-isotope labeled peptides are used and subjected to mass spectrometry using LS/MS/MS for each predetermined concentration level, to prepare a calibration curve. The calibration curve is prepared by adding a determined amount of stable-isotope labeled peptide to non-labeled peptides of several concentration levels, and measuring by LS/MS/MS. Area ratio of MS spectrum or peak height ratio of non-labeled peptide and stable-isotope labeled peptide at each concentration is calculated to prepare a calibration curve. The amount of non-labeled peptide is preferred to be within the linear measurement range of the mass spectrometry.

In the present invention, the prepared calibration curve is used to quantify a plasma membrane protein sample. For measurement, a stable-isotope labeled peptide is added to the peptide fragment obtained by fragmentizing a plasma membrane protein to be quantified of a sample with the same protease used for selecting the subject peptide for quantification, to perform mass spectrometry by using LS/MS/MS, the mass spectrum area ratio of the plasma membrane protein peptide to be quantified to a stable-isotope labeled peptide is calculated, and the quantitative level is calculated from the area ratio by using the calibration curve. The flow of the method for quantifying a plasma membrane protein of the present invention is shown in FIG. 1.

Figure 2A:
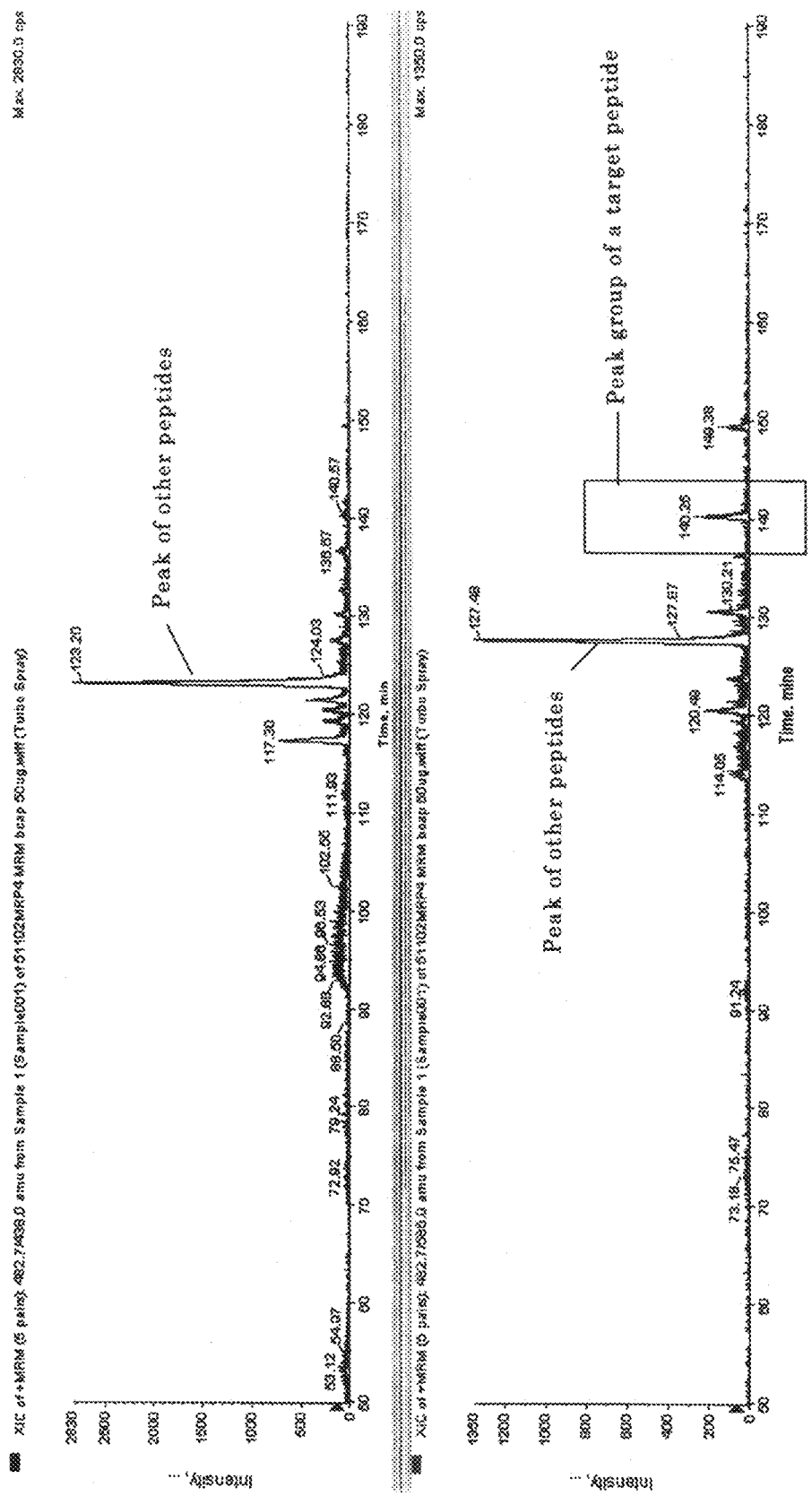
FIG. 2*a* It is a figure showing the results of LS/MS/MS measurement of a peptide library of a sample containing the subject membrane protein using the prepared 5 channels, when quantifying by peptide multichannel using LS/MS/MS in the present invention.
Figure 2B:
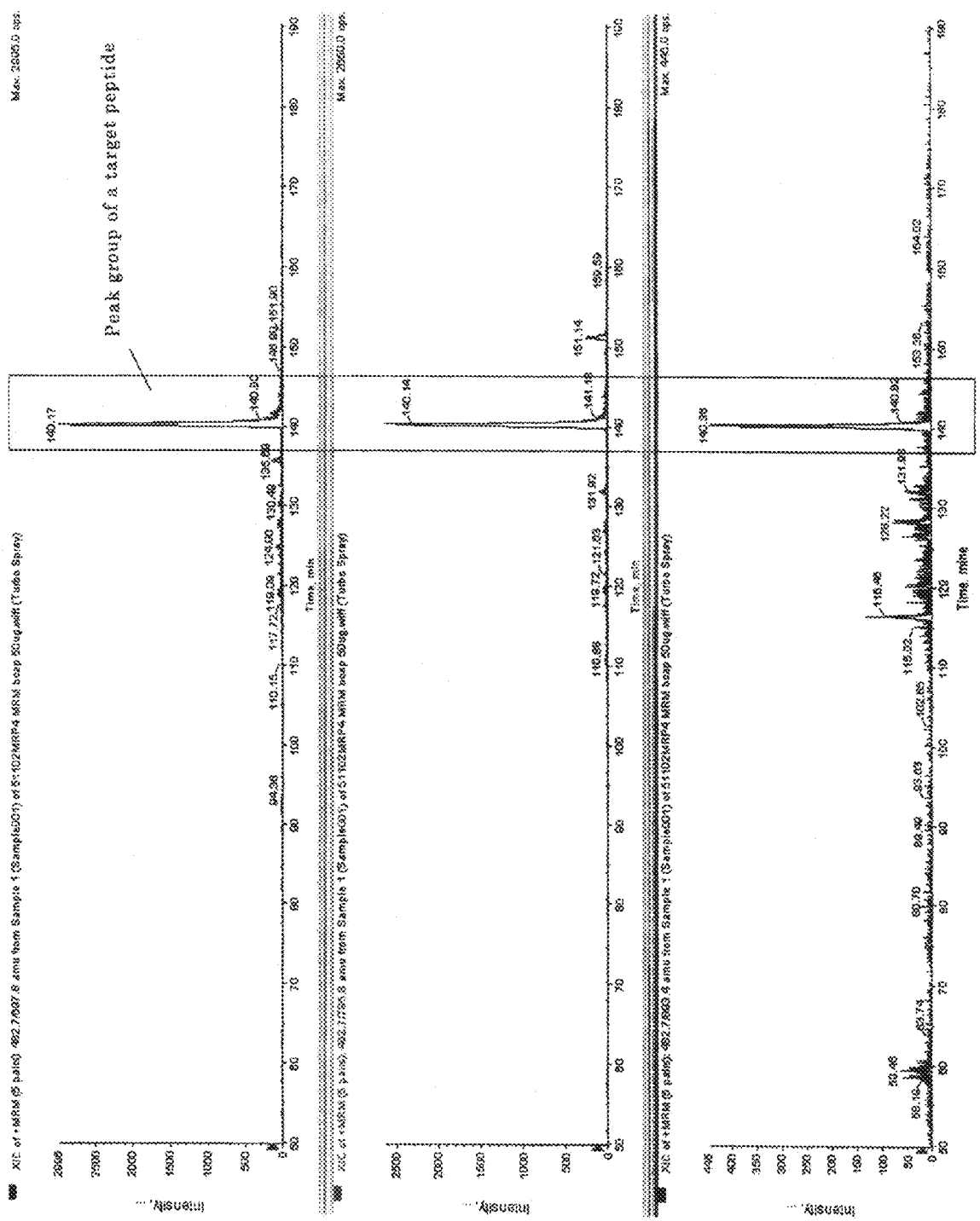
FIG. 2*b* It is a figure showing the results of LS/MS/MS measurement of a peptide library of a sample containing the subject membrane protein using the prepared 5 channels, when quantifying by peptide multichannel using LS/MS/MS in the present invention.

In the present invention, it is preferred to improve the quantitative accuracy by peptide multichannel by using LS/MS/MS. In the present invention, by using LS/MS/MS analysis, plural specific measurement channels are prepared by combining parent ion (m/z) and peptide fragment ion (m/z) for peptide sequence candidates selected according to the criteria and measured. It is preferred to prepare 5 or more specific measurement channels. It is preferred to select a divalent ion of the candidate peptide as MS spectrum, and to select 5 monovalent ions in descending order in terms of the mass for MSMS spectrum. By using the prepared 5 channels, a peptide library of a sample containing the subject membrane protein is measured with LS/MS/MS, and the ion peak of the candidate peptide is confirmed by the prepared channel. The ion peaks in which the detecting time conforms within plus minus 1.0 sec for 3 or more out of 5 channels are identified as the intended peptide peak. The measurement results of mass spectrometry of the 5 prepared channels are shown in FIG. 2.

The present invention encompasses a method for quantifying the above-mentioned present ABC transporters, present SLC transporters (group A: those transporting drugs, and those which drug transporting function is estimated from amino acid sequence identity), present SLC transporters (group B: those transporting endogenous substances, and those which endogenous substance function is estimated from amino acid sequence identity), present SLC transporters (group C: those which transporting function is not estimated), present MATE transporter, and "the suitable transporters of the present invention", by using the method for quantifying a plasma membrane protein of the present invention.

In the quantification by mass spectrometry of human ABCG2 of the present invention (ATP binding cassette transporter G2; Humann Mol. Genet. 5(10), 1649-1655, 1996); its sequence is registered at the data base of the Gene Bank with the accession no.: NM_004827), a quantification with high accuracy can be performed by using a peptide which amino acid sequence is ENLQFSAALR (SEQ ID No: 1), LAEIYVNSSFYK (SEQ ID No: 2), LFDSLTLLASGR (SEQ ID No: 3), SSLLDVLAAR (SEQ ID No: 4), and VIQELGLDK (SEQ ID No: 5), which has been selected in the present invention, as a subject peptide for quantification and a stable-isotope labeled peptide.

In the quantification by mass spectrometry of P-glycoprotein (P-glycoprotein; Medicine, Stanford University School of Medicine, Stanford, Calif. 94306, USA; Nature 323(6090), 728-731, 1986; Biochem. Biophys. Res. Commun. 162(1), 224-231, 1989; its sequence is registered at the data base of the Gene Bank with the accession no.: AF016535, NM_000927, M14758), a quantification with high accuracy can be performed by using a peptide which amino acid sequence is SEIDALEMSSNDSR (SEQ ID No: 6), EALDESIPPVSFWR (SEQ ID No: 7), IATEAIENFR (SEQ ID No: 8), NADVIAGFDDGVIVEK (SEQ ID No: 9), LYDPTEGMVSVDGQDIR (SEQ ID No: 10), ILLLDEATSALDTESEAVVQVALDK (SEQ ID No: 11), TVVSLTQEQK (SEQ ID No: 12), STVVQLLER (SEQ ID No: 13), ENVTMDEIEK (SEQ ID No: 14), NTTGALTTR (SEQ ID No: 15), VVQEALDK (SEQ ID No: 16), FYDPLAGK (SEQ ID No: 17), and STTVQLMQR (SEQ ID No: 18), which has been selected in the present invention, as a subject peptide for quantification and a stable-isotope labeled peptide.

In the quantification by mass spectrometry of human ABCC4 (Curr. Opin. Genet. Dev., 5, 779-B5, 1995; its sequence is registered in the data base of the Gene Bank with the accession no.: NM_005845), a quantification with high accuracy can be performed by using a peptide which amino acid sequence is SQHLGEELQGFWDK (SEQ ID No: 19), MDTELAESGSNFSVGQR (SEQ ID. No: 20), DGALESQDTENVPVTLSEENR (SEQ ID No: 21), ITILVTHQLQYLK (SEQ ID No: 22), IAYVSQQPWVFSGTLR (SEQ ID No: 23), IQTFLLLDEISQR (SEQ ID No: 24), DLQLLEDGDLTVIGDR (SEQ ID No: 25), MVHVQDFTAFWDK (SEQ ID No: 26), VFFWWLNPLFK (SEQ ID No: 27), DNEESEQPPVPGTPTLR (SEQ ID No: 28), APVLFFDR (SEQ ID No: 29), VAMZHMIYR (SEQ ID No: 30), SSLLSAVLGELAPSHGLVSVHGR (SEQ ID No: 31), TFSESSVWSQQSSRPSLK (SEQ ID No: 32), VSEAIVSIR (SEQ ID No: 33), SGIDFGSLLK (SEQ ID No: 34), DLQLLEDGDLTVIGDR (SEQ ID No: 35), and MSIIPQEPVLFTGTMR (SEQ ID No: 36), which has been selected in the present invention, as a subject peptide for quantification and a stable-isotope labeled peptide.

Similarly, as the above plasma membrane protein to be quantified, human ABCA1 can be exemplified. As a subject peptide for quantification and a stable-isotope labeled peptide used for measuring human ABCA1, one or more peptides selected from a peptide having an amino acid sequence shown by SEQ ID No: 37, SEQ ID No: 38, SEQ ID No: 39, SEQ ID No: 40, SEQ ID No: 41, SEQ ID No: 42, SEQ ID No: 43, SEQ ID No: 44, SEQ ID No: 45, SEQ ID No: 46, SEQ ID No: 47, SEQ ID No: 48, SEQ ID No: 49, SEQ ID No: 50, SEQ ID No: 51, SEQ ID No: 52, and SEQ ID No: 53 of the sequence listing can be specifically exemplified.

Similarly, as the above plasma membrane protein to be quantified, human ABCA2 can be exemplified. As a subject peptide for quantification and a stable-isotope labeled peptide used for measuring human ABCA2, one or more peptides selected from a peptide having an amino acid sequence shown by SEQ ID No: 54, SEQ ID No: 55, SEQ ID No: 56, SEQ ID No: 57, SEQ ID No: 58, SEQ ID No: 59, SEQ ID No: 60, SEQ ID No: 61, SEQ ID No: 62, SEQ ID No: 63, SEQ ID No: 64, SEQ ID No: 65, SEQ ID No: 66, SEQ ID No: 67, SEQ ID No: 68, SEQ ID No: 69, SEQ ID No: 70, SEQ ID No: 71, SEQ ID No: 72, SEQ ID No: 73, SEQ ID No: 74, and SEQ ID No: 75 of the sequence listing can be specifically exemplified.

Similarly, as the above plasma membrane protein to be quantified, human ABCA3 can be exemplified. As a subject peptide for quantification and a stable-isotope labeled peptide used for measuring human ABCA3, one or more peptides selected from a peptide having an amino acid sequence shown by SEQ ID No: 76, SEQ ID No: 77, SEQ ID No: 78, SEQ ID No: 79, SEQ ID No: 80, SEQ ID No: 81, SEQ ID No: 82, SEQ ID No: 83, SEQ ID No: 84, SEQ ID No: 85, SEQ ID No: 86, SEQ ID No: 87, SEQ ID No: 88, SEQ ID No: 89, SEQ ID No: 90, SEQ ID No: 91, and SEQ ID No: 92 of the sequence listing can be specifically exemplified.

Similarly, as the above plasma membrane protein to be quantified, human ABCA4 can be exemplified. As a subject peptide for quantification and a stable-isotope labeled peptide used for measuring human ABCA4, one or more peptides selected from a peptide having an amino acid sequence shown by SEQ ID No: 93, SEQ ID No: 94, SEQ ID No: 95, SEQ ID No: 96, SEQ ID No: 97, SEQ ID No: 98, SEQ ID No: 99, SEQ ID No: 100, SEQ ID No: 101, SEQ ID No: 102, SEQ ID No: 103, SEQ ID No: 104, and SEQ ID No: 105 of the sequence listing can be specifically exemplified.

Similarly, as the above plasma membrane protein to be quantified, human ABCA5 can be exemplified. As a subject peptide for quantification and a stable-isotope labeled peptide used for measuring human ABCA5, one or more peptides selected from a peptide having an amino acid sequence shown by SEQ ID No: 106, SEQ ID No: 107, SEQ ID No: 108, SEQ ID No: 109, SEQ ID No: 110, SEQ ID No: 111, SEQ ID No: 112, SEQ ID No: 113, SEQ ID No: 114, and SEQ ID No: 115 of the sequence listing can be specifically exemplified.

Similarly, as the above plasma membrane protein to be quantified, human ABCA6 can be exemplified. As a subject peptide for quantification and a stable-isotope labeled peptide used for measuring human ABCA6, one or more peptides selected from a peptide having an amino acid sequence shown by SEQ ID No: 116, SEQ ID No: 117, SEQ ID No: 118, SEQ ID No: 119, SEQ ID No: 120, SEQ ID No: 121, SEQ ID No: 122, SEQ ID No: 123, SEQ ID No: 124, SEQ ID No: 125, SEQ ID No: 125, SEQ ID No: 126, SEQ ID No: 127, SEQ ID No: 128, SEQ ID No: 129, SEQ ID No: 130, SEQ ID No: 131, SEQ ID No: 132, and SEQ ID No: 133 of the sequence listing can be specifically exemplified.

Similarly, as the above plasma membrane protein to be quantified, human ABCA7 can be exemplified. As a subject peptide for quantification and a stable-isotope labeled peptide used for measuring human ABCA7, one or more peptides selected from a peptide having an amino acid sequence shown by SEQ ID No: 134 of the sequence listing can be specifically exemplified.

Similarly, as the above plasma membrane protein to be quantified, human ABCA8 can be exemplified. As a subject peptide for quantification and a stable-isotope labeled peptide used for measuring human ABCA8, one or more peptides selected from a peptide having an amino acid sequence shown by SEQ ID No: 135 of the sequence listing can be specifically exemplified.

Similarly, as the above plasma membrane protein to be quantified, human ABCA9 can be exemplified. As a subject peptide for quantification and a stable-isotope labeled peptide used for measuring human ABCA9, one; or more peptides selected from a peptide having an amino acid sequence shown by SEQ ID No: 136 of the sequence listing can be specifically exemplified.

Similarly, as the above plasma membrane protein to be quantified, human ABCA10 can be exemplified. As a subject peptide for quantification and a stable-isotope labeled peptide used for measuring human ABCA10, one or more peptides selected from a peptide having an amino acid sequence shown by SEQ ID No: 137 of the sequence listing can be specifically exemplified.

Similarly, as the above plasma membrane protein to be quantified, human ABCA12 can be exemplified. As a subject peptide for quantification and a stable-isotope labeled peptide used for measuring human ABCA12, one or more peptides selected from a peptide having an amino acid sequence shown by SEQ ID No: 138 of the sequence listing can be specifically exemplified.

Similarly, as the above plasma membrane protein to be quantified, human ABCA13 can be exemplified. As a subject peptide for quantification and a stable-isotope labeled peptide used for measuring human. ABCA13, one or more peptides selected from a peptide having an amino acid sequence shown by SEQ ID No: 139 of the sequence listing can be specifically exemplified.

Similarly, as the above plasma membrane protein to be quantified, human ABCB1 can be exemplified. As a subject peptide for quantification and a stable-isotope labeled peptide used for measuring human ABCB1, one or more peptides selected from a peptide having an amino acid sequence shown by SEQ ID No: 140 of the sequence listing can be specifically exemplified.

Similarly, as the above plasma membrane protein to be quantified, human ABCB4 can be exemplified. As a subject peptide for quantification and a stable-isotope labeled peptide used for measuring human ABCB4, one or more peptides selected from a peptide having an amino acid sequence shown by SEQ ID No: 141 of the sequence listing can be specifically exemplified.

Similarly, as the above plasma membrane protein to be quantified, human ABCB5 can be exemplified. As a subject peptide for quantification and a stable-isotope labeled peptide used for measuring human ABCB5, one or more peptides selected from a peptide having an amino acid sequence shown by SEQ ID No: 142 of the sequence listing can be specifically exemplified.

Similarly, as the above plasma membrane protein to be quantified, human ABCB11 can be exemplified. As a subject peptide for quantification and a stable-isotope labeled peptide used for measuring human ABCB11, one or more peptides selected from a peptide having an amino acid sequence shown by SEQ ID No: 143 of the sequence listing can be specifically exemplified.

Similarly, as the above plasma membrane protein to be quantified, human ABCC1 can be exemplified. As a subject peptide for quantification and a stable-isotope labeled peptide used for measuring human ABCC1, one or more peptides selected from a peptide having an amino acid sequence shown by SEQ ID No: 144, SEQ ID No: 145, SEQ ID No: 146, SEQ ID No: 147, SEQ ID No: 148, SEQ ID No: 149, SEQ ID No: 150, SEQ ID No: 151, SEQ ID No: 152, SEQ ID No: 153, SEQ ID No: 154, SEQ ID No: 155, SEQ ID No: 156, SEQ ID No: 157, and SEQ ID No: 158 of the sequence listing can be specifically exemplified.

Similarly, as the above plasma membrane protein to be quantified, human ABCC2 can be exemplified. As a subject peptide for quantification and a stable-isotope labeled peptide used for measuring human ABCC2, one or more peptides selected from a peptide having an amino acid sequence shown by SEQ ID No: 159, SEQ ID No: 160, SEQ ID No: 161, SEQ ID No: 162, SEQ ID No: 163, SEQ ID No: 164, SEQ ID No: 165, SEQ ID No: 166, SEQ ID No: 167, SEQ ID No: 168, SEQ ID No: 169, SEQ ID No: 170, SEQ ID No: 171, and SEQ ID No: 172; of the sequence listing can be specifically exemplified.

Similarly, as the above plasma membrane protein to be quantified, human ABCC3 can be exemplified. As a subject peptide for quantification and a stable-isotope labeled peptide used for measuring human ABCC3, one or more peptides selected from a peptide having an amino acid sequence shown by SEQ ID No: 173, SEQ ID No: 174, SEQ ID No: 175, SEQ ID No: 176, SEQ ID No: 177, SEQ ID No: 178, SEQ ID No: 179, SEQ ID No: 180, SEQ ID No: 181, SEQ ID No: 182, SEQ ID No: 183, SEQ ID No: 184, SEQ ID No: 185, and SEQ ID No: 186 of the sequence listing can be specifically exemplified.

Similarly, as the above plasma membrane protein to be quantified, human ABCC5 can be exemplified. As a subject peptide for quantification and a stable-isotope labeled peptide used for measuring human ABCC5, one or more peptides selected from a peptide having an amino acid sequence shown by SEQ ID No: 187 of the sequence listing can be specifically exemplified.

Similarly, as the above plasma membrane protein to be quantified, human ABCC6 can be exemplified. As a subject peptide for quantification and a stable-isotope labeled peptide used for measuring human ABCC6, one or more peptides selected from a peptide having an amino acid sequence shown by SEQ ID No: 188, SEQ ID No: 189, SEQ ID No: 190, SEQ ID No: 191, SEQ ID No: 192, SEQ ID No: 193, SEQ ID No: 194, SEQ ID No: 195, SEQ ID No: 196, SEQ ID No: 197, SEQ ID No: 198, SEQ ID No: 199, SEQ ID No: 200, SEQ ID No: 201, SEQ ID No: 202, SEQ ID No: 203, and SEQ ID No: 204 of the sequence listing can be specifically exemplified.

Similarly, as the above plasma membrane protein to be quantified, human ABCC7 can be exemplified. As a subject peptide for quantification and a stable-isotope labeled peptide used for measuring human ABCC7, one or more peptides selected from a peptide having an amino acid sequence shown by SEQ ID No: 205, SEQ ID No: 206, SEQ ID No: 207, SEQ ID No: 208, SEQ ID No: 209, SEQ ID No: 210, SEQ ID No: 211, SEQ ID No: 212, SEQ ID No: 212, SEQ ID No: 213, and SEQ ID No: 214 of the sequence listing can be specifically exemplified.

Similarly, as the above plasma membrane protein to be quantified, human ABCC8 can be exemplified. As a subject peptide for quantification and a stable-isotope labeled peptide used for measuring human ABCC8, one or more peptides selected from a peptide having an amino acid sequence shown by SEQ ID No. 215, SEQ ID No: 216, SEQ ID No: 217, SEQ ID No: 218, SEQ ID No: 219, SEQ ID No: 220, SEQ ID No: 221, SEQ ID No: 222, SEQ ID No: 223, and SEQ ID No: 224 of the sequence listing can be specifically exemplified.

Similarly, as the above plasma membrane protein to be quantified, human ABCC9 can be exemplified. As a subject peptide for quantification and a stable-isotope labeled peptide used for measuring human ABCC9, one or more peptides selected from a peptide having an amino acid sequence shown by SEQ ID No: 225, SEQ ID No: 226, SEQ ID No: 227, SEQ ID No: 228, SEQ ID No: 229, SEQ ID No: 230, SEQ ID No: 231, and SEQ ID No: 232 of the sequence listing can be specifically exemplified.

Similarly, as the above plasma membrane protein to be quantified, human ABCC10 can be exemplified. As a subject peptide for quantification and a stable-isotope labeled peptide used for measuring human ABCC10, one or more peptides selected from a peptide having an amino acid sequence shown by SEQ ID No: 233, SEQ ID No: 234, SEQ ID No: 235, SEQ ID No: 236, SEQ ID No: 237, SEQ ID No: 238, SEQ ID No: 239, SEQ ID No: 240, SEQ ID No: 241, SEQ. ID No: 242, SEQ ID No: 243, SEQ ID No: 244, SEQ ID No: 245, and SEQ ID No: 246, SEQ ID No: 247, SEQ ID No: 248, SEQ ID No: 249, SEQ ID No: 250, SEQ ID No: 251, SEQ ID No: 252, SEQ ID No: 253, SEQ ID No: 254, and SEQ ID No: 255 of the sequence listing can be specifically exemplified.

Similarly, as the above plasma membrane protein to be quantified, human ABCC11 can be exemplified. As a subject peptide for quantification and a stable-isotope labeled peptide used for measuring human ABCC11, one or more peptides selected from a peptide having an amino acid sequence shown by SEQ ID No: 256, SEQ ID No: 257, SEQ ID No: 258, SEQ ID No: 259, SEQ ID No: 260, SEQ ID No: 261, SEQ ID No: 262, SEQ ID No: 263, SEQ ID No: 264, SEQ ID No: 265, SEQ ID No: 266, and SEQ ID No: 267 of the sequence listing can be; specifically exemplified.

Similarly, as the above plasma membrane protein to be quantified, human ABCC12 can be exemplified. As a subject peptide for quantification and a stable-isotope labeled peptide used for measuring human ABCC12', one or more peptides selected from a peptide having an amino acid sequence shown by SEQ ID No: 268, and SEQ ID No: 269 of the sequence listing can be specifically exemplified.

Similarly, as the above plasma membrane protein to be quantified, human ABCC13 can be exemplified. As a subject peptide for quantification and a stable-isotope labeled peptide used for measuring human ABCC13, one or more peptides selected from a peptide having an amino acid sequence shown by SEQ ID No: 270 of the sequence listing can be specifically exemplified.

Similarly, as the above plasma membrane protein to be quantified, human ABCG1 can be exemplified. As a subject peptide for quantification and a stable-isotope labeled peptide used for measuring human ABCG1, one or more peptides selected from a peptide having an amino acid sequence shown by SEQ ID No: 271, SEQ ID No: 272, SEQ ID No: 273, SEQ ID No: 274, and SEQ ID No: 275 can be specifically exemplified.

Similarly, as the above plasma membrane protein to be quantified, human ABCG4 can be exemplified. As a subject peptide for quantification and a stable-isotope labeled peptide used for measuring human ABCG4, one or more peptides selected from a peptide having an amino acid sequence shown by SEQ ID No: 276, SEQ ID No: 277, and SEQ ID No: 278 of the sequence listing can be specifically exemplified.

Similarly, as the above plasma membrane protein to be quantified, human ABCG5 can be exemplified. As a subject peptide for quantification and a stable-isotope labeled peptide used for measuring human ABCG5, one or more peptides selected from a peptide having an amino acid sequence shown by SEQ ID No: 279, SEQ ID No: 280, SEQ ID No: 281, SEQ ID No: 282, and SEQ ID No: 283 of the sequence listing can be specifically exemplified.

Similarly, as the above plasma membrane protein to be quantified, human ABCG8 can be exemplified. As a subject peptide for quantification and a stable-isotope labeled peptide used for measuring human ABCG8, one or more peptides selected from a peptide having an amino acid sequence shown by SEQ ID No: 284 of the sequence listing can be specifically exemplified.

Similarly, as the above plasma membrane protein to be quantified, human SLC10A1 can be exemplified. As a subject peptide for quantification and a stable-isotope labeled peptide used for measuring human SLC10A1, one or more peptides selected from a peptide having an amino acid sequence shown by SEQ ID No: 285 of the sequence listing can be specifically exemplified.

Similarly, as the above plasma membrane protein to be quantified, human SLC15A1 can be exemplified. As a subject peptide for quantification and a stable-isotope labeled peptide used for measuring human SLC15A1, one or more peptides selected from a peptide having an amino acid sequence shown by SEQ ID No: 286 of the sequence listing can be specifically exemplified.

Similarly, as the above plasma membrane protein to be quantified, human SLC15A2 can be exemplified. As a subject peptide for quantification and a stable-isotope labeled peptide used for measuring human SLC15A2, one or more peptides selected from a peptide having an amino acid sequence shown by SEQ ID No: 287 of the sequence listing can be specifically exemplified.

Similarly, as the above plasma membrane protein to be quantified, human SLC16A1 can be exemplified. As a subject peptide for quantification and a stable-isotope labeled peptide used for measuring human SLC16A1, one or more peptides selected from a peptide having an amino acid sequence shown by SEQ ID No: 288 of the sequence listing can be specifically exemplified.

Similarly, as the above plasma membrane protein to be quantified, human SLC16A7 can be exemplified. As a subject peptide for quantification and a stable-isotope labeled peptide used for measuring human SLC16A7, one or more peptides selected from a peptide having an amino acid sequence shown by SEQ ID No: 289 of the sequence listing can be specifically exemplified.

Similarly, as the above plasma membrane protein to be quantified, human SLC21A2 can be exemplified. As a subject peptide for quantification and a stable-isotope labeled peptide used for measuring human SLC21A2, one or more peptides selected from a peptide having an amino acid sequence shown by SEQ ID No: 290 of the sequence listing can be specifically exemplified.

Similarly, as the above plasma membrane protein to be quantified, human SLC21A3 can be exemplified. As a subject peptide for quantification and a stable-isotope labeled peptide used for measuring human SLC21A3, one or more peptides selected from a peptide having an amino acid sequence shown by SEQ ID No: 291 of the sequence listing can be specifically exemplified.

Similarly, as the above plasma membrane protein to be quantified, human SLC21A6 can be exemplified. As a subject peptide for quantification and a stable-isotope labeled peptide used for measuring human SLC21A6, one or more peptides selected from a peptide having an amino acid sequence shown by SEQ ID No: 292 of the sequence listing can be specifically exemplified.

Similarly, as the above plasma membrane protein to be quantified, human SLC21A8 can be exemplified. As a subject peptide for quantification and a stable-isotope labeled peptide used for measuring human SLC21A8, one or more peptides selected from a peptide having an amino acid sequence shown by SEQ ID No: 293 of the sequence listing can be specifically exemplified.

Similarly, as the above plasma membrane protein to be quantified, human SLC21A9 can be exemplified. As a subject peptide for quantification and a stable-isotope labeled peptide used for measuring human SLC21A9, one or more peptides selected from a peptide having an amino acid sequence shown by SEQ ID No: 294 of the sequence listing can be specifically exemplified.

Similarly, as the above plasma membrane protein to be quantified, human SLC21A11 can be exemplified. As a subject peptide for quantification and a stable-isotope labeled peptide used for measuring human SLC21A11, one or more peptides selected from a peptide having an amino acid sequence shown by SEQ ID No: 295 of the sequence listing can be specifically exemplified.

Similarly, as the above plasma membrane protein to be quantified, human SLC21A12 can be exemplified. As a subject peptide for quantification and a stable-isotope labeled peptide used for measuring human SLC21A12, one or more peptides selected from a peptide having an amino acid sequence shown by SEQ ID No: 296 of the sequence listing can be specifically exemplified.

Similarly, as the above plasma membrane protein to be quantified, human SLC21A14 can be exemplified. As a subject peptide for quantification and a stable-isotope labeled peptide used for measuring human SLC21A14, one or more peptides selected from a peptide having an amino acid sequence shown by SEQ ID No: 297 of the sequence listing can be specifically exemplified.

Similarly, as the above plasma membrane protein to be quantified, human SLC21A15 can be exemplified. As a subject peptide for quantification and a stable-isotope labeled peptide used for measuring human SLC21A15, one or more peptides selected from a peptide having an amino acid sequence shown by SEQ ID No: 298 of the sequence listing can be specifically exemplified.

Similarly, as the above plasma membrane protein to be quantified, human SLC21A19 can be exemplified. As a subject peptide for quantification and a stable-isotope labeled peptide used for measuring human SLC21A19, one or more peptides selected from a peptide having an amino acid sequence shown by SEQ ID No: 299 of the sequence listing can be specifically exemplified.

Similarly, as the above plasma membrane protein to be quantified, human SLC21A20 can be exemplified. As a subject peptide for quantification and a stable-isotope labeled peptide used for measuring human SLC21A20, one or more peptides selected from a peptide having an amino acid sequence shown by SEQ ID No: 300 of the sequence listing can be specifically exemplified.

Similarly, as the above plasma membrane protein to be quantified, human SLC22A1 can be exemplified. As a subject peptide for quantification and a stable-isotope labeled peptide used for measuring human SLC22A1 one or more peptides selected from a peptide having an amino acid sequence shown by SEQ ID No: 301 of the sequence listing can be specifically exemplified.

Similarly, as the above plasma membrane protein to be quantified, human SLC22A2 can be exemplified. As a subject peptide for quantification and a stable-isotope labeled peptide used for measuring human SLC22A2, one or more peptides selected from a peptide having an amino acid sequence shown by SEQ ID No: 302 of the sequence listing can be specifically exemplified.

Similarly, as the above plasma membrane protein to be quantified, human SLC22A3 can be exemplified. As a subject peptide for quantification and a stable-isotope labeled peptide used for measuring human SLC22A3, one or more peptides selected from a peptide having an amino acid sequence shown by SEQ ID No: 303 of the sequence listing can be specifically exemplified.

Similarly, as the above plasma membrane protein to be quantified, human SLC22A4 can be exemplified. As a subject peptide for quantification and a stable-isotope labeled peptide used for measuring human SLC22A4, one or more peptides selected from a peptide having an amino acid sequence shown by SEQ ID No: 304 of the sequence listing can be specifically exemplified.

Similarly, as the above plasma membrane protein to be quantified, human SLC22A5 can be exemplified. As a subject peptide for quantification and a stable-isotope labeled peptide used for measuring human SLC22A5, one or more peptides selected from a peptide having an amino acid sequence shown by SEQ ID No: 305 of the sequence listing can be specifically exemplified.

Similarly, as the above plasma membrane protein to be quantified, human SLC22A6 can be exemplified. As a subject peptide for quantification and a stable-isotope labeled peptide used for measuring human SLC22A6, one or more peptides selected from a peptide having an amino acid sequence shown by SEQ ID No: 306 of the sequence listing can be specifically exemplified.

Similarly, as the above plasma membrane protein to be quantified, human SLC22A7 can be exemplified. As a subject peptide for quantification and a stable-isotope labeled peptide used for measuring human SLC22A7, one or more peptides selected from a peptide having an amino acid sequence shown by SEQ ID No: 307 of the sequence listing can be specifically exemplified.

Similarly, as the above plasma membrane protein to be quantified, human SLC22A8 can be exemplified. As a subject peptide for quantification and a stable-isotope labeled peptide used for measuring human SLC22A8, one or more peptides selected from a peptide having an amino acid sequence shown by SEQ ID No: 308 of the sequence listing can be specifically exemplified.

Similarly, as the above plasma membrane protein to be quantified, human SLC22A9 can be exemplified. As a subject peptide for quantification and a stable-isotope labeled peptide used for measuring human SLC22A9, one or more peptides selected from a peptide having an amino acid sequence shown by SEQ ID No: 309 of the sequence listing can be specifically exemplified.

Similarly, as the above plasma membrane protein to be quantified, human SLC22A10 can be exemplified. As a subject peptide for quantification and a stable-isotope labeled peptide used for measuring human SLC22A10, one or more peptides selected from a peptide having an amino acid sequence shown by SEQ ID No: 310 of the sequence listing can be specifically exemplified.

Similarly, as the above plasma membrane protein to be quantified, human SLC22A11 can be exemplified. As a subject peptide for quantification and a stable-isotope labeled peptide used for measuring human SLC22A11, one or more peptides selected from a peptide having an amino acid sequence shown by SEQ ID No: 311 of the sequence listing can be specifically exemplified.

Similarly, as the above plasma membrane protein to be quantified, human SLC22A12 can be exemplified. As a subject peptide for quantification and a stable-isotope labeled peptide used for measuring human SLC22A12, one or more peptides selected from a peptide having an amino acid sequence shown by SEQ ID No: 312 of the sequence listing can be specifically exemplified.

Similarly, as the above plasma membrane protein to be quantified, human SLC22A13 can be exemplified. As a subject peptide for quantification and a stable-isotope labeled peptide used for measuring human SLC22A13, one or more peptides selected from a peptide having an amino acid sequence shown by SEQ ID No: 313 of the sequence listing can be specifically exemplified.

Similarly, as the above plasma membrane protein to be quantified, human SLC22A14 can be exemplified. As a subject peptide for quantification and a stable-isotope labeled peptide used for measuring human SLC22A14, one or more peptides selected from a peptide having an amino acid sequence shown by SEQ ID No: 314 of the sequence listing can be specifically exemplified.

Similarly, as the above plasma membrane protein to be quantified, human SLC22A15 can be exemplified. As a subject peptide for quantification and a stable-isotope labeled peptide used for measuring human SLC22A15, one or more peptides selected from a peptide having an amino-acid sequence shown by SEQ ID No: 315 of the sequence listing can be specifically exemplified.

Similarly, as the above plasma membrane protein to be quantified, human SLC22A16 can be exemplified. As a subject peptide for quantification and a stable-isotope labeled peptide used for measuring human SLC22A16, one or more peptides selected from a peptide having an amino acid sequence shown by SEQ ID No: 316 of the sequence listing can be specifically exemplified.

Similarly, as the above plasma membrane protein to be quantified, human SLC22A17 can be exemplified. As a subject peptide for quantification and a stable-isotope labeled peptide used for measuring human SLC22A17, one or more peptides selected from a peptide having an amino acid sequence shown by SEQ ID No: 317 of the sequence listing can be specifically exemplified.

Similarly, as the above plasma membrane protein to be quantified, human SLC22A18 can be exemplified. As a subject peptide for quantification and a stable-isotope labeled peptide used for measuring human SLC22A18, one or more peptides selected from a peptide having an amino acid sequence shown by SEQ ID No: 318 of the sequence listing can be specifically exemplified.

Similarly, as the above plasma membrane protein to be quantified, human SLC29A1 can be exemplified. As a subject peptide for quantification and a stable-isotope labeled peptide used for measuring human SLC29A1, one or more peptides selected from a peptide having an amino acid sequence shown by SEQ ID No: 319 of the sequence listing can be specifically exemplified.

Similarly, as the above plasma membrane protein to be quantified, human SLC29A2 can be exemplified. As a subject peptide for quantification and a stable-isotope labeled peptide used for measuring human SLC29A2, one or more peptides selected from a peptide having an amino acid sequence shown by SEQ ID No: 320 of the sequence listing can be specifically exemplified.

Similarly, as the above plasma membrane protein to be quantified, human SLC28A1 can be exemplified. As a subject peptide for quantification and a stable-isotope labeled peptide used for measuring human SLC28A1, one or more peptides selected from a peptide having an amino acid sequence shown by SEQ ID No: 321 of the sequence listing can be specifically exemplified.

Similarly, as the above plasma membrane protein to be quantified, human SLC28A3 can be exemplified. As a subject peptide for quantification and a stable-isotope labeled peptide used for measuring human SLC28A3, one or more peptides selected from a peptide having an amino acid sequence shown by SEQ ID No: 322 of the sequence listing can be specifically exemplified.

Similarly, as the above plasma membrane protein to be quantified, human SLC19A1 can be exemplified. As a subject peptide for quantification and a stable-isotope labeled peptide used for measuring human SLC19A1, one or more peptides selected from a peptide having an amino acid sequence shown by SEQ ID No: 323 of the sequence listing can be specifically exemplified.

Similarly, as the above plasma membrane protein to be quantified, human SLC1A1 can be exemplified. As a subject peptide for quantification and a stable-isotope labeled peptide used for measuring human SLC1A1, one or more peptides selected from a peptide having an amino acid sequence shown by SEQ ID No: 324 of the sequence listing can be specifically exemplified.

Similarly, as the above plasma membrane protein to be quantified, human SLC1A2 can be exemplified. As a subject peptide for quantification and a stable-isotope labeled peptide used for measuring human SLC1A2, one or more peptides selected from a peptide having an amino acid sequence shown by SEQ ID No: 325 of the sequence listing can be specifically exemplified.

Similarly, as the above plasma membrane protein to be quantified, human SLC1A3 can be exemplified. As a subject peptide for quantification and a stable-isotope labeled peptide used for measuring human SLC1A3, one or more peptides selected from a peptide having an amino acid sequence shown by SEQ ID No: 326 of the sequence listing can be specifically exemplified.

Similarly, as the above plasma membrane protein to be quantified, human SLC1A4 can be exemplified. As a subject peptide for quantification and a stable-isotope labeled peptide used for measuring human SLC1A4, one or more peptides selected from a peptide having an amino acid sequence shown by SEQ ID No: 327 of the sequence listing can be specifically exemplified.

Similarly, as the above plasma membrane protein to be quantified, human SLC1A5 can be exemplified. As a subject peptide for quantification and a stable-isotope labeled peptide used for measuring human SLC1A5, one or more peptides selected from a peptide having an amino acid sequence shown by SEQ ID No: 328 of the sequence listing can be specifically exemplified.

Similarly, as the above plasma membrane protein to be quantified, human SLC1A6 can be exemplified. As a subject peptide for quantification and a stable-isotope labeled peptide used for measuring human SLC1A6, one or more peptides selected from a peptide having an amino acid sequence shown by SEQ ID No: 329 of the sequence listing can be specifically exemplified.

Similarly, as the above plasma membrane protein to be quantified, human SLC1A7 can be exemplified. As a subject peptide for quantification and a stable-isotope labeled peptide used for measuring human SLC1A7, one or more peptides selected from a peptide having an amino acid sequence shown by SEQ ID No: 330 of the sequence listing can be specifically exemplified.

Similarly, as the above plasma membrane protein to be quantified, human SLC2A1 can be exemplified. As a subject peptide for quantification and a stable-isotope labeled peptide used for measuring human SLC2A1, one or more peptides selected from a peptide having an amino acid sequence shown by SEQ ID No: 331 of the sequence listing can be specifically exemplified.

Similarly, as the above plasma membrane protein to be quantified, human SLC6A12 can be exemplified. As a subject peptide for quantification and a stable-isotope labeled peptide used for measuring human SLC6A12, one or more peptides selected from a peptide having an amino acid sequence shown by SEQ ID No: 332 of the sequence listing can be specifically exemplified.

Similarly, as the above plasma membrane protein to be quantified, human SLC7A5 can be exemplified. As a subject peptide for quantification and a stable-isotope labeled peptide used for measuring human SLC7A5, one or more peptides selected from a peptide having an amino acid sequence shown by SEQ ID No: 333 of the sequence listing can be specifically exemplified.

Similarly, as the above plasma membrane protein to be quantified, human SLC17A1 can be exemplified. As a subject peptide for quantification and a stable-isotope labeled peptide used for measuring human SLC17A1, one or more peptides selected from a peptide having an amino acid sequence shown by SEQ ID No: 334 of the sequence listing can be specifically exemplified.

Similarly, as the above plasma membrane protein to be quantified, human SLC17A2 can be exemplified. As a subject peptide for quantification and a stable-isotope labeled peptide used for measuring human SLC17A2, one or more peptides selected from a peptide having an amino acid sequence shown by SEQ ID No: 335 of the sequence listing can be specifically exemplified.

Similarly, as the above plasma membrane protein to be quantified, human SLC17A3 can be exemplified. As a subject peptide for quantification and a stable-isotope labeled peptide used for measuring human SLC17A3, one or more peptides selected from a peptide having an amino acid sequence shown by SEQ ID No: 336 of the sequence listing can be specifically exemplified.

Similarly, as the above plasma membrane protein to be quantified, human SLC17A4 can be exemplified. As a subject peptide for quantification and a stable-isotope labeled peptide used for measuring human SLC17A4, one or more peptides selected from a peptide having an amino acid sequence shown by SEQ ID No: 337 of the sequence listing can be specifically exemplified.

Similarly, as the above plasma membrane protein to be quantified, human SLC17A5 can be exemplified. As a subject peptide for quantification and a stable-isotope labeled peptide used for measuring human SLC17A5, one or more peptides selected from a peptide having an amino acid sequence shown by SEQ ID No: 338 of the sequence listing can be specifically exemplified.

Similarly, as the above plasma membrane protein to be quantified, human SLC17A6 can be exemplified. As a subject peptide for quantification and a stable-isotope labeled peptide used for measuring human SLC17A6, one or more peptides selected from a peptide having an amino acid sequence shown by SEQ ID No: 339 of the sequence listing can be specifically exemplified.

Similarly, as the above plasma membrane protein to be quantified, human SLC17A7 can be exemplified. As a subject peptide for quantification and a stable-isotope labeled peptide used for measuring human SLC17A7, one or more peptides selected from a peptide having an amino acid sequence shown by SEQ ID No: 340 of the sequence listing can be specifically exemplified.

Similarly, as the above plasma membrane protein to be quantified, human SLC17A8 can be exemplified. As a subject peptide for quantification and a stable-isotope labeled peptide used for measuring human SLC17A8, one or more peptides selected from a peptide having an amino acid sequence shown by SEQ ID No: 341 of the sequence listing can be specifically exemplified.

Similarly, as the above plasma membrane protein to be quantified, human SLC29A4 can be exemplified. As a subject peptide for quantification and a stable-isotope labeled peptide used for measuring human SLC29A4, one or more peptides selected from a peptide having an amino acid sequence shown by SEQ ID No: 342 of the sequence listing can be specifically exemplified.

Similarly, as the above plasma membrane protein to be quantified, human SLC44A1 can be exemplified. As a subject peptide for quantification and a stable-isotope labeled peptide used for measuring human SLC44A1, one or more peptides selected from a peptide having an amino acid sequence shown by SEQ ID No: 343 of the sequence listing can be specifically exemplified.

Similarly, as the above plasma membrane protein to be quantified, human SLC44A2 can be exemplified. As a subject peptide for quantification and a stable-isotope labeled peptide used for measuring human SLC44A2, one or more peptides selected from a peptide having an amino acid sequence shown by SEQ ID No: 344 of the sequence listing can be specifically exemplified.

Similarly, as the above plasma membrane protein to be quantified, human SLC44A3 can be exemplified. As a subject peptide for quantification and a stable-isotope labeled peptide used for measuring human SLC44A3, one or more peptides selected from a peptide having an amino acid sequence shown by SEQ ID No: 345 of the sequence listing can be specifically exemplified.

Similarly, as the above plasma membrane protein to be quantified, human SLC44A4 can be exemplified. As a subject peptide for quantification and a stable-isotope labeled peptide used for measuring human SLC44A4, one or more peptides selected from a peptide having an amino acid sequence shown by SEQ ID No: 346 of the sequence listing can be specifically exemplified.

Similarly, as the above plasma membrane protein to be quantified, human SLC44A5 can be exemplified. As a subject peptide for quantification and a stable-isotope labeled peptide used for measuring human SLC44A5, one or more peptides selected from a peptide having an amino acid sequence shown by SEQ ID No: 347 of the sequence listing can be specifically exemplified.

Similarly, as the above plasma membrane protein to be quantified, human MATE1 can be exemplified. As a subject peptide for quantification and a stable-isotope labeled peptide used for measuring human MATE1, one or more peptides selected from a peptide having an amino acid sequence shown by SEQ ID No: 348 of the sequence listing can be specifically exemplified.

Similarly, as the above plasma membrane protein to be quantified, human MATE2 can be exemplified. As a subject peptide for quantification and a stable-isotope labeled peptide used for measuring human MATE2, one or more peptides selected from a peptide having an amino acid sequence shown by SEQ ID No: 349 of the sequence listing can be specifically exemplified.

Similarly, as the above plasma membrane protein to be quantified, human SLC2A2 can be exemplified. As a subject peptide for quantification and a stable-isotope labeled peptide used for measuring human SLC2A2, one or more peptides selected from a peptide having an amino acid sequence shown by SEQ ID No: 350 and SEQ ID NO: 351 of the sequence listing can be specifically exemplified.

Similarly, as the above plasma membrane protein to be quantified, human SLC2A8 can be exemplified. As a subject peptide for quantification and a stable-isotope labeled peptide used for measuring human SLC2A8, one or more peptides selected from a peptide having an amino acid sequence shown by SEQ ID No: 352 and SEQ ID NO: 353 of the sequence listing can be specifically exemplified.

Similarly, as the above plasma membrane protein to be quantified, human SLC2A9 can be exemplified. As a subject peptide for quantification and a stable-isotope labeled peptide used for measuring human SLC2A9, one or more peptides selected from a peptide having an amino acid sequence shown by SEQ ID No: 354, SEQ ID NO: 355 and SEQ ID NO: 356 of the sequence listing can be specifically exemplified.

Similarly, as the above plasma membrane protein to be quantified, human SLC2A10 can be exemplified. As a subject peptide for quantification and a stable-isotope labeled peptide used for measuring human SLC2A10, one or more peptides selected from a peptide having an amino acid sequence shown by SEQ ID No: 357, SEQ ID No: 358, SEQ ID No: 359, and SEQ ID No: 360 of the sequence listing can be specifically exemplified.

Similarly, as the above plasma membrane protein to be quantified, human SLC4A5 can be exemplified. As a subject peptide for quantification and a stable-isotope labeled peptide used for measuring human SLC4A5, one or more peptides selected from a peptide having an amino acid sequence shown by SEQ ID No: 361, SEQ ID No: 362, SEQ ID No: 363, SEQ ID NO: 364, SEQ ID No: 365, SEQ ID No: 366, SEQ ID No:

367, SEQ ID No: 368, SEQ ID No: 369, SEQ ID No: 370, SEQ ID No: 371, SEQ ID No: 372, and SEQ ID No: 373 of the sequence listing can be specifically exemplified.

Similarly, as the above plasma membrane protein to be quantified, human SLC4A7 can be exemplified. As a subject peptide for quantification and a stable-isotope labeled peptide used for measuring human SLC4A7, one or more peptides selected from a peptide having an amino acid sequence shown by SEQ ID No: 374, SEQ ID No: 375, SEQ ID No: 376, SEQ ID No: 377, SEQ ID No: 378, and SEQ ID No: 379 of the sequence listing can be specifically exemplified.

Similarly, as the above plasma membrane protein to be quantified, human SLC5A9 can be exemplified. As a subject peptide for quantification and a stable-isotope labeled peptide used for measuring human SLC5A9, one or more peptides selected from a peptide having an amino acid sequence shown by SEQ ID No: 380 and SEQ ID NO: 381 of the sequence listing can be specifically exemplified.

Similarly, as the above plasma membrane protein to be quantified, human SLC5A11 can be exemplified. As a subject peptide for quantification and a stable-isotope labeled peptide used for measuring human SLC5A11, one or more peptides selected from a peptide having an amino acid sequence shown by SEQ ID No: 382, SEQ ID No: 383, SEQ ID No: 384, and SEQ ID No: 385 of the sequence listing can be specifically exemplified.

Similarly, as the above plasma membrane protein to be quantified, human SLC6A9 can be exemplified. As a subject peptide for quantification and a stable-isotope labeled peptide used for measuring human SLC6A9, one or more peptides selected from a peptide having an amino acid sequence shown by SEQ ID No: 386 and SEQ ID NO: 387 of the sequence listing can be specifically exemplified.

Similarly, as the above plasma membrane protein to be quantified, human SLC6A13 can be exemplified. As a subject peptide for quantification and a stable-isotope labeled peptide used for measuring human SLC6A13, one or more peptides selected from a peptide having an amino acid sequence shown by SEQ ID No: 388 of the sequence listing can be specifically exemplified.

Similarly, as the above plasma membrane protein to be quantified, human SLC7A2 can be exemplified. As a subject peptide for quantification and a stable-isotope labeled peptide used for measuring human SLC7A2, one or more peptides selected from a peptide having an amino acid sequence shown by SEQ ID No: 389, SEQ ID No: 390, SEQ ID No: 391, SEQ ID No: 392, SEQ ID No: 393, SEQ ID No: 394, SEQ ID No: 395, SEQ ID No: 396, SEQ ID No: 397 of the sequence listing can be specifically exemplified.

Similarly, as the above plasma membrane protein to be quantified, human SLC7A6 can be exemplified. As a subject peptide for quantification and a stable-isotope labeled peptide used for measuring human SLC7A6, one or more peptides selected from a peptide having an amino acid sequence shown by SEQ ID No: 398, SEQ ID No: 399, and SEQ ID No: 400 of the sequence listing can be specifically exemplified.

Similarly, as the above plasma membrane protein to be quantified, human SLC7A9 can be exemplified. As a subject peptide for quantification and a stable-isotope labeled peptide used for measuring human SLC7A9, one or more peptides selected from a peptide having an amino acid sequence shown by SEQ ID No: 401 of the sequence listing can be specifically exemplified.

Similarly, as the above plasma membrane protein to be quantified, human SLC10A6 can be exemplified. As a subject peptide for quantification and a stable-isotope labeled peptide used for measuring human SLC10A6, one or more peptides selected from a peptide having an amino acid sequence shown by SEQ ID No: 402 and SEQ ID No: 403 of the sequence listing can be specifically exemplified.

Similarly, as the above plasma membrane protein to be quantified, human SLC13A3 can be exemplified. As a subject peptide for quantification and a stable-isotope labeled peptide used for measuring human SLC13A3, one or more peptides selected from a peptide having an amino acid sequence shown by SEQ ID No: 404, SEQ ID No: 405, SEQ ID No: 406, and SEQ ID No: 407 of the sequence listing can be specifically exemplified.

Similarly, as the above plasma membrane protein to be quantified, human SLC13A5 can be exemplified. As a subject peptide for quantification and a stable-isotope labeled peptide used for measuring human SLC13A5, one or more peptides selected from a peptide having an amino acid sequence shown by SEQ ID No: 408 of the sequence listing can be specifically exemplified.

Similarly, as the above plasma membrane protein to be quantified, human SLC16A2 can be exemplified. As a subject peptide for quantification and a stable-isotope labeled peptide used for measuring human SLC16A2, one or more peptides selected from a peptide having an amino acid sequence shown by SEQ ID No: 409, SEQ ID No: 410, and SEQ ID No: 411 of the sequence listing can be specifically exemplified.

Similarly, as the above plasma membrane protein to be quantified, human SLC16A4 can be exemplified. As a subject peptide for quantification and a stable-isotope labeled peptide used for measuring human SLC16A4, one or more peptides selected from a peptide having an amino acid sequence shown by SEQ ID No: 412, SEQ ID No: 413, and SEQ ID No: 414 of the sequence listing can be specifically exemplified.

Similarly, as the above plasma membrane protein to be quantified, human SLC10A2 can be exemplified. As a subject peptide for quantification and a stable-isotope labeled peptide used for measuring human SLC10A2, one or more peptides selected from a peptide having an amino acid sequence shown by SEQ ID No: 415 of the sequence listing can be specifically exemplified.

Similarly, as the above plasma membrane protein to be quantified, human SLC10A3 can be exemplified. As a subject peptide for quantification and a stable-isotope labeled peptide used for measuring human SLC10A3, one or more peptides selected from a peptide having an amino acid sequence shown by SEQ ID No: 416, and SEQ ID No: 417 of the sequence listing can be specifically exemplified.

Similarly, as the above plasma membrane protein to be quantified, human SLC10A4 can be exemplified. As a subject peptide for quantification and a stable-isotope labeled peptide used for measuring human SLC10A4, one or more peptides selected from a peptide having an amino acid sequence shown by SEQ ID No: 418 of the sequence listing can be specifically exemplified.

Similarly, as the above plasma membrane protein to be quantified, human SLC10A5 can be exemplified. As a subject peptide for quantification and a stable-isotope labeled peptide used for measuring human SLC10A5, one or more peptides selected from a peptide having an amino acid sequence shown by SEQ ID No: 419, SEQ ID No: 420, and SEQ ID No: 421 of the sequence listing can be specifically exemplified.

Similarly, as the above plasma membrane protein to be quantified, human SLC11A1 can be exemplified. As a subject peptide for quantification and a stable-isotope labeled peptide used for measuring human SLC11A1, one or more peptides selected from a peptide having an amino acid sequence shown by SEQ ID No: 422 of the sequence listing can be specifically exemplified.

Similarly, as the above plasma membrane protein to be quantified, human SLC11A2 can be exemplified. As a subject peptide for quantification and a stable-isotope labeled peptide used for measuring human SLC11A2, one or more peptides selected from a peptide having an amino acid sequence shown by SEQ ID No: 423 of the sequence listing can be specifically exemplified.

Similarly, as the above plasma membrane protein to be quantified, human SLC12A1 can be exemplified. As a subject peptide for quantification and a stable-isotope labeled peptide used for measuring human SLC12A1, one or more peptides selected from a peptide having an amino acid sequence shown by SEQ ID No: 424, SEQ ID No: 425, SEQ ID No: 426, and SEQ ID No: 427 of the sequence listing can be specifically exemplified.

Similarly, as the above plasma membrane protein to be quantified, human SLC12A2 can be exemplified. As a subject peptide for quantification and a stable-isotope labeled peptide used for measuring human SLC12A2, one or more peptides selected from a peptide having an amino acid sequence shown by SEQ ID No: 428, SEQ ID No: 429, SEQ ID No: 430, SEQ ID No: 431, and SEQ ID No: 432 of the sequence listing can be specifically exemplified.

Similarly, as the above plasma membrane protein to be quantified, human SLC12A3 can be exemplified. As a subject peptide for quantification and a stable-isotope labeled peptide used for measuring human SLC12A3, one or more peptides selected from a peptide having an amino acid sequence shown by SEQ ID No: 433, SEQ ID No: 434, and SEQ ID No: 435 of the sequence listing can be specifically exemplified.

Similarly, as the above plasma membrane protein to be quantified, human SLC12A4 can be exemplified. As a subject peptide for quantification and a stable-isotope labeled peptide used for measuring human SLC12A4, one or more peptides selected from a peptide having an amino acid sequence shown by SEQ ID No: 436, SEQ ID No: 437, SEQ ID No: 438, SEQ ID No: 439, SEQ ID No: 440, and SEQ ID No: 441 of the sequence listing can be specifically exemplified.

Similarly, as the above plasma membrane protein to be quantified, human SLC12A5 can be exemplified. As a subject peptide for quantification and a stable-isotope labeled peptide used for measuring human SLC12A5, one or more peptides selected from a peptide having an amino acid sequence shown by SEQ ID No: 442, SEQ ID No: 443, SEQ ID No: 444, and SEQ ID No: 445 of the sequence listing can be specifically exemplified.

Similarly, as the above plasma membrane protein to be quantified, human SLC12A6 can be exemplified. As a subject peptide for quantification and a stable-isotope labeled peptide used for measuring human SLC12A6, one or more peptides selected from a peptide having an amino acid sequence shown by SEQ ID No: 446, SEQ ID No: 447, SEQ ID No: 448, SEQ ID No: 449, SEQ ID No: 450, SEQ ID No: 451, SEQ ID No: 452, SEQ ID No: 453, and SEQ ID No: 454 of the sequence listing can be specifically exemplified.

Similarly, as the above plasma membrane protein to be quantified, human SLC12A7 can be exemplified. As a subject peptide for quantification and a stable-isotope labeled peptide used for measuring human SLC12A7, one or more peptides selected from a peptide having an amino acid sequence shown by SEQ ID No: 455, SEQ ID No: 456, SEQ ID No: 457, SEQ ID No: 458, SEQ ID No: 459, SEQ ID No: 460, SEQ ID No: 461, SEQ ID No: 462, SEQ ID No: 463, and SEQ ID No: 464 of the sequence listing can be specifically exemplified.

Similarly, as the above plasma membrane protein to be quantified, human SLC12A8 can be exemplified. As a subject peptide for quantification and a stable-isotope labeled peptide used for measuring human SLC12A8, one or more peptides selected from a peptide having an amino acid sequence shown by SEQ ID No: 465, and SEQ ID No: 466 of the sequence listing can be specifically exemplified.

Similarly, as the above plasma membrane protein to be quantified, human SLC12A9 can be exemplified. As a subject peptide for quantification and a stable-isotope labeled peptide used for measuring human SLC12A9, one or more peptides selected from a peptide having an amino acid sequence shown by SEQ ID No: 467, SEQ ID No: 468, SEQ ID No: 469, SEQ ID No: 470, SEQ ID No: 471, SEQ ID No: 472, SEQ ID No: 473, SEQ ID No: 474, SEQ ID No: 475, and SEQ ID No: 476 of the sequence listing can be specifically exemplified.

Similarly, as the above plasma membrane protein to be quantified, human SLC13A1 can be exemplified. As a subject peptide for quantification and a stable-isotope labeled peptide used for measuring human SLC13A1, one or more peptides selected from a peptide having an amino acid sequence shown by SEQ ID No: 477 of the sequence listing can be specifically exemplified.

Similarly, as the above plasma membrane protein to be quantified, human SLC13A2 can be exemplified. As a subject peptide for quantification and a stable-isotope labeled peptide used for measuring human SLC13A2, one or more peptides selected from a peptide having an amino acid sequence shown by SEQ ID No: 478, and SEQ ID No: 479 of the sequence listing can be specifically exemplified.

Similarly, as the above plasma membrane protein to be quantified, human SLC13A4 can be exemplified. As a subject peptide for quantification and a stable-isotope labeled peptide used for measuring human SLC13A4, one or more peptides selected from a peptide having an amino acid sequence shown by SEQ ID No: 480, and SEQ ID No: 481 of the sequence listing can be specifically exemplified.

Similarly, as the above plasma membrane protein to be quantified, human SLC14A1 can be exemplified. As a subject peptide for quantification and a stable-isotope labeled peptide used for measuring human SLC14A1, one or more peptides selected from a peptide having an amino acid sequence shown by SEQ ID No: 482 of the sequence listing can be specifically exemplified.

Similarly, as the above plasma membrane protein to be quantified, human SLC14A2 can be exemplified. As a subject peptide for quantification and a stable-isotope labeled peptide used for measuring human SLC14A2, one or more peptides selected from a peptide having an amino acid sequence shown by SEQ ID No: 483 of the sequence listing can be specifically exemplified.

Similarly, as the above plasma membrane protein to be quantified, human SLC15A3 can be exemplified. As a subject peptide for quantification and a stable-isotope labeled peptide used for measuring human SLC15A3, one or more peptides selected from a peptide having an amino acid sequence shown by SEQ ID No: 484, SEQ ID No: 485, SEQ ID No: 486, SEQ ID No: 487, and SEQ ID No: 488 of the sequence listing can be specifically exemplified.

Similarly, as the above plasma membrane protein to be quantified, human SLC15A4 can be exemplified. As a subject peptide for quantification and a stable-isotope labeled peptide used for measuring human SLC15A4, one or more peptides selected from a peptide having an amino acid sequence shown by SEQ ID No: 489, and SEQ ID No: 490 of the sequence listing can be specifically exemplified.

Similarly, as the above plasma membrane protein to be quantified, human SLC16A10 can be exemplified. As a subject peptide for quantification and a stable-isotope labeled peptide used for measuring human SLC16A10, one or more peptides selected from a peptide having an amino acid sequence shown by SEQ ID No: 491 of the sequence listing can be specifically exemplified.

Similarly, as the above plasma membrane protein to be quantified, human SLC16A11 can be exemplified. As a subject peptide for quantification and a stable-isotope labeled peptide used for measuring human SLCA11, one or more peptides selected from a peptide having an amino acid sequence shown by SEQ ID No: 492, and SEQ ID No: 493 of the sequence listing can be specifically exemplified.

Similarly, as the above plasma membrane protein to be quantified, human SLC16A12 can be exemplified. As a subject peptide for quantification and a stable-isotope labeled peptide used for measuring human SLC16A12, one or more peptides selected from a peptide having an amino acid sequence shown by SEQ ID No: 494 of the sequence listing can be specifically exemplified.

Similarly, as the above plasma membrane protein to be quantified, human SLC16A13 can be exemplified. As a subject peptide for quantification and a stable-isotope labeled peptide used for measuring human SLC16A13, one or more peptides selected from a peptide having an amino acid sequence shown by SEQ ID No: 495 of the sequence listing can be specifically exemplified.

Similarly, as the above plasma membrane protein to be quantified, human SLC16A14 can be exemplified. As a subject peptide for quantification and a stable-isotope labeled peptide used for measuring human SLC16A14, one or more peptides selected from a peptide having an amino acid sequence shown by SEQ ID No: 496 of the sequence listing can be specifically exemplified.

Similarly, as the above plasma membrane protein to be quantified, human SLC16A3 can be exemplified. As a subject peptide for quantification and a stable-isotope labeled peptide used for measuring human SLC16A3, one or more peptides selected from a peptide having an amino acid sequence shown by SEQ ID No: 497, and SEQ ID No: 498 of the sequence listing can be specifically exemplified.

Similarly, as the above plasma membrane protein to be quantified, human SLC16A5 can be exemplified. As a subject peptide for quantification and a stable-isotope labeled peptide used for measuring human SLC16A5, one or more peptides selected from a peptide having an amino acid sequence shown by SEQ ID No: 499 of the sequence listing can be specifically exemplified.

Similarly, as the above plasma membrane protein to be quantified, human SLC16A6 can be exemplified. As a subject peptide for quantification and a stable-isotope labeled peptide used for measuring human SLC16A6, one or more peptides selected from a peptide having an amino acid sequence shown by SEQ ID No: 500 of the sequence listing can be specifically exemplified.

Similarly, as the above plasma membrane protein to be quantified, human SLC16A8 can be exemplified. As a subject peptide for quantification and a stable-isotope labeled peptide used for measuring human SLC16A8, one or more peptides selected from a peptide having an amino acid sequence shown by SEQ ID No: 501, SEQ ID No: 502, and SEQ ID No: 503 of the sequence listing can be specifically exemplified.

Similarly, as the above plasma membrane protein to be quantified, human SLC16A9 can be exemplified. As a subject peptide for quantification and a stable-isotope labeled peptide used for measuring human SLC16A9, one or more peptides selected from a peptide having an amino acid sequence shown by SEQ ID No: 504, SEQ ID No: 505, and SEQ ID No: 506 of the sequence listing can be specifically exemplified.

Similarly, as the above plasma membrane protein to be quantified, human SLC18A1 can be exemplified. As a subject peptide for quantification and a stable-isotope labeled peptide used for measuring human SLC18A1, one or more peptides selected from a peptide having an amino acid sequence shown by SEQ ID No: 507, and SEQ ID No: 508 of the sequence listing can be specifically exemplified.

Similarly, as the above plasma membrane protein to be quantified, human SLC18A2 can be exemplified. As a subject peptide for quantification and a stable-isotope labeled peptide used for measuring human SLC18A2, one or more peptides selected from a peptide having an amino acid sequence shown by SEQ ID. No: 509, and SEQ ID No: 510 of the sequence listing can be specifically exemplified.

Similarly, as the above plasma membrane protein to be quantified, human SLC18A3 can be exemplified. As a subject peptide for quantification and a stable-isotope labeled peptide used for measuring human SLC18A3, one or more peptides selected from a peptide having an amino acid sequence shown by SEQ ID No: 511, SEQ ID No: 512, SEQ ID No: 513, SEQ ID No: 514, and SEQ ID No: 515 of the sequence listing can be specifically exemplified.

Similarly, as the above plasma membrane protein to be quantified, human SLC19A2 can be exemplified. As a subject peptide for quantification and a stable-isotope labeled peptide used for measuring human SLC19A2, one or more peptides selected from a peptide having an amino acid sequence shown by SEQ ID No: 516, and SEQ ID No: 517 of the sequence listing can be specifically exemplified.

Similarly, as the above plasma membrane protein to be quantified, human SLC19A3 can be exemplified. As a subject peptide for quantification and a stable-isotope labeled peptide used for measuring human SLC19A3, one or more peptides selected from a peptide having an amino acid sequence shown by SEQ ID No: 518, and SEQ ID No: 519 of the sequence listing can be specifically exemplified.

Similarly, as the above plasma membrane protein to be quantified, human SLC20A1 can be exemplified. As a subject peptide for quantification and a stable-isotope labeled peptide used for measuring human SLC20A1, one or more peptides selected from a peptide having an amino acid sequence shown by SEQ ID No: 520, SEQ ID No: 521, SEQ ID No: 522, SEQ ID No: 523, SEQ ID No: 524, SEQ ID No: 525, SEQ ID No: 526, SEQ ID No: 527, SEQ ID No: 528, SEQ ID No: 529, SEQ ID No: 530, SEQ ID No: 531, and SEQ ID No: 532 of the sequence listing can be specifically exemplified.

Similarly, as the above plasma membrane protein to be quantified, human SLC20A2 can be exemplified. As a subject peptide for quantification and a stable-isotope labeled peptide used for measuring human SLC20A2, one or more peptides selected from a peptide having an amino acid sequence shown by SEQ ID No: 533, SEQ ID No: 534, SEQ ID No: 535, SEQ ID No: 536, SEQ ID No: 537, SEQ ID No: 538, SEQ ID No: 539, SEQ ID No: 540, SEQ ID No: 541, SEQ ID No: 542, SEQ ID No: 543, SEQ ID No: 544, SEQ ID No: 545, and SEQ ID No: 546 of the sequence listing can be specifically exemplified.

Similarly, as the above plasma membrane protein to be quantified, human SLC23A1 can be exemplified. As a subject peptide for quantification and a stable-isotope labeled peptide used for measuring human SLC23A1, one or more peptides selected from a peptide having an amino acid sequence shown by SEQ ID No: 547, SEQ ID No: 548, SEQ ID No: 549, and SEQ ID No: 550 of the sequence listing can be specifically exemplified.

Similarly, as the above plasma membrane protein to be quantified, human SLC23A2 can be exemplified. As a subject peptide for quantification and a stable-isotope labeled peptide used for measuring human SLC23A2, one or more peptides selected from a peptide having an amino acid sequence shown by SEQ ID No: 551, SEQ ID No: 552, SEQ ID No: 553, SEQ ID No: 554, and SEQ ID No: 555 of the sequence listing can be specifically exemplified.

Similarly, as the above plasma membrane protein to be quantified, human SLC23A3 can be exemplified. As a subject peptide for quantification and a stable-isotope labeled peptide used for measuring human SLC23A3, one or more peptides selected from a peptide having an amino acid sequence shown by SEQ ID No: 556, SEQ ID No: 557, SEQ ID No: 558, SEQ ID No: 559, and SEQ ID No: 560 of the sequence listing can be specifically exemplified.

Similarly, as the above plasma membrane protein to be quantified, human SLC24A1 can be exemplified. As a subject peptide for quantification and a stable-isotope labeled peptide used for measuring human SLC24A1, one or more peptides selected from a peptide having an amino acid sequence shown by SEQ ID No: 561, SEQ ID No: 562, SEQ ID No: 563, SEQ ID No: 564, SEQ ID No: 565, SEQ ID No: 566, SEQ ID No: 567, SEQ ID No: 568, SEQ ID No: 569, SEQ ID No: 570, SEQ ID No: 571, SEQ ID No: 572, SEQ ID No: 573, and SEQ ID No: 574 of the sequence listing can be specifically exemplified.

Similarly, as the above plasma membrane protein to be quantified, human SLC24A2 can be exemplified. As a subject peptide for quantification and a stable-isotope labeled peptide used for measuring human SLC24A2, one or more peptides selected from a peptide having an amino acid sequence shown by SEQ ID No: 575, SEQ ID No: 576, SEQ ID No: 577, SEQ ID No: 578, SEQ ID No: 579, and SEQ ID No: 580 of the sequence listing can be specifically exemplified.

Similarly, as the above plasma membrane protein to be quantified, human SLC24A3 can be exemplified. As a subject peptide for quantification and a stable-isotope labeled peptide used for measuring human SLC24A3, one or more peptides selected from a peptide having an amino acid sequence shown by SEQ ID No: 581, SEQ ID No: 582, SEQ ID No: 583, and SEQ ID No: 584 of the sequence listing can be specifically exemplified.

Similarly, as the above plasma membrane protein to be quantified, human SLC24A4 can be exemplified. As a subject peptide for quantification and a stable-isotope labeled peptide used for measuring human SLC24A4, one or more peptides selected from a peptide having an amino acid sequence shown by SEQ ID No: 585, and SEQ ID No: 586 of the sequence listing can be specifically exemplified.

Similarly, as the above plasma membrane protein to be quantified, human SLC24A5 can be exemplified. As a subject peptide for quantification and a stable-isotope labeled peptide used for measuring human SLC24A5, one or more peptides selected from a peptide having an amino acid sequence shown by SEQ ID No: 587 of the sequence listing can be specifically exemplified.

Similarly, as the above plasma membrane protein to be quantified, human SLC24A6 can be exemplified. As a subject peptide for quantification and a stable-isotope labeled peptide used for measuring human SLC24A6, one or more peptides selected from a peptide having an amino acid sequence shown by SEQ ID No: 588, SEQ ID No: 589, and SEQ ID No: 590 of the sequence listing can be specifically exemplified.

Similarly, as the above plasma membrane protein to be quantified, human SLC25A1 can be exemplified. As a subject peptide for quantification and a stable-isotope labeled peptide used for measuring human SLC25A1, one or more peptides selected from a peptide having an amino acid sequence shown by SEQ ID No: 591, SEQ ID No: 592, SEQ ID No: 593, SEQ ID No: 594, SEQ ID No: 595, SEQ ID No: 596, and SEQ ID No: 597 of the sequence listing can be specifically exemplified.

Similarly, as the above plasma membrane protein to be quantified, human SLC25A10 can be exemplified. As a subject peptide for quantification and a stable-isotope labeled peptide used for measuring human SLC25A10, one or more peptides selected from a peptide having an amino acid sequence shown by SEQ ID No: 598, SEQ ID No: 599, SEQ ID No: 600, and SEQ ID No: 601 of the sequence listing can be specifically exemplified.

Similarly, as the above plasma membrane protein to be quantified, human SLC25A11 can be exemplified. As a subject peptide for quantification and a stable-isotope labeled peptide used for measuring human SLC25A11, one or more peptides selected from a peptide having an amino acid sequence shown by SEQ ID No: 602, SEQ ID No: 603, SEQ ID No: 604, SEQ ID No: 605, SEQ ID No: 606, and SEQ ID No: 607 of the sequence listing can be specifically exemplified.

Similarly, as the above plasma membrane protein to be quantified, human SLC25A12 can be exemplified. As a subject peptide for quantification and a stable-isotope labeled peptide used for measuring human SLC25A12, one or more peptides selected from a peptide having an amino acid sequence shown by SEQ ID No: 608, SEQ ID No: 607, SEQ ID No: 608, SEQ ID No: 609, SEQ ID No: 610, SEQ ID No: 611, SEQ ID No: 612, SEQ ID No: 613, SEQ ID No: 614, SEQ ID No: 615, SEQ ID No: 616, SEQ ID No: 617, SEQ ID No: 618, SEQ ID No: 619, SEQ. ID No: 620, SEQ ID No: 621, SEQ ID No: 622, SEQ ID No: 623, SEQ ID No: 624, SEQ ID No: 625, SEQ ID No: 626, and SEQ ID No: 627 of the sequence listing can be specifically exemplified.

Similarly, as the above plasma membrane protein to be quantified, human SLC25A13 can be exemplified. As a subject peptide for quantification and a stable-isotope labeled peptide used for measuring human SLC25A13, one or more peptides selected from a peptide having an amino acid sequence shown by SEQ ID No: 628, SEQ ID No: 629, SEQ ID No: 630, SEQ ID No: 631, SEQ ID No: 632, SEQ ID No: 633, SEQ ID No: 634, SEQ ID No: 635, SEQ ID No: 636, SEQ ID No: 637, SEQ ID No: 638, SEQ ID No: 639, SEQ ID No: 640, SEQ ID No: 641, SEQ ID No: 642, SEQ ID No: 643, SEQ ID No: 644, and SEQ ID No: 645 of the sequence listing can be specifically exemplified.

Similarly, as the above plasma membrane protein to be quantified, human SLC25A14 can be exemplified. As a subject peptide for quantification and a stable-isotope labeled peptide used for measuring human SLC25A14, one or more peptides selected from a peptide having an amino acid sequence shown by SEQ ID No: 646, SEQ ID No: 647, SEQ ID No: 648, SEQ ID No: 649 and SEQ ID No: 650 of the sequence listing can be specifically exemplified.

Similarly, as the above plasma membrane protein to be quantified, human SLC25A15 can be exemplified. As a subject peptide for quantification and a stable-isotope labeled peptide used for measuring human SLC25A15, one or more peptides selected from a peptide having an amino acid sequence shown by SEQ ID No: 651, SEQ ID No: 652, and SEQ ID No: 653 of the sequence listing can be specifically exemplified.

Similarly, as the above plasma membrane protein to be quantified, human SLC25A16 can be exemplified. As a subject peptide for quantification and a stable-isotope labeled peptide used for measuring human SLC25A16, one or more peptides selected from a peptide having an amino acid sequence shown by SEQ ID No: 654, SEQ ID No: 655, SEQ ID No: 656, SEQ ID No: 657, SEQ ID No: 658, SEQ ID No: 659, SEQ ID No: 660, SEQ ID No: 661, SEQ ID No: 662, SEQ ID No: 663, SEQ ID No: 664, SEQ ID No: 665, and SEQ ID No: 666 of the sequence listing can be specifically exemplified.

Similarly, as the above plasma membrane protein to be quantified, human SLC25A17 can be exemplified. As a subject peptide for quantification and a stable-isotope labeled peptide used for measuring human SLC25A17, one or more peptides selected from a peptide having an amino acid sequence shown by SEQ ID No: 667, SEQ ID No: 668, SEQ ID No: 669, SEQ ID No: 670, SEQ ID No: 671, SEQ ID No: 672, SEQ ID No: 673, SEQ ID No: 674, and SEQ ID No: 675 of the sequence listing can be specifically exemplified.

Similarly, as the above plasma membrane protein to be quantified, human SLC25A18 can be exemplified. As a subject peptide for quantification and a stable-isotope labeled peptide used for measuring human SLC25A18, one or more peptides selected from a peptide having an amino acid sequence shown by SEQ ID No: 676, SEQ ID No: 677, SEQ ID No: 678, SEQ ID No: 679, and SEQ ID No: 680 of the sequence listing can be specifically exemplified.

Similarly, as the above plasma membrane protein to be quantified, human SLC25A19 can be exemplified. As a subject peptide for quantification and a stable-isotope labeled peptide used for measuring human SLC25A19, one or more peptides selected from a peptide having an amino acid sequence shown by SEQ ID No: 681, SEQ ID No: 682, SEQ ID No: 683, SEQ ID No: 684, SEQ ID No: 685, SEQ ID No: 686, and SEQ ID No: 687 of the sequence listing can be specifically exemplified.

Similarly, as the above plasma membrane protein to be quantified, human SLC25A2 can be exemplified. As a subject peptide for quantification and a stable-isotope labeled peptide used for measuring human SLC25A2, one or more peptides selected from a peptide having an amino acid sequence shown by SEQ ID No: 688, SEQ ID No: 689, SEQ ID No: 690, SEQ ID No: 691, and SEQ ID No: 692 of the sequence listing can be specifically exemplified.

Similarly, as the above plasma membrane protein to be quantified, human SLC25A21 can be exemplified. As a subject peptide for quantification and a stable-isotope labeled peptide used for measuring human SLC25A21, one or more peptides selected from a peptide having an amino acid sequence shown by SEQ ID No: 697, SEQ ID No: 698, SEQ ID No: 699, SEQ ID No: SEQ ID No: 700, SEQ ID No: 701, SEQ ID No: 702, and SEQ ID No: 703 of the sequence listing can be specifically exemplified.

Similarly, as the above plasma membrane protein to be quantified, human SLC25A21 can be exemplified. As a subject peptide for quantification and a stable-isotope labeled peptide used for measuring human SLC25A21, one or more peptides selected from a peptide having an amino acid sequence shown by SEQ ID No: 697, SE ID No: 698, SEQ ID No: SEQ ID No: 700, SEQ ID No: 701, SEQ ID No: 702, and SEQ ID No: 703 of the sequence listing can be specifically exemplified.

Similarly, as the above plasma membrane protein to be quantified, human SLC25A22 can be exemplified. As a subject peptide for quantification and a stable-isotope labeled peptide used for measuring human SLC25A22, one or more peptides selected from a peptide having an amino acid sequence shown by SEQ ID No: 704, SEQ ID No: 705, SEQ ID No: 706, SEQ ID No: 707, SEQ ID No: 708, SEQ ID No: 709, SEQ ID No: 710, SEQ ID No: 711, SEQ ID No: 712, and SEQ ID No: 713 of the sequence listing can be specifically exemplified.

Similarly, as the above plasma membrane protein to be quantified, human SLC25A23 can be exemplified. As a subject peptide for quantification and a stable-isotope labeled peptide used for measuring human SLC25A23, one or more peptides selected from a peptide having an amino acid sequence shown by SEQ ID No: 714, SEQ ID No: 715, SEQ ID No: 716, SEQ ID No: 717, SEQ ID No: 718, SEQ ID No: 719, SEQ ID No: 720, SEQ ID No: 721, SEQ ID No: 722, SEQ ID No: 723, SEQ ID No: 724, SEQ ID No: 725, and SEQ ID No: 726 of the sequence listing can be specifically exemplified.

Similarly, as the above plasma membrane protein to be quantified, human SLC25A24 can be exemplified. As a subject peptide for quantification and a stable-isotope labeled peptide used for measuring human SLC25A24, one or more peptides selected from a peptide having an amino acid sequence shown by SEQ ID No: 727, SEQ ID No: 728, SEQ ID No: 729, SEQ ID No: 730, SEQ ID No: 731, SEQ ID No: 732, SEQ ID No: 733, SEQ ID No: 734, SEQ ID No: 735, SEQ ID No: 736, SEQ ID No: 737, SEQ ID No: 738, SEQ ID No: 739, and SEQ ID No: 740 of the sequence listing can be specifically exemplified.

Similarly, as the above plasma membrane protein to be quantified, human SLC25A25 can be exemplified. As a subject peptide for quantification and a stable-isotope labeled peptide used for measuring human SLC25A25, one or more peptides selected from a peptide having an amino acid sequence shown by SEQ ID No: 741, SEQ ID No: 742, SEQ ID No: 743, SEQ ID No: 744, SEQ ID No: 745, SEQ ID No: 746, SEQ ID No: 747, SEQ ID No: 748, SEQ ID No: 749, SEQ ID No: 750, SEQ ID No: 751, and SEQ ID No: 752 of the sequence listing can be specifically exemplified.

Similarly, as the above plasma membrane protein to be quantified, human SLC25A26 can be exemplified. As a subject peptide for quantification and a stable-isotope labeled peptide used for measuring human SLC25A26, one or more peptides selected from a peptide having an amino acid sequence shown by SEQ ID No: 753, SEQ ID No: 754, SEQ ID No: 755, and SEQ ID No: 756 of the sequence listing can be specifically exemplified.

Similarly, as the above plasma membrane protein to be quantified, human SLC25A27 can be exemplified. As a subject peptide for quantification and a stable-isotope labeled peptide used for measuring human SLC25A27, one or more peptides selected from a peptide having an amino acid sequence shown by SEQ ID No: 757, SEQ ID No: 758, SEQ ID No: 759, SEQ ID No: 760, SEQ ID No: 761, SEQ ID No: 762, SEQ ID No: 763, and SEQ ID No: 764 of the sequence listing can be specifically exemplified.

Similarly, as the above plasma membrane protein to be quantified, human SLC25A28 can be exemplified. As a subject peptide for quantification and a stable-isotope labeled peptide used for measuring human SLC25A28, one or more peptides selected from a peptide having an amino acid sequence shown by SEQ ID No: 765, and SEQ ID No: 766 of the sequence listing can be specifically exemplified.

Similarly, as the above plasma membrane protein to be quantified, human SLC25A29 can be exemplified. As a subject peptide for quantification and a stable-isotope labeled peptide used for measuring human SLC25A29, one or more peptides selected from a peptide having an amino acid sequence shown by SEQ ID No: 767, SEQ ID No: 768, SEQ ID No: 769, SEQ ID No: 770, SEQ ID No: 771, and SEQ ID No: 772 of the sequence listing can be specifically exemplified.

Similarly, as the above plasma membrane protein to be quantified, human SLC25A3 can be exemplified. As a subject peptide for quantification and a stable-isotope labeled peptide used for measuring human SLC25A3, one or more peptides selected from a peptide having an amino acid sequence shown by SEQ ID No: 773, SEQ ID No: 774, SEQ ID No: 775, SEQ ID No: 776, and SEQ ID No: 777 of the sequence listing can be specifically exemplified.

Similarly, as the above plasma membrane protein to be quantified, human SLC25A30 can be exemplified. As a subject peptide for quantification and a stable-isotope labeled peptide used for measuring human SLC25A30, one or more peptides selected from a peptide having an amino acid sequence shown by SEQ ID No: 778, SEQ ID No: 779, SEQ ID No: 780, SEQ ID No: 781, SEQ ID No: 782, and SEQ ID No: 783 of the sequence listing can be specifically exemplified.

Similarly, as the above plasma membrane protein to be quantified, human SLC25A31 can be exemplified. As a subject peptide for quantification and a stable-isotope labeled peptide used for measuring human SLC25A31, one or more peptides selected from a peptide having an amino acid sequence shown by SEQ ID No: 784, SEQ ID No: 785, SEQ ID No: 786, SEQ ID No: 787, SEQ ID No: 798, SEQ ID No: 789, SEQ ID No: 790, SEQ ID No: 791, SEQ ID No: 792, SEQ ID No: 793, SEQ ID No: 794, SEQ ID No: 795, SEQ ID No: 796, and SEQ ID No: 797 of the sequence listing can be specifically exemplified.

Similarly, as the above plasma membrane protein to be quantified, human SLC25A32 can be exemplified. As a subject peptide for quantification and a stable-isotope labeled peptide used for measuring human SLC25A32, one or more peptides selected from a peptide having an amino acid sequence shown by SEQ ID No: 798, SEQ ID No: 799, SEQ ID No: 800, and SEQ ID No: 801 of the sequence listing can be specifically exemplified.

Similarly, as the above plasma membrane protein to be quantified, human SLC25A34 can be exemplified. As a subject peptide for quantification and a stable-isotope labeled peptide used for measuring human SLC25A34, one or more peptides selected from a peptide having an amino acid sequence shown by SEQ ID No: 802, SEQ ID No: 803, SEQ ID No: 804, SEQ ID No: 805, SEQ ID No: 806, SEQ ID No: 807, and SEQ ID No: 808 of the sequence listing can be specifically exemplified.

Similarly, as the above plasma membrane protein to be quantified, human SLC25A35 can be exemplified. As a subject peptide for quantification and a stable-isotope labeled peptide used for measuring human SLC25A35, one or more peptides selected from a peptide having an amino acid sequence shown by SEQ ID No: 809, SEQ ID No: 810, SEQ ID No: 811, SEQ ID No: 812, SEQ ID No: 813, SEQ ID No: 814, SEQ ID No: 815, and SEQ ID No: 816 of the sequence listing can be specifically exemplified.

Similarly, as the above plasma membrane protein to be quantified, human SLC25A36 can be exemplified. As a subject peptide for quantification and a stable-isotope labeled peptide used for measuring human SLC25A36, one or more peptides selected from a peptide having an amino acid sequence shown by SEQ ID No: 817, SEQ ID No: 818, SEQ ID No: 819, SEQ ID No: 820, SEQ ID No: 821, and SEQ ID No: 822 of the sequence listing can be specifically exemplified.

Similarly, as the above plasma membrane protein to be quantified, human SLC25A37 can be exemplified. As a subject peptide for quantification and a stable-isotope labeled peptide used for measuring human SLC35A37, one or more peptides selected from a peptide having an amino acid sequence shown by SEQ ID No: 823, SEQ ID No: 824, SEQ ID No: 825, and SEQ ID No: 826 of the sequence listing can be specifically exemplified.

Similarly, as the above plasma membrane protein to be quantified, human SLC25A4 can be exemplified. As a subject peptide for quantification and a stable-isotope labeled peptide used for measuring human SLC25A4, one or more peptides selected from a peptide having an amino acid sequence shown by SEQ ID No: 827, SEQ ID No: 828, and SEQ ID No: 829 of the sequence listing can be specifically exemplified.

Similarly, as the above plasma membrane protein to be quantified, human SLC25A5 can be exemplified. As a subject peptide for quantification and a stable-isotope labeled peptide used for measuring human SLC25A5, one or more peptides selected from a peptide having an amino acid sequence shown by SEQ ID No: 830, and SEQ ID No: 831 of the sequence listing can be specifically exemplified.

Similarly, as the above plasma membrane protein to be quantified, human SLC25A6 can be exemplified. As a subject peptide for quantification and a stable-isotope labeled peptide used for measuring human SLC25A6, one or more peptides selected from a peptide having an amino acid sequence shown by SEQ ID No: 832, SEQ ID No: 833, and SEQ ID No: 834 of the sequence listing can be specifically exemplified.

Similarly, as the above plasma membrane protein to be quantified, human SLC25A7 can be exemplified. As a subject peptide for quantification and a stable-isotope labeled peptide used for measuring human SLC25A7, one or more peptides selected from a peptide having an amino acid sequence shown by SEQ ID No: 835, SEQ ID No: 836, SEQ ID No: 837, SEQ ID No: 838, and SEQ ID No: 839 of the sequence listing can be specifically exemplified.

Similarly, as the above plasma membrane protein to be quantified, human SLC25A8 can be exemplified. As a subject peptide for quantification and a stable-isotope labeled peptide used for measuring human SLC25A8, one or more peptides selected from a peptide having an amino acid sequence shown by SEQ ID No: 840, SEQ ID No: 841, SEQ ID No: 842, SEQ ID No: 843, SEQ ID No: 844, and SEQ ID No: 845 of the sequence listing can be specifically exemplified.

Similarly, as the above plasma membrane protein to be quantified, human SLC25A9 can be exemplified. As a subject peptide for quantification and a stable-isotope labeled peptide used for measuring human SLC25A9, one or more peptides selected from a peptide having an amino acid sequence shown by SEQ ID No: 846, SEQ ID No: 847, and SEQ ID No: 848 of the sequence listing can be specifically exemplified.

Similarly, as the above plasma membrane protein to be quantified, human SLC26A1 can be exemplified. As a subject peptide for quantification and a stable-isotope labeled peptide used for measuring human SLC26A1, one or more peptides selected from a peptide having an amino acid sequence shown by SEQ ID No: 849, SEQ ID No: 850, SEQ ID No: 851, SEQ ID No: 852, SEQ ID No: 853, SEQ ID No: 854, SEQ ID No: 855, SEQ ID No: 856, SEQ ID No: 857, and SEQ ID No: 858 of the sequence listing can be specifically exemplified.

Similarly, as the above plasma membrane protein to be quantified, human SLC26A10 can be exemplified. As a subject peptide for quantification and a stable-isotope labeled peptide used for measuring human SLC26A10, one or more peptides selected from a peptide having an amino acid sequence shown by SEQ ID No: 859, SEQ ID No: 860, SEQ ID No: 861, SEQ ID No: 862, SEQ ID No: 863, SEQ ID No: 864, SEQ ID No: 865, SEQ ID No: 866, SEQ ID No: 867, SEQ ID No: 868, SEQ ID No: 869, SEQ ID No: 870, and SEQ ID No: 871 of the sequence listing can be specifically exemplified.

Similarly, as the above plasma membrane protein to be quantified, human SLC26A11 can be exemplified. As a subject peptide for quantification and a stable-isotope labeled peptide used for measuring human SLC26A11, one or more peptides selected from a peptide having an amino acid sequence shown by SEQ ID No: 872, SEQ ID No: 873, SEQ ID No: 874, SEQ ID No: 875, SEQ ID No: 876, SEQ ID No: 877, SEQ ID No: 878, SEQ ID No: 879, SEQ ID No: 880, and SEQ ID No: 881 of the sequence listing can be specifically exemplified.

Similarly, as the above plasma membrane protein to be quantified, human SLC26A2 can be exemplified. As a subject peptide for quantification and a stable-isotope labeled peptide used for measuring human SLC26A2, one or more peptides selected from a peptide having an amino acid sequence shown by SEQ ID No: 882, SEQ ID No: 883, SEQ ID No: 884, SEQ ID No: 885, SEQ ID No: 886, SEQ ID No: 887, SEQ ID No: 888, SEQ ID No: 889, SEQ ID No: 890, SEQ ID No: 891, and SEQ ID No: 892 of the sequence listing can be specifically exemplified.

Similarly, as the above plasma membrane protein to be quantified, human SLC26A3 can be exemplified. As a subject peptide for quantification and a stable-isotope labeled peptide used for measuring human SLC26A3, one or more peptides selected from a peptide having an amino acid sequence shown by SEQ ID No: 893, SEQ ID No: 894, SEQ ID No: 895, SEQ ID No: 896, SEQ ID No: 897, SEQ ID No: 898, SEQ ID No: 899, SEQ ID No: 900, SEQ ID No: 901, SEQ ID No: 902, SEQ ID No: 903, SEQ ID No: 904, SEQ ID No: 905, and SEQ ID No: 906 of the sequence listing can be specifically exemplified.

Similarly, as the above plasma membrane protein to be quantified, human SLC26A4 can be exemplified. As a subject peptide for quantification and a stable-isotope labeled peptide used for measuring human SLC26A4, one or more peptides selected from a peptide having an amino acid sequence shown by SEQ ID No: 907, SEQ ID No: 908, SEQ ID No: 909, SEQ ID No: 910, SEQ ID No: 911, SEQ ID No: 912, SEQ ID No: 913, and SEQ ID No: 914 of the sequence listing can be specifically exemplified.

Similarly, as the above plasma membrane protein to be quantified, human SLC26A5 can be exemplified. As a subject peptide for quantification and a stable-isotope labeled peptide used for measuring human SLC26A5, one or more peptides selected from a peptide having an amino acid sequence shown by SEQ ID No: 915, SEQ ID No: 916, and SEQ ID No: 917 of the sequence listing can be specifically exemplified.

Similarly, as the above plasma membrane protein to be quantified, human SLC26A6 can be exemplified. As a subject peptide for quantification and a stable-isotope labeled peptide used for measuring human SLC26A6, one or more peptides selected from a peptide having an amino acid sequence shown by SEQ ID No: 918, SEQ ID No: 919, SEQ ID No: 920, SEQ ID No: 921, SEQ ID No: 922, SEQ ID No: 923, SEQ ID No: 924, SEQ ID No: 925, SEQ ID No: 926, and SEQ ID No: 927 of the sequence listing can be specifically exemplified.

Similarly, as the above plasma membrane protein to be quantified, human SLC26A7 can be exemplified. As a subject peptide for quantification and a stable-isotope labeled peptide used for measuring human SLC26A7, one or more peptides selected from a peptide having an amino acid sequence shown by SEQ ID No: 928, and SEQ ID No: 929 of the sequence listing can be specifically exemplified.

Similarly, as the above plasma membrane protein to be quantified, human SLC26A8 can be exemplified. As a subject peptide for quantification and a stable-isotope labeled peptide used for measuring human SLC26A8, one or more peptides selected from a peptide having an amino acid sequence shown by SEQ ID No: 930, SEQ ID No: 931, and SEQ ID No: 932 of the sequence listing can be specifically exemplified.

Similarly, as the above plasma membrane protein to be quantified, human SLC26A9 can be exemplified. As a subject peptide for quantification and a stable-isotope labeled peptide used for measuring human SLC26A9, one or more peptides selected from a peptide having an amino acid sequence shown by SEQ ID No: 933, SEQ ID No: 934, SEQ ID No: 935, SEQ ID No: 936, SEQ ID No: 937, SEQ ID No: 938, SEQ ID No: 939, SEQ ID No: 940, SEQ ID No: 941, SEQ ID No: 942, SEQ ID No: 943, SEQ ID No: 944, and SEQ ID No: 945 of the sequence listing can be specifically exemplified.

Similarly, as the above plasma membrane protein to be quantified, human SLC27A1 can be exemplified. As a subject peptide for quantification and a stable-isotope labeled peptide used for measuring human SLC27A1 one or more peptides selected from a peptide having an amino acid sequence shown by SEQ ID No: 946, SEQ ID No: 947, and SEQ ID No: 948 of the sequence listing can be specifically exemplified.

Similarly, as the above plasma membrane protein to be quantified, human SLC27A2 can be exemplified. As a subject peptide for quantification and a stable-isotope labeled peptide used for measuring human SLC27A2, one or more peptides selected from a peptide having an amino acid sequence shown by SEQ ID No: 949, SEQ ID No: 950, SEQ ID No: 951, SEQ ID No: 952, and SEQ ID No: 953 of the sequence listing can be specifically exemplified.

Similarly, as the above plasma membrane protein to be quantified, human SLC27A3 can be exemplified. As a subject peptide for quantification and a stable-isotope labeled peptide used for measuring human SLC27A3, one or more peptides selected from a peptide having an amino acid sequence shown by SEQ ID No: 954, SEQ ID No: 955, SEQ ID No: 956, and SEQ ID No: 957 of the sequence listing can be specifically exemplified.

Similarly, as the above plasma membrane protein to be quantified, human SLC27A4 can be exemplified. As a subject peptide for quantification and a stable-isotope labeled peptide used for measuring human SLC27A4, one or more peptides selected from a peptide having an amino acid sequence shown by SEQ ID No: 958, SEQ ID No: 959, SEQ ID No: 960, SEQ ID No: 961, and SEQ ID No: 962 of the sequence listing can be specifically exemplified.

Similarly, as the above plasma membrane protein to be quantified, human SLC27A5 can be exemplified. As a subject peptide for quantification and a stable-isotope labeled peptide used for measuring human SLC27A5, one or more peptides selected from a peptide having an amino acid sequence shown by SEQ ID No: 963, SEQ ID No: 964, and SEQ ID No: 965 of the sequence listing can be specifically exemplified.

Similarly, as the above plasma membrane protein to be quantified, human SLC27A6 can be exemplified. As a subject peptide for quantification and a stable-isotope labeled peptide used for measuring human SLC27A6, one or more peptides selected from a peptide having an amino acid sequence shown by SEQ ID No: 966, SEQ ID No: 967, SEQ ID No: 968, and SEQ ID No: 969 of the sequence listing can be specifically exemplified.

Similarly, as the above plasma membrane protein to be quantified, human SLC28A2 can be exemplified. As a subject peptide for quantification and a stable-isotope labeled peptide used for measuring human SLC28A2, one or more peptides selected from a peptide having an amino acid sequence shown by SEQ ID No: 970, SEQ ID No: 971, and SEQ ID No: 972 of the sequence listing can be specifically exemplified.

Similarly, as the above plasma membrane protein to be quantified, human SLC29A3 can be exemplified. As a subject peptide for quantification and a stable-isotope labeled peptide used for measuring human SLC29A3, one or more peptides selected from a peptide having an amino acid sequence shown by SEQ ID No: 973, SEQ ID No: 974, SEQ ID No: 975, and SEQ ID No: 976 of the sequence listing can be specifically exemplified.

Similarly, as the above plasma membrane protein to be quantified, human SLC2A11 can be exemplified. As a subject peptide for quantification and a stable-isotope labeled peptide used for measuring human SLC2A11, one or more peptides selected from a peptide having an amino acid sequence shown by SEQ ID No: 977, SEQ ID No: 978, SEQ ID No: 979, and SEQ ID No: 980 of the sequence listing can be specifically exemplified.

Similarly, as the above plasma membrane protein to be quantified, human SLC2A12 can be exemplified. As a subject peptide for quantification and a stable-isotope labeled peptide used for measuring human SLC2A12, one or more peptides selected from a peptide having an amino acid sequence shown by SEQ ID No: 981, and SEQ ID No: 982 of the sequence listing can be specifically exemplified.

Similarly, as the above plasma membrane protein to be quantified, human SLC2A13 can be exemplified. As a subject peptide for quantification and a stable-isotope labeled peptide used for measuring human SLC2A13, one or more peptides selected from a peptide having an amino acid sequence shown by SEQ ID No: 983, SEQ ID No: 984, SEQ ID No: 985, SEQ ID No: 986, SEQ ID No: 987, and SEQ ID No: 988 of the sequence listing can be specifically exemplified.

Similarly, as the above plasma membrane protein to be quantified, human SLC2A14 can be exemplified. As a subject peptide for quantification and a stable-isotope labeled peptide used for measuring human SLC2A14, one or more peptides selected from a peptide having an amino acid sequence shown by SEQ ID No: 989, SEQ ID No: 990, and SEQ ID No: 991 of the sequence listing can be specifically exemplified.

Similarly, as the above plasma membrane protein to be quantified, human SLC2A3 can be exemplified. As a subject peptide for quantification and a stable-isotope labeled peptide used for measuring human SLC2A3, one or more peptides selected from a peptide having an amino acid sequence shown by SEQ ID No: 992, SEQ ID No: 993, SEQ ID No: 994 and SEQ ID No: 995 of the sequence listing can be specifically exemplified.

Similarly, as the above plasma membrane protein to be quantified, human SLC2A4 can be exemplified. As a subject peptide for quantification and a stable-isotope labeled peptide used for measuring human SLC2A4, one or more peptides selected from a peptide having an amino acid sequence shown by SEQ ID No: 996, and SEQ ID No: 997 of the sequence listing can be specifically exemplified.

Similarly, as the above plasma membrane protein to be quantified, human SLC2A5 can be exemplified. As a subject peptide for quantification and a stable-isotope labeled peptide used for measuring human SLC2A5, one or more peptides selected from a peptide having an amino acid sequence shown by SEQ ID No: 998, and SEQ ID No: 999 of the sequence listing can be specifically exemplified.

Similarly, as the above plasma membrane protein to be quantified, human SLC2A6 can be exemplified. As a subject peptide for quantification and a stable-isotope labeled peptide used for measuring human SLC2A6, one or more peptides selected from a peptide having an amino acid sequence shown by SEQ ID No: 1000, and SEQ ID No: 1001 of the sequence listing can be specifically exemplified.

Similarly, as the above plasma membrane protein to be quantified, human SLC2A7 can be exemplified. As a subject peptide for quantification and a stable-isotope labeled peptide used for measuring human SLC2A7, one or more peptides selected from a peptide having an amino acid sequence shown by SEQ ID NO: 1002 of the sequence listing can be specifically exemplified.

Similarly, as the above plasma membrane protein to be quantified, human SLC30A1 can be exemplified. As a subject peptide for quantification and a stable-isotope labeled peptide used for measuring human SLC30A1, one or more peptides selected from a peptide having an amino acid sequence shown by SEQ ID No: 1003, SEQ ID No: 1004, and SEQ ID No: 1005 of the sequence listing can be specifically exemplified.

Similarly, as the above plasma membrane protein to be quantified, human SLC30A10 can be exemplified. As a subject peptide for quantification and a stable-isotope labeled peptide used for measuring human SLC30A10, one or more peptides selected from a peptide having an amino acid sequence shown by SEQ ID No: 1006, and SEQ ID No: 1007 of the sequence listing can be specifically exemplified.

Similarly, as the above plasma membrane protein to be quantified, human SLC30A11 can be exemplified. As a subject peptide for quantification and a stable-isotope labeled peptide used for measuring human SLC30A11, one or more peptides selected from a peptide having an amino acid sequence shown by SEQ ID No: 1008, SEQ ID No: 1009, and SEQ ID No: 1010 of the sequence listing can be specifically exemplified.

Similarly, as the above plasma membrane protein to be quantified, human SLC30A2 can be exemplified. As a subject peptide for quantification and a stable-isotope labeled peptide used for measuring human SLC30A2, one or more peptides selected from a peptide having an amino acid sequence shown by SEQ ID No: 1011, and SEQ ID No: 1012 of the sequence listing can be specifically exemplified.

Similarly, as the above plasma membrane protein to be quantified, human SLC30A3 can be exemplified. As a subject peptide for quantification and a stable-isotope labeled peptide used for measuring human SLC30A3, one or more peptides selected from a peptide having an amino acid sequence shown by SEQ ID No: 1013, SEQ ID No: 1014, SEQ ID No: 1015, and SEQ ID No: 1016 of the sequence listing can be specifically exemplified.

Similarly, as the above plasma membrane protein to be quantified, human SLC30A4 can be exemplified. As a subject peptide for quantification and a stable-isotope labeled peptide used for measuring human SLC30A4, one or more peptides selected from a peptide having an amino acid sequence shown by SEQ ID No: 1017, SEQ ID No: 1018, SEQ ID No: 1019, SEQ ID No: 1020, and SEQ ID No: 1021 of the sequence listing can be specifically exemplified.

Similarly, as the above plasma membrane protein to be quantified, human SLC30A5 can be exemplified. As a subject peptide for quantification and a stable-isotope labeled peptide used for measuring human SLC30A5, one or more peptides selected from a peptide having an amino acid sequence shown by SEQ ID No: 1022, and SEQ ID No: 1023 of the sequence listing can be specifically exemplified.

Similarly, as the above plasma membrane protein to be quantified, human SLC30A6 can be exemplified. As a subject peptide for quantification and a stable-isotope labeled peptide used for measuring human SLC30A6, one or more peptides selected from a peptide having an amino acid sequence shown by SEQ ID No: 1024, SEQ ID No: 1025, and SEQ ID No: 1026 of the sequence listing can be specifically exemplified.

Similarly, as the above plasma membrane protein to be quantified, human SLC30A7 can be exemplified. As a subject peptide for quantification and a stable-isotope labeled peptide used for measuring human SLC30A7, one or more peptides selected from a peptide having an amino acid sequence shown by SEQ ID No: 1027, SEQ ID No: 1028, and SEQ ID No: 1029 of the sequence listing can be specifically exemplified.

Similarly, as the above plasma membrane protein to be quantified, human SLC30A8 can be exemplified. As a subject peptide for quantification and a stable-isotope labeled peptide used for measuring human SLC30A8, one or more peptides selected from a peptide having an amino acid sequence shown by SEQ ID No: 1030, SEQ ID No: 1031, SEQ ID No: 1032, SEQ ID No: 1033, and SEQ ID No: 1034 of the sequence listing can be specifically exemplified.

Similarly, as the above plasma membrane protein to be quantified, human SLC30A9 can be exemplified. As a subject peptide for quantification and a stable-isotope labeled peptide used for measuring human SLC30A9, one or more peptides selected from a peptide having an amino acid sequence shown by SEQ ID No: 1035, SEQ ID No: 1036, SEQ ID No: 1037, SEQ ID No: 1038, SEQ ID No: 1039, and SEQ ID No: 1040 of the sequence listing can be specifically exemplified.

Similarly, as the above plasma membrane protein to be quantified, human SLC31A1 can be exemplified. As a subject peptide for quantification and a stable-isotope labeled peptide used for measuring human SLC31A1, one or more peptides selected from a peptide having an amino acid sequence shown by SEQ ID No: 1041, and SEQ ID No: 1042 of the sequence listing can be specifically exemplified.

Similarly, as the above plasma membrane protein to be quantified, human SLC31A2 can be exemplified. As a subject peptide for quantification and a stable-isotope labeled peptide used for measuring human SLC31A2, one or more peptides selected from a peptide having an amino acid sequence shown by SEQ ID No: 1043 of the sequence listing can be specifically exemplified.

Similarly, as the above plasma membrane protein to be quantified, human SLC32A1 can be exemplified. As a subject peptide for quantification and a stable-isotope labeled peptide used for measuring human SLC32A1, one or more peptides selected from a peptide having an amino acid sequence shown by SEQ ID No: 1044, SEQ ID No: 1045, and SEQ ID No: 1046 of the sequence listing can be specifically exemplified.

Similarly, as the above plasma membrane protein to be quantified, human SLC33A1 can be exemplified. As a subject peptide for quantification and a stable-isotope labeled peptide used for measuring human SLC33A1, one or more peptides selected from a peptide having an amino acid sequence shown by SEQ ID No: 1047, and SEQ ID No: 1048 of the sequence listing can be specifically exemplified.

Similarly, as the above plasma membrane protein to be quantified, human SLC34A1 can be exemplified. As a subject peptide for quantification and a stable-isotope labeled peptide used for measuring human SLC34A1, one or more peptides selected from a peptide having an amino acid sequence shown by SEQ ID No: 1049, SEQ ID No: 1050, SEQ ID No: 1051, SEQ ID No: 1052, and SEQ ID No: 1053 of the sequence listing can be specifically exemplified.

Similarly, as the above plasma membrane protein to be quantified, human SLC34A2 can be exemplified. As a subject peptide for quantification and a stable-isotope labeled peptide used for measuring human SLC34A2, one or more peptides selected from a peptide having an amino acid sequence shown by SEQ ID No: 1054, SEQ ID No: 1055, and SEQ ID No: 1056 of the sequence listing can be specifically exemplified.

Similarly, as the above plasma membrane protein to be quantified, human SLC34A3 can be exemplified. As a subject peptide for quantification and a stable-isotope labeled peptide used for measuring human SLC34A3, one or more peptides selected from a peptide having an amino acid sequence shown by SEQ ID No: 1057, SEQ ID No: 1058, SEQ ID No: 1059, SEQ ID No: 1060, and SEQ ID No: 1061 of the sequence listing can be specifically exemplified.

Similarly, as the above plasma membrane protein to be quantified, human SLC35A1 can be exemplified. As a subject peptide for quantification and a stable-isotope labeled peptide used for measuring human SLC35A1, one or more peptides selected from a peptide having an amino acid sequence shown by SEQ ID No: 1062 of the sequence listing can be specifically exemplified.

Similarly, as the above plasma membrane protein to be quantified, human SLC35A2 can be exemplified. As a subject peptide for quantification and a stable-isotope labeled peptide used for measuring human SLC35A2, one or more peptides selected from a peptide having an amino acid sequence shown by SEQ ID No: 1063, SEQ ID No: 1064, and SEQ ID No: 1065 of the sequence listing can be specifically exemplified.

Similarly, as the above plasma membrane protein to be quantified, human SLC35A3 can be exemplified. As a subject peptide for quantification and a stable-isotope labeled peptide used for measuring human SLC35A3, one or more peptides selected from a peptide having an amino acid sequence shown by SEQ ID No: 1066, and SEQ ID No: 1067 of the sequence listing can be specifically exemplified.

Similarly, as the above plasma membrane protein to be quantified, human SLC35A4 can be exemplified. As a subject peptide for quantification and a stable-isotope labeled peptide used for measuring human SLC35A4, one or more peptides selected from a peptide having an amino acid sequence shown by SEQ ID No: 1068, and SEQ ID No: 1069 of the sequence listing can be specifically exemplified.

Similarly, as the above plasma membrane protein to be quantified, human SLC35A5 can be exemplified. As a subject peptide for quantification and a stable-isotope labeled peptide used for measuring human SLC35A5, one or more peptides selected from a peptide having an amino acid sequence shown by SEQ ID No: 1070, SEQ ID No: 1071, and SEQ ID No: 1072 of the sequence listing can be specifically exemplified.

Similarly, as the above plasma membrane protein to be quantified, human SLC35B1 can be exemplified. As a subject peptide for quantification and a stable-isotope labeled peptide used for measuring human SLC35B1, one or more peptides selected from a peptide having an amino acid sequence shown by SEQ ID No: 1073 of the sequence listing can be specifically exemplified.

Similarly, as the above plasma membrane protein to be quantified, human SLC35B2 can be exemplified. As a subject peptide for quantification and a stable-isotope labeled peptide used for measuring human SLC35B2, one or more peptides selected from a peptide having an amino acid sequence shown by SEQ ID No: 1074, SEQ ID No: 1075, SEQ ID No: 1076, and SEQ ID No: 1077 of the sequence listing can be specifically exemplified.

Similarly, as the above plasma membrane protein to be quantified, human SLC35B3 can be exemplified. As a subject peptide for quantification and a stable-isotope labeled peptide used for measuring human SLC35B3, one or more peptides selected from a peptide having an amino acid sequence shown by SEQ ID No: 1078, SEQ ID No: 1079, and SEQ ID No: 1080 of the sequence listing can be specifically exemplified.

Similarly, as the above plasma membrane protein to be quantified, human SLC35B4 can be exemplified. As a subject peptide for quantification and a stable-isotope labeled peptide used for measuring human SLC35B4, one or more peptides selected from a peptide having an amino acid sequence shown by SEQ ID No: 1081, and SEQ ID No: 1082 of the sequence listing can be specifically exemplified.

Similarly, as the above plasma membrane protein to be quantified, human SLC35C1 can be exemplified. As a subject peptide for quantification and a stable-isotope labeled peptide used for measuring human SLC35C1, one or more peptides selected from a peptide having an amino acid sequence shown by SEQ ID No: 1083, and SEQ ID No: 1084 of the sequence listing can be specifically exemplified.

Similarly, as the above plasma membrane protein to be quantified, human SLC35C2 can be exemplified. As a subject peptide for quantification and a stable-isotope labeled peptide used for measuring human SLC35C2, one or more peptides selected from a peptide having an amino acid sequence shown by SEQ ID No: 1085, SEQ ID No: 1086 and SEQ ID No: 1087 of the sequence listing can be specifically exemplified.

Similarly, as the above plasma membrane protein to be quantified, human SLC35D1 can be exemplified. As a subject peptide for quantification and a stable-isotope labeled peptide used for measuring human SLC35D1, one or more peptides selected from a peptide having an amino acid sequence shown by SEQ ID No: 1088, and SEQ ID No: 1089 of the sequence listing can be specifically exemplified.

Similarly, as the above plasma membrane protein to be quantified, human SLC35D2 can be exemplified. As a subject peptide for quantification and a stable-isotope labeled peptide used for measuring human SLC35D2, one or more peptides selected from a peptide having an amino acid sequence shown by SEQ ID No: 1090, SEQ ID No: 1091, and SEQ ID No: 1092 of the sequence listing can be specifically exemplified.

Similarly, as the above plasma membrane protein to be quantified, human SLC35D3 can be exemplified. As a subject peptide for quantification and a stable-isotope labeled peptide used for measuring human SLC35D3, one or more peptides selected from a peptide having an amino acid sequence shown by SEQ ID No: 1093, SEQ ID No: 1094, and SEQ ID No: 1095 of the sequence listing can be specifically exemplified.

Similarly, as the above plasma membrane protein to be quantified, human SLC35E1 can be exemplified. As a subject peptide for quantification and a stable-isotope labeled peptide used for measuring human SLC35E1, one or more peptides selected from a peptide having an amino acid sequence shown by SEQ ID No: 1096, SEQ ID No: 1097, and SEQ ID No: 1098 of the sequence listing can be specifically exemplified.

Similarly, as the above plasma membrane protein to be quantified, human SLC35E2 can be exemplified. As a subject peptide for quantification and a stable-isotope labeled peptide used for measuring human SLC35E2, one or more peptides selected from a peptide having an amino acid sequence shown by SEQ ID No: 1099, SEQ ID No: 1100, SEQ ID No: 1101, SEQ ID No: 1102, SEQ ID No: 1103, SEQ ID No: 1104, SEQ ID No: 1105, SEQ ID No: 1106, and SEQ ID No: 1107 of the sequence listing can be specifically exemplified.

Similarly, as the above plasma membrane protein to be quantified, human SLC35E3 can be exemplified. As a subject peptide for quantification and a stable-isotope labeled peptide used for measuring human SLC35E3, one or more peptides selected from a peptide having an amino acid sequence shown by SEQ ID No: 1108, SEQ ID No: 1109, and SEQ ID No: 1110 of the sequence listing can be specifically exemplified.

Similarly, as the above plasma membrane protein to be quantified, human SLC35E4 can be exemplified. As a subject peptide for quantification and a stable-isotope labeled peptide used for measuring human SLC35E4, one or more peptides selected from a peptide having an amino acid sequence shown by SEQ ID No: 1111, and SEQ ID No: 1112 of the sequence listing can be specifically exemplified.

Similarly, as the above plasma membrane protein to be quantified, human SLC35F1 can be exemplified. As a subject peptide for quantification and a stable-isotope labeled peptide used for measuring human SLC35F1, one or more peptides selected from a peptide having an amino acid sequence shown by SEQ ID No: 1113 of the sequence listing can be specifically exemplified.

Similarly, as the above plasma membrane protein to be quantified, human SLC35F2 can be exemplified. As a subject peptide for quantification and a stable-isotope labeled peptide used for measuring human SLC35F2, one or more peptides selected from a peptide having an amino acid sequence shown by SEQ ID No: 1114, and SEQ ID No: 1115 of the sequence listing can be specifically exemplified.

Similarly, as the above plasma membrane protein to be quantified, human SLC35F3 can be exemplified. As a subject peptide for quantification and a stable-isotope labeled peptide used for measuring human SLC35F3, one or more peptides selected from a peptide having an amino acid sequence shown by SEQ ID No: 1116, and SEQ ID No: 1117 of the sequence listing can be specifically exemplified.

Similarly, as the above plasma membrane protein to be quantified, human SLC35F5 can be exemplified. As a subject peptide for quantification and a stable-isotope labeled peptide used for measuring human SLC35F5, one or more peptides selected from a peptide having an amino acid sequence shown by SEQ ID No: 1118, and SEQ ID No: 1119 of the sequence listing can be specifically exemplified.

Similarly, as the above plasma membrane protein to be quantified, human SLC36A1 can be exemplified. As a subject peptide for quantification and a stable-isotope labeled peptide used for measuring human SLC36A1, one or more peptides selected from a peptide having an amino acid sequence shown by SEQ ID No: 1120 of the sequence listing can be specifically exemplified.

Similarly, as the above plasma membrane protein to be quantified, human SLC36A2 can be exemplified. As a subject peptide for quantification and a stable-isotope labeled peptide used for measuring human SLC36A2, one or more peptides selected from a peptide having an amino acid sequence shown by SEQ ID No: 1121, SEQ ID No: 1122, and SEQ ID No: 1123 of the sequence listing can be specifically exemplified.

Similarly, as the above plasma membrane protein to be quantified, human SLC36A3 can be exemplified. As a subject peptide for quantification and a stable-isotope labeled peptide used for measuring human SLC36A3, one or more peptides selected from a peptide having an amino acid sequence shown by SEQ ID No: 1124, and SEQ ID No: 1125 of the sequence listing can be specifically exemplified.

Similarly, as the above plasma membrane protein to be quantified, human SLC36A4 can be exemplified. As a subject peptide for quantification and a stable-isotope labeled peptide used for measuring human SLC36A4, one or more peptides selected from a peptide having an amino acid sequence shown by SEQ ID No: 1126, SEQ ID No: 1127, SEQ ID No: 1128, and SEQ ID No: 1129 of the sequence listing can be specifically exemplified.

Similarly, as the above plasma membrane protein to be quantified, human SLC37A1 can be exemplified. As a subject peptide for quantification and a stable-isotope labeled peptide used for measuring human SLC37A1, one or more peptides selected from a peptide having an amino acid sequence shown by SEQ ID No: 1130, SEQ ID No: 1131, and SEQ ID No: 1132 of the sequence listing can be specifically exemplified.

Similarly, as the above plasma membrane protein to be quantified, human SLC37A2 can be exemplified. As a subject peptide for quantification and a stable-isotope labeled peptide used for measuring human SLC37A2, one or more peptides selected from a peptide having an amino acid sequence shown by SEQ ID No: 1133, and SEQ ID No: 1134 of the sequence listing can be specifically exemplified.

Similarly, as the above plasma membrane protein to be quantified, human SLC37A3 can be exemplified. As a subject peptide for quantification and a stable-isotope labeled peptide used for measuring human SLC37A3, one or more peptides selected from a peptide having an amino acid sequence shown by SEQ ID No: 1135, SEQ ID No: 1136, and SEQ ID No: 1137 of the sequence listing can be specifically exemplified.

Similarly, as the above plasma membrane protein to be quantified, human SLC37A4 can be exemplified. As a subject peptide for quantification and a stable-isotope labeled peptide used for measuring human SLC37A4, one or more peptides selected from a peptide having an amino acid sequence shown by SEQ ID No: 1138, and SEQ ID No: 1139 of the sequence listing can be specifically exemplified.

Similarly, as the above plasma membrane protein to be quantified, human SLC38A1 can be exemplified. As a subject peptide for quantification and a stable-isotope labeled peptide used for measuring human SLC38A1, one or more peptides selected from a peptide having an amino acid sequence shown by SEQ ID No: 1140, and SEQ ID No: 1141 of the sequence listing can be specifically exemplified.

Similarly, as the above plasma membrane protein to be quantified, human SLC38A2 can be exemplified. As a subject peptide for quantification and a stable-isotope labeled peptide used for measuring human SLC38A2, one or more peptides selected from a peptide having an amino acid sequence shown by SEQ ID No: 1142, SEQ ID No: 1143, and SEQ ID No: 1144 of the sequence listing can be specifically exemplified.

Similarly, as the above plasma membrane protein to be quantified, human SLC38A3 can be exemplified. As a subject peptide for quantification and a stable-isotope labeled peptide used for measuring human SLC38A3, one or more peptides selected from a peptide having an amino acid sequence shown by SEQ ID No: 1145, SEQ ID No: 1146, and SEQ ID No: 1147 of the sequence listing can be specifically exemplified.

Similarly, as the above plasma membrane protein to be quantified, human SLC38A4 can be exemplified. As a subject peptide for quantification and a stable-isotope labeled peptide used for measuring human SLC38A4, one or more peptides selected from a peptide having an amino acid sequence shown by SEQ ID No: 1148, and SEQ ID No: 1149 of the sequence listing can be specifically exemplified.

Similarly, as the above plasma membrane protein to be quantified, human SLC38A5 can be exemplified. As a subject peptide for quantification and a stable-isotope labeled peptide used for measuring human SLC38A5, one or more peptides selected from a peptide having an amino acid sequence shown by SEQ ID No: 1150, SEQ ID No: 1151, SEQ ID No: 1152, SEQ ID No: 1153, and SEQ ID No: 1154 of the sequence listing can be specifically exemplified.

Similarly, as the above plasma membrane protein to be quantified, human SLC38A6 can be exemplified. As a subject peptide for quantification and a stable-isotope labeled peptide used for measuring human SLC38A6, one or more peptides selected from a peptide having an amino acid sequence shown by SEQ ID No: 1155, SEQ ID No: 1156, and SEQ ID No: 1157 of the sequence listing can be specifically exemplified.

Similarly, as the above plasma membrane protein to be quantified, human SLC39A1 can be exemplified. As a subject peptide for quantification and a stable-isotope labeled peptide used for measuring human SLC39A1, one or more peptides selected from a peptide having an amino acid sequence shown by SEQ ID No: 1158, and SEQ ID No: 1159 of the sequence listing can be specifically exemplified.

Similarly, as the above plasma membrane protein to be quantified, human SLC39A10 can be exemplified. As a subject peptide for quantification and a stable-isotope labeled peptide used for measuring human SLC39A10, one or more peptides selected from a peptide having an amino acid sequence shown by SEQ ID No: 1160, SEQ ID No: 1161, and SEQ ID No: 1162 of the sequence listing can be specifically exemplified.

Similarly, as the above plasma membrane protein to be quantified, human SLC39A11 can be exemplified. As a subject peptide for quantification and a stable-isotope labeled peptide used for measuring human SLC39A11, one or more peptides selected from a peptide having an amino acid sequence shown by SEQ ID No: 1163, and SEQ ID No: 1164 of the sequence listing can be specifically exemplified.

Similarly, as the above plasma membrane protein to be quantified, human SLC39A12 can be exemplified. As a subject peptide for quantification and a stable-isotope labeled peptide used for measuring human SLC39A12, one or more peptides selected from a peptide having an amino acid sequence shown by SEQ ID No: 1165, and SEQ ID No: 1166 of the sequence listing can be specifically exemplified.

Similarly, as the above plasma membrane protein to be quantified, human SLC39A13 can be exemplified. As a subject peptide for quantification and a stable-isotope labeled peptide used for measuring human SLC39A13, one or more peptides selected from a peptide having an amino acid sequence shown by SEQ ID No: 1167, SEQ ID No: 1168, and SEQ ID No: 1169 of the sequence listing can be specifically exemplified.

Similarly, as the above plasma membrane protein to be quantified, human SLC39A14 can be exemplified. As a subject peptide for quantification and a stable-isotope labeled peptide used for measuring human SLC39A14, one or more peptides selected from a peptide having an amino acid sequence shown by SEQ ID No: 1170, and SEQ ID No: 1171 of the sequence listing can be specifically exemplified.

Similarly, as the above plasma membrane protein to be quantified, human SLC39A2 can be exemplified. As a subject peptide for quantification and a stable-isotope labeled peptide used for measuring human SLC39A2, one or more peptides selected from a peptide having an amino acid sequence shown by SEQ ID No: 1172, SEQ ID No: 1173, SEQ ID No: 1174, and SEQ ID No: 1175 of the sequence listing can be specifically exemplified.

Similarly, as the above plasma membrane protein to be quantified, human SLC39A3 can be exemplified. As a subject peptide for quantification and a stable-isotope labeled peptide used for measuring human SLC39A3, one or more peptides selected from a peptide having an amino acid sequence shown by SEQ ID No: 1176, SEQ ID No: 1177, SEQ ID No: 1178, SEQ ID No: 1179 of the sequence listing can be specifically exemplified.

Similarly, as the above plasma membrane protein to be quantified, human SLC39A4 can be exemplified. As a subject peptide for quantification and a stable-isotope labeled peptide used for measuring human SLC39A4, one or more peptides selected from a peptide having an amino acid sequence shown by SEQ ID No: 1180, SEQ ID No: 1181, SEQ ID No: 1182, and SEQ ID No: 1183 of the sequence listing can be specifically exemplified.

Similarly, as the above plasma membrane protein to be quantified, human SLC39A5 can be exemplified. As a subject peptide for quantification and a stable-isotope labeled peptide used for measuring human SLC39A5, one or more peptides selected from a peptide having an amino acid sequence shown by SEQ ID No: 1184, SEQ ID No: 1185, and SEQ ID No: 1186 of the sequence listing can be specifically exemplified.

Similarly, as the above plasma membrane protein to be quantified, human SLC39A6 can be exemplified. As a subject peptide for quantification and a stable-isotope labeled peptide used for measuring human SLC39A6, one or more peptides selected from a peptide having an amino acid sequence shown by SEQ ID No: 1187, SEQ ID No: 1188, and SEQ ID No: 1189 of the sequence listing can be specifically exemplified.

Similarly, as the above plasma membrane protein to be quantified, human SLC39A7 can be exemplified. As a subject peptide for quantification and a stable-isotope labeled peptide used for measuring human SLC39A7, one or more peptides selected from a peptide having an amino acid sequence shown by SEQ ID No: 1190, SEQ ID No: 1191, and SEQ ID No: 1192 of the sequence listing can be specifically exemplified.

Similarly, as the above plasma membrane protein to be quantified, human SLC39A8 can be exemplified. As a subject peptide for quantification and a stable-isotope labeled peptide used for measuring human SLC39A8, one or more peptides selected from a peptide having an amino acid sequence shown by SEQ ID No: 1193, SEQ ID No: 1194, and SEQ ID No: 1195 of the sequence listing can be specifically exemplified.

Similarly, as the above plasma membrane protein to be quantified, human SLC39A9 can be exemplified. As a subject peptide for quantification and a stable-isotope labeled peptide used for measuring human SLC39A9, one or more peptides selected from a peptide having an amino acid sequence shown by SEQ ID No: 1196, SEQ ID No: 1197, and SEQ ID No: 1198 of the sequence listing can be specifically exemplified.

Similarly, as the above plasma membrane protein to be quantified, human SLC3A1 can be exemplified. As a subject peptide for quantification and a stable-isotope labeled peptide used for measuring human SLC3A1, one or more peptides selected from a peptide having an amino acid sequence shown by SEQ ID No: 1199, SEQ ID No: 1200, SEQ ID No: 1201, SEQ ID No: 1202, and SEQ ID No: 1203 of the sequence listing can be specifically exemplified.

Similarly, as the above plasma membrane protein to be quantified, human SLC3A2 can be exemplified. As a subject peptide for quantification and a stable-isotope labeled peptide used for measuring human SLC3A2, one or more peptides selected from a peptide having an amino acid sequence shown by SEQ ID No: 1204, SEQ ID No: 1205, SEQ ID No: 1206, SEQ ID No: 1207, and SEQ ID No: 1208 of the sequence listing can be specifically exemplified.

Similarly, as the above plasma membrane protein to be quantified, human SLC40A1 can be exemplified. As a subject peptide for quantification and a stable-isotope labeled peptide used for measuring human SLC40A1, one or more peptides selected from a peptide having an amino acid sequence shown by SEQ ID No: 1209, SEQ ID No: 1210, and SEQ ID No: 1211 of the sequence listing can be specifically exemplified.

Similarly, as the above plasma membrane protein to be quantified, human SLC41A1 can be exemplified. As a subject peptide for quantification and a stable-isotope labeled peptide used for measuring human SLC41A1, one or more peptides selected from a peptide having an amino acid sequence shown by SEQ ID No: 1212, SEQ ID No: 1213, and SEQ ID No: 1214 of the sequence listing can be specifically exemplified.

Similarly, as the above plasma membrane protein to be quantified, human SLC41A2 can be exemplified. As a subject peptide for quantification and a stable-isotope labeled peptide used for measuring human SLC41A2, one or more peptides selected from a peptide having an amino acid sequence shown by SEQ ID No: 1215, SEQ ID No: 1216, and SEQ ID No: 1217 of the sequence listing can be specifically exemplified.

Similarly, as the above plasma membrane protein to be quantified, human SLC41A3 can be exemplified. As a subject peptide for quantification and a stable-isotope labeled peptide used for measuring human SLC41A3, one or more peptides selected from a peptide having an amino acid sequence shown by SEQ ID No: 1218, and SEQ ID No: 1219 of the sequence listing can be specifically exemplified.

Similarly, as the above plasma membrane protein to be quantified, human SLC42A1 can be exemplified. As a subject peptide for quantification and a stable-isotope labeled peptide used for measuring human SLC42A1, one or more peptides selected from a peptide having an amino acid sequence shown by SEQ ID No: 1220, and SEQ ID No: 1221 of the sequence listing can be specifically exemplified.

Similarly, as the above plasma membrane protein to be quantified, human SLC42A2 can be exemplified. As a subject peptide for quantification and a stable-isotope labeled peptide used for measuring human SLC42A2, one or more peptides selected from a peptide having an amino acid sequence shown by SEQ ID No: 1222, and SEQ ID No: 1223 of the sequence listing can be specifically exemplified.

Similarly, as the above plasma membrane protein to be quantified, human SLC42A3 can be exemplified. As a subject peptide for quantification and a stable-isotope labeled peptide used for measuring human SLC42A3, one or more peptides selected from a peptide having an amino acid sequence shown by SEQ ID No: 1224, SEQ ID No: 1225, SEQ ID No: 1226, and SEQ ID No: 1227 of the sequence listing can be specifically exemplified.

Similarly, as the above plasma membrane protein to be quantified, human SLC43A1 can be exemplified. As a subject peptide for quantification and a stable-isotope labeled peptide used for measuring human SLC43A1, one or more peptides selected from a peptide having an amino acid sequence shown by SEQ ID No: 1228, SEQ ID No: 1229, and SEQ ID No: 1230 of the sequence listing can be specifically exemplified.

Similarly, as the above plasma membrane protein to be quantified, human SLC43A2 can be exemplified. As a subject peptide for quantification and a stable-isotope labeled peptide used for measuring human SLC43A2, one or more peptides selected from a peptide having an amino acid sequence shown by SEQ ID No: 1231, SEQ ID No: 1232, and SEQ ID No: 1233 of the sequence listing can be specifically exemplified.

Similarly, as the above plasma membrane protein to be quantified, human SLC43A3 can be exemplified. As a subject peptide for quantification and a stable-isotope labeled peptide used for measuring human SLC43A3, one or more peptides selected from a peptide having an amino acid sequence shown by SEQ ID No: 1234, SEQ ID No: 1235, and SEQ ID No: 1236 of the sequence listing can be specifically exemplified.

Similarly, as the above plasma membrane protein to be quantified, human SLC45A1 can be exemplified. As a subject peptide for quantification and a stable-isotope labeled peptide used for measuring human SLC45A1, one or more peptides selected from a peptide having an amino acid sequence shown by SEQ ID No: 1237, SEQ ID No: 1238, SEQ ID No: 1239, SEQ ID No: 1240 of the sequence listing can be specifically exemplified.

Similarly, as the above plasma membrane protein to be quantified, human SLC45A2 can be exemplified. As a subject peptide for quantification and a stable-isotope labeled peptide used for measuring human SLC45A2, one or more peptides selected from a peptide having an amino acid sequence shown by SEQ ID No: 1241, SEQ ID No: 1242, and SEQ ID No: 1243 of the sequence listing can be specifically exemplified.

Similarly, as the above plasma membrane protein to be quantified, human SLC45A3 can be exemplified. As a subject peptide for quantification and a stable-isotope labeled peptide used for measuring human SLC45A3, one or more peptides selected from a peptide having an amino acid sequence shown by SEQ ID No: 1244, SEQ ID No: 1245, SEQ ID No: 1246, SEQ ID No: 1247, SEQ ID No: 1248 of the sequence listing can be specifically exemplified.

Similarly, as the above plasma membrane protein to be quantified, human SLC45A4 can be exemplified. As a subject peptide for quantification and a stable-isotope labeled peptide used for measuring human SLC45A4, one or more peptides selected from a peptide having an amino acid sequence shown by SEQ ID No: 1249, SEQ ID No: 1250, SEQ ID No: 1251 of the sequence listing can be specifically exemplified.

Similarly, as the above plasma membrane protein to be quantified, human SLC4A1 can be exemplified. As a subject peptide for quantification and a stable-isotope labeled peptide used for measuring human SLC4A1, one or more peptides selected from a peptide having an amino acid sequence shown by SEQ ID No: 1252, SEQ ID No: 1253, SEQ ID No: 1254, SEQ ID No: 1255, SEQ ID No: 1256, SEQ ID No: 1257, and SEQ ID No: 1258 of the sequence listing can be specifically exemplified.

Similarly, as the above plasma membrane protein to be quantified, human SLC4A10 can be exemplified. As a subject peptide for quantification and a stable-isotope labeled peptide used for measuring human SLC4A10, one or more peptides selected from a peptide having an amino acid sequence shown by SEQ ID No: 1259, SEQ ID No: 1260, SEQ ID No: 1261, SEQ ID No: 1262, SEQ ID No: 1263, SEQ ID No: 1264, and SEQ ID No: 1265 of the sequence listing can be specifically exemplified.

Similarly, as the above plasma membrane protein to be quantified, human SLC4A11 can be exemplified. As a subject peptide for quantification and a stable-isotope labeled peptide used for measuring human SLC4A11, one or more peptides selected from a peptide having an amino acid sequence shown by SEQ ID No: 1266, SEQ ID No: 1267, SEQ ID No: 1268, SEQ ID No: 1269, SEQ ID No: 1270, SEQ ID No: 1271, SEQ ID No: 1272, and SEQ ID No: 1273 of the sequence listing can be specifically exemplified.

Similarly, as the above plasma membrane protein to be quantified, human SLC4A2 can be exemplified. As a subject peptide for quantification and a stable-isotope labeled peptide used for measuring human SLC4A2, one or more peptides selected from a peptide having an amino acid sequence shown by SEQ ID No: 1274, SEQ ID No: 1275, SEQ ID No: 1276, SEQ ID No: 1277, SEQ ID No: 1278, SEQ ID No: 1279, SEQ ID No: 1280, SEQ ID No: 1281, and SEQ ID No: 1282 of the sequence listing can be specifically exemplified.

Similarly, as the above plasma membrane protein to be quantified, human SLC4A3 can be exemplified. As a subject peptide for quantification and a stable-isotope labeled peptide used for measuring human SLC4A3, one or more peptides selected from a peptide having an amino acid sequence shown by SEQ ID No: 1283, SEQ ID No: 1284, SEQ ID No: 1285, SEQ ID No: 1286, SEQ ID No: 1287, SEQ ID No: 1288, SEQ ID No: 1289, SEQ ID No: 1290, SEQ ID No: 1291, SEQ ID No: 1292, SEQ ID No: 1293 of the sequence listing can be specifically exemplified.

Similarly, as the above plasma membrane protein to be quantified, human SLC4A4 can be exemplified. As a subject peptide for quantification and a stable-isotope labeled peptide used for measuring human SLC4A4, one or more peptides selected from a peptide having an amino acid sequence shown by SEQ ID No: 1294, SEQ ID No: 1295, SEQ ID No: 1296, SEQ ID No: 1297, SEQ ID No: 1298, SEQ ID No: 1299, and SEQ ID No: 1300 of the sequence listing can be specifically exemplified.

Similarly, as the above plasma membrane protein to be quantified, human SLC4A8 can be exemplified. As a subject peptide for quantification and a stable-isotope labeled peptide used for measuring human SLC4A8, one or more peptides selected from a peptide having an amino acid sequence shown by SEQ ID No: 1301, SEQ ID No: 1302, SEQ ID No: 1303, SEQ ID No: 1304, SEQ ID No: 1305, SEQ ID No: 1306, SEQ ID No: 1307 of the sequence listing can be specifically exemplified.

Similarly, as the above plasma membrane protein to be quantified, human SLC4A9 can be exemplified. As a subject peptide for quantification and a stable-isotope labeled peptide used for measuring human SLC4A9, one or more peptides selected from a peptide having an amino acid sequence shown by SEQ ID No: 1308, SEQ ID No: 1309, SEQ ID No: 1310, and SEQ ID No: 1311 of the sequence listing can be specifically exemplified.

Similarly, as the above plasma membrane protein to be quantified, human SLC5A1 can be exemplified. As a subject peptide for quantification and a stable-isotope labeled peptide used for measuring human SLC5A1, one or more peptides selected from a peptide having an amino acid sequence shown by SEQ ID No: 1312 of the sequence listing can be specifically exemplified.

Similarly, as the above plasma membrane protein to be quantified, human SLC5A12 can be exemplified. As a subject peptide for quantification and a stable-isotope labeled peptide used for measuring human SLC5A12, one or more peptides selected from a peptide having an amino acid sequence shown by SEQ ID No: 1313 of the sequence listing can be specifically exemplified.

Similarly, as the above plasma membrane protein to be quantified, human SLC5A2 can be exemplified. As a subject peptide for quantification and a stable-isotope labeled peptide used for measuring human SLC5A2, one or more peptides selected from a peptide having an amino acid sequence shown by SEQ ID No: 1314, SEQ ID No: 1315, SEQ ID No: 1316, and SEQ ID No: 1317 of the sequence listing can be specifically exemplified.

Similarly, as the above plasma membrane protein to be quantified, human SLC5A3 can be exemplified. As a subject peptide for quantification and a stable-isotope labeled peptide used for measuring human SLC5A3, one or more peptides selected from a peptide having an amino acid sequence shown by SEQ ID No: 1318, and SEQ ID No: 1319 of the sequence listing can be specifically exemplified.

Similarly, as the above plasma membrane protein to be quantified, human SLC5A4 can be exemplified. As a subject peptide for quantification and a stable-isotope labeled peptide used for measuring human SLC5A4, one or more peptides selected from a peptide having an amino acid sequence shown by SEQ ID No: 1320, and SEQ ID No: 1321 of the sequence listing can be specifically exemplified.

Similarly, as the above plasma membrane protein to be quantified, human SLC5A5 can be exemplified. As a subject peptide for quantification and a stable-isotope labeled peptide used for measuring human SLC5A5, one or more peptides selected from a peptide having an amino acid sequence shown by SEQ ID No: 1322, SEQ ID No: 1323, and SEQ ID No: 1324 of the sequence listing can be specifically exemplified.

Similarly, as the above plasma membrane protein to be quantified, human SLC6A1 can be exemplified. As a subject peptide for quantification and a stable-isotope labeled peptide used for measuring human SLC6A1, one or more peptides selected from a peptide having an amino acid sequence shown by SEQ ID No: 1325, and SEQ ID No: 1326 of the sequence listing can be specifically exemplified.

Similarly, as the above plasma membrane protein to be quantified, human SLC6A11 can be exemplified. As a subject peptide for quantification and a stable-isotope labeled peptide used for measuring human SLC6A11, one or more peptides selected from a peptide having an amino acid sequence shown by SEQ ID No: 1327, SEQ ID No: 1328, and SEQ ID No: 1329 of the sequence listing can be specifically exemplified.

Similarly, as the above plasma membrane protein to be quantified, human SLC6A14 can be exemplified. As a subject peptide for quantification and a stable-isotope labeled peptide used for measuring human SLC6A14, one or more peptides selected from a peptide having an amino acid sequence shown by SEQ ID No: 1330 of the sequence listing can be specifically exemplified.

Similarly, as the above plasma membrane protein to be quantified, human SLC6A15 can be exemplified. As a subject peptide for quantification and a stable-isotope labeled peptide used for measuring human SLC6A15, one or more peptides selected from a peptide having an amino acid sequence shown by SEQ ID No: 1331, and SEQ ID No: 1332 of the sequence listing can be specifically exemplified.

Similarly, as the above plasma membrane protein to be quantified, human SLC6A16 can be exemplified. As a subject peptide for quantification and a stable-isotope labeled peptide used for measuring human SLC6A16, one or more peptides selected from a peptide having an amino acid sequence shown by SEQ ID No: 1333 of the sequence listing can be specifically exemplified.

Similarly, as the above plasma membrane protein to be quantified, human SLC6A17 can be exemplified. As a subject peptide for quantification and a stable-isotope labeled peptide used for measuring human SLC6A17, one or more peptides selected from a peptide having an amino acid sequence shown by SEQ ID No: 1334, and SEQ ID No: 1335 of the sequence listing can be specifically exemplified.

Similarly, as the above plasma membrane protein to be quantified, human SLC6A18 can be exemplified. As a subject peptide for quantification and a stable-isotope labeled peptide used for measuring human SLC6A18, one or more peptides selected from a peptide having an amino acid sequence shown by SEQ ID No: 1336 of the sequence listing can be specifically exemplified.

Similarly, as the above plasma membrane protein to be quantified, human SLC6A19 can be exemplified. As a subject peptide for quantification and a stable-isotope labeled peptide used for measuring human SLC6A19, one or more peptides selected from a peptide having an amino acid sequence shown by SEQ ID No: 1337 of the sequence listing can be specifically exemplified.

Similarly, as the above plasma membrane protein to be quantified, human SLC6A2 can be exemplified. As a subject peptide for quantification and a stable-isotope labeled peptide used for measuring human SLC6A2, one or more peptides selected from a peptide having an amino acid sequence shown by SEQ ID No: 1338 of the sequence listing can be specifically exemplified.

Similarly, as the above plasma membrane protein to be quantified, human SLC6A2 can be exemplified. As a subject peptide for quantification and a stable-isotope labeled peptide used for measuring human SLC6A2, one or more peptides selected from a peptide having an amino acid sequence shown by SEQ ID No: 1339, SEQ ID No: 1340, and SEQ ID No: 1341 of the sequence listing can be specifically exemplified.

Similarly, as the above plasma membrane protein to be quantified, human SLC6A3 can be exemplified. As a subject peptide for quantification and a stable-isotope labeled peptide used for measuring human SLC6A3, one or more peptides selected from a peptide having an amino acid sequence shown by SEQ ID No: 1342, SEQ ID No: 1343, and SEQ ID No: 1344 of the sequence listing can be specifically exemplified.

Similarly, as the above plasma membrane protein to be quantified, human SLC6A4 can be exemplified. As a subject peptide for quantification and a stable-isotope labeled peptide used for measuring human SLC6A4, one or more peptides selected from a peptide having an amino acid sequence shown by SEQ ID No: 1345, SEQ ID No: 1346, and SEQ ID No: 1347 of the sequence listing can be specifically exemplified.

Similarly, as the above plasma membrane protein to be quantified, human SLC6A5 can be exemplified. As a subject peptide for quantification and a stable-isotope labeled peptide used for measuring human SLC6A5, one or more peptides selected from a peptide having an amino acid sequence shown by SEQ ID No: 1348, and SEQ ID No: 1349 of the sequence listing can be specifically exemplified.

Similarly, as the above plasma membrane protein to be quantified, human SLC6A6 can be exemplified. As a subject peptide for quantification and a stable-isotope labeled peptide used for measuring human SLC6A6, one or more peptides selected from a peptide having an amino acid sequence shown by SEQ ID No: 1350, SEQ ID No: 1351, SEQ ID No: 1352, SEQ ID No: 1353, and SEQ ID No: 1354 of the sequence listing can be specifically exemplified.

Similarly, as the above plasma membrane protein to be quantified, human SLC6A7 can be exemplified. As a subject peptide for quantification and a stable-isotope labeled peptide used for measuring human SLC6A7, one or more peptides selected from a peptide having an amino acid sequence shown by SEQ ID No: 1355, SEQ ID No: 1356, and SEQ ID No: 1357 of the sequence listing can be specifically exemplified.

Similarly, as the above plasma membrane protein to be quantified, human SLC6A8 can be exemplified. As a subject peptide for quantification and a stable-isotope labeled peptide used for measuring human SLC6A8, one or more peptides selected from a peptide having an amino acid sequence shown by SEQ ID No: 1358, SEQ ID No: 1359, and SEQ ID No: 1360 of the sequence listing can be specifically exemplified.

Similarly, as the above plasma membrane protein to be quantified, human SLC7A1 can be exemplified. As a subject peptide for quantification and a stable-isotope labeled peptide used for measuring human SLC7A1, one or more peptides selected from a peptide having an amino acid sequence shown by SEQ ID No: 1361 of the sequence listing can be specifically exemplified.

Similarly, as the above plasma membrane protein to be quantified, human SLC7A10 can be exemplified. As a subject peptide for quantification and a stable-isotope labeled peptide used for measuring human SLC7A10, one or more peptides selected from a peptide having an amino acid sequence shown by SEQ ID No: 1362 of the sequence listing can be specifically exemplified.

Similarly, as the above plasma membrane protein to be quantified, human SLC7A11 can be exemplified. As a subject peptide for quantification and a stable-isotope labeled peptide used for measuring human SLC7A11, one or more peptides selected from a peptide having an amino acid sequence shown by SEQ ID No: 1363, SEQ ID No: 1364, SEQ ID No: 1365, SEQ ID No: 1366, SEQ ID No: 1367, and SEQ ID No: 1368 of the sequence listing can be specifically exemplified.

Similarly, as the above plasma membrane protein to be quantified, human SLC7A13 can be exemplified. As a subject peptide for quantification and a stable-isotope labeled peptide used for measuring human SLC7A13, one or more peptides selected from a peptide having an amino acid sequence shown by SEQ ID No: 1369, and SEQ ID No: 1370 of the sequence listing can be specifically exemplified.

Similarly, as the above plasma membrane protein to be quantified, human SLC7A14 can be exemplified. As a subject peptide for quantification and a stable-isotope labeled peptide used for measuring human SLC7A14, one or more peptides selected from a peptide having an amino acid sequence shown by SEQ ID No: 1371 of the sequence listing can be specifically exemplified.

Similarly, as the above plasma membrane protein to be quantified, human SLC7A3 can be exemplified. As a subject peptide for quantification and a stable-isotope labeled peptide used for measuring human SLC7A3, one or more peptides selected from a peptide having an amino acid sequence shown by SEQ ID No: 1372, and SEQ ID No: 1373 of the sequence listing can be specifically exemplified.

Similarly, as the above plasma membrane protein to be quantified, human SLC7A4 can be exemplified. As a subject peptide for quantification and a stable-isotope labeled peptide used for measuring human SLC7A4, one or more peptides selected from a peptide having an amino acid sequence shown by SEQ ID No: 1374, and SEQ ID No: 1375 of the sequence listing can be specifically exemplified.

Similarly, as the above plasma membrane protein to be quantified, human SLC7A7 can be exemplified. As a subject peptide for quantification and a stable-isotope labeled peptide used for measuring human SLC7A7, one or more peptides selected from a peptide having an amino acid sequence shown by SEQ ID No: 1376 of the sequence listing can be specifically exemplified.

Similarly, as the above plasma membrane protein to be quantified, human SLC7A8 can be exemplified. As a subject peptide for quantification and a stable-isotope labeled peptide used for measuring human SLC7A8, one or more peptides selected from a peptide having an amino acid sequence shown by SEQ ID No: 1377, SEQ ID No: 1378, and SEQ ID No: 1379 of the sequence listing can be specifically exemplified.

Similarly, as the above plasma membrane protein to be quantified, human SLC8A1 can be exemplified. As a subject peptide for quantification and a stable-isotope labeled peptide used for measuring human SLC8A1, one or more peptides selected from a peptide having an amino acid sequence shown by SEQ ID No: 1380, SEQ ID No: 1381, SEQ ID No: 1382 of the sequence listing can be specifically exemplified.

Similarly, as the above plasma membrane protein to be quantified, human SLC8A2 can be exemplified. As a subject peptide for quantification and a stable-isotope labeled peptide used for measuring human SLC8A2, one or more peptides selected from a peptide having an amino acid sequence shown by SEQ ID No: 1383, and SEQ ID No: 1384 of the sequence listing can be specifically exemplified.

Similarly, as the above plasma membrane protein to be quantified, human SLC8A3 can be exemplified. As a subject peptide for quantification and a stable-isotope labeled peptide used for measuring human SLC8A3, one or more peptides selected from a peptide having an amino acid sequence shown by SEQ ID No: 1385, and SEQ ID No: 1386 of the sequence listing can be specifically exemplified.

Similarly, as the above plasma membrane protein to be quantified, human SLC9A1 can be exemplified. As a subject peptide for quantification and a stable-isotope labeled peptide used for measuring human SLC9A1, one or more peptides selected from a peptide having an amino acid sequence shown by SEQ ID No: 1387, SEQ ID No: 1388, SEQ ID No: 1389, SEQ ID No: 1390, SEQ ID No: 1391, SEQ ID No: 1392, and SEQ ID No: 1393 of the sequence listing can be specifically exemplified.

Similarly, as the above plasma membrane protein to be quantified, human SLC9A2 can be exemplified. As a subject peptide for quantification and a stable-isotope labeled peptide used for measuring human SLC9A2, one or more peptides selected from a peptide having an amino acid sequence shown by SEQ ID No: 1394, SEQ ID No: 1395, SEQ ID No: 1396, SEQ ID No: 1397, SEQ ID No: 1398, SEQ ID No: 1399, SEQ ID No: 1400, SEQ ID No: 1401, SEQ ID No: 1402, SEQ ID No: 1403, and SEQ ID No: 1404 of the sequence listing can be specifically exemplified.

Similarly, as the above plasma membrane protein to be quantified, human SLC9A3 can be exemplified. As a subject peptide for quantification and a stable-isotope labeled peptide used for measuring human SLC9A3, one or more peptides selected from a peptide having an amino acid sequence shown by SEQ ID No: 1405, SEQ ID No: 1406, and SEQ ID No: 1407 of the sequence listing can be specifically exemplified.

Similarly, as the above plasma membrane protein to be quantified, human SLC9A4 can be exemplified. As a subject peptide for quantification and a stable-isotope labeled peptide used for measuring human SLC9A4, one or more peptides selected from a peptide having an amino acid sequence shown by SEQ ID No: 1408, SEQ ID No: 1409, SEQ ID No: 1410, and SEQ ID No: 1411 of the sequence listing can be specifically exemplified.

Similarly, as the above plasma membrane protein to be quantified, human SLC9A5 can be exemplified. As a subject peptide for quantification and a stable-isotope labeled peptide used for measuring human SLC9A5, one or more peptides selected from a peptide having an amino acid sequence shown by SEQ ID No: 1412, and SEQ ID No: 1413 of the sequence listing can be specifically exemplified.

Similarly, as the above plasma membrane protein to be quantified, human SLC9A6 can be exemplified. As a subject peptide for quantification and a stable-isotope labeled peptide used for measuring human SLC9A6, one or more peptides selected from a peptide having an amino acid sequence shown by SEQ ID No: 1414 of the sequence listing can be specifically exemplified.

Similarly, as the above plasma membrane protein to be quantified, human SLC9A7 can be exemplified. As a subject peptide for quantification and a stable-isotope labeled peptide used for measuring human SLC9A7, one or more peptides selected from a peptide having an amino acid sequence shown by SEQ ID No: 1415, SEQ ID No: 1416, and SEQ ID No: 1417 of the sequence listing can be specifically exemplified.

Similarly, as the above plasma membrane protein to be quantified, human SLC9A8 can be exemplified. As a subject peptide for quantification and a stable-isotope labeled peptide used for measuring human SLC9A8, one or more peptides selected from a peptide having an amino acid sequence shown by SEQ ID No: 1418 of the sequence listing can be specifically exemplified.

Similarly, as the above plasma membrane protein to be quantified, human SLC9A9 can be exemplified. As a subject peptide for quantification and a stable-isotope labeled peptide used for measuring human SLC9A9, one or more peptides selected from a peptide having an amino acid sequence shown by SEQ ID No: 1419, and SEQ ID No: 1420 of the sequence listing can be specifically exemplified.

The present invention will be explained in detail by referring to Examples, while the technical scope of the present invention will not be limited by these exemplifications.

Example 1

Preparation of a Peptide Sample

Human ABCG2 (human ATB binding cassette transporter G2) was selected as a plasma membrane protein, and a peptide sample was prepared to select a peptide that can be selected by LS/MS/MS. First, a plasma membrane of human ABCG2-expressing cell was used as a peptide source, and the peptide sample was prepared as follows. That is, ABCC2-expressing plasma membrane protein was denatured in buffer solution of 7 M guanidine hydrochloride, 0.1 M Tris-HCl, 10 mM EDTA ph 8.5, and a reduction treatment by DTT and a carbamidemethylation treatment by Iodo acetamide were performed in order to protect SH group of cysteine residue. After a dialysis against 50 mM hydrogen carbonate ammonium buffer solution, trypsin was added in an amount of 1/100 of protein mass, the mixture was enzymatically digested at 37° C. for 16 hours, to obtain a peptide sample.

(Preparation of a Subject Peptide for Quantification and a Stable-Isotope Labeled Peptide)

Human ABCG2-expressing plasma membrane peptide sample was measured by LS/MS/MS. From the measurement results, according to the criteria for selecting a subject peptide for quantification, 5 peptides derived from human ABCG2 protein were selected: ENLQFSAALR (SEQ ID No: 1), LAEIYVNSSFYK (SEQ ID No:2), LFDSLTLLASGR (SEQ ID No:3), SSLLDVLAAR (SEQ ID No:4), and VIQEL-GLDK (SEQ ID No:5). The applied criteria for ENLQF-SAALR (SEQ ID No:1) were (1), (2), (3), (4), (5), (8), (9), and (10). The applied criteria for LAEIYVNSSFYK (SEQ ID No:2) were (1), (2), (3), (4), (5), (6), (7), (8), (9), and (10). The applied criteria for LFDSLTLLASGR (SEQ ID No:3) were (1), (2), (3), (4), (5), (6), (7), (8), (9), (10) and (11). The applied criteria for SSLLDVLAAR (SEQ ID No:4) were (1), (2), (3), (4), (5), (6), (7), (8), (9), (10) and (11). The applied criteria for VIQELGLDK (SEQ ID No:5) were (1), (2), (3), (4), (5), (6), (7), (8), (9), and (10). Among these, the peptide SSLLDVLAAR (SEQ ID No:4), which is the same amino acid sequence as those of rats and mice, was set as a measurement subject. By selecting a peptide having homology among species, the quantification of not only human-derived sample, but rat and mouse-derived sample can be performed by using the same standard peptide. For the subject peptide, a non-labeled peptide, and a stable-isotope peptide in which the 7 th leucine is labeled with $^{13}C_6$, and $^{15}N$, were synthesized by F-moc method: SSLLDVL($^{13}C_6$, $^{15}N$)AAR. It was confirmed that the intended peptide was synthesized, by mass spectrometry by using LS/MS/MS.

Figure 3B:
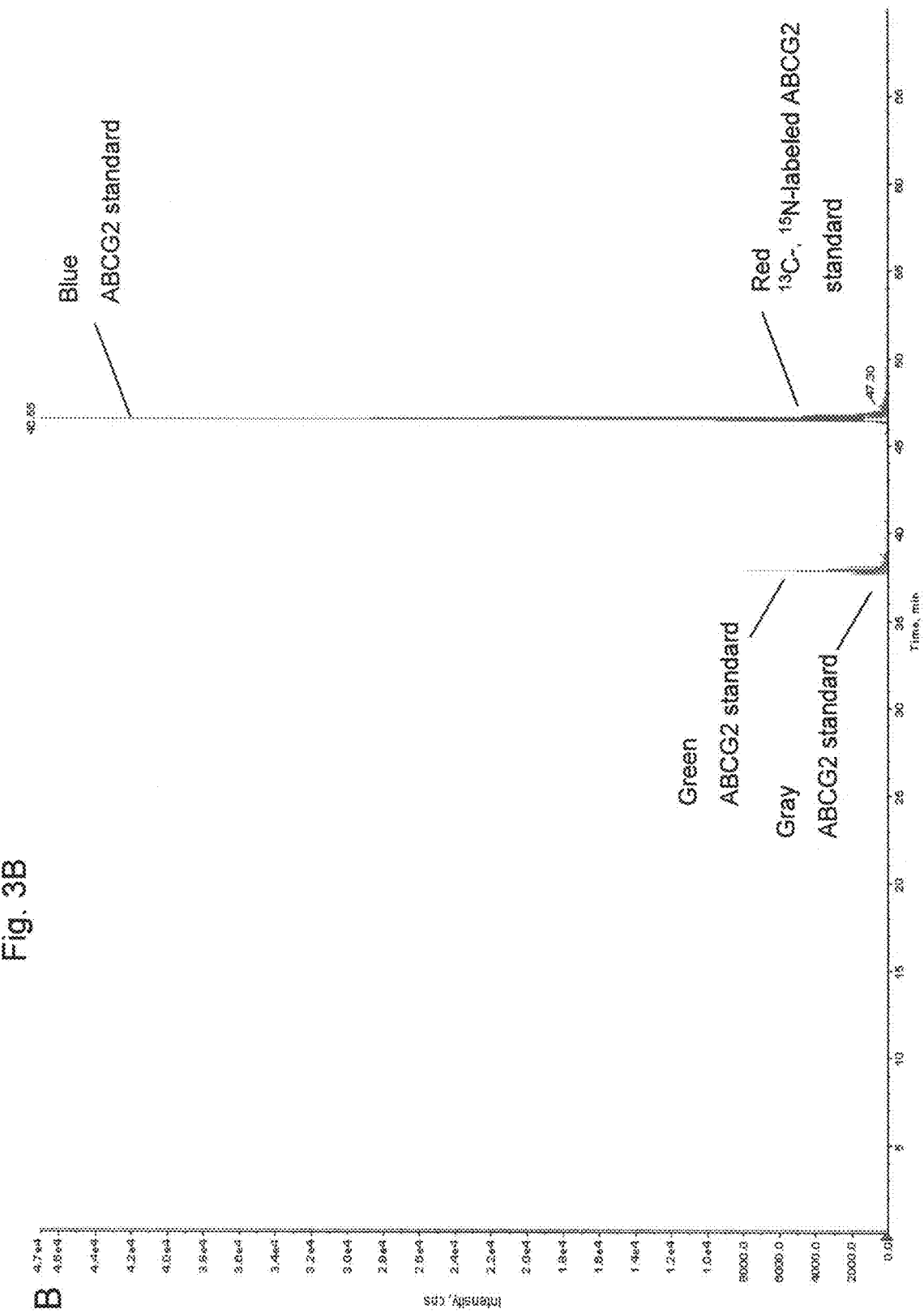
FIG. 3b It is a figure showing the results of mass spectrometry by human ABCG2 peptide in an Example of the present invention. B) shows the MS spectrum of 50 fmol standard peptide and 50 fmol, $^{13}C_6-$, $^{15}N$-labeled peptide.
Figure 4:
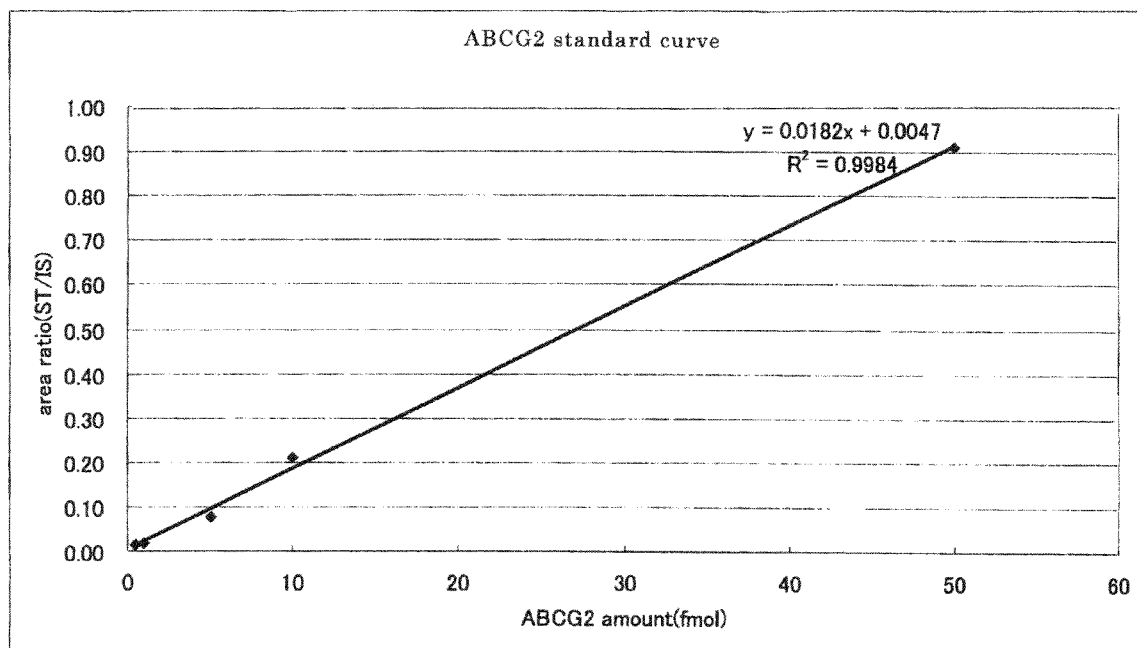
FIG. 4 It is a figure showing a calibration curve prepared by adding 10 fmol of $^{13}C_6-$, $^{15}N$-labeled peptide, to 0.5 fmol, 1 fmol, 5 fmol, 10 fmol, and 50 fmol of standard peptide, respectively in an Example of the present invention. The calibration curve was prepared by calculating MS spectrum area ratio (standard peptide/$^{13}C_6-$, $^{15}N$-labeled peptide).

(Preparation of a calibration curve) By using the selected subject peptide for quantification (non-labeled peptide: SSLLDVLAAR) and the synthesized stable-isotope labeled peptide (isotope labeled peptide: SSLLDVL($^{13}C_6$, $^{15}N$)AAR), a calibration curve was prepared (consideration of linearity). 10 f mol of $^{13}C_6$—, $^{15}N$-labeled peptide was added to each of 0.5 fmol, 1 fmol, 5 fmol, 10 fmol, 50 fmol of non-labeled peptide, respectively, and measured by LS/MS/MS (FIG. 3). The MS spectrum area ratio (non-labeled peptide/$^{13}C_6$—, $^{15}N$-labeled peptide) was calculated to prepare a calibration curve (FIG. 4). The linearity of the calibration curve within the measured range, 0.5 fmol-50 fmol, was shown, and it was confirmed that quantification was possible within this range.

(Quantification of ABCG2 Protein Sample)

As ABCG2 protein source, a plasma membrane protein of mouse conditionally immortalized brain capillary endothelial cell strain was selected and quantified. First, the cultured cells were suspended in 10 mM Tris-HCl, 250 mM Sucrose, 1 mM EGTA pH 7.4. High nitrogen gas filling method was conducted for 15 min, and the solution was centrifuged at 10,000×g, for 15 min. Further, the supernatant was added on 38% sucrose solution, which mixture was centrifuged at 10,000×g for 40 min to obtain a plasma membrane sample.

Figure 5:
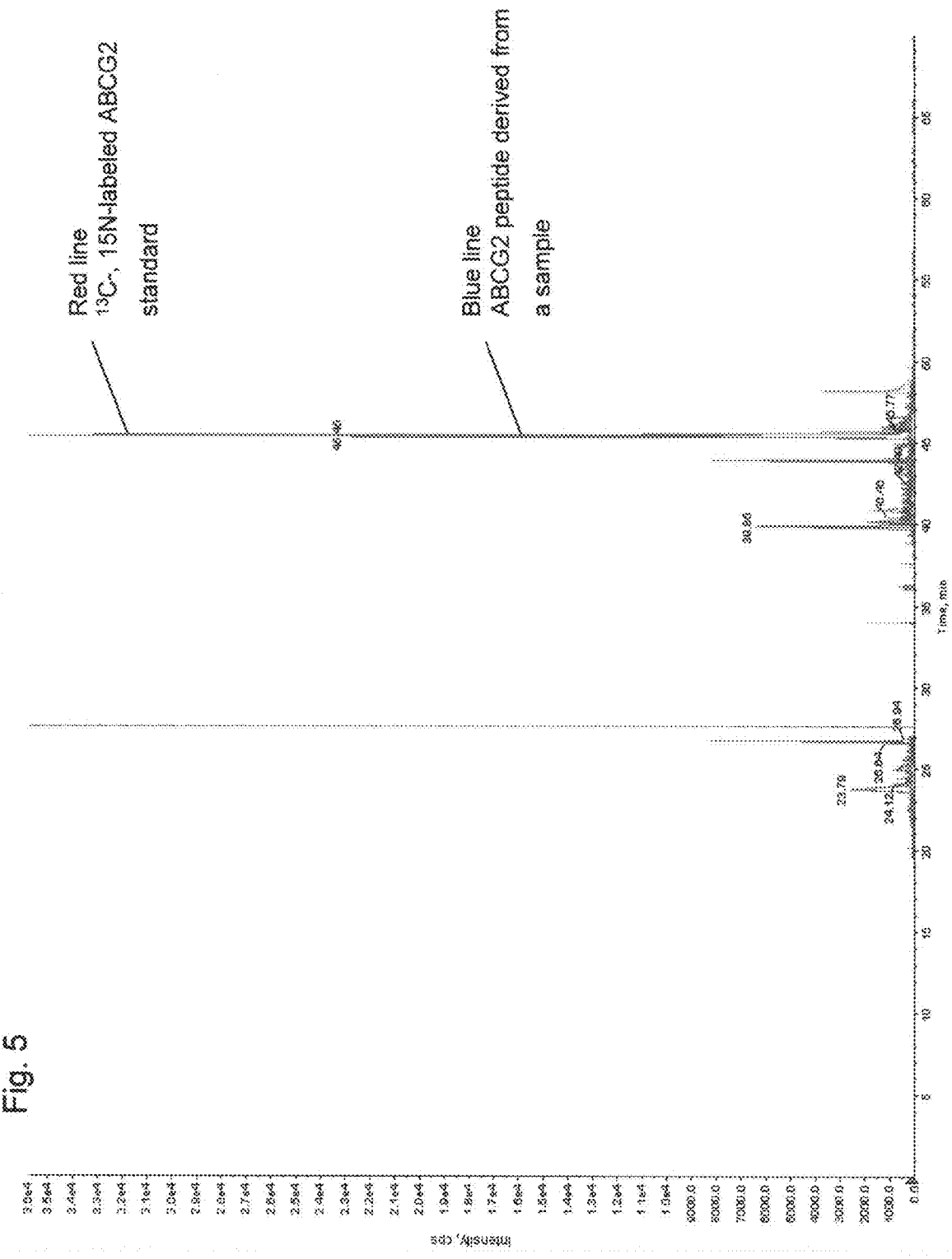
FIG. 5 It is a figure showing the results of mass spectrometry in an experiment for quantifying ABCG2 content in 1 µg of a plasma membrane peptide sample of a conditionally immortalized brain capillary endothelial cell strain, in an Example of the present invention. 10 fmol of $^{13}C_6-$, $^{15}N$-labeled peptide was added to a sample and measured. The ABCG2 content in the sample calculated from the calibration curve was 4.7 fmol/µg.

With the method described in the above section "(Preparation of a peptide sample)", a peptide sample was prepared from a plasma membrane sample. In 1 μg of the plasma membrane peptide sample thus obtained from mouse conditionally immortalized brain capillary endothelial cell strain, 10 fmol of $^{13}C_6$—, $^{15}N$-labeled peptide was added and the resultant was measured by LS/MS/MS (FIG. 5). After measurement, MS spectrum area ratio (endogenous ABCG2 peptide $^{13}C_6$—, $^{15}N$-labeled peptide) was calculated, and the quantitative level was calculated by using the above calibration curve. As a result, the ABCG2 protein mass of a plasma membrane of mouse conditionally immortalized brain capillary endothelial cell strain was calculated to be 4.7 fmol/μg.

As criteria for selecting a subject peptide for quantification, criteria (1), (2), (3), (4), (5), (6), (7), (8), (9), and (10) were applied as well as (11) according to need. Subject peptides for quantification for the proteins listed on the following Table 1 were synthesized in the same manner as Example 1, and their linearity was considered by preparing a calibration curve. 500 f mol of a stable-isotope labeled peptide was added to each of 10 fmol, 50 fmol, 100 fmol, 500 fmol, 1000 fmol of non-labeled peptide, respectively, and measured by LS/MS/MS. In each of the peptides, the linearity of the calibration curve was shown within 10 f mol-1000 fmol, and it was confirmed that quantification of the target protein is possible within this range (FIG. 6). Moreover, a plasma membrane of protein of human leukemia cell strain was selected as a transporter protein source, and quantified. The quantification threshold value and the quantitative level of plasmid membrane of leukemia cells of the obtained calibration curve are shown in Table 1.

TABLE 1

| protein | sequence | Isotope sequence | Quantitative threshold (fmol) | Quantitative level of leukemia cells (fmol/μg) |
|---|---|---|---|---|
| ABCB1 | EALDESIPPVSF ($^{13}C_9$, $^{15}N$)WR | EALDESIPPVSF($^{13}C_9$, $^{15}N$)WR | 10 | <0.12 |
| ABCB4 | IATEAIENIR | IATEA($^{13}C_3$, $^{15}N$)IENIR | 1 | 0 |

TABLE 1-continued

| protein | sequence | Isotope sequence | Quantitative threshold (fmol) | Quantitative level of leukemia cells (fmol/μg) |
|---|---|---|---|---|
| ABCB5 | SADLIVTLK | SADLIVTL($^{13}C_6$, $^{15}N$)K | 5 | 0.15 |
| ABCB11 | STALQLIQR | STALQL($^{13}C_6$, $^{15}N$)IQR | 1 | 0.45 |
| ABCC1 | TPSGNLVNR | TPSGNL($^{13}C_6$, $^{15}N$)VNR | 5 | 0.67 |
| ABCC2 | QLLNNILR | QLLNNIL($^{13}C_6$, $^{15}N$)R | 10 | <0.01 |
| ABCC3 | AEGEISDPFR | AEGEISDPF($^{13}C_9$, $^{15}N$)R | 5 | <0.06 |
| ABCC4 | APVLFFDR | APVL($^{13}C_6$, $^{15}N$)FFDR | 5 | 0.65 |
| ABCC5 | SLSEASVAVDR | SL($^{13}C_6$, $^{15}N$)SEASVAVDR | 10 | 0.28 |
| ABCC6 | APETEPFLR | APETEPFL($^{13}C_6$, $^{15}N$)R | 1 | 0 |
| ABCC7 | GLPLVHTLITVSK | GLPLVHTLITV($^{13}C_5$, $^{15}N$)SK | 10 | <0.22 |
| ABCC8 | TVVTIAHR | TVVTIA($^{13}C_3$, $^{15}N$)HR | 5 | <0.06 |
| ABCC9 | NLHHNLLNK | NLHHNLL($^{13}C_6$, $^{15}N$)NK | 50 | <0.29 |
| ABCC10 | VFTALALVR | VFTALAL($^{13}C_6$, $^{15}N$)VR | 5 | <0.01 |
| ABCC11 | FNLDPFDR | FNLDPF($^{13}C_9$, $^{15}N$)DR | 5 | <0.11 |
| ABCC12 | FSIAILPFSIK | FSIAILPF($^{13}C_9$, $^{15}N$)SIK | 50 | <0.43 |
| ABCC13 | EDLFELK | EDLFEL($^{13}C_6$, $^{15}N$)K | 5 | 0 |
| ABCG1 | GAVLINGLPR | GAVLINGL($^{13}C_6$, $^{15}N$)PR | 5 | 0 |
| ABCG4 | GVVTNLIIPYLK | GVVTNLIPYL($^{13}C_6$, $^{15}N$)K | 5 | <0.21 |
| ABCG5 | DSPGVFSK | DSPGVF($^{13}C_9$, $^{15}N$)SK | 50 | <0.09 |
| ABCG8 | ASLLDVITGR | ASLL($^{13}C_6$, $^{15}N$)DVITGR | 5 | 0 |

As criteria for selecting a subject peptide for quantification, criteria (1), (2), (3), (4), (5), (6), (7), (8), (9), and (10) were applied as well as (11) according to need, subject peptides for quantification for the proteins listed on the following Table 2 were synthesized in the same manner as Example 1, and their linearity was considered by preparing a calibration curve. 100 fmol of a stable-isotope labeled peptide was added to each of 1 fmol, 5 fmol, 10 fmol, 50 fmol, 100 fmol, 500 fmol, and 1000 fmol of non-labeled peptide, respectively, and measured by LS/MS/MS. In each of the peptides, the linearity of the calibration curve was shown, and it was confirmed that quantification of the intended peptide is possible. The quantification threshold value and the quantitative level of plasma membrane of leukemia cells of the obtained calibration curve are shown in Table 2.

TABLE 2

| protein | sequence | Isotope sequence | Quantitative threshold (fmol) |
|---|---|---|---|
| SLC10A1 | GIYDGDLK | GIYDGDL($^{13}C_6$, $^{15}N$)K | 5 |
| SLC15A1 | TLPVFPK | TLPVFP($^{13}C_5$, $^{15}N$)K | 5 |
| SLC15A2 | SQDFHFHLK | SQDFHFHL($^{13}C_6$, $^{15}N$)K | 10 |
| SLC21A2 | VNTAAVNLVPGDPR | VNTAAVNLVPGDP($^{13}C_5$, 15N)R | 5 |
| SLC21A6 | LNTVGIAK | LNTVGI($^{13}C_6$, $^{15}N$)AK | 1 |
| SLC21A8 | IYNSVFFGR | IYNSVFF($^{13}C_9$, $^{15}N$)GR | 5 |
| SLC21A9 | VLLQTLR | VLLQTL($^{13}C_6$, $^{15}N$)R | 5 |
| SLC22A1 | LSPSFADLFR | LSPSFADL($^{13}C_6$, $^{15}N$)FR | 5 |
| SLC22A3 | FLQGVFGK | FLQGVF($^{13}C_9$, $^{15}N$)GK | 5 |

TABLE 2-continued

| protein | sequence | Isotope sequence | Quantitative threshold(fmol) |
|---|---|---|---|
| SLC22A7 | NVALLALPR | NVALLAL($^{13}C_6$, $^{15}N$)PR | 10 |
| SLC22A9 | DTLTLEILK | DTLTLEIL($^{13}C_6$, $^{15}N$)K | 50 |
| SLC22A10 | NLPLPDTIK | NLPLPDTI($^{13}C_6$, $^{15}N$)K | 5 |
| SLC22A15 | VGGIIAPFIPSLK | VGGIIAPFIPSL($^{13}C_6$, $^{15}N$)K | 5 |

INDUSTRIAL APPLICABILITY

With the method for quantifying a plasma membrane protein by mass spectrometry by using a stable-isotope labeled peptide of the present invention, it is possible to quantify insoluble and high molecular membrane proteins in a simple, rapid and accurate manner, which was difficult with the conventional methods. Further, with the method for quantifying a plasma membrane protein of the present invention, it is possible to quantify the membrane protein without using an antibody. Therefore, the step of preparing an antibody which took much time in the conventional methods can be omitted, and the quantification of a membrane protein to which an antibody cannot be prepared became also possible. Therefore, a method for quantifying accurately a plasma membrane protein widely applicable can be provided. Therefore, a method for quantifying a plasma membrane protein of the present invention can be expected to contribute significantly for elucidating functions of a plasma membrane protein having important functions as receptor against factors acting on organisms, transporter of biological substances, ion channel, and plasma membrane antigen; screening of active substances, test, diagnosis, etc. using the expression of the protein. Particularly, when developing a novel drug, the absolute quantification of a protein such as membrane proteins by a simple and accurate method, is very critical for testing a novel drug candidate. The method for quantifying a plasma membrane protein of the present invention is expected to contribute greatly for promoting development in this field.

The invention claimed is:

1. A method for quantifying a plasma membrane protein by liquid chromatography-tandem mass spectrometry (LC/MS/MS) using a stable-isotope labeled peptide, comprising the following steps (a) to (e):
   (a) preparing and identifying a peptide fragment by fragmenting a separated plasma membrane protein target molecule to be quantified; and selecting a subject peptide for quantification that can be ionized by ESI method based on criteria consisting of at least (1) and (2) set forth below and based on selective criteria (3) to (11) set forth below, each selective criterion having a score value, wherein a peptide is preferentially selected as the subject peptide for quantification if it meets at least criteria (1) and (2) and if it has a high total score value based on said score values of selective criteria (3) to (11):
      (1) the peptide is obtained by fragmenting with a protease selected from trypsin, endoproteinase, and pepsin;
      (2) the peptide sequence is specific to the target molecule;
      (3) where it is a peptide wherein the content of hydrophobic amino acids is 80% or less and wherein not more than 10 hydrophobic amino acids are consecutive, where hydrophobic amino acids are selected from tryptophan, tyrosine, valine, leucine, isoleucine and phenylalanine, score 2 is given;
      (4) where it is a peptide wherein the number of amino acid residues is 4 to 30, score 3 is given;
      (5) where it is a peptide that does not contain the sequence of asparagine-X-serine, asparagine-X-threonine, or asparagine-X-cysteine as specific amino acid sequence conditions, wherein X represents an amino acids other than proline, score 2 is given;
      (6) where, except when a post-translational modified protein is being quantified, it is a peptide that does not contain a post-translation modified site, score 3 is given;
      (7) where it is a peptide that does not contain a single nucleotide polymorphism (SNP) site, score 4 is given;
      (8) where it is a peptide wherein a cleavage site of the protease is not arginine-arginine, arginine-lysine, lysine-arginine, or lysine-lysine, score 5 is given;
      (9) where it is a peptide that does not contain a transmembrane domain when the protein structure is determined or estimated, score 2 is given; and
      (10) where it is a peptide that does not contain methionine or cysteine, score 3 is given; and
      (11) where it is a peptide that does not contain tryptophan or glutamic acid, score 1 is given;
   (b) preparing a stable-isotope labeled peptide having the same sequence as the subject peptide for quantification and labeled with a stable-isotope by a peptide synthesis method;
   (c) preparing a calibration curve by using the subject peptide for quantification and the stable-isotope labeled peptide and performing mass spectrometry using LC/MS/MS for each predetermined concentration level;
   (d) performing mass spectrometry by using LC/MS/MS by adding the stable-isotope labeled peptide to the peptide fragment obtained by fragmenting the plasma membrane protein to be quantified and calculating the mass spectrum area ratio of the peptide fragment to the stable-isotope labeled peptide; and (e) calculating a quantitative level of the plasma membrane protein from the mass spectrum area ratio by using the calibration curve.

2. The method for quantifying a plasma membrane protein according to claim 1, wherein the hydrophobic amino acid content in selective criterion (3) is 50% or less, and the number of amino acid residues in selective criterion (4) is 8 to 12.

3. The method for quantifying a plasma membrane protein according to claim 1, further comprising an additional criterion (12):
(12) the same amino acid sequence of the peptide is found in plural animal species;
wherein the peptide is preferentially selected as the subject peptide for quantification if it meets at least criteria (1), (2) and (12) and if it has a high total score value based on said score values of selective criteria (3) to (11).

4. The method for quantifying a plasma membrane protein according to claim 1, wherein plural specific measurement channels are prepared by combining parent ion (m/z) and peptide fragment ion (m/z) of candidate peptides selected according to the criteria for selecting subject peptide for quantification, and measured.

5. The method for quantifying a plasma membrane protein according to claim 4, wherein the plural specific channels are prepared for plural candidate peptides of the same protein and for a candidate peptide for plural proteins, and measured at the same time.

6. The method for quantifying a plasma membrane protein according to claim 1, wherein the stable-isotope labeled peptide is labeled with an amino acid containing any one of $^{15}N$, $^{13}C$, $^{18}O$, or $^{2}H$.

7. The method for quantifying a plasma membrane protein according to claim 1, wherein a source of plasma membrane protein is a tissue sample.

8. The method for quantifying a plasma membrane protein according to claim 1, wherein the plasma membrane protein is one or more proteins selected from the group consisting of human ABCA1, human ABCA2, human ABCA3, human ABCA4, human ABCA5, human ABCA6, human ABCA7, human ABCA8, human ABCA9, human ABCA10, human ABCA12, human ABCA13, human ABCB1, human ABCB4, human ABCB5, human ABCB11, human ABCC1, human ABCC2, human ABCC3, human ABCC4, human ABCC5, human ABCC6, human ABCC7, human ABCC8, human ABCC9, human ABCC10, human ABCC11, human ABCC12, human ABCC13, human ABCG1, human ABCG2, human ABCG4, human ABCG5, human ABCG8, and human P-glycoprotein.

9. The method for quantifying a plasma membrane protein according to claim 1, wherein the plasma membrane protein is one or more proteins selected from the group consisting of human SLC10A1, human SLC10A2, human SLC15A1, human SLC15A2, human SLC16A1, human SLC16A7, human SLC19A1, human SLC19A2, human SLC19A3, human SLC21A1, human SLC21A10, human SLC21A11, human SLC21A12, human SLC21A13, human SLC21A14, human SLC21A15, human SLC21A19, human SLC21A2, human SLC21A20, human SLC21A3, human SLC21A4, human SLC21A5, human SLC21A6, human SLC21A7, human SLC21A8, human SLC21A9, human SLC22A1, human SLC22A10, human SLC22A11, human SLC22A12, human SLC22A13, human SLC22A14, human SLC22A15, human SLC22A16, human SLC22A17, human SLC22A18, human SLC22A2, human SLC22A3, human SLC22A4, human SLC22A5, human SLC22A6, human SLC22A7, human SLC22A8, human SLC22A9, human SLC23A1, human SLC23A2, human SLC28A1, human SLC28A2, human SLC28A3, human SLC29A1, human SLC29A2, human SLC29A3, human SLC29A4, human SLC31A1, human SLC3A2, human SLC43A1, human SLC43A2, human SLC43A3, human SLC7A5, human SLC7A6, and human SLC7A8.

10. The method for quantifying a plasma membrane protein according to claim 1, wherein the plasma membrane protein is one or more proteins selected from the group consisting of human SLC10A3, human SLC10A4, human SLC10A5, human SLC10A6, human SLC11A1, human SLC11A2, human SLC12A1, human SLC12A2, human SLC12A3, human SLC12A4, human SLC12A5, human SLC12A6, human SLC12A7, human SLC12A8, human SLC12A9, human SLC13A1, human SLC13A2, human SLC13A3, human SLC13A4, human SLC13A5, human SLC14A1, human SLC14A2, human SLC15A3, human SLC15A4, human SLC16A10, human SLC16A11, human SLC16A1, human SLC16A13, human SLC16A14, human SLC16A2, human SLC16A3, human SLC16A4, human SLC16A5, human SLC16A6, human SLC16A8, human SLC16A9, human SLC17A1, human SLC17A2, human SLC17A3, human SLC17A4, human SLC17A5, human SLC17A6, human SLC17A7, human SLC17A8, human SLC18A1, human SLC18A2, human SLC18A3, human SLC1A1, human SLC1A2, human SLC1A3, human SLC1A4, human SLC1A5, human SLC1A6, human SLC1A7, human SLC20A1, human SLC20A2, human SLC23A3, human SLC24A1, human SLC24A2, human SLC24A3, human SLC24A4, human SLC24A5, human SLC24A6, human SLC25A1, human SLC25A10, human SLC25A11, human SLC25A12, human SLC25A13, human SLC25A14, human SLC25A15, human SLC25A16, human SLC25A17, human SLC25A18, human SLC25A19, human SLC25A2, human SLC25A20, human SLC25A21, human SLC25A22, human SLC25A23, human SLC25A24, human SLC25A25, human SLC25A26, human SLC25A27, human SLC25A28, human SLC25A29, human SLC25A3, human SLC25A30, human SLC25A31, human SLC25A32, human SLC25A33, human SLC25A34, human SLC25A35, human SLC25A36, human SLC25A37, human SLC25A4, human SLC25A5, human SLC25A6, human SLC25A7, human SLC25A8, human SLC25A9, human SLC26A1, human SLC26A10, human SLC26A11, human SLC26A2, human SLC26A3, human SLC26A4, human SLC26A5, human SLC26A6, human SLC26A7, human SLC26A8, human SLC26A9, human SLC27A1, human SLC27A2, human SLC27A3, human SLC27A4, human SLC27A5, human SLC27A6, human SLC2A1, human SLC2A10, human SLC2A11, human SLC2A12, human SLC2A13, human SLC2A14, human SLC2A2, human SLC2A3, human SLC2A4, human SLC2A5, human SLC2A6, human SLC2A7, human SLC2A8, human SLC2A9, human SLC30A1, human SLC30A10, human SLC30A11, human SLC30A2, human SLC30A3, human SLC30A4, human SLC30A5, human SLC30A6, human SLC30A7, human SLC30A8, human SLC30A9, human SLC31A2, human SLC32A1, human SLC33A1, human SLC34A1, human SLC34A2, human SLC34A3, human SLC35B1, human SLC35B2, human SLC35B3, human SLC35B4, human SLC35C1, human SLC35C2, human SLC35D1, human SLC35D2, human SLC35D3, human SLC36A1, human SLC36A2, human SLC36A3, human SLC36A4, human SLC37A1, human SLC37A2, human SLC37A3, human SLC37A4, human SLC38A1, human SLC38A2, human SLC38A3, human SLC38A4, human SLC38A5, human SLC38A6, human SLC3A1, human SLC40A1, human SLC41A1, human SLC41A2, human SLC41A3, human SLC44A1, human SLC44A2, human SLC44A3, human SLC44A4, human SLC44A5, human SLC45A1, human SLC45A2, human SLC45A3, human SLC45A4, human SLC4A1, human SLC4A10, human SLC4A11, human SLC4A2, human SLC4A3, human SLC4A4, human SLC4A5, human SLC4A7, human SLC4A8, human SLC4A9, human SLC5A1, human SLC5A11, human SLC5A12, human SLC5A2, human SLC5A3, human SLC5A4, human SLC5A5, human SLC5A9, human SLC6A1, human SLC6A10, human SLC6A11, human SLC6A12, human SLC6A13, human SLC6A14, human SLC6A15, human SLC6A16, human SLC6A17, human SLC6A18, human SLC6A19, human SLC6A2, human SLC6A20, human SLC6A3, human SLC6A4, human SLC6A5, human SLC6A6, human SLC6A7, human SLC6A8, human SLC6A9, human SLC7A1, human SLC7A10, human SLC7A11, human SLC7A13, human SLC7A14, human SLC7A2, human SLC7A3, human SLC7A4, human SLC7A7, human SLC7A9, human SLC8A1, human SLC8A2, human SLC8A3, human SLC9A1, human SLC9A2, human SLC9A3, human SLC9A4, human SLC9A5, human SLC9A6, human SLC9A7, human SLC9A8, and human SLC9A9.

11. The method for quantifying a plasma membrane protein according to claim 1, wherein the plasma membrane protein is one or more proteins selected the group consisting from human SLC35A1, human SLC35A2, human SLC35A3, human SLC35A4, human SLC35A5, human SLC35E1, human SLC35E2, human SLC35E3, human SLC35E4, human SLC35F1, human SLC35F2, human SLC35F3, human SLC35F5, human SLC39A1, human SLC39A10, human SLC39A11, human SLC39A12, human SLC39A13, human SLC39A14, human SLC39A2, human SLC39A3, human SLC39A4, human SLC39A5, human SLC39A6, human SLC39A7, human SLC39A8, human SLC39A9, human SLC42A1, human SLC42A2, and human SLC42A3.

12. The method for quantifying a plasma membrane protein according to claim 1, wherein the plasma membrane protein is human MATE1 or human MATE2.

13. The method for quantifying a plasma membrane protein according to claim 1, wherein the plasma membrane protein is one or more proteins selected from the group consisting of human ABCA1, human ABCA2, human ABCA3, human ABCA4, human ABCA5, human ABCA6, human ABCA7, human ABCA8, human ABCA9, human ABCA10, human ABCA12, human ABCA13, human ABCB1, human ABCB4, human ABCB5, human ABCB11, human ABCC1, human ABCC2, human ABCC3, human ABCC4, human ABCC5, human ABCC6, human ABCC10, human ABCC11, human ABCC12, human ABCC13, human ABCG1, human ABCG2, human ABCG4, human ABCG5, human ABCG8, human MATE1, human MATE2, human SLC3A2, human SLC7A5, human SLC7A6, human SLC10A1, human SLC10A2, human SLC15A1, human SLC15A2, human SLC16A1, human SLC16A7, human SLC19A1, human SLC21A2, human SLC21A3, human SLC21A4, human SLC21A5, human SLC21A6, human SLC21A7, human SLC21A8, human SLC21A9, human SLC21A11, human SLC21A12, human SLC21A13, human SLC21A14, human SLC21A15, human SLC21A19, human SLC21A20, human SLC22A1, human SLC22A2, human SLC22A3, human SLC22A4, human SLC22A5, human SLC22A6, human SLC22A7, human SLC22A8, human SLC22A9, human SLC22A10, human SLC22A11, human SLC22A12, human SLC22A13, human SLC22A14, human SLC22A15, human SLC22A16, human SLC22A17, human SLC23A1, human SLC23A2, human SLC28A1, human SLC28A2, human SLC28A3, human SLC29A1, human SLC29A2, and human SLC31A1.

* * * * *

UNITED STATES PATENT AND TRADEMARK OFFICE
CERTIFICATE OF CORRECTION

Page 1 of 1

PATENT NO. : 7,901,942 B2
APPLICATION NO. : 12/093133
DATED : March 8, 2011
INVENTOR(S) : Junichi Kamiie, Sumio Otsuki and Tetsuya Terasaki It is certified that error appears in the above-identified patent and that said Letters Patent is hereby corrected as shown below:

Column 532, Claim 10, line 18, please amend "SLC16A1" to read "SLC16A12"

Signed and Sealed this
Thirty-first Day of May, 2011

David J. Kappos
*Director of the United States Patent and Trademark Office*